(12) United States Patent
Munakata et al.

(10) Patent No.: US 9,242,973 B2
(45) Date of Patent: Jan. 26, 2016

(54) CHROMANE COMPOUNDS

(71) Applicant: CoMentis, Inc., South San Francisco, CA (US)

(72) Inventors: Ryosuke Munakata, Tokyo (JP); Makoto Inoue, Tokyo (JP); Hiroaki Tominaga, Tokyo (JP); Shingo Yamasaki, Tokyo (JP); Yasuhiro Shiina, Tokyo (JP); Kiyohiro Samizu, Tokyo (JP); Hisao Hamaguchi, Tokyo (JP); Lin Hong, Edmond, OK (US)

(73) Assignee: COMENTIS, INC., South San Francisco, CA (US)

( * ) Notice: Subject to any disclaimer, the term of this patent is extended or adjusted under 35 U.S.C. 154(b) by 0 days.

(21) Appl. No.: 14/603,110

(22) Filed: Jan. 22, 2015

(65) Prior Publication Data

US 2015/0225386 A1 Aug. 13, 2015

Related U.S. Application Data

(60) Division of application No. 14/192,667, filed on Feb. 27, 2014, now Pat. No. 8,975,415, which is a continuation of application No. PCT/US2013/043016, filed on May 29, 2013.

(60) Provisional application No. 61/782,038, filed on Mar. 14, 2013, provisional application No. 61/653,321, filed on May 30, 2012.

(51) Int. Cl.
| C07D 263/52 | (2006.01) |
| C07D 493/00 | (2006.01) |
| C07D 413/14 | (2006.01) |
| C07D 498/10 | (2006.01) |
| C07D 498/20 | (2006.01) |
| C07D 519/00 | (2006.01) |

(52) U.S. Cl.
CPC .......... *C07D 413/14* (2013.01); *C07D 263/52* (2013.01); *C07D 498/10* (2013.01); *C07D 498/20* (2013.01); *C07D 519/00* (2013.01)

(58) Field of Classification Search
CPC .................................................. C07D 263/52
USPC ........................................ 548/216; 549/330
See application file for complete search history.

(56) References Cited

U.S. PATENT DOCUMENTS

| 6,545,127 B1 | 4/2003 | Tang et al. |
| 8,501,733 B2 | 8/2013 | Motoki et al. |
| 8,975,415 B2 | 3/2015 | Munakata et al. |
| 2004/0121947 A1 | 6/2004 | Ghosh et al. |
| 2006/0111370 A1 | 5/2006 | Zhu et al. |
| 2007/0203116 A1 | 8/2007 | Quagliato et al. |
| 2010/0087429 A1 | 4/2010 | White et al. |
| 2011/0152253 A1 | 6/2011 | Motoki et al. |
| 2011/0218192 A1 | 9/2011 | Dillard et al. |
| 2012/0065195 A1 | 3/2012 | Clark et al. |
| 2012/0302549 A1 | 11/2012 | Narquizian et al. |
| 2013/0338177 A1 | 12/2013 | Minatti et al. |

FOREIGN PATENT DOCUMENTS

| WO | WO-03/039454 A2 | 5/2003 |
| WO | WO-03/039454 A3 | 5/2003 |
| WO | WO-2005/058311 A1 | 6/2005 |
| WO | WO-2007/100536 A1 | 9/2007 |
| WO | WO-2010/013302 A1 | 2/2010 |
| WO | WO-2010/013794 A1 | 2/2010 |
| WO | WO-2010/021680 A2 | 2/2010 |
| WO | WO-2010/021680 A3 | 2/2010 |
| WO | WO-2010/030954 A1 | 3/2010 |
| WO | WO-2010/105179 A2 | 9/2010 |
| WO | WO-2010/105179 A3 | 9/2010 |
| WO | WO-2010/128058 A1 | 11/2010 |
| WO | WO-2011/072064 A1 | 6/2011 |
| WO | WO-2011/106414 A1 | 9/2011 |
| WO | WO-2011/115928 A1 | 9/2011 |
| WO | WO-2011/115938 A1 | 9/2011 |
| WO | WO-2011/123674 A1 | 10/2011 |
| WO | WO-2011/130741 A1 | 10/2011 |
| WO | WO-2012/040641 A2 | 3/2012 |
| WO | WO-2012/040641 A3 | 3/2012 |
| WO | WO-2012/054510 A1 | 4/2012 |
| WO | WO-2012/071279 A1 | 5/2012 |
| WO | WO-2012/071458 A1 | 5/2012 |
| WO | WO-2012/087237 A1 | 6/2012 |
| WO | WO-2012/109165 A1 | 8/2012 |
| WO | WO-2012/112462 A1 | 8/2012 |
| WO | WO-2012/163790 A1 | 12/2012 |
| WO | WO-2013/044092 A1 | 3/2013 |
| WO | WO-2013/054108 A1 | 4/2013 |
| WO | WO-2012/181202 A3 | 12/2013 |
| WO | WO-2013/178322 A1 | 12/2013 |
| WO | WO-2013/181202 A2 | 12/2013 |

OTHER PUBLICATIONS

Anderson, R.N. et al. (Oct. 12, 2001). "Deaths: Leading Causes for 1999," *National Vital Statistics Reports* 49(11): 88 pages.

(Continued)

*Primary Examiner* — Nizal Chandrakumar

(74) *Attorney, Agent, or Firm* — Morrison & Foerster LLP

(57) ABSTRACT

The present invention provides a hydrate of N-[(4S)-2-amino-2',2'-dimethyldispiro[1,3-oxazole-4,4'-chromene-3',3''-oxetan]-6'-yl]-5-chloropyridine-2-carboxamide which is useful as an active ingredient of a pharmaceutical composition, in particular, a pharmaceutical composition for preventing or treating diseases or conditions associated with and/or mediated by β-secretase activity, hydrolysis of a β-secretase site of a β-amyloid precursor protein, and/or β-amyloid protein accumulation, including a pharmaceutical composition for preventing or treating diseases including, but not limited to, Glaucoma, MCI (Mild cognitive impairment) or Alzheimer's disease, especially, Alzheimer's disease.

2 Claims, 3 Drawing Sheets

(56) References Cited

OTHER PUBLICATIONS

Christlieb, M. et al. (Nov. 21, 2001, e-published Oct. 30, 2001). "The Stereoselective Synthesis of Oxetanes; Exploration of a New, Mitsunobu-Style Procedure for the Cyclisation of 1,3-diols," *J Chem Soc* 22:2983-2996.

Coulson, D.T.R. et al. (2010). "BACE1 mRNA Expression in Alzheimer's Disease Postmortem Brain Tissue," *Journal of Alzheimer's Disease* 22(4):1111-1122.

Destrooper, B. et al. (Jan. 22, 1998). "Deficiency of Presenilin-1 Inhibits the Normal Cleavage of Amyloid Precursor Protein," *Nature* 391:387-390.

Ermolieff, J. et al. (Oct. 10, 2000). "Proteolytic Activation of Recombinant Pro-Memapsin 2 (Pro-β-Secretase) Studied With New Fluorogenic Substrates," *Biochemistry* 39(40):12450-12456.

Halliday, G.M. et al. (2011). "Striatal β-Amyloid in Dementia with Lewy Bodies But Not Parkinson's Disease," *Journal of Neural Transmission* 118(5):713-719.

Huang, H. et al. (Nov. 8, 2012, e-published Sep. 11, 2012). Structure- and Property-Based Design of Aminooxazoline Xanthenes as Selective, Orally Efficacious, and CNS Penetrable BACE Inhibitors for the Treatment of Alzheimer's Disease, *Journal of Medicinal Chemistry* 55(21):9156-9169.

Hunt, K.W. (Apr. 25, 2013, e-published Apr. 16, 2013). "Spirocyclic β-Site Amyloid Precursor Protein Cleaving Enzyme 1 (BACE1) Inhibitors: From Hit to Lowering of Cerebrospinal Fluid (CSF) Amyloid β in a Higher Species," *Journal of Medicinal Chemistry* 56(8):3379-3403.

International Search Report mailed on Nov. 22, 2013, for PCT Patent Application No. PCT/US13/43016, filed on May 29, 2013, 3 pages.

Jamieson, C. et al. (Aug. 24, 2006, e-published Jul. 27, 2006). "Medicinal Chemistry of hERG Optimizations: Highlights and Hang-ups," *J Med Chem* 49(17):5029-5046.

Kongsamut, S. et al. (Aug. 16, 2002). "A Comparison of the Receptor Binding and HERG Channel Affinities for a Series of Antipsychotic Drugs," *Eur J Pharmacol* 450:37-41.

Lin, X. et al. (Feb. 15, 2000). "Human Aspartic Protease Memapsin 2 Cleaves the β-Secretase Site of β-Amyloid Precursor Protein," *Proc Natl Acad Sci USA* 97(4):1456-1460.

Micheli, F. et al. (Jan. 14, 2010, e-published Nov. 5, 2009). "1,2,4-Triazolyl Azabicyclo[3.1.0]Hexanes: a New Series of Potent and Selective Dopamine $D_3$ Receptor Antagonists," *J Med Chem* 53(1):374-391.

Miners, J.S. et al. (2011). "Accumulation of Insoluble Amyloid-β in Down's Syndrome is Associated with Increased BACE-1 and Neprilysin Activities," *Journal of Alzheimer's Disease* 23(1):101-108.

Mitsuru, H. (1985). "Chemical Structures of Prodrugs and Their Classification," *Prog Med* 5(7):2157-2161.

Pajouhesh, H. et al. (2012). "Structure-Activity Relationships of Trimethoybenzyl Piperazine N-Type Calcium Channel Inhibitors" *Biorg Med Chem Lett* 22:4153-4158.

Selkoe, D.J. (Jun. 24, 1999). "Translating Cell Biology Into Therapeutic Advances in Alzheimer's Disease," *Nature* 399(6738 Suppl):A23-A31.

Wen, Y. et al. (May 29, 2004). "Increased β-Secretase Activity and Expression in Rats Following Transient Cerebral Ischemia," *Brain Research* 1009(1-2):1-8.

Woltering, T.J. et al. (2013). "BACE1 Inhibitors: A Head Group Scan on a Series of Amides," *Biorganic & Medicinal Chemistry Letters* 23:4239-4243.

Written Opinion originally mailed on Nov. 22, 2013, re-issued as corrected on Dec. 16, 2013, for PCT Patent Application No. PCT/US2013/43016, filed on May 29, 2013, 4 pages.

CHROMANE COMPOUNDS

CROSS REFERENCE TO RELATED APPLICATIONS

This application is a divisional of U.S. patent application Ser. No. 14/192,667 filed Feb. 27, 2014 (now U.S. Pat. No. 8,975,415), which is a continuation of International Application No. PCT/US2013/043016 having an international filing date of May 29, 2013, which claims priority benefit of U.S. Provisional Patent Application Nos. 61/653,321 filed May 30, 2012 and 61/782,038 filed Mar. 14, 2013, the disclosures of which are incorporated herein by reference in their entirety.

INCORPORATION BY REFERENCE

The content of the following submission on ASCII text file (ST.25 text format) is incorporated herein by reference in its entirety: a computer readable form (CRF) of the Sequence Listing (file name is "322732001040_Sequence_Listing.txt"; date recorded: May 9, 2013; and the size of the ASCII text file in bytes is 4,096 bytes).

TECHNICAL FIELD

The present invention relates to a chromane compound which is useful as an active ingredient of a pharmaceutical composition, in particular, a pharmaceutical composition for preventing or treating diseases or conditions associated with and/or mediated by β-secretase activity, hydrolysis of a β-secretase site of an amyloid precursor protein, and/or β-amyloid protein accumulation, including a pharmaceutical composition for preventing or treating diseases including, but not limited to, Glaucoma, MCI (Mild cognitive impairment) or Alzheimer's disease, especially, Alzheimer's disease.

BACKGROUND OF THE INVENTION

Alzheimer's disease is a progressive mental deterioration in a human resulting, inter alia, in loss of memory, confusion and disorientation. Alzheimer's disease accounts for the majority of senile dementia and is a leading cause of death in adults (Non-Patent Document 1). Histologically, the brain of persons afflicted with Alzheimer's disease is characterized by a distortion of the intracellular neurofibrils and the presence of senile plaques composed of granular or filamentous argentophilic masses with an amyloid protein core, largely due to the accumulation of β-amyloid protein (Aβ) in the brain. Aβ accumulation plays a role in the pathogenesis and progression of the disease (Non-Patent Document 2) and is a proteolytic fragment of amyloid precursor protein (APP). APP is cleaved initially by β-secretase followed by γ-secretase to generate Aβ (Non-Patent Document 3 and 4).

It is known that inhibition of BACE may have a therapeutic effect in the prevention of dementia after stroke recovery (Non-Patent Document 5). It is reported that inhibition of BACE1 (beta-secretase 1) may have a therapeutic effect in Down syndrome (Non-Patent Document 6). The relationship between BACE1 mRNA levels and Parkinson's disease (PD) and Dementia with Lewy bodies (DLB) is also reported (Non-Patent Document 7 and 8).

In Patent Document 1, it is described that compounds (A) which are BACE inhibitors and are useful as therapeutic agents in the treatment, prevention, and amelioration of a disease or disorder characterized by elevated β-amyloid deposits or β-amyloid levels in a patient.

[Scheme 1]

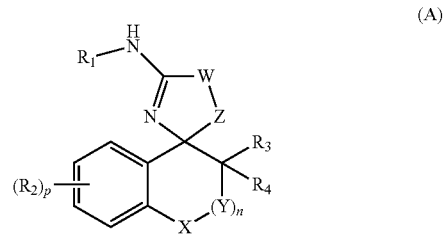

(for the symbols in the formula, refer to the patent publication).

In Patent Document 2, it is described that compounds (B) which are useful for inhibition of β-secretase enzymatic activity and for therapy and/or prophylaxis of neurodegenerative diseases associated therewith, particularly Alzheimer's Disease.

[Scheme 2]

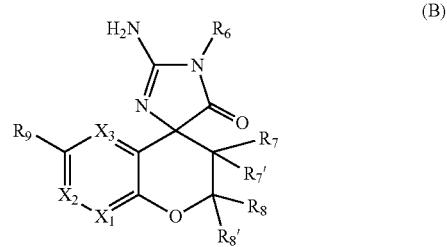

(for the symbols in the formula, refer to the patent publication).

In Patent Document 3, it is described that compounds (C) which are BACE inhibitors and are useful as therapeutic agents in the treatment, prevention, and amelioration of a disease or disorder characterized by elevated β-amyloid deposits or β-amyloid levels in a patient.

[Scheme 3]

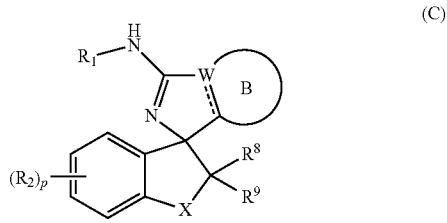

(for the symbols in the formula, refer to the patent publication).

In Patent Document 4, it is described that compounds (D) which are BACE inhibitors and are useful as therapeutic agents in the treatment, prevention, and amelioration of a disease or disorder characterized by elevated β-amyloid deposits or β-amyloid levels in a patient.

[Scheme 4]

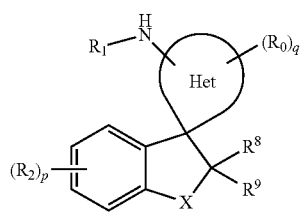
(D)

(for the symbols in the formula, refer to the patent publication).

In Patent Document 5 and 6, it is described that compounds (E) have BACE1 inhibitory activity and are useful as prophylactic or therapeutic agent for a neurodegenerative disease caused by Aβ and typified by Alzheimer type dementia, and pharmaceutical use thereof.

[Scheme 5]

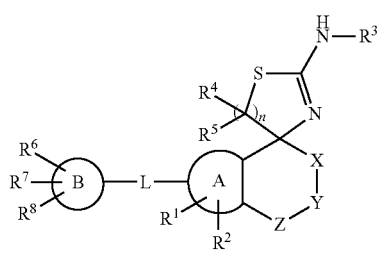
(E)

(for the symbols in the formula, refer to the patent publication).

In Patent Document 7, it is described that compounds (F) are useful for the modulation of the beta-secretase activity and are useful for the treatment of Alzheimer's disease and beta-secretase and/or plaque mediated disorders.

[Scheme 6]

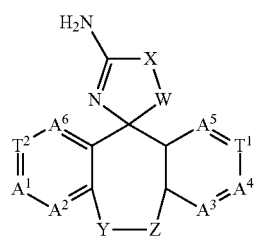
(F)

(for the symbols in the formula, refer to the patent publication).

In Patent Document 8, it is described that compounds (G) are useful for the modulation of the beta-secretase activity and are useful for the treatment of Alzheimer's disease and beta-secretase and/or plaque mediated disorders.

[Scheme 7]

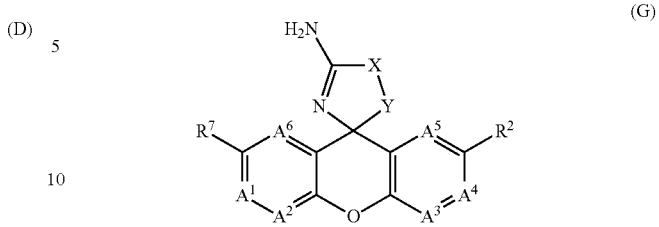
(G)

(for the symbols in the formula, refer to the patent publication).

In Patent Document 9, it is described that compounds (H) are useful for the modulation of the beta-secretase activity and are useful for the treatment of Alzheimer's disease and beta-secretase and/or plaque mediated disorders.

[Scheme 8]

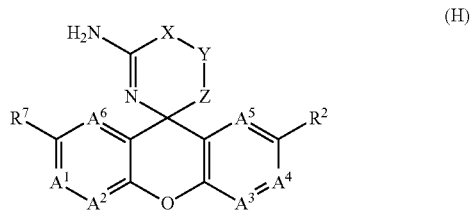
(H)

(for the symbols in the formula, refer to the patent publication).

In Patent Document 10, it is described that compounds (I) are useful for inhibition of β-secretase enzyme activity and the therapy and/or prophylaxis of neurodegenerative diseases associated therewith, such as Alzheimer's disease.

[Scheme 9]

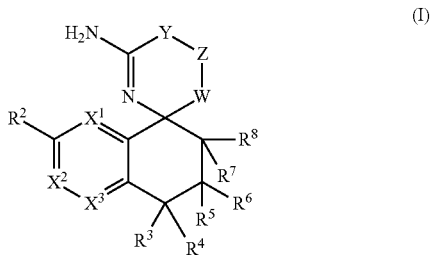
(I)

(for the symbols in the formula, refer to the patent publication).

In Patent Document 11, it is described that compounds (J) are inhibitors of beta-secretase-2 (BACE2) and the compounds may therefore be useful in the treatment of type 2 diabetes and other metabolic disorders.

[Scheme 10]

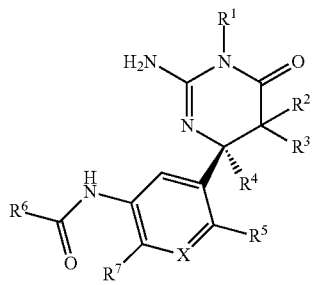

(J)

(for the symbols in the formula, refer to the patent publication).

In Patent Document 12, it is described that compounds (K) are useful for inhibition of β-secretase enzyme activity and the therapy and/or prophylaxis of neurodegenerative diseases associated therewith, such as Alzheimer's disease.

[Scheme 11]

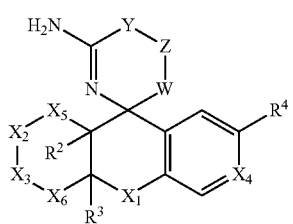

(K)

(for the symbols in the formula, refer to the patent publication).

In Patent Document 13, it is described that compounds (L) are inhibitors of β-secretase and hence inhibit the formation of amyloid β (Aβ) peptides and are useful for treatment and/or prevention of Aβ-related pathologies such as Alzheimer's disease, and so on.

[Scheme 12]

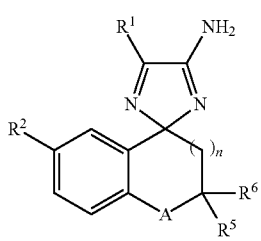

(L)

(for the symbols in the formula, refer to the patent publication).

In any of these Patent Documents, there is no specific disclosure of the compound of the present invention.

REFERENCES

Patent Document 1: Pamphlet of International Publication WO 2010/021680
Patent Document 2: Pamphlet of International Publication WO 2011/072064
Patent Document 3: Pamphlet of International Publication WO 2011/106414
Patent Document 4: Pamphlet of International Publication WO 2010/105179
Patent Document 5: Pamphlet of International Publication WO 2010/013302
Patent Document 6: Pamphlet of International Publication WO 2010/013794
Patent Document 7: Pamphlet of International Publication WO 2010/030954
Patent Document 8: Pamphlet of International Publication WO 2011/115938
Patent Document 9: Pamphlet of International Publication WO 2011/115928
Patent Document 10: Pamphlet of International Publication WO2011/123674
Patent Document 11: Pamphlet of International Publication WO2010/128058
Patent Document 12: Pamphlet of International Publication WO2012/071458
Patent Document 13: Pamphlet of International Publication WO2012/087237
Non-Patent Document 1: Anderson, R. N., et al., Natl. Vital Stat. Rep. 49:1-87 (2001)
Non-Patent Document 2: Selkoe, D. J., Nature 399: 23-31 (1999)
Non-Patent Document 3: Lin, X., et al., Proc. Natl. Acad. Sci. USA 97:1456-1460 (2000)
Non-Patent Document 4: De Stropper, B., et al., Nature 391: 387-390 (1998)
Non-Patent Document 5: Wen Y., et al., Brain Res. 1009 (1-2):1-8 (2004)
Non-Patent Document 6: Miners J. S., et al., J. Alzheimer's Dis. 23 (1):101-108 (2011)
Non-Patent Document 7: Coulson D T., et al., J. Alzheimer's Dis. 22 (4):1111-1122 (2010)
Non-Patent Document 8: Halliday G M., et al., J. Neural Transm. 118 (5):713-719 (2011)

SUMMARY OF THE INVENTION

Figure 1:
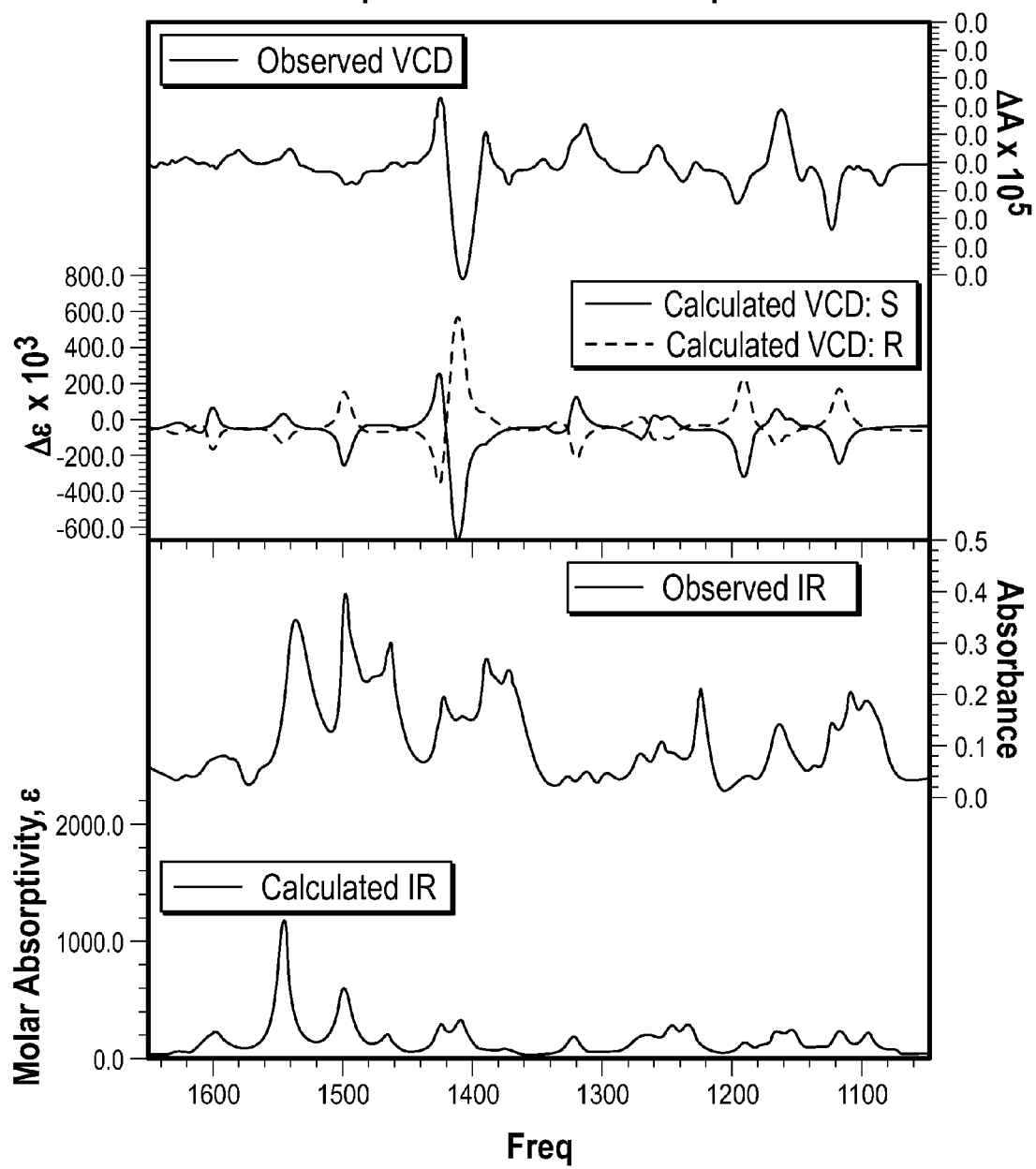
FIG. 1 Drawing shows VCD spectra of Ex. 228b compound.
Figure 2:
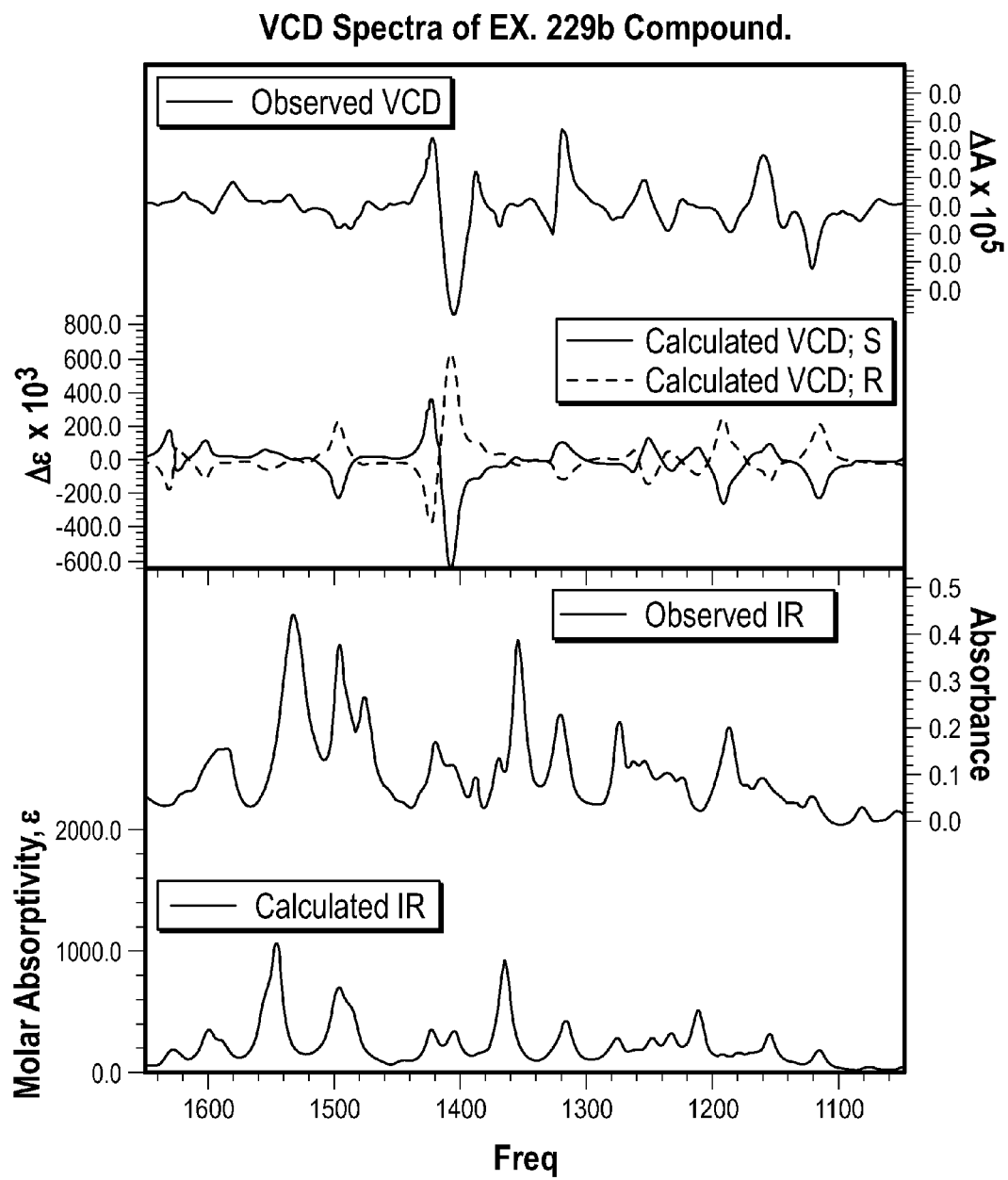
FIG. 2 Drawing shows VCD spectra of Ex. 229b compound.
Figure 3:
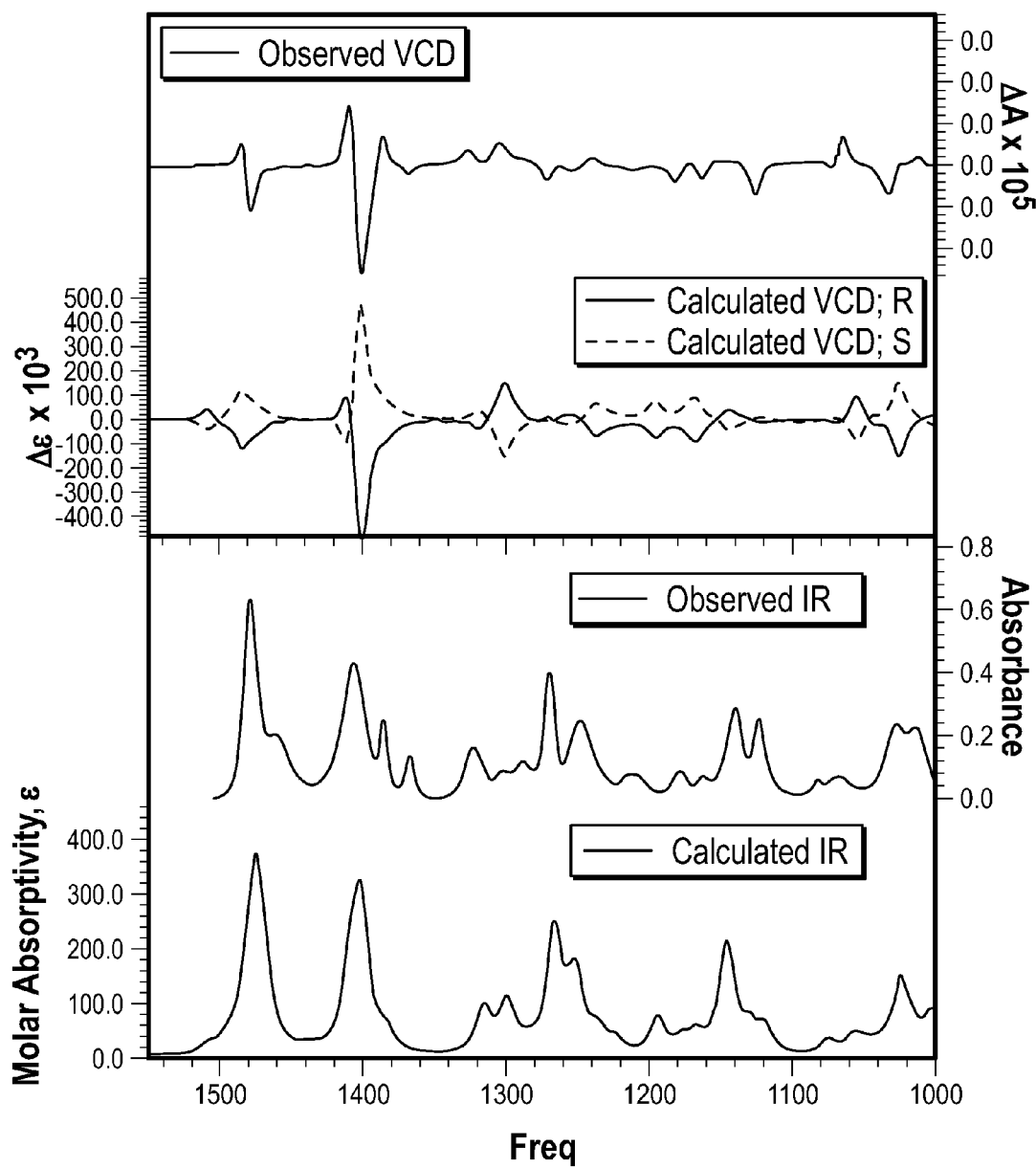
FIG. 3 Drawing shows VCD spectra of Reference Example 225a compound.

The present invention provides a compound which is useful as an active ingredient of a pharmaceutical composition, in particular, a pharmaceutical composition for preventing or treating diseases or conditions associated with and/or mediated by β-secretase activity, hydrolysis of a β-secretase site of a β-amyloid precursor protein, and/or β-amyloid protein accumulation, including a pharmaceutical composition for preventing or treating diseases including, but not limited to, Glaucoma, MCI (Mild cognitive impairment) or Alzheimer's disease, especially, Alzheimer's disease.

Means for Solving the Problems

The present inventors have extensively studied compounds having beta-secretase inhibitory activity, and as a result, they have found that chromane compounds which are the compounds of the present invention have excellent beta-secretase inhibitory activity, and are therefore useful as agents for preventing or treating diseases or conditions associated with and/or mediated by β-secretase activity, hydrolysis of a β-secretase site of a β-amyloid precursor protein, and/or β-amyloid protein accumulation, including a pharmaceutical composition for preventing or treating diseases including, but not limited to, Glaucoma, MCI (Mild cognitive impairment) or Alzheimer's disease, especially, Alzheimer's disease, thereby completing the present invention.

The present invention relates to compounds of the formula (I) or a salt thereof:

[Scheme 13]

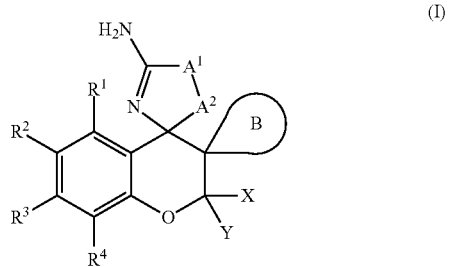

wherein
A$^1$ is O, S, —C(R$^{411}$R$^{412}$)-T-, or -T-C(R$^{411}$R$^{412}$)—;
A$^2$ is —C(R$^{421}$R$^{422}$)—;
T is a single bond, O, or S;
R$^{411}$, R$^{412}$, R$^{421}$ and R$^{422}$ are, independently, H or halogen; or
R$^{411}$, R$^{412}$, R$^{421}$ and R$^{422}$ are combined with each other to form an aryl group, which is unsubstituted or substituted;
B is a hetero ring group which is unsubstituted or substituted, or cycloalkyl which is unsubstituted or substituted;
X and Y are independently selected from the group consisting of H, lower alkyl, which is unsubstituted or substituted, and cycloalkyl, which is unsubstituted or substituted; or
X and Y are combined with each other to form a cycloalkyl group, which is unsubstituted or substituted; and
R$^1$, R$^2$, R$^3$ and R$^4$ are independently selected from the group consisting of H, halogen, lower alkyl, which is unsubstituted or substituted, lower alkenyl, which is unsubstituted or substituted, —N(H)-(hetero ring group), wherein said hetero ring group is unsubstituted or substituted, —N(H)—C(O)-(hetero ring group), wherein said hetero ring group is unsubstituted or substituted, cycloalkenyl, which is unsubstituted or substituted, aryl, which is unsubstituted or substituted, and a hetero ring group, which is unsubstituted or substituted.

Further, unless specifically described otherwise, in the case where the symbols in any of the formulae in the present specification are also used in other formulae, the same symbols denote the same meanings.

Furthermore, the present invention relates to pharmaceutical compositions, comprising compounds of formula (I) or a salt thereof, as described herein, and a pharmaceutically acceptable carrier. Moreover, the present invention relates to pharmaceutical compositions for preventing or treating diseases or conditions associated with and/or mediated by β-secretase activity, hydrolysis of a β-secretase site of a β-amyloid precursor protein, and/or β-amyloid protein accumulation, including compounds of formula (I) or a salt thereof, as described herein, that are agents for preventing or treating diseases or conditions associated with and/or mediated by β-secretase activity, hydrolysis of a β-secretase site of a β-amyloid precursor protein, and/or β-amyloid protein accumulation, including compounds of formula (I) or a salt thereof.

Furthermore, the present invention relates to use of compounds of formula (I) or a salt thereof, as described herein, for preparation of a pharmaceutical composition (e.g., medicament) for preventing or treating diseases or conditions associated with and/or mediated by β-secretase activity, hydrolysis of a β-secretase site of a β-amyloid precursor protein, and/or β-amyloid protein accumulation, use of compounds of formula (I) or a salt thereof for preventing or treating diseases or conditions associated with and/or mediated by β-secretase activity, hydrolysis of a β-secretase site of a β-amyloid precursor protein, and/or β-amyloid protein accumulation, and methods for preventing or treating diseases or conditions associated with and/or mediated by β-secretase activity, hydrolysis of a β-secretase site of a β-amyloid precursor protein, and/or β-amyloid protein accumulation, including administering to a subject in need thereof an effective amount of the compounds of formula (I) or a salt thereof.

The present invention also relates to compounds of formula (I) or a salt thereof, as described herein, for use in the prevention or treatment of diseases or conditions associated with and/or mediated by β-secretase activity, hydrolysis of a β-secretase site of a β-amyloid precursor protein, and/or β-amyloid protein accumulation, the compounds of formula (I) or a salt thereof for preventing or treating diseases or conditions associated with and/or mediated by β-secretase activity, hydrolysis of a β-secretase site of a β-amyloid precursor protein, and/or β-amyloid protein accumulation. The present invention also relates to a method for preventing or treating diseases or conditions associated with and/or mediated by β-secretase activity, hydrolysis of a β-secretase site of a β-amyloid precursor protein, and/or β-amyloid protein accumulation, including administering to a subject an effective amount of the compounds of formula (I) or a salt thereof.

Effects of the Invention

The compounds of formula (I) or a salt thereof have beta-secretase inhibitory activity, and therefore can be used as an agent for preventing or treating diseases or conditions associated with and/or mediated by β-secretase activity, hydrolysis of a β-secretase site of a β-amyloid precursor protein, and/or β-amyloid protein accumulation, including, but not limited to, diseases such as Glaucoma, MCI (Mild cognitive impairment) or Alzheimer's disease, especially, Alzheimer's disease, or the like. In some embodiments, the compounds of formula (I) or a salt thereof can be used as an agent for preventing or treating diseases or conditions including, but not limited to, stroke, cerebrovascular dementia, Down syndrome, Parkinson's disease (PD), and dementia with Lewy bodies (DLB).

DETAILED DESCRIPTION

The present invention will be explained in more detail herein below. Further, "the compounds of formula (I) or a salt thereof" may be denoted as "the compounds (I) of the present invention" or "the compounds (I)" below in some cases.

In the present specification, the term "lower alkyl" refers to a straight (linear) or branched chain alkyl having 1 to 6 carbon atoms (hereinafter simply referred to as C$_{1-6}$), for example, methyl, ethyl, n-propyl, isopropyl, n-butyl, isobutyl, sec-butyl, tert-butyl, n-pentyl, n-hexyl, and the like. In another embodiment, it is $C_{1-4}$ alkyl, and in a further embodiment, $C_{1-3}$ alkyl.

The term "lower alkenyl" refers to a straight (linear) or branched chain $C_{2-6}$ alkenyl, for example, vinyl, propenyl, butenyl, pentenyl, 1-methylvinyl, 1-methyl-2-propenyl, 1,3-butadienyl, 1,3-pentadienyl, or the like. In another embodiment, it is $C_{2-4}$ alkenyl, and in a still another embodiment, $C_{2-3}$ alkenyl.

The term "lower alkynyl" refers to a linear or branched chain $C_{2-6}$ alkynyl, for example, ethynyl, propynyl, butynyl, pentynyl, 1-methyl-2-propynyl, 1,3-butadiynyl, 1,3-pentadiynyl, or the like. In another embodiment, it is $C_{2-4}$ alkynyl.

The term "cycloalkyl" refers to a $C_{3-10}$ saturated hydrocarbon ring group, which may have a bridge. It is, for example, cyclopropyl, cyclobutyl, cyclopentyl, cyclohexyl, cycloheptyl, cyclooctyl, adamantyl, or the like, in another embodiment, $C_{3-8}$ cycloalkyl, and in a further embodiment, $C_{3-6}$ cycloalkyl.

The term "cycloalkenyl" refers to a $C_{4-15}$ hydrocarbon ring group having at least one double bond in the ring (provided that an aromatic hydrocarbon ring group is excluded), which may have a bridge, and includes a ring group fused (e.g., condensed) with a benzene ring at a double bond site. It is, for example, cyclopentenyl, cyclopentadienyl, cyclohexenyl, cyclohexadienyl, 1-tetrahydronaphthyl, 1-indenyl, 9-fluorenyl, or the like. In another embodiment, it is $C_{5-10}$ cycloalkenyl, in a further embodiment, $C_{5-8}$ cycloalkenyl, and in a further embodiment, $C_{5-7}$ cycloalkenyl.

The term "aryl" refers to a $C_{6-14}$ monocyclic to tricyclic aromatic hydrocarbon ring group, and includes a ring group fused with $C_{5-8}$ cycloalkene at its double bond site. It is, for example, phenyl, naphthyl, 5-tetrahydronaphthyl, 4-indenyl, 1-fluorenyl, or the like. And the term "aryl" does not encompass aryl rings containing hetero atoms (such as S, N, O).

The term "hetero ring" means a ring group containing i) a monocyclic 3- to 8-membered hetero ring containing 1 to 4 hetero atoms selected from oxygen, sulfur, and nitrogen, and in another embodiment, a 5- to 7-membered hetero ring containing 1 to 4 hetero atoms selected from oxygen, sulfur, and nitrogen, and ii) a bicyclic or tricyclic hetero ring (in which the bicyclic or tricyclic heterocyclic ring may include a spiro ring) containing 1 to 5 hetero atoms selected from oxygen, sulfur, and nitrogen, formed by condensation or ring-fusion of the monocyclic hetero ring with one or two rings selected from the group consisting of a monocyclic hetero ring, a benzene ring, $C_{5-8}$ cycloalkane, and $C_{5-8}$ cycloalkene. The ring atom, sulfur or nitrogen, may be oxidized to form an oxide or a dioxide.

Examples of the "hetero ring" group include the following embodiments:

(1) Monocyclic Saturated Hetero Ring Groups, which mean monocyclic 3- to 8-membered saturated rings containing 1 to 4 hetero atoms selected from oxygen, sulfur, and nitrogen, and in another embodiment, 5- to 7-membered hetero rings containing 1 to 4 hetero atoms selected from oxygen, sulfur, and nitrogen.

(a) those containing 1 to 4 nitrogen atoms, for example, azepanyl, diazepanyl, aziridinyl, azetidinyl, pyrrolidinyl, imidazolidinyl, piperidyl, piperazolidinyl, piperazinyl, azocanyl, hexamethyleneimino, homopiperazinyl, and the like;

(b) those containing 1 to 3 nitrogen atoms and 1 to 2 sulfur atoms and/or 1 to 2 oxygen atoms, for example, thiomorpholinyl, thiazolidinyl, isothiazolidinyl, oxazolidinyl, morpholinyl, and the like;

(c) those containing 1 to 2 sulfur atoms, for example, tetrahydrothiopyranyl and the like;

(d) those containing 1 to 2 sulfur atoms and 1 to 2 oxygen atoms, for example, oxathiolanyl and the like; and (e) those containing 1 to 2 oxygen atoms, for example, oxiranyl, oxetanyl, dioxolanyl, tetrahydrofuranyl, tetrahydropyranyl, 1,4-dioxanyl, and the like;

(2) Monocyclic Unsaturated Hetero Ring Groups, which mean monocyclic 3- to 8-membered unsaturated rings containing 1 to 4 hetero atoms selected from oxygen, sulfur, and nitrogen, and in another embodiment, 5- to 7-membered hetero rings containing 1 to 4 hetero atoms selected from oxygen, sulfur, and nitrogen.

(a) those containing 1 to 4 nitrogen atoms, for example, pyrrolyl, 2-pyrrolinyl, imidazolyl, 2-imidazolinyl, pyrazolyl, 2-pyrazolinyl, pyridyl, dihydropyridyl, tetrahydropyridinyl, pyrimidinyl, pyrazinyl, pyridazinyl, triazolyl, tetrazolyl, triazinyl, dihydrotriazinyl, azepinyl, and the like;

(b) those containing 1 to 3 nitrogen atoms and 1 to 2 sulfur atoms and/or 1 to 2 oxygen atoms, for example, thiazolyl, isothiazolyl, thiadiazolyl, dihydrothiazinyl, oxazolyl, isoxazolyl, oxadiazolyl, oxazinyl, and the like;

(c) those containing 1 to 2 sulfur atoms, for example, thienyl, thiepinyl, dihydrodithiopyranyl, dihydrodithionyl, 2H-thiopyranyl, and the like;

(d) those containing 1 to 2 sulfur atoms and 1 to 2 oxygen atoms, for example, dihydroxythiopyranyl and the like; and (e) those containing 1 to 2 oxygen atoms, for example, furyl, dihydrofuryl, pyranyl, 2H-pyranyl, oxepinyl, dioxolyl, and the like;

(3) Fused Polycyclic Saturated Hetero Ring Groups, which mean bicyclic or tricyclic saturated hetero rings (in which the bicyclic or tricyclic heterocyclic ring may include a spiro ring) containing 1 to 5 hetero atoms selected from oxygen, sulfur, and nitrogen, formed by condensation or ring-fusion of the monocyclic saturated hetero ring with one or two rings selected from the group consisting of a monocyclic saturated hetero ring, and $C_{5-8}$ cycloalkane.

(a) those containing 1 to 5 nitrogen atoms, for example, quinuclidinyl, 7-azabicyclo[2.2.1]heptyl, 3-azabicyclo[3.2.2]nonanyl, 2,8-diazaspiro[4.5]decan-8-yl, 2,3,6,8-tetraazaspiro[4.5]decan-8-yl, and the like;

(b) those containing 1 to 4 nitrogen atoms and 1 to 3 sulfur atoms, and/or 1 to 3 oxygen atoms, for example, trithiadiazaindenyl, dioxoloimidazolidinyl, 6-oxa-2,8-diazaspiro[4.5]decan-8-yl, 6-thia-2,8-diazaspiro[4.5]decan-8-yl, and the like; and (c) those containing 1 to 3 sulfur atoms and/or 1 to 3 oxygen atoms, for example, 2,6-dioxabicyclo[3.2.2]oct-7-yl, 2-oxa-6-thiaspiro[4.5]decan-8-yl, and the like;

(4) Fused Polycyclic Unsaturated Hetero Ring Groups, which mean bicyclic or tricyclic unsaturated hetero rings (in which the bicyclic or tricyclic heterocyclic ring may include a spiro ring) containing 1 to 5 hetero atoms selected from oxygen, sulfur, and nitrogen, formed by condensation or ring-fusion of the monocyclic hetero ring with one or two rings selected from the group consisting of a monocyclic hetero ring, a benzene ring, $C_{5-8}$ cycloalkane, and $C_{5-8}$ cycloalkene.

(a) those containing 1 to 5 nitrogen atoms, for example, indolyl, isoindolyl, indolinyl, indolizinyl, benzimidazolyl, dihydrobenzimidazolyl, tetrahydrobenzimidazolyl, quinolyl, tetrahydroquinolyl, isoquinolyl, tetrahydroisoquinolyl, indazolyl, imidazopyridyl, benzotriazolyl, tetrazolopyridazinyl, carbazolyl, acridinyl, quinoxalinyl, dihydroquinoxalinyl, tetrahydroquinoxalinyl, phthalazinyl, dihydroindazolyl, benzopyrimidinyl, naphthyridinyl, quinazolinyl, cinnolinyl, pyridopyrrolidinyl, triazolopiperidinyl, 9,10-dihydroacridinyl, 2,8-diazaspiro[4.5]deca-3-en-8-yl, 2,3,6,8-tetraazaspiro[4.5]deca-1-en-8-yl, and the like;

(b) those containing 1 to 4 nitrogen atoms, and 1 to 3 sulfur atoms and/or 1 to 3 oxygen atoms, for example, benzothiazolyl, dihydrobenzothiazolyl, benzothiadiazolyl, imidazothiazolyl, imidazothiadiazolyl, benzoxazolyl, dihydrobenzoxazolyl, dihydrobenzoxazinyl, benzoxadiazolyl, benzoisothiazolyl, benzoisoxazolyl, thiazolopiperidinyl, 10H-phenothiazinyl, 6-oxa-2,8-diazaspiro[4.5]deca-3-en-8-yl, 6-thia-2,8-diazaspiro[4.5]deca-3-en-8-yl, and the like;

(c) those containing 1 to 3 sulfur atoms, for example, benzothienyl, benzodithiopyranyl, dibenzo[b,d]thienyl, and the like;

(d) those containing 1 to 3 sulfur atoms and 1 to 3 oxygen atoms, for example, benzoxathiopyranyl, 2-oxa-6-thiaspiro[4.5]deca-3-en-8-yl, and the like; and (e) those containing 1 to 3 oxygen atoms, for example, benzodioxolyl, benzofuranyl, dihydrobenzofuranyl, isobenzofuranyl, chromanyl, chromenyl, isochromenyl, dibenzo[b,d]furanyl, methylenedioxyphenyl, ethylenedioxyphenyl, xanthenyl, and the like; etc.

Further, the terms "aryl", "cycloalkyl", and "hetero ring" groups as described above are meant to be monovalent groups, but these may be divalent or higher groups in some cases. For example, when aryl in the $R^2$ is substituted, this aryl is described by monovalent group, but this aryl means divalent or higher groups.

The term "nitrogen-containing hetero ring" group refers to one containing at least one nitrogen atom, including, but not limited to, such as groups in (1)(a), (1)(b), (2)(a), (2)(b), (3)(a), (3)(b), (4)(a), and (4)(b), among the "hetero ring" groups above.

The term "oxygen-containing monocyclic saturated hetero ring" group refers to one containing at least one oxygen atom, including, but not limited to, such as groups containing at least one oxygen atom in (1)(b) or such as groups in (1)(d), and (1)(e), among the "(1) Monocyclic Saturated Hetero Ring Groups" above.

The term "cyclic ether" group refers to one containing only at least one oxygen atom as hetero atom, including, but not limited to, such as groups in, (1)(e), among the "oxygen-containing monocyclic saturated hetero ring" group above.

The term "nitrogen-containing monocyclic hetero ring" group refers to one containing at least one nitrogen atom, including, but not limited to, such as groups in (1)(a), (1)(b), (2)(a), and (2)(b), among the "Monocyclic Saturated Hetero Ring Groups" and "Monocyclic Unsaturated Hetero Ring Groups" above.

The term "halogen" means F, Cl, Br, or I.

In the present specification, the term "substituted" represents being substituted with 1 to 5 substituents. In some embodiments, the term "substituted" represents being substituted with 1, 2, 3, 4 or 5 substituents. Further, if a plurality of substituents are included, the substituents may be the same as or different from one another.

In some embodiments, the term "substituted with one or more substituents" represents being substituted with 1 to 5 substituents. In some embodiments, the term "substituted with one or more substituents" represents being substituted with 1, 2, 3, 4 or 5 substituents.

In the present specification, both B and

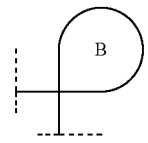

represent a group that shares a carbon atom with the chromane ring to which it is attached, as shown in formula (I). For example, when B is oxetanyl, this means that

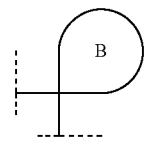

is

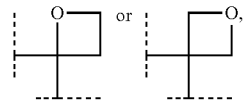

and when B is cyclopropyl, this means that

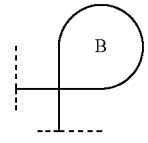

is

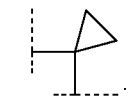

In some embodiments, the B group may be substituted at one or more available positions, as described herein.

"$R^{411}$, $R^{412}$, $R^{421}$ and $R^{422}$ are combined with each other to form an aryl group" indicates that $R^{411}$, $R^{412}$, $R^{421}$ and $R^{422}$ combined with each carbon atom to which they are bonded to form a $C_{6-14}$ monocyclic to tricyclic aromatic hydrocarbon ring group, and includes a ring group fused with $C_{5-8}$ cycloalkene at its double bond site. It is, for example, phenyl, naphthyl, 5-tetrahydronaphthyl, 4-indenyl, 1-fluorenyl, or the like.

For example, when $R^{411}$, $R^{412}$, $R^{421}$ and $R^{422}$ are combined with each other to form phenyl, a structure of the compound of formula (I) is as below.

[Scheme 14]

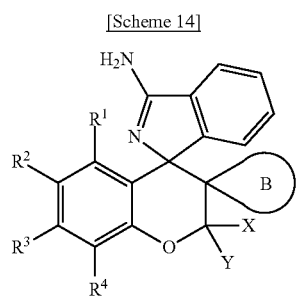

"X and Y are combined with each other to form a cycloalkyl group" indicates that X and Y combined with a carbon atom to which they are bonded to form a C$_{3-10}$ saturated hydrocarbon ring group, which may have a bridge. It is, for example, cyclopropyl, cyclobutyl, cyclopentyl, cyclohexyl, cycloheptyl, cyclooctyl, adamantyl, or the like, in another embodiment, C$_{3-8}$ cycloalkyl, and in a further embodiment, C$_{3-6}$ cycloalkyl.

For example, when X and Y are combined with each other to form cyclobutyl or cyclopentyl structures of the compound of formula (I) are as below.

[Scheme 15]

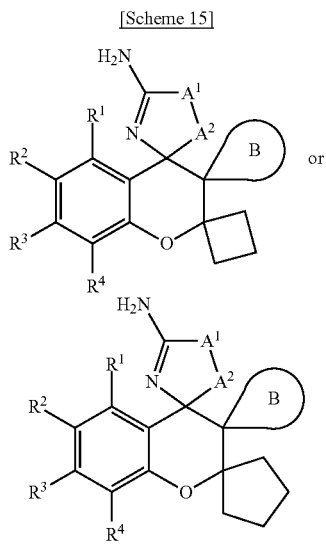

"Amyloid precursor protein," or "APP," as used herein, refers to an amyloid precursor polypeptide comprising a β-secretase cleavage site.

A "β-secretase cleavage site" is an amino acid sequence that is cleaved by an active memapsin 2 (also referred to as beta-secretase 1 or BACE-1, or active fragment thereof, such as described in U.S. Pat. No. 6,545,127). Specific β-secretase cleavage sites have also been previously set forth and discussed in detail in U.S. Application No. 20040121947, and International Application No. PCT/US02/34324 (Publication No. WO 03/039454), which are herein incorporated by reference for all purposes in their entirety, and include the Swedish mutation sequence, and the native amyloid precursor protein cleavage sequence. Thus, β-secretase inhibitors may be tested for their ability to decrease the hydrolysis of the β-secretase cleavage site of a substrate, such as the amyloid precursor protein, compounds of amyloid precursor protein, or fragments of amyloid precursor protein.

A "beta-secretase inhibitor" (i.e. β-secretase inhibitor) refers to a compound capable of reducing the proteolytic activity of memapsin-2 relative to the activity in the absence of inhibitor.

"Memapsin-2," as used herein, refers to proteins identified by National Center for Biotechnology Information ("NCBI") accession number NP_036236 (sometimes referred to as "β-site APP-cleaving enzyme 1" or "BACE1" or generically as "β-secretase" or "beta-secretase"), including homologs, isoforms and subdomains thereof that retain proteolytic activity. Sequence identities of active memapsin 2 proteins and protein fragments (and nucleic acid coding sequences thereof) have been previously disclosed and discussed in detail in U.S. Application No. 20040121947, and International Application No. PCT/US02/34324 (Publication No. WO 03/039454, International publication WO 01/00663, U.S. Pat. No. 6,545,127), which are herein incorporated by reference for all purposes in their entirety.

"Amyloid beta (Aβ or Abeta)" refers to a peptide of 36-43 amino acids. While best known as a component of amyloid plaques in association with Alzheimer's disease, as Aβ is the main component of certain deposits found in the brains of patients with Alzheimer's disease. The different Aβ isoforms (for example, Aβ40, Aβ42, and so on) refer to cleavage products of transmembranous APP via the β-secretase pathway. The cleavage by β-secretase (BACE1) liberates the Aβ N-terminus, together with sAPPβ and a C-terminal fragment C99. C99 is subsequently cleaved by γ-secretase to yield Aβ.

"Diseases or conditions associated with and/or mediated by β-secretase activity, hydrolysis of a β-secretase cleavage site of an amyloid precursor protein, and/or β-amyloid protein accumulation" as used herein, includes, but is not limited to, diseases such as Glaucoma, MCI (Mild cognitive impairment) or Alzheimer's disease. In another embodiment, the term includes, but is not limited to, MCI (Mild cognitive impairment) or Alzheimer's disease. In another embodiment, the term includes, but is not limited to, Alzheimer's disease. In another embodiment, the term includes, but is not limited to, MCI (Mild cognitive impairment). In some embodiments, the compounds of formula (I) or a salt thereof can be used as agent for preventing or treating diseases or conditions including, but not limited to, stroke, cerebrovascular dementia, Down syndrome, Parkinson's disease (PD), and dementia with Lewy bodies (DLB).

As used herein and in the appended claims, the singular forms "a," "an," and "the" include plural reference unless the context clearly indicates otherwise.

The term, "effective amount," and cognates of this term, as used herein, refer to an amount that results in a desired pharmacological and/or physiological effect for a specified condition (e.g., disease, disorder, etc.) or one or more of its symptoms and/or to completely or partially prevent the occurrence of the condition or symptom thereof and/or may be therapeutic in terms of a partial or complete cure for the condition and/or adverse effect attributable to the condition. In reference to conditions mediated by memapsin 2 (β-secretase) or diseases or conditions associated with and/or mediated by β-secretase activity, hydrolysis of a β-secretase cleavage site of an amyloid precursor protein, and/or β-amyloid protein accumulation, a pharmaceutically or therapeutically effective amount comprises an amount sufficient to, among other things, cause antagonism or inhibition of memapsin 2 (β-secretase). In reference to glaucoma, a pharmaceutically or therapeutically effective amount comprises an amount sufficient to, among other things, decrease intraocular pressure; and/or halt, reverse, and/or diminish the loss of retinal ganglion cells (RGCs). In certain embodiments, the pharmaceutically effective amount is sufficient to prevent the condition, as in being administered to an individual prophylactically.

The "effective amount" will vary depending on the composition being administered, the condition being treated/prevented, the severity of the condition being treated or prevented, the age and relative health of the individual, the route and form of administration, the judgment of the attending medical or veterinary practitioner, and other factors appreciated by the skilled artisan in view of the teaching provided herein.

The "subject" means the animal which needs its prevention or treatment and the human who needs its prevention or treatment, in some embodiments it means the human who needs its prevention or treatment.

When used with respect to methods of treatment/prevention and the use of the compounds and compositions thereof described herein, a subject "in need thereof" may be an individual who has been diagnosed with or previously treated for the condition to be treated. With respect to prevention, the subject in need thereof may also be an individual who is at risk for a condition (e.g., a family history of the condition, lifestyle factors indicative of risk for the condition, etc.).

In some variations, the subject has been identified as having one or more of the conditions described herein. In some embodiments, the subject has been identified as susceptible to one or more of the conditions as described herein. The susceptibility of a subject may be based on any one or more of a number of risk factors and/or diagnostic approaches appreciated by the skilled artisan, including, but not limited to, genetic profiling, family history, medical history (e.g., appearance of related conditions), lifestyle or habits.

Examples of the embodiment of the substituent acceptable in the "$R^{411}$, $R^{412}$, $R^{421}$ and $R^{422}$ are combined with each other to form an aryl group, which is substituted" include, but are not limited to, e.g., halogen.

Examples of the embodiment of the substituent acceptable in the "a hetero ring group, which is substituted" in B include, but are not limited to, e.g., halogen.

Examples of the embodiment of the substituent acceptable in the "cycloalkyl, which is substituted" in B include, but are not limited to, e.g., halogen.

Examples of the embodiment of the substituent acceptable in the "lower alkyl, which is substituted" in X and Y include, but are not limited to, the groups shown in i) to iii) below.

i) halogen, ii) cycloalkyl, or iii) aryl.

Examples of the embodiment of the substituent acceptable in the "cycloalkyl, which is substituted" in X and Y include, but are not limited to, the groups shown in i) to iii) below.

i) halogen, ii) cycloalkyl, or iii) aryl.

Examples of the embodiment of the substituent acceptable in the "X and Y are combined with each other to form a cycloalkyl group, which is substituted" include, but are not limited to, the groups shown in i) to iii) below.

i) halogen, ii) cycloalkyl, or iii) aryl.

Examples of the embodiment of the substituent acceptable in the "a hetero ring group, which is substituted" in $R^1$, $R^2$, $R^3$ and $R^4$ include, but are not limited to, the groups shown in i) to vi) below.

i) halogen, ii) lower alkyl, which is unsubstituted or substituted with one or more substituents selected from the group consisting of halogen and —O-(lower alkyl), iii) lower alkynyl, which is unsubstituted or substituted with one or more substituents selected from the group consisting of —O-(lower alkyl) and cycloalkyl, iv) —O-(lower alkyl), wherein said lower alkyl is unsubstituted or substituted with halogen, v) cycloalkyl, or vi) —CN.

Examples of the embodiment of the substituent acceptable in the "lower alkyl, which is substituted" in $R^1$, $R^2$, $R^3$ and $R^4$ include, but are not limited to, —O-(lower alkyl), or aryl, wherein said aryl is unsubstituted or substituted with lower alkyl.

Examples of the embodiment of the substituent acceptable in the "lower alkenyl, which is substituted" in $R^1$, $R^2$, $R^3$ and $R^4$ include, but are not limited to, —O-(lower alkyl).

Examples of the embodiment of the substituent acceptable in the "—N(H)-(hetero ring group), wherein said hetero ring group is substituted" in $R^1$, $R^2$, $R^3$ and $R^4$ include, but are not limited to, halogen or —O-(lower alkyl).

Examples of embodiments of substituents acceptable in the "—N(H)—C(O)-(hetero ring group), wherein said hetero ring group is substituted" in $R^1$, $R^2$, $R^3$ and $R^4$ include, but are not limited to, the groups shown in i) to vii) below.

i) halogen, ii) lower alkyl, which is unsubstituted or substituted with one or more substituents selected from the group consisting of halogen, —O-(lower alkyl), and a hetero ring group, iii) —CN, iv) —O-(lower alkyl), wherein said lower alkyl is unsubstituted or substituted with halogen, v) cycloalkyl, vi) aryl, or vii) a hetero ring group.

Examples of other embodiments of substituents acceptable in the "—N(H)—C(O)-(hetero ring group), wherein said hetero ring group is substituted" in $R^1$, $R^2$, $R^3$ and $R^4$ include, but are not limited to, the groups shown in i) to vii) below.

i) halogen, ii) lower alkyl, which is unsubstituted or substituted with one or more substituents selected from the group consisting of halogen, —O-(lower alkyl), and a nitrogen-containing monocyclic hetero ring group, iii) —CN, iv) —O-(lower alkyl), wherein said lower alkyl is unsubstituted or substituted with halogen, v) cycloalkyl, vi) aryl, or vii) a nitrogen-containing monocyclic hetero ring group.

Examples of other embodiments of the substituent acceptable in the "—N(H)—C(O)-(hetero ring group), wherein said hetero ring group is substituted" in $R^1$, $R^2$, $R^3$ and $R^4$ include, but are not limited to, the groups shown in i) to iv) below.

i) halogen, ii) lower alkyl, iii) —CN, or iv) —O-(lower alkyl).

Examples of embodiments of substituents acceptable in the "cycloalkenyl, which is substituted" in $R^1$, $R^2$, $R^3$ and $R^4$ include, but are not limited to, lower alkyl.

Examples of the embodiment of the substituent acceptable in the "aryl, which is substituted" in $R^1$, $R^2$, $R^3$ and $R^4$ include, but are not limited to, the groups shown in i) to ix) below.
  i) —OH,
  ii) halogen,
  iii) lower alkyl, which is unsubstituted or substituted with halogen,
  iv) —O-(lower alkyl), wherein said lower alkyl is unsubstituted or substituted with halogen,
  v) —S-(lower alkyl),
  vi) cycloalkyl,
  vii) —CN,
  viii) lower alkenyl, which is unsubstituted or substituted with —CN, or
  ix) —C(O)—N(H)-(lower alkyl).

Examples of the embodiment of groups of compounds of formula (I) of the present invention are shown below.
(1)
(1-1)
  $A^1$ is O or S;
  $A^2$ is —C($R^{A21}R^{A22}$)—; and
  $R^{A21}$ and $R^{A22}$ are H.
(1-2)
(1-2-1)
  $A^1$ is O;
  $A^2$ is —C($R^{A21}R^{A22}$)—; and
  $R^{A21}$ and $R^{A22}$ are H.
(2)
(2-1)
(2-1-1)
  B is a hetero ring group, wherein said hetero ring group is unsubstituted or substituted with halogen, or cycloalkyl, wherein said cycloalkyl is unsubstituted or substituted with halogen.
(2-1-2)
  B is a hetero ring group or cycloalkyl, wherein said cycloalkyl is unsubstituted or substituted with halogen.
(2-1-3)
  B is an oxygen-containing monocyclic saturated hetero ring group or cycloalkyl, wherein said cycloalkyl is unsubstituted or substituted with halogen.
(2-1-4)
  B is an oxygen-containing monocyclic saturated hetero ring group or $C_{3-6}$ cycloalkyl, wherein said $C_{3-6}$ cycloalkyl is unsubstituted or substituted with halogen.
(2-1-5)
  B is an oxygen-containing monocyclic saturated hetero ring group or $C_{3-6}$ cycloalkyl, wherein said $C_{3-6}$ cycloalkyl is unsubstituted or substituted with F.
(2-1-6)
  B is a cyclic ether group or cycloalkyl, wherein said cycloalkyl is unsubstituted or substituted with halogen.
(2-1-7)
  B is a cyclic ether group or $C_{3-6}$ cycloalkyl, wherein said $C_{3-6}$ cycloalkyl is unsubstituted or substituted with halogen.
(2-1-8)
  B is a cyclic ether group or $C_{3-6}$ cycloalkyl, wherein said $C_{3-6}$ cycloalkyl is unsubstituted or substituted with F.
(2-1-9)
  B is oxetanyl, tetrahydropyranyl, cyclopropyl, cyclobutyl, or 3,3-difluorocyclobutan-1-yl.
(2-1-10)
  B is oxetanyl, tetrahydrofuranyl, cyclopropyl, cyclobutyl, or 3,3-difluorocyclobutan-1-yl.
(2-2)
(2-2-1)
  B is a hetero ring group.
(2-2-2)
  B is an oxygen-containing monocyclic saturated hetero ring group.
(2-2-3)
  B is a cyclic ether group.
(2-2-4)
  B is oxetanyl or tetrahydropyranyl.
(2-2-5)
  B is oxetanyl.
(2-2-6)
  B is oxetanyl or tetrahydrofuranyl.
(2-3)
(2-3-1)
  B is cycloalkyl, wherein said cycloalkyl is unsubstituted or substituted with halogen.
(2-3-2)
  B is $C_{3-6}$ cycloalkyl, wherein said $C_{3-6}$ cycloalkyl is unsubstituted or substituted with halogen.
(2-3-3)
  B is $C_{3-6}$ cycloalkyl, wherein said $C_{3-6}$ cycloalkyl is unsubstituted or substituted with F.
(2-3-4)
  B is cyclopropyl, cyclobutyl, or 3,3-difluorocyclobutan-1-yl.
(2-3-5)
  B is cyclopropyl.
(3)
(3-1)
  X is lower alkyl; and
  Y is lower alkyl.
(3-2)
  X is methyl; and
  Y is methyl.
(4)
(4-1)
(4-1-1)
  $R^1$, $R^2$, $R^3$ and $R^4$ are independently selected from the group consisting of
  H,
  halogen, and
  —N(H)—C(O)-(hetero ring group), wherein said hetero ring group is unsubstituted or substituted with one or more substituents selected from the group consisting of halogen, lower alkyl which is unsubstituted or substituted with halogen,
  —CN, and
  —O-(lower alkyl).
(4-1-2)
  $R^1$ and $R^4$ are H;
  $R^3$ is H or halogen; and
  $R^2$ is —N(H)—C(O)-(hetero ring group), wherein said hetero ring group is unsubstituted or substituted with one or more substituents selected from the group consisting of halogen,
  lower alkyl which is unsubstituted or substituted with halogen,
  —CN, and
  —O-(lower alkyl).
(4-1-3)
  $R^1$ and $R^4$ are H;
  $R^3$ is H or halogen; and
  $R^2$ is —N(H)—C(O)-(nitrogen-containing monocyclic hetero ring group), wherein said nitrogen-containing monocyclic hetero ring group is unsubstituted or substituted with one or more substituents selected from the group consisting of halogen,
lower alkyl which is unsubstituted or substituted with halogen,
—CN, and
—O-(lower alkyl).

(4-1-4)
  $R^1$ and $R^4$ are H;
  $R^3$ is H or halogen; and
  $R^2$ is selected from the group consisting of
    —N(H)—C(O)-(pyridyl), wherein said pyridyl is unsubstituted or substituted with one or more substituents selected from the group consisting of
    halogen,
    lower alkyl which is unsubstituted or substituted with halogen,
    —CN, and
    —O-(lower alkyl),
    —N(H)—C(O)-(pyrazinyl), wherein said pyrazinyl is unsubstituted or substituted with one or more substituents selected from the group consisting of
    halogen,
    lower alkyl which is unsubstituted or substituted with halogen,
    —CN, and
    —O-(lower alkyl), and
    —N(H)—C(O)-(pyrimidinyl), wherein said pyrimidinyl is unsubstituted or substituted with one or more substituents selected from the group consisting of
    halogen,
    lower alkyl which is unsubstituted or substituted with halogen,
    —CN, and
    —O-(lower alkyl).

(4-1-5)
  $R^1$ and $R^4$ are H;
  $R^3$ is H or halogen; and
  $R^2$ is selected from the group consisting of
    —N(H)—C(O)-(pyridyl), wherein said pyridyl is unsubstituted or substituted with one or more substituents selected from the group consisting of
    halogen,
    lower alkyl, and
    —CN,
    —N(H)—C(O)-(pyrazinyl), wherein said pyrazinyl is unsubstituted or substituted with —O-(lower alkyl) or lower alkyl which is unsubstituted or substituted with halogen, and
    —N(H)—C(O)-(pyrimidinyl), wherein said pyrimidinyl is unsubstituted or substituted with halogen.

(4-1-6)
  $R^1$ and $R^4$ are H;
  $R^3$ is H or halogen; and
  $R^2$ is —N(H)—C(O)-(pyridyl), wherein said pyridyl is unsubstituted or substituted with one or more substituents selected from the group consisting of
  halogen,
  lower alkyl, and
  —CN.

(4-1-6-1)
  $R^1$ and $R^4$ are H;
  $R^3$ is H or halogen; and
  $R^2$ is —N(H)—C(O)-(pyridyl), wherein said pyridyl is unsubstituted or substituted with halogen.

(4-1-7)
  $R^1$ and $R^4$ are H;
  $R^3$ is H or halogen; and
  $R^2$ is —N(H)—C(O)-(pyrazinyl), wherein said pyrazinyl is unsubstituted or substituted with —O-(lower alkyl) or lower alkyl which is unsubstituted or substituted with halogen.

(4-1-8)
  $R^1$ and $R^4$ are H;
  $R^3$ is H or halogen; and
  $R^2$ is —N(H)—C(O)-(pyrimidinyl), wherein said pyrimidinyl is unsubstituted or substituted with halogen.

(4-2)
  The groups of any one of (4-1),
  wherein $R^3$ is H.

Furthermore, still other embodiments of the compounds of formula (I) of the present invention include the compounds including a combination of two or more of the groups described in (1) to (4) above, specifically, the following compounds.

(5) The compound of formula (I), wherein B is as described in (2).
(6) The compound as described in (5), wherein X and Y are as described in (3).
(7) The compound as described in (5) or (6), wherein $R^1$, $R^2$, $R^3$ and $R^4$ are as described in (4).
(8) The compound as described in (5), (6) or (7), wherein $A^1$ and $A^2$ are as described in (1).

Furthermore, still other embodiments of the compounds of formula (I) of the present invention include the compounds including a combination of two or more of the groups described in (1) to (4) above, specifically, the following compounds.

(9) The compound of formula (I), wherein $A^1$ and $A^2$ are as described in (1-2-1), B is as described in (2-1-3), X and Y are as described in (3-1) and $R^1$, $R^2$, $R^3$ and $R^4$ are as described in (4-1-2).
(10) The compound of formula (I), wherein $A^1$ and $A^2$ are as described in (1-2-1), B is as described in (2-1-3), X and Y are as described in (3-1) and $R^1$, $R^2$, $R^3$ and $R^4$ are as described in (4-1-5).
(11) The compound of formula (I), wherein $A^1$ and $A^2$ are as described in (1-2-1), B is as described in (2-2-2), X and Y are as described in (3-1) and $R^1$, $R^2$, $R^3$ and $R^4$ are as described in (4-1-5).
(12) The compound of formula (I), wherein $A^1$ and $A^2$ are as described in (1-2-1), B is as described in (2-3-1), X and Y are as described in (3-1) and $R^1$, $R^2$, $R^3$ and $R^4$ are as described in (4-1-5).
(13) The compound of formula (I), wherein $A^1$ and $A^2$ are as described in (1-2-1), B is as described in (2-2-5), X and Y are as described in (3-1) and $R^1$, $R^2$, $R^3$ and $R^4$ are as described in (4-1-5).
(14) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-5).
(15) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-6).
(16) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-6-1).
(17) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-7).

(18) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-8).

(19) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-6), wherein $R^3$ is H.

(20) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-6-1), wherein $R^3$ is H.

(21) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-7), wherein $R^3$ is H.

(22) The compound of formula (I), wherein $A^1$ and $A^2$ are as described in (1-2-1), B is as described in (2-2-5), X and Y are as described in (3-2) and $R^1$, $R^2$, $R^3$ and $R^4$ are as described in (4-1-8), wherein $R^3$ is H.

(23) The compound of formula (I), wherein $A^1$ and $A^2$ are as described in (1-2-1), B is as described in (2-3-5), X and Y are as described in (3-1) and $R^1$, $R^2$, $R^3$ and $R^4$ are as described in (4-1-5).

(24) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-5).

(25) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-6).

(26) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-6-1).

(27) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-7).

(28) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-8).

(29) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-6), wherein $R^3$ is H.

(30) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-6-1), wherein $R^3$ is H.

(31) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-7), wherein $R^3$ is H.

(32) The compound of formula (I), wherein $A^1$ and $A^2$ are as described in (1-2-1), B is as described in (2-3-5), X and Y are as described in (3-2) and $R^1$, $R^2$, $R^3$ and $R^4$ are as described in (4-1-8), wherein $R^3$ is H.

(33) The compound of formula (I), wherein $A^1$ and $A^2$ are as described in (1-2-1), B is as described in (2-1-3), X and Y are as described in (3-1) and $R^1$, $R^2$, $R^3$ and $R^4$ are as described in (4-1-3).

(34) The compound of formula (I), wherein $A^1$ and $A^2$ are as described in (1-2-1), B is as described in (2-1-3), X and Y are as described in (3-1) and $R^1$, $R^2$, $R^3$ and $R^4$ are as described in (4-1-4).

(35) The compound as described in (5) to (34), wherein the compound of formula (I) is the compound of formula (II) as below.

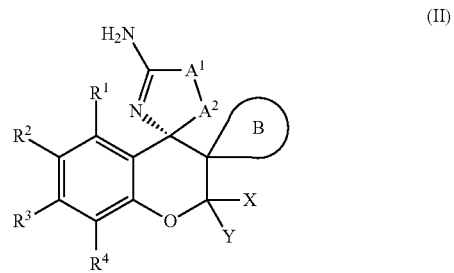

Examples of the specific compounds encompassed by the present invention include the following compounds. Nomenclature of some compounds described herein may be identified using IUPAC or other naming conventions including ACD/Name ver. 12.02, available from Advanced Chemistry Development, Inc., Toronto, Ontario, Canada.

N-(2-amino-2',2'-dimethyldispiro[1,3-oxazole-4,4'-chromene-3',3''-oxetan]-6'-yl)-5-chloropyridine-2-carboxamide, N-(2-amino-2',2'-dimethyldispiro[1,3-oxazole-4,4'-chromene-3',3''-oxetan]-6'-yl)-5-fluoropyridine-2-carboxamide, N-(2-amino-2',2'-dimethyldispiro[1,3-oxazole-4,4'-chromene-3',3''-oxetan]-6'-yl)-5-chloro-3-fluoropyridine-2-carboxamide, N-(2-amino-2',2'-dimethyldispiro[1,3-oxazole-4,4'-chromene-3',3''-oxetan]-6'-yl)-5-bromopyrimidine-2-carboxamide, N-(2-amino-2',2'-dimethyldispiro[1,3-oxazole-4,4'-chromene-3',3''-oxetan]-6'-yl)-5-chloro-3-methyl pyridine-2-carboxamide, N-(2-amino-2',2'-dimethyldispiro[1,3-oxazole-4,4'-chromene-3',3''-oxetan]-6'-yl)-5-cyanopyridine-2-carboxamide, N-(2-amino-2',2'-dimethyldispiro[1,3-oxazole-4,4'-chromene-3',3''-oxetan]-6'-yl)-5-methoxypyrazine-2-carboxamide, N-[(4S)-2-amino-2',2'-dimethyldispiro[1,3-oxazole-4,4'-chromene-3',3''-oxetan]-6'-yl]-5-chloropyridine-2-carboxamide, N-[(4'R)-2''-amino-2',2'-dimethyldispiro[cyclopropane-1,3'-chromene-4',4''-[1,3]oxazol]-6'-yl]-5-methoxypyrazine-2-carboxamide, N-[(4'R)-2''-amino-2',2'-dimethyldispiro[cyclopropane-1,3'-chromene-4',4''-[1,3]oxazol]-6'-yl]-5-(difluoromethyl)pyrazine-2-carboxamide, N-[(4S)-2-amino-2',2'-dimethyldispiro[1,3-oxazole-4,4'-chromene-3',3''-oxetan]-6'-yl]-5-methoxypyrazine-2-carboxamide, N-[(4S)-2-amino-2',2'-dimethyldispiro[1,3-oxazole-4,4'-chromene-3',3''-oxetan]-6'-yl]-5-bromopyridine-2-carboxamide, N-[(4'R)-2''-amino-2',2'-dimethyldispiro[cyclopropane-1,3'-chromene-4',4''-[1,3]oxazol]-6'-yl]-5-chloropyridine-2-carboxamide, and N-[(4'R)-2"-amino-2',2'-dimethyldispiro[cyclopropane-1,3'-chromene-4',4"-[1,3]oxazol]-6'-yl]-5-fluoropyridine-2-carboxamide.

Other examples of the specific compounds encompassed by the present invention include the following compounds. Nomenclature of some compounds described herein may be identified using IUPAC or other naming conventions including ACD/Name ver. 12.02, available from Advanced Chemistry Development, Inc., Toronto, Ontario, Canada.

N-[(4S)-2-amino-2',2'-dimethyldispiro[1,3-oxazole-4,4'-chromene-3',3"-oxetan]-6'-yl]-5-chloropyridine-2-carboxamide, N-[(4'R)-2"-amino-2',2'-dimethyldispiro[cyclopropane-1,3'-chromene-4',4"-[1,3]oxazol]-6'-yl]-5-methoxypyrazine-2-carboxamide, and N-[(4'R)-2"-amino-2',2'-dimethyldispiro[cyclopropane-1,3'-chromene-4',4"-[1,3]oxazol]-6'-yl]-5-(difluoromethyl)pyrazine-2-carboxamide.

The present invention relates to a hydrate of the compound or a salt, wherein said compound is N-[(4S)-2-amino-2',2'-dimethyldispiro[1,3-oxazole-4,4'-chromene-3',3"-oxetan]-6'-yl]-5-chloropyridine-2-carboxamide.

In some embodiments, $A^1$ is O;

$A^2$ is $CH_2$;

B is

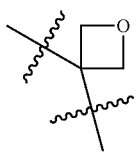 [SMILES: *C1(*)COC1]

or cyclopropyl;

X and Y are both methyl, or X and Y are both H;

$R^1$, $R^3$, and $R^4$ are H; and $R^2$ is —N(H)—C(O)-(hetero ring group), wherein the hetero ring group of $R^2$ is selected from the group consisting of each of

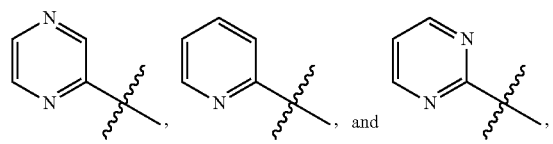 [SMILES: *c1cnccn1 ; *c1ccccn1 ; *c1ncccn1]

each of which is substituted with 1 or 2 substituents independently selected from the group consisting of halogen, cyano, unsubstituted —O-lower alkyl, unsubstituted lower alkyl, lower alkyl substituted with one or more halogen, —O-lower alkyl substituted with one or more halogen, lower alkyl substituted with —$OCH_3$, unsubstituted lower alkynyl, and unsubstituted cycloalkyl. In some embodiments, B is

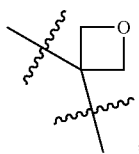

and X and Y are both methyl. In some embodiments, B is cyclopropyl, and X and Y are both H. In some embodiments, $R^2$ is selected from the group consisting of

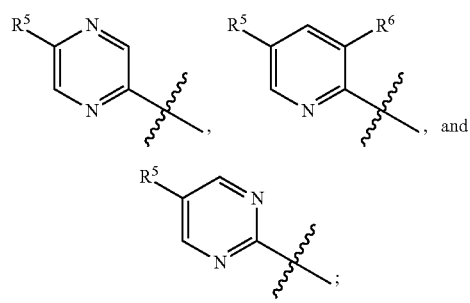

and wherein $R^5$ and $R^6$ are independently selected from the group consisting of hydrogen, fluoro, chloro, bromo, cyano, —$OCH_3$, methyl, —$CHF_2$, —$OCHF_2$, —$OCH_2CHF_2$, —$CH_2OCH_3$, —C≡C—$CH_3$, and cyclopropyl. In some embodiments, $R^5$ is chloro or —$OCH_3$, and $R^6$ is hydrogen or fluoro. In some embodiments, $R^5$ is —$CHF_2$ or —$OCHF_2$, and $R^6$ is hydrogen.

In some embodiments, $A^1$ is O;

$A^2$ is $CH_2$; and $R^2$ is —N(H)—C(O)-(hetero ring group), wherein the hetero ring group is

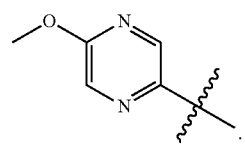 [SMILES: *c1cnc(OC)cn1]

In some embodiments, the compound is selected from the group consisting of

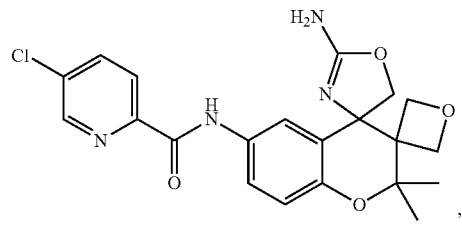 [SMILES: CC1(C)Oc2ccc(NC(=O)c3ccc(Cl)cn3)cc2C2(COC(N)=N2)C12COC2]

-continued

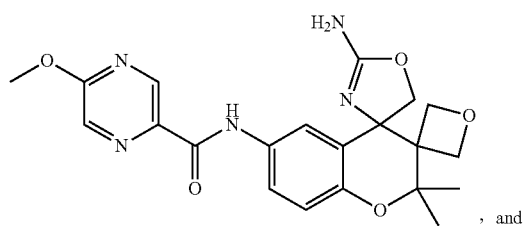, and

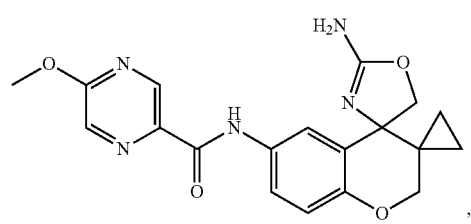, or a salt thereof.

In some embodiments, the compound is

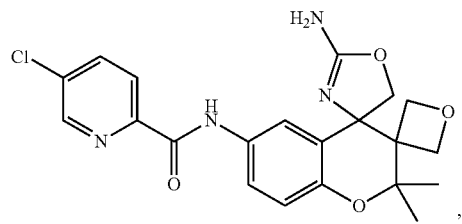, or a salt thereof.

In some embodiments, the compound is

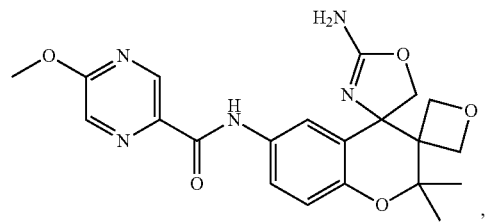 [SMILES: COc1cnc(C(=O)Nc2ccc3c(c2)C2(COC(N)=N2)C2(COC2)C(C)(C)O3)cn1], or a salt thereof.

In some embodiments, the compound is

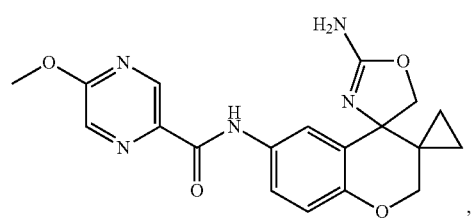 [SMILES: COc1cnc(C(=O)Nc2ccc3c(c2)C2(COC(N)=N2)C2(CC2)CO3)cn1], or a salt thereof.

In some embodiments, the compound is selected from the group consisting of

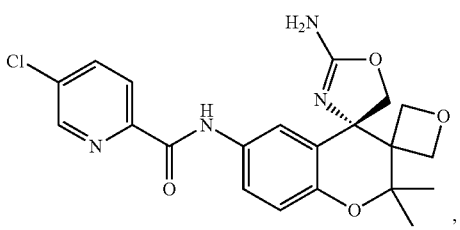 [SMILES: CC1(C)Oc2ccc(NC(=O)c3ccc(Cl)cn3)cc2[C@@]2(COC(N)=N2)C12COC2],

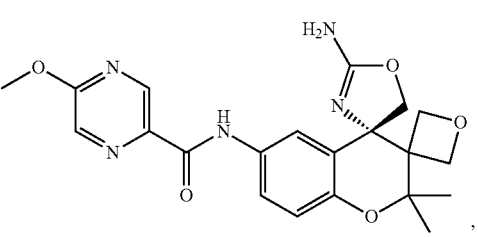 [SMILES: COc1cnc(C(=O)Nc2ccc3c(c2)[C@@]2(COC(N)=N2)C2(COC2)C(C)(C)O3)cn1], and

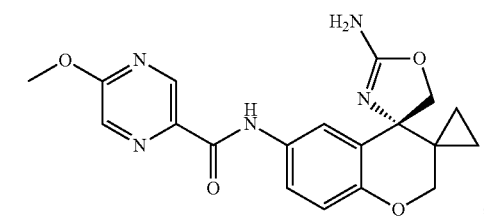, or a salt thereof.

In some embodiments, the compound is

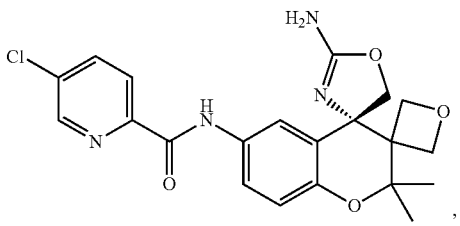, or a salt thereof.

In some embodiments, the compound is

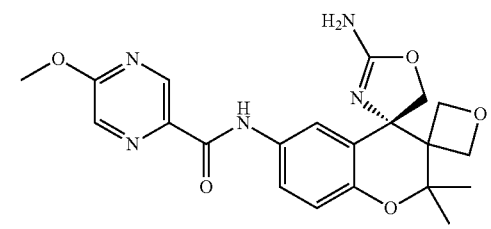, or a salt thereof.

In some embodiments, the compound is
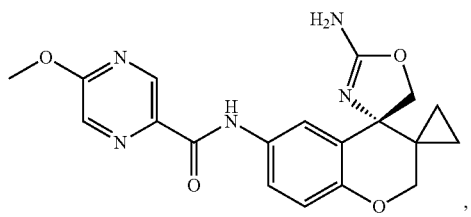 [SMILES: COc1cnc(C(=O)Nc2ccc3c(c2)[C@@]2(COC(N)=N2)C2(CC2)CO3)cn1]
or a salt thereof.
In some embodiments, the compound is selected from the group consisting of
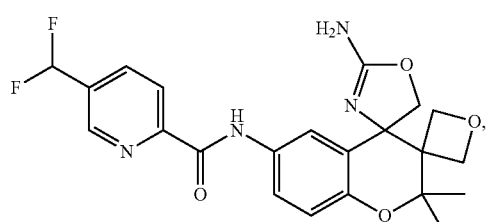
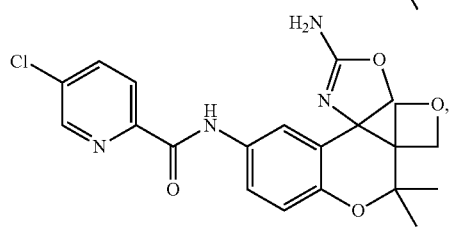
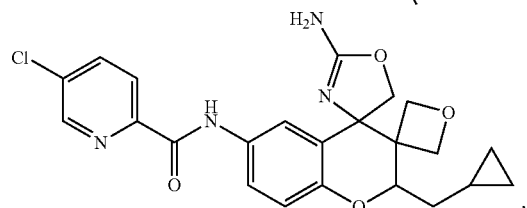
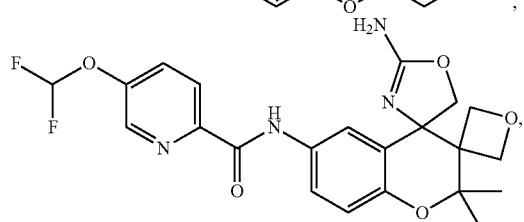
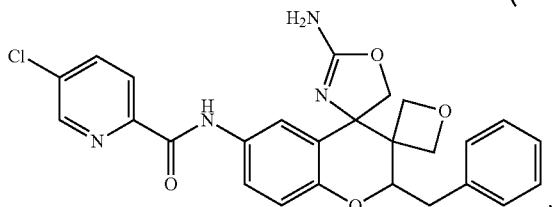
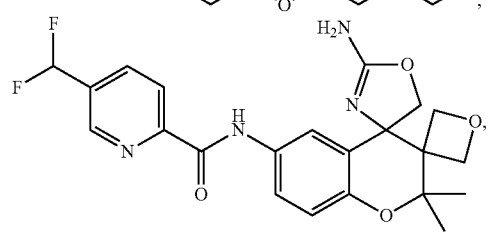
-continued
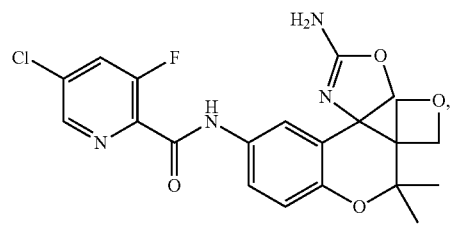
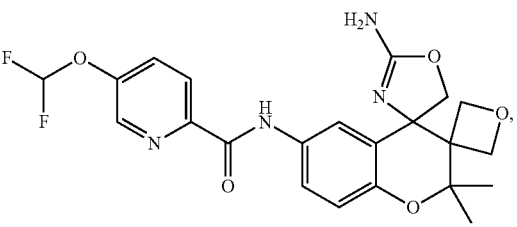
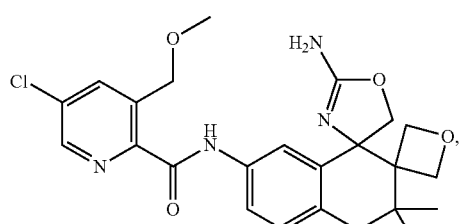
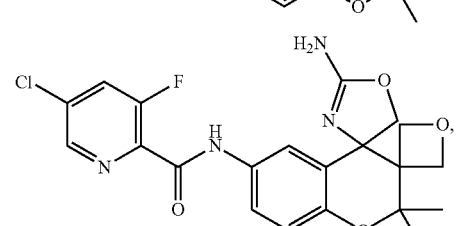
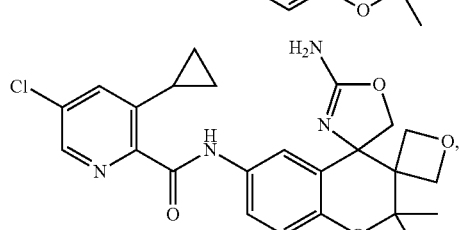
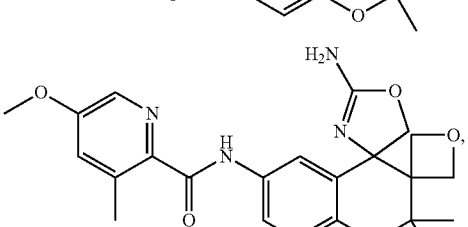
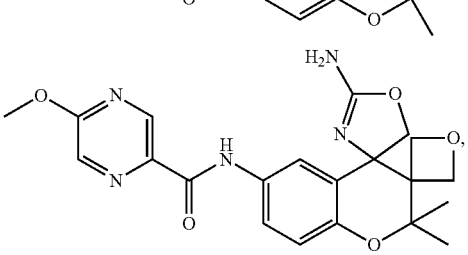

-continued
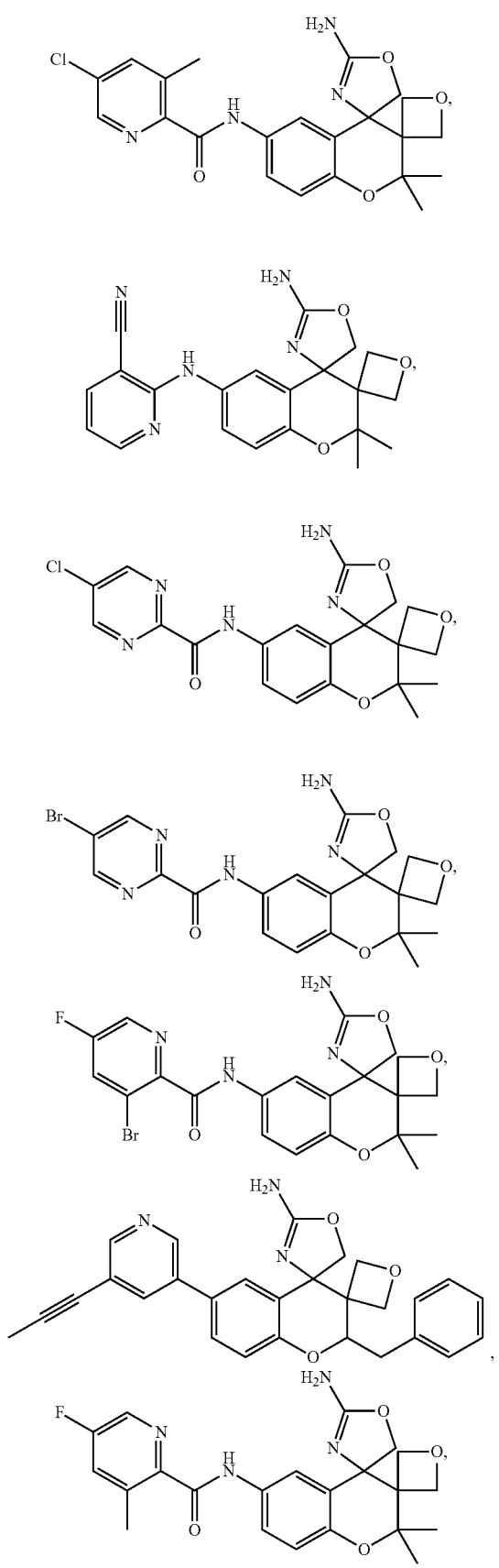
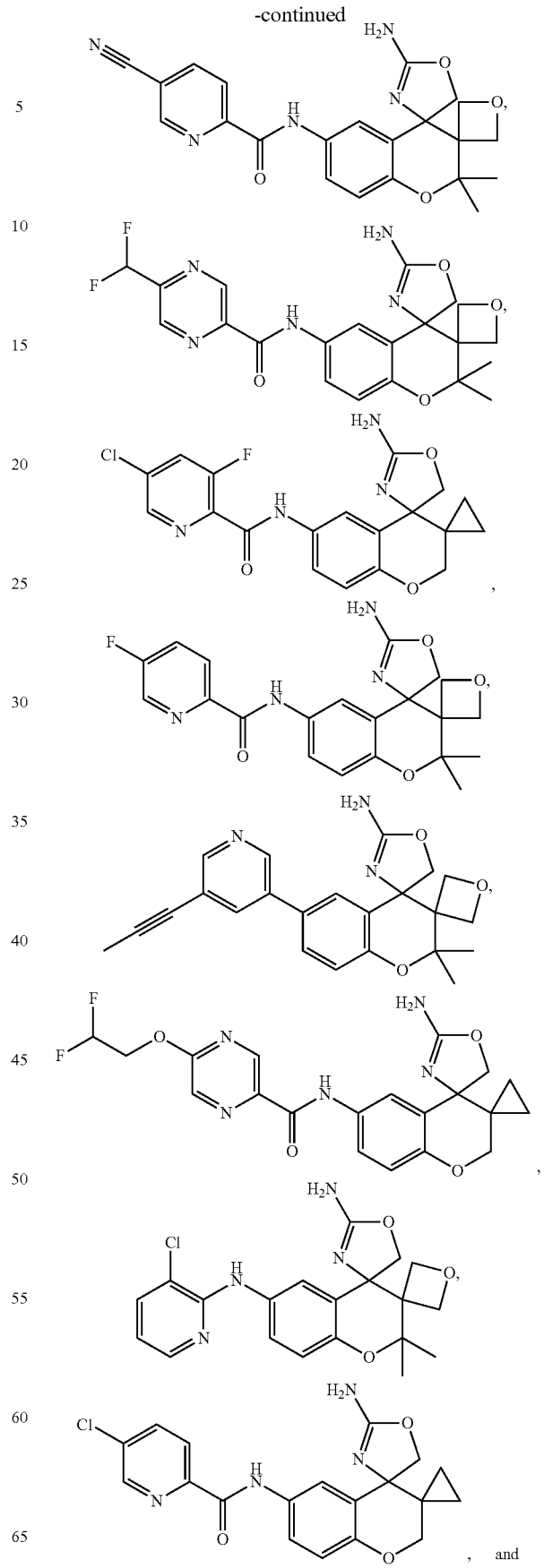
, and

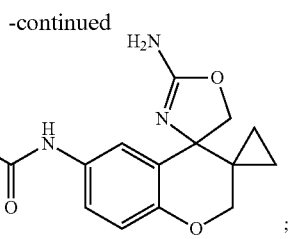

or a salt thereof.

The compound of the formula (I) may exist in the form of tautomers or geometrical isomers depending on the kind of substituents. In the present specification, the compound of the formula (I) shall be described in only one form of isomer, yet the present invention includes such an isomer, isolated forms of the isomers, or a mixture thereof.

In addition, the compound of the formula (I) may have asymmetric carbon atoms or axial asymmetry in some cases, and correspondingly, it may exist in the form of optical isomers. The present invention includes both an isolated form of the optical isomers of the compound of the formula (I) or a mixture thereof.

Moreover, the present invention also includes a pharmaceutically acceptable prodrug of the compound of the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and Pharmaceutical Research and Development, Drug Design, Hirokawa Publishing Company (1990), Vol. 7, 163-189, which is incorporated by reference herein in its entirety.

Furthermore, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystal substances of the compound of the formula (I) and a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the functional group) at the stage from starting material to an intermediate may be effective depending on the type of the functional group in the production technology in some cases. The protective group for such a functional group may include for example, the protective groups described in "Greene's Protective Groups in Organic Synthesis (4$^{th}$ Ed., 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be produced by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Unless otherwise indicated, in any of the foregoing schemes, $A^1$, $A^2$, $R^1$, $R^2$, $R^3$, $R^4$, X, Y, and B are as described for formula (I) or any applicable variation thereof. Further, the preparation methods of the compound of the formula (I) are not limited to the examples as shown below.

(Production Process 1)

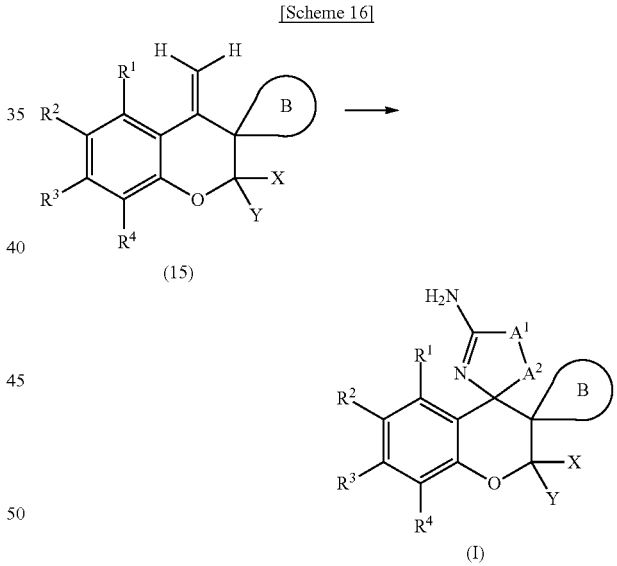

A compound (I) can be obtained by subjecting a compound (15) to addition and cyclization reactions.

In the addition reaction, the compound (15) and an equivalent amount or an excess amount of iodine and silver cyanate or silver thiocyanate are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent. Examples of the solvent as used herein are not particularly limited, but include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof.

In the cyclization reaction, the crude mixture after the addition reaction and an equivalent amount or an excess amount of $NH_3$ dissolved in solvent such as $H_2O$ or ethanol (EtOH), and so on, are used, and a mixture thereof is stirred under any temperature condition from cooling to heating to refluxing, preferably at 0° C. to 200° C., and still more preferably at 20° C. to 120° C., usually for 0.1 hours to 5 days, in a solvent which is inert to the reaction or without a solvent. Examples of the solvent as used herein are not particularly limited, but include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, water and a mixture thereof. It may be advantageous in some cases for the smooth progress of the reaction to carry out the reaction in the presence of an organic base such as triethylamine, N,N-diisopropylethylamine, N-methylmorpholine, and the like, or an inorganic base such as sodium tert-butoxide, potassium carbonate, sodium bis(trimethylsilyl)amide, sodium carbonate, potassium hydroxide, and the like.

In some embodiments of Production Process 1, the compound (I) is a compound of formula (Ie):

[Scheme 17]

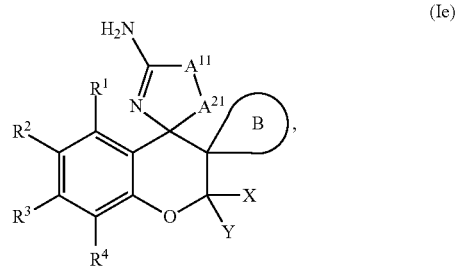

(Ie)

wherein $A^{11}$ represents O or S, and $A^{21}$ represents $CH_2$.

(Production Process 2)

[Scheme 18]

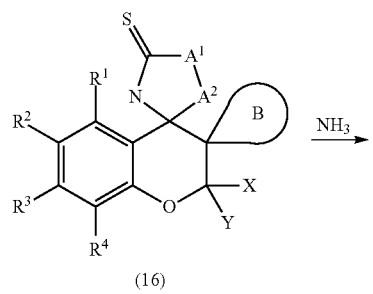

(16)

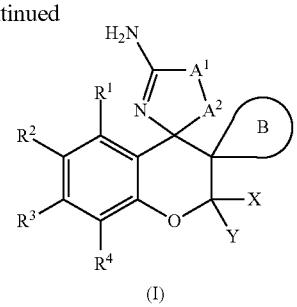

(I)

A compound (I) can be obtained by subjecting a compound (16) and $NH_3$ to a substitution reaction.

In this reaction, the compound (16) and an equivalent amount or an excess amount of $NH_3$ dissolved in solvent such as $H_2O$ or EtOH, and so on, are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent. It may be advantageous in some cases for the smooth progress of the reaction to carry out the reaction under microwave irradiation. Examples of the solvent as used herein are not particularly limited, but include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to carry out the reaction in the presence of tert-butyl hydroperoxide, and the like.

(Other Production Processes)

Furthermore, several substituents in the formula (I) can also be easily converted into other functional groups by using the compound of the present invention (I) as a starting material by means of the reactions apparent to a person skilled in the art, or modified methods thereof. The reaction can be carried out by any combination of the processes that can be usually employed by a person skilled in the art, such as hydrolysis, alkylation, halogenation, hydrogenation, and the like. Several examples thereof are presented below.

(Production Process 3)

[Scheme 19]

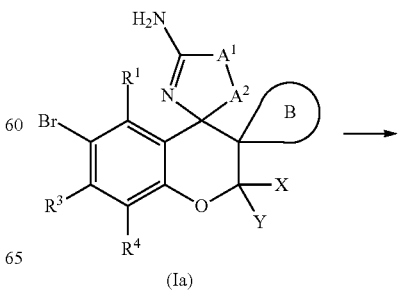

(Ia)

-continued

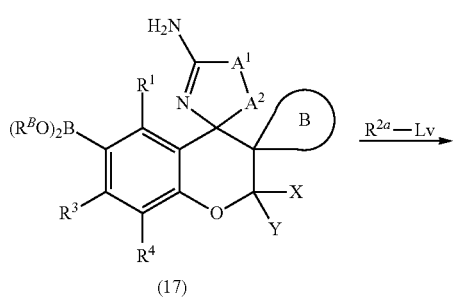

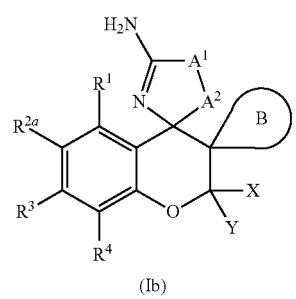

(wherein $R^B$ represents H or lower alkyl, or two $R^B$'s are combined with each other to form $C_{2-7}$ alkylene, Lv represents a leaving group, and $R^{2a}$ represents a group in $R^2$ with the exception that $R^{2a}$ cannot be H or halogen. In some embodiments, $R^{2a}$ represents aryl or a hetero ring group which has aromaticity in $R^2$. Moreover, said aryl may be substituted with substituents acceptable in the "aryl" of $R^1$, $R^2$, $R^3$ and $R^4$, and said hetero ring group may be substituted with substituents acceptable in the "a hetero ring group" of $R^1$, $R^2$, $R^3$ and $R^4$).

First, the compound (17) can be obtained by subjecting the compound (Ia) to a cross-coupling reaction with a borylation reagent.

In this reaction, a mixture of the compound (Ia) and a borylation reagent in equivalent amounts, or with either thereof in an excess amount is stirred under any temperature condition from cooling to heating, and preferably −20° C. to 60° C., usually for 0.1 hours to 5 days, in a solvent which is inert to the reaction, in the presence of an organometallic compound. The solvent as used herein is not particularly limited, but examples thereof include aromatic hydrocarbons such as benzene, toluene or xylene, and the like, halogenated hydrocarbons such as dichloromethane, 1,2-dichloroethane, chloroform, and the like, ethers such as diethyl ether, tetrahydrofuran, dioxane, dimethoxyethane, and the like, DMF, DMSO, EtOAc, acetonitrile, water, and a mixture thereof. Examples of the borylation reagent include bis(pinacolato) diboron, and the like. It may be advantageous in some cases for the smooth progress of the reaction to carry out the reaction in the presence of inorganic base, such as potassium acetate or potassium phenolate, and the like. Examples of an organometallic compound include palladium catalysts, such as [1,1'-Bis(diphenylphosphino)ferrocene]palladium(II) dichloride. It may be advantageous in some cases for the smooth progress of the reaction to carry out the reaction after protecting —NH₂ of a compound (Ia).

Moreover, the compound (Ib) can be obtained by subjecting the compound (17) and the $R^{2a}$-Lv to a coupling reaction. Herein, examples of the leaving group Lv include halogen, a trifluoromethanesulfonyloxy group, and the like.

In this reaction, a mixture of the compound (17) and an equivalent amount or an excess amount of $R^{2a}$-Lv is stirred under any temperature condition from cooling to heating and refluxing, and preferably at 0° C. to 80° C., usually for 0.1 hours to 5 days, in a solvent which is inert to the reaction or without a solvent by using a catalyst used for Suzuki-Miyaura cross-coupling reaction. The solvent as used herein is not particularly limited, but examples thereof include aromatic hydrocarbons such as benzene, toluene, xylene, and the like, ethers such as dimethyl ether, diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. The catalyst as used herein is not particularly limited, but tetrakis (triphenylphosphine)palladium(0), palladium(II) acetate, dichloro[1,1'-bis(diphenylphosphino)ferrocene]palladium (II), bis(triphenylphosphine)palladium(II) chloride, tris (dibenzylideneacetone)dipalladium(0)-2-dicyclohexylphosphino-2',6'-dimethoxybiphenyl or the like can be used. In addition, metal palladium(0) can also be used to carry out the coupling reaction. It may be advantageous in some cases for the smooth progress of the reaction to carry out the reaction after protecting —NH₂ of a compound (17).

(Production Process 4)

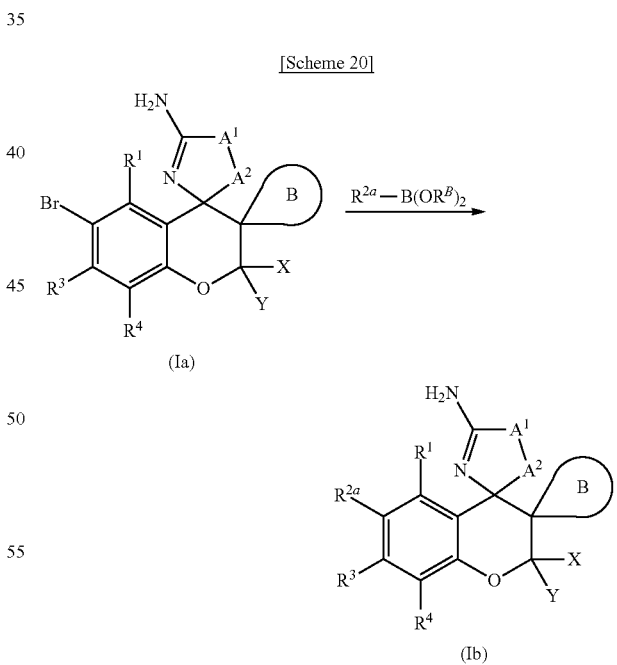

[Scheme 20]

A compound (Ib) can be obtained by subjecting a compound (Ia) and $R^2$—$B(OR^B)_2$ to a coupling reaction. This reaction can be conducted by the same condition of the said reaction of (Production Process 3). It may be advantageous in some cases for the smooth progress of the reaction to carry out the reaction after protecting —NH₂ of a compound (Ia).

(Production Process 5)

[Scheme 21]

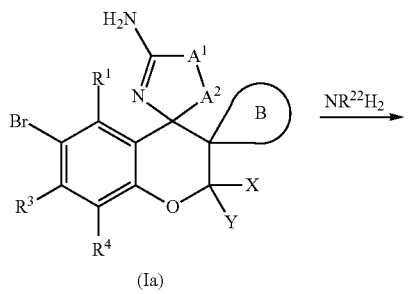

(Ia)

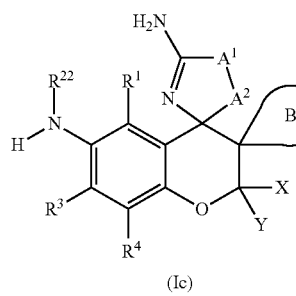

(Ic)

(wherein R' represents a hetero ring group which may be substituted with substituents acceptable in the "—N(H)-(hetero ring group)" of $R^1$, $R^2$, $R^3$ and $R^4$.

A compound (Ic) among the compounds (I) of the present invention can be obtained by subjecting a compound (Ia) and $NR^{22}H_2$ to a substitution reaction.

In this reaction, the compound (Ia) and an equivalent amount or an excess amount of $NR^{22}H_2$ are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent. It may be advantageous in some cases for the smooth progress of the reaction to carry out the reaction under microwave irradiation. Examples of the solvent as used herein are not particularly limited, but include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to carry out the reaction in the presence of an organic base such as triethylamine, N,N-diisopropylethylamine, N-methylmorpholine, and the like, or an inorganic base such as sodium tert-butoxide, potassium carbonate, caesium carbonate, sodium bis(trimethylsilyl)amide, sodium carbonate, potassium hydroxide, and the like. It may be advantageous in some cases for the smooth progress of the reaction to carry out the reaction after protecting —$NH_2$ of a compound (Ia).

Moreover, the reaction may be carried out using a catalyst which is not particularly limited, but includes catalysts used for Ullmann reaction, Buchwald-Hartwig reaction, or the like. The catalyst for Buchwald-Hartwig reaction as used herein is not particularly limited, but a suitable combination of tris(dibenzylideneacetone)palladium (0), tetrakis(triphenylphosphine)palladium (0), or the like with 4,5-bis(diphenylphosphino)-9,9'-dimethylxanthene (Xantphos), 2-dicyclohexylphosphino-2',6'-dimethoxybiphenyl (SPhos), 2-dicyclohexylphosphino-2',4',6'-triisopropylbiphenyl (XPhos), and the like can be used. The catalyst for Ullmann reaction as used herein is not particularly limited, but a suitable combination of copper(I) iodide, or the like with (1R*, 2R*)-N,N'-dimethylcyclohexane-1,2-diamine, 1,10-phenanthroline and the like can be used.

(Production Process 6)

[Scheme 22]

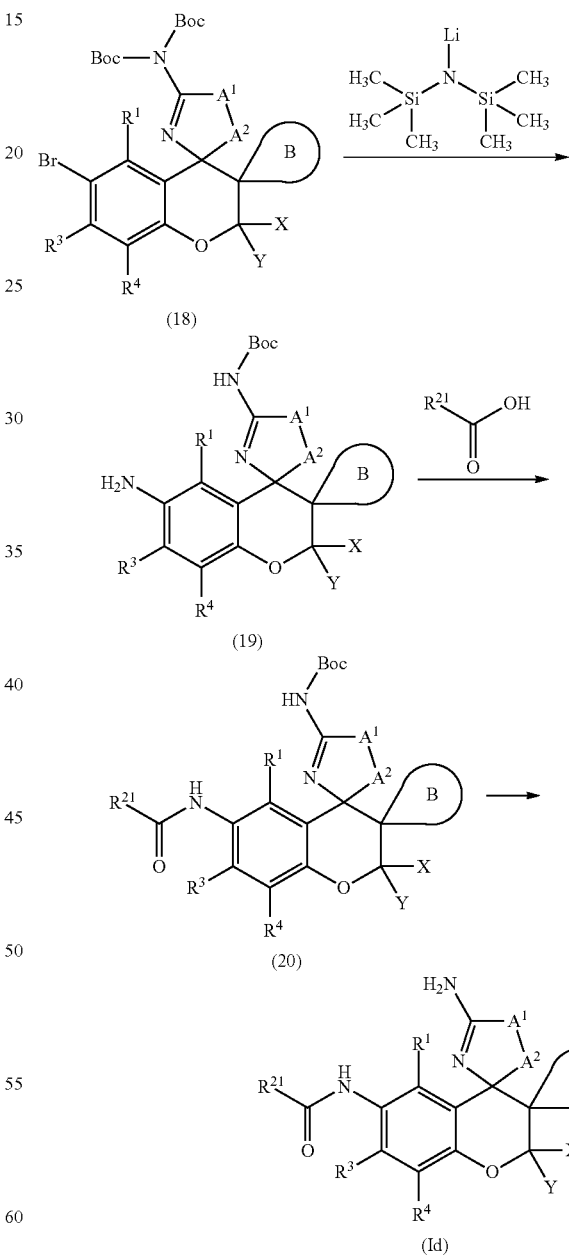

(wherein $R^{21}$ represents a hetero ring group which may be substituted with substituents acceptable in the "—N(H)—C(O)-(hetero ring group)" of $R^1$, $R^2$, $R^3$ and $R^4$, Boc represents a tert-butoxylcarbonyl group.)

A compound (19) can be obtained by subjecting a compound (18) which is obtained by the protection reaction of (Ia) and lithium bis(trimethylsilyl)amide to an amination reaction.

In this reaction, the compound (18) and an equivalent amount or an excess amount of lithium bis(trimethylsilyl) amide are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent in the presence of a palladium catalyst. The palladium catalyst can be prepared in situ from bis(dibenzylideneacetone)palladium (0) and tri-tert-butylphosphonium tetrafluoroborate. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, and a mixture thereof.

A compound (20) can be obtained by subjecting a compound (19) to an amination reaction. For the reaction, the compound (19) and an equivalent amount or an excess amount of $R^{21}$—C(=O)—OH are used, and a mixture thereof is stirred in a range of from cooling to heating, preferably at a temperature from −20° C. to 60° C., usually for about 0.1 hours to 5 days, in a solvent which is inert to the reaction, in the presence of a condensing agent. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, DMF, DMSO, EtOAc, acetonitrile, or water, and a mixture thereof. Examples of the condensing agent include, but are not limited to, CDI, diphenylphosphoryl azide, phosphorus oxychloride, WSC (Water-Soluble Carbodiimide, trademark, 1-(3-dimethylaminopropyl)-3-ethylcarbodiimide, and the like), and DCC (dicyclohexylcarbodiimide). It may be in some cases preferable for the reaction to use an additive for example, 1-hydroxybenzotriazole. It is in some cases advantageous for smooth progress of the reaction to carry out the reaction in the presence of organic bases such as triethylamine, N,N-diisopropylethylamine, N-methylmorpholine, DBU, DMAP, and the like, or inorganic bases such as potassium carbonate, sodium carbonate, potassium hydroxide, and the like.

Furthermore, it is also possible to use a method in which a reactive derivative of $R^{21}$—C(=O)—OH is used, and reacted with the compound (19). Examples of the reactive derivative of the carboxylic acid include acid halides that can be obtained by the reaction with a halogenating agent such as phosphorus oxychloride, thionyl chloride, and the like, mixed acid anhydrides that can be obtained by the reaction with isobutyl chloroformate or the like, activated esters that can be obtained by condensation with 1-hydroxybenzotriazole or the like, etc. The reaction of the reactive derivative with the compound (19) can be carried out in a range of from cooling to heating, and preferably from −20° C. to 60° C., in a solvent which is inert to the reaction, such as halogenated hydrocarbons, aromatic hydrocarbons, ethers, and the like.

A compound (Id) can be obtained by subjecting a compound (20) to a deprotection reaction. The deprotection reaction can be carried out with reference to, for example, "Greene's Protective Groups in Organic Synthesis (4th Ed., 2006)", P. G. M. Wuts and T. W. Greene.

Moreover, each reaction in (Production Process 6) can be conducted with using a compound protected by protective group except a Boc group, and each reaction may be conducted with using a non-protective compound.

(Starting Material Synthesis 1)

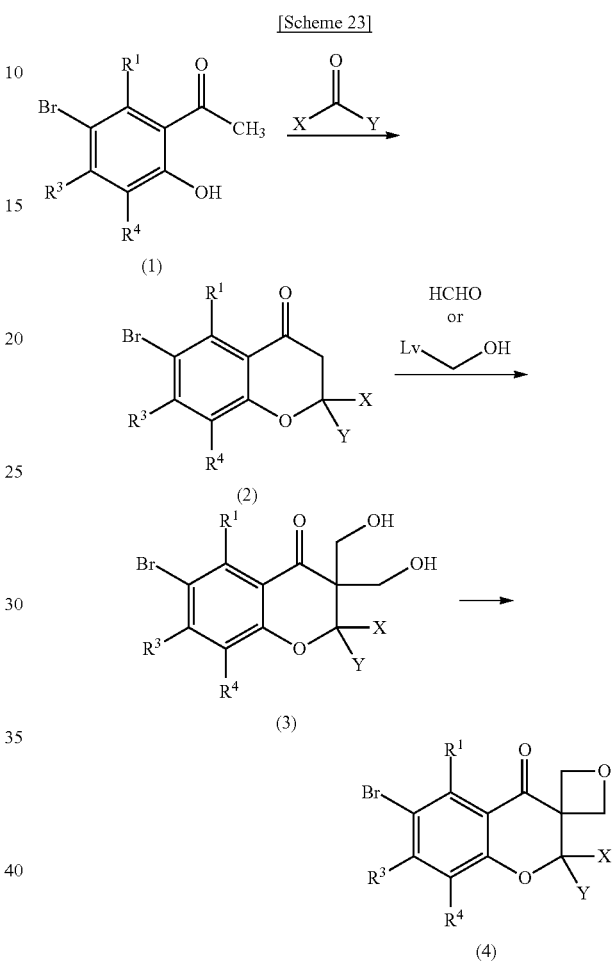

A compound (2) can be obtained by subjecting a compound (1) and X—(C=O)—Y to a cyclization reaction.

In this reaction, the compound (1) and an equivalent amount or an excess amount of X—(C=O)—Y are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent. Examples of the solvent as used herein are not particularly limited, but include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to carry out the reaction in the presence of an organic acid or organic base. Examples of the organic acid as used herein are not particularly limited, but include acetic acid, trifluoroacetic acid and the like, and examples of the organic base as used herein are not particularly limited, but include pyrrolidine, triethylamine, N,N-diisopropylethylamine, N-methylmorpholine, and the like, or an inorganic base such as sodium tert-butoxide, potassium carbonate, sodium bis (trimethylsilyl)amide, sodium carbonate, potassium hydroxide, caesium carbonate, and the like.

A compound (3) can be obtained by subjecting a compound (2) and HCHO or Lv-CH$_2$—OH to a substitution reaction in the presence of a base. Herein, examples of the leaving group Lv include a benzotriazolyl group, and the like.

In this reaction, the compound (2) and an equivalent amount or an excess amount of HCHO or Lv-CH$_2$—OH are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent. Examples of the solvent as used herein are not particularly limited, but include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, water, and a mixture thereof. Examples of the organic base as used herein are not particularly limited, but include pyrrolidine, triethylamine, N,N-diisopropylethylamine, N-methylmorpholine, and the like, or an inorganic base such as sodium tert-butoxide, potassium carbonate, sodium bis(trimethylsilyl)amide, calcium hydroxide, sodium carbonate, potassium hydroxide, caesium carbonate, and the like.

A compound (4) can be obtained by subjecting a compound (3) to a modified Mitsunobu reaction as described in Warren et al. *J. Chem. Soc., Perkin Trans.* 1, 2001, 2983.

In this reaction, a compound (3) is treated under any temperature condition from cooling to heating, and preferably −20° C. to 80° C., usually for 0.1 hours to 3 days, in a solvent which is inert to the reaction, in the presence of zinc bis (dimethyldithiocarbamate), an azo compound and a phosphorous compound. Examples of the solvent as used herein are not particularly limited, but include ethers such as diethyl ether, tetrahydrofuran, dioxane, dimethoxyethane, and the like, halogenated hydrocarbons such as dichloromethane, 1,2-dichloroethane, chloroform, and the like, aromatic hydrocarbons such as benzene, toluene, xylene, and the like, N,N-dimethylformamide, dimethylsulfoxide, and a mixture thereof. As the azo compound, diesters of azodicarboxylic acid, such as, diethyl azodicarboxylate, or diisopropyl azodicarboxylate can be used, and as the phosphorous compound, for example, triphenylphosphine is suitably used.

(Starting Material Synthesis 2)

[Scheme 24]

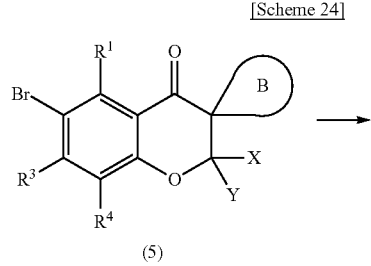

(5)

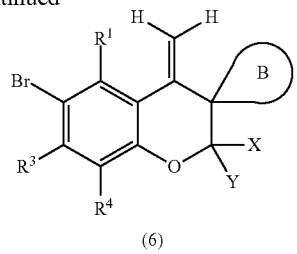

(6)

A compound (6) can be obtained by subjecting the compound (5) to Wittig reaction.

In this reaction, the compound (5) is treated under any temperature condition from cooling to heating, and preferably −20° C. to 80° C., usually for 0.1 hours to 3 days, in a solvent which is inert to the reaction, in the presence of an equivalent amount or an excess amount of methyltriphenylphosphonium halide such as methyltriphenylphosphonium bromide in the presence of a base. Examples of the solvent as used herein are not particularly limited, but include ethers such as diethyl ether, tetrahydrofuran, dioxane, dimethoxyethane, and the like, aromatic hydrocarbons such as benzene, toluene, xylene, and the like, N,N-dimethylformamide, dimethylsulfoxide, and a mixture thereof. Examples of the base as used herein are not particularly limited, but include sodium bis(trimethylsilyl)amide, n-butyllithium, potassium tert-butoxide, sodium ethoxide, sodium methoxide, sodium hydride, and the like.

(Starting Material Synthesis 3)

[Scheme 25]

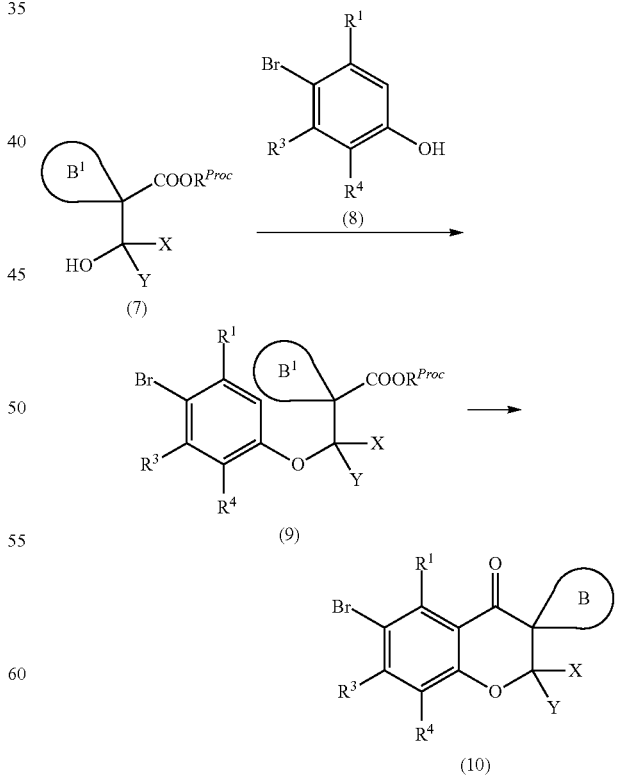

(wherein $R^{Proc}$ represents a protective group, $B^1$ represents a cycloalkyl group which may be substituted).

A compound (9) can be obtained by subjecting a compound (7) and a compound (8) to a substitution reaction. Herein, the reaction is conducted after converting —OH group of a compound (7) to a leaving group, such as mesyloxy group (methanesulfonyloxy group).

In this reaction, a mesylate derivative of the compound (7) and an equivalent amount or an excess amount of compound (8) are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to carry out the reaction in the presence of an acid or a base. Examples of the organic acid as used herein are not particularly limited, but include, acetic acid, trifluoroacetic acid, p-toluenesulfonic acid, methanesulfonic acid and the like, examples of the inorganic acid as used herein are not particularly limited, but include, hydrochloric acid, sulfuric acid, potassium hydrogen sulfate and the like, and examples of the organic base as used herein are not particularly limited, but include, pyridine, 2,6-lutidine (2,6-dimethylpyridine), triethylamine, diisopropylethylamine, 1,8-diazabicyclo [5.4.0]undec-7-ene and the like, examples of the inorganic base as used herein are not particularly limited, but include, sodium carbonate, potassium carbonate, sodium bicarbonate, potassium phosphate, caesium carbonate and the like.

A compound (10) can be obtained by converting an ester group of a compound (9) to a carboxylic acid group by a hydrolysis reaction, and then performing a cyclization reaction.

First, the hydrolysis reaction can be carried out with reference to, for example, "Greene's Protective Groups in Organic Synthesis (4$^{th}$ Ed., 2006)", P. G. M. Wuts and T. W. Greene.

Next, the hydrolysis product obtained from the compound (9) is stirred under any temperature condition from cooling to heating and refluxing, and preferably at 0° C. to 80° C., usually for 0.1 hours to 5 days, in a solvent which is inert to the reaction or without a solvent. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It is in some cases advantageous in advancing the reaction smoothly to carry out the reaction under an acidic condition. Examples of the acid as used herein are not particularly limited, but include organic acids such as p-toluenesulfonic acid, acetic acid, and the like, and inorganic acids such as hydrochloric acid, sulfuric acid, and the like.

(Starting Material Synthesis 4)

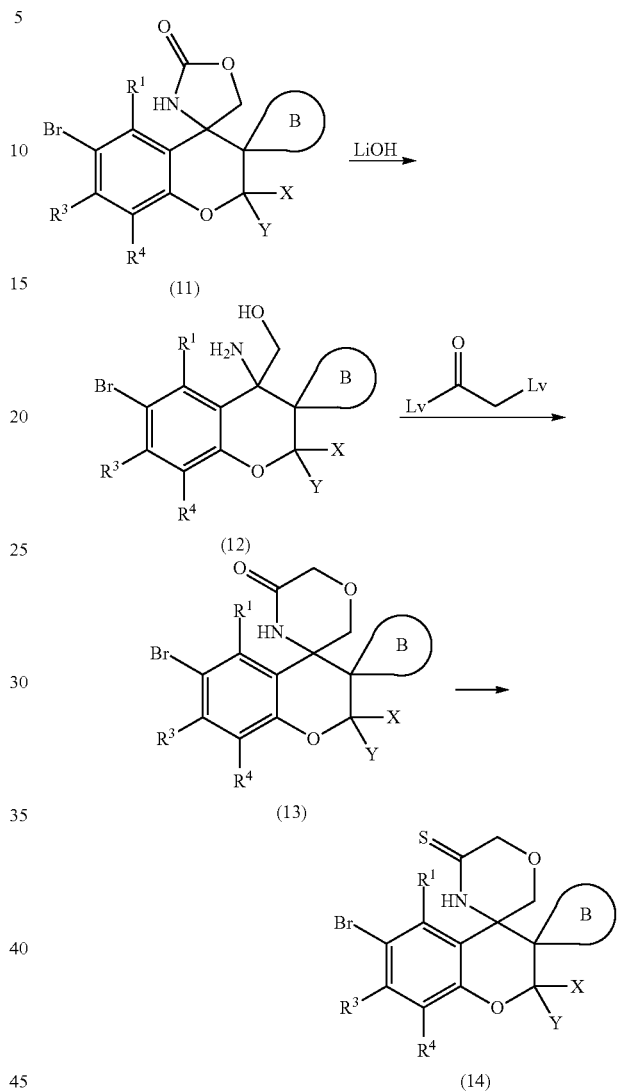

A compound (12) can be obtained by hydrolysis reaction.

In this reaction, the compound (11) is stirred under any temperature condition from cooling to heating and refluxing, and preferably at 0° C. to 80° C., usually for 0.1 hours to 5 days, in a solvent which is inert to the reaction or without a solvent in the presence of a base such as lithium hydroxide. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, alcohols such as methanol, ethanol, tert-butanol, and the like, N,N-dimethylformamide, dimethylsulfoxide, acetonitrile, water and a mixture thereof.

A compound (13) can be obtained by subjecting a compound (12) and Lv-C(=O)—CH$_2$-Lv to a substitution reaction and cyclization reaction.

In the substitution reaction, the compound (12) and an equivalent amount or an excess amount of Lv-C(=O)—CH$_2$-Lv are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to carry out the reaction in the presence of an acid or base. Examples of the organic acid as used herein are not particularly limited, but include, acetic acid, trifluoroacetic acid, p-toluenesulfonic acid, methanesulfonic acid and the like, examples of the inorganic acid as used herein are not particularly limited, but include, hydrochloric acid, sulfuric acid, potassium hydrogen sulfate and the like, and examples of the organic base as used herein are not particularly limited, but include, pyridine, 2,6-lutidine (2,6-dimethylpyridine), triethylamine, diisopropylethylamine, 1,8-diazabicyclo[5.4.0]undec-7-ene and the like, examples of the inorganic base as used herein are not particularly limited, but include, sodium carbonate, potassium carbonate, sodium bicarbonate, potassium phosphate, caesium carbonate and the like.

In the cyclization reaction, the compound after substitution reaction of a compound (12) is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent. Examples of the solvent as used herein are not particularly limited, but include alcohols such as methanol, ethanol, tert-butanol, 2-methylbutan-2-ol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to carry out the reaction in the presence of an acid or base. Examples of the organic acid as used herein are not particularly limited, but include, acetic acid, trifluoroacetic acid, p-toluenesulfonic acid, methanesulfonic acid and the like, examples of the inorganic acid as used herein are not particularly limited, but include, hydrochloric acid, sulfuric acid, potassium hydrogen sulfate and the like, and examples of the organic base as used herein are not particularly limited, but include, pyridine, 2,6-lutidine (2,6-dimethylpyridine), triethylamine, diisopropylethylamine, potassium tert-butoxide, 1,8-diazabicyclo[5.4.0]undec-7-ene and the like, examples of the inorganic base as used herein are not particularly limited, but include, sodium carbonate, potassium carbonate, sodium bicarbonate, potassium phosphate, caesium carbonate and the like.

A compound (14) can be obtained by a reaction of a compound (13) and Lawesson's reagent.

In this reaction, the compound (13) is stirred under any temperature condition from cooling to heating and refluxing, and preferably at 0° C. to 80° C., usually for 0.1 hours to 5 days, in a solvent which is inert to the reaction or without a solvent in the presence of Lawesson's reagent (2,4-bis(4-methoxyphenyl)-1,3,2,4-dithiadiphosphetane-2,4-disulfide). Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, dimethylsulfoxide, acetonitrile, and a mixture thereof.

(Starting Material Synthesis 5)

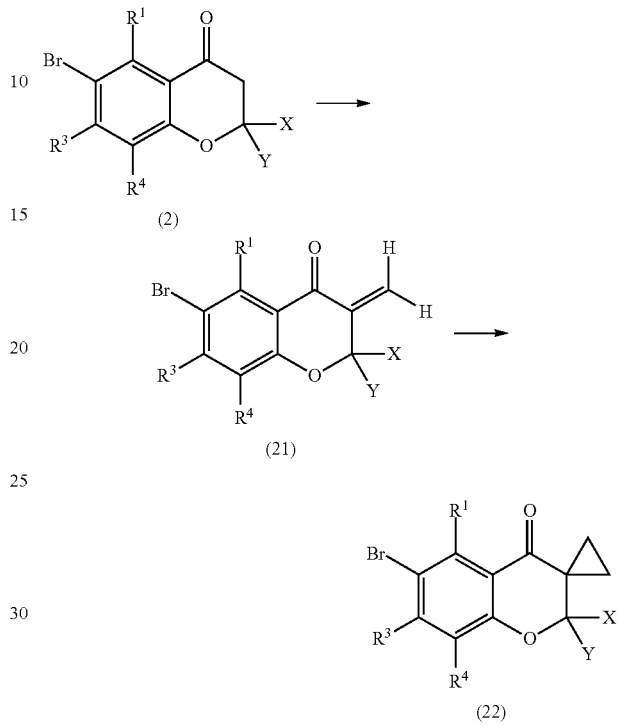

[Scheme 27]

A compound (21) can be obtained by Mannich reaction and elimination reaction of compound (2).

In this reaction, a mixture of the compound (2), N,N,N',N'-tetramethylmethanediamine, and acetic acid is stirred under any temperature condition from cooling to heating and refluxing, and preferably at 0° C. to 80° C., usually for 0.1 hours to 5 days, in a solvent which is inert to the reaction or without a solvent. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. Subsequently, acetic anhydride is added to the mixture and the mixture is stirred under any temperature condition from cooling to heating and refluxing, and preferably at 0° C. to 80° C., usually for 0.1 hours to 5 days, in a solvent which is inert to the reaction or without a solvent. Examples of the solvent as used herein are described above.

A compound (22) can be obtained by subjecting a compound (21) to a Corey-Chaykovsky type reaction.

In this reaction, the compound (21) and an equivalent amount or an excess amount of trimethylsulfoxonium iodide are used, and a mixture thereof is stirred under any temperature condition from cooling to heating and refluxing, preferably at 0° C. to 200° C., and still more preferably at 20° C. to 120° C., usually for 0.1 hours to 5 days, in a solvent which is inert to the reaction or without a solvent in the presence of a base. Examples of the solvent as used herein are not particularly limited, but include alcohols such as methanol, ethanol, tert-butanol, and the like, aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile, and a mixture thereof. It may be advantageous in some cases for the smooth progress of the reaction to use a pre-formed mixture of a base and trimethylsulfoxonium iodide and add the mixture to the compound (21). Examples of the inorganic base as used herein are not particularly limited, but include, sodium hydride, potassium hydroxide, sodium carbonate, potassium carbonate, sodium bicarbonate, potassium phosphate, caesium carbonate, and the like.

(Starting Material Synthesis 6)

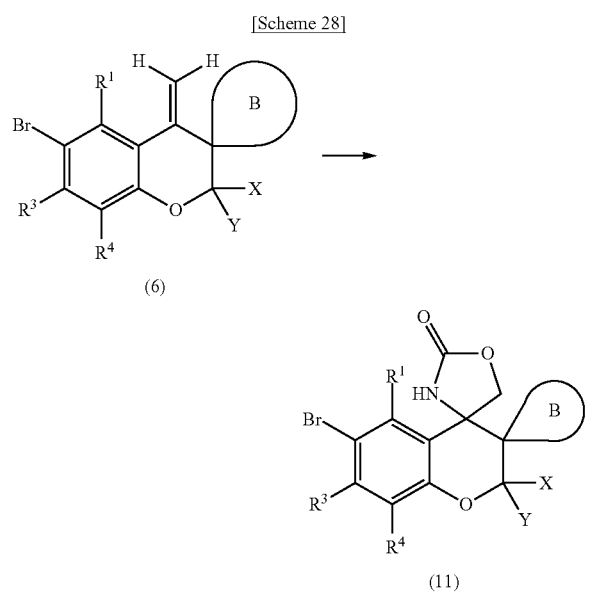

A compound (11) can be obtained by subjecting a compound (6) to reaction with silver cyanate. This reaction can be carried out using similar conditions as for the reaction of a compound (15) with silver cyanate in (Production Process 1), except for use of excess tert-butanol in the presence of triethylamine, instead of excess NH$_3$, in the cyclization step.

(Starting Material Synthesis 7)

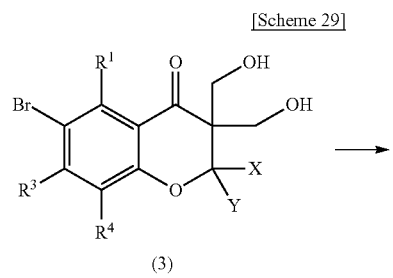

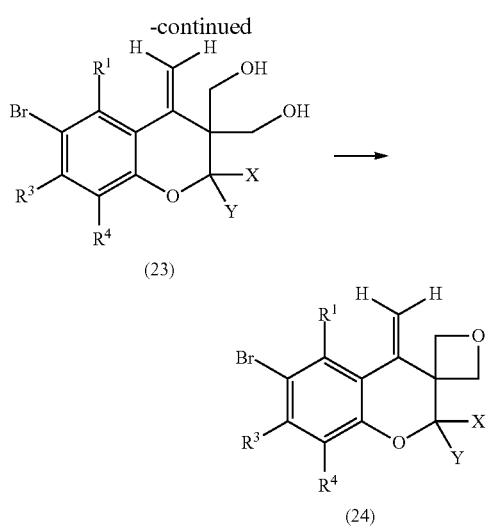

A compound (23) can be obtained by subjecting a compound (3) to reaction with nucleophilic methylation reagent and dehydration reaction.

In this reaction, a mixture of the compound (3) and nucleophilic methylation reagent is stirred under any temperature condition from cooling to heating and refluxing, and preferably at −78° C. to 80° C., usually for 0.1 hours to 5 days, in a solvent which is inert to the reaction or without a solvent. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like and a mixture thereof. Examples of the nucleophilic methylation reagent as used herein are not particularly limited, but include methylmagnesium bromide, methylmagnesium chloride, methylmagnesium iodide, methyllithium, and the like.

After the methylation step, an acid is added to the reaction mixture. And, the reaction mixture is stirred under any temperature condition from cooling to heating and refluxing, and preferably at 0° C. to 80° C., usually for 0.1 hours to 5 days. Examples of the organic acid as used herein are not particularly limited, but include, acetic acid, trifluoroacetic acid, p-toluenesulfonic acid, methanesulfonic acid and the like, examples of the inorganic acid as used herein are not particularly limited, but include, hydrochloric acid, sulfuric acid, potassium hydrogen sulfate and the like.

A compound (24) can be obtained by subjecting a compound (23) to a cyclization reaction.

First, a mixture of the compound (23) and a sulfonyl halide is stirred under any temperature condition from cooling to heating and refluxing, and preferably at −18° C. to 50° C., usually for 0.1 hours to 5 days, in a solvent which is inert to the reaction or without a solvent in the presence of a base. Examples of the sulfonyl halide as used herein are not particularly limited, but include methanesulfonyl chloride, tosyl chloride, and the like. Examples of the solvent as used herein are not particularly limited, but include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, ethyl acetate, acetonitrile, and a mixture thereof. Examples of the organic base as used herein are not particularly limited, but include pyridine, triethylamine, N,N-diisopropylethylamine, N-methylmorpholine, methyllithium, n-butyllithium and the like, or an inorganic base such as potassium carbonate, sodium bis(trimethylsilyl)amide, sodium carbonate, potassium hydroxide, caesium carbonate, sodium hydroxide, sodium hydride and the like. In some cases, compound (23) can be pretreated with the base for the smooth progress of the reaction before addition of the sulfonyl halide.

After the sulfonylation step, a base is added to the reaction mixture. And, the reaction mixture is stirred under any temperature condition from cooling to heating and refluxing, and preferably at 0° C. to 80° C., usually for 0.1 hours to 5 days. Examples of an organic base as used herein are not particularly limited, but include pyridine, triethylamine, N,N-diisopropylethylamine, N-methylmorpholine, methyllithium, n-butyllithium and the like, or an inorganic base such as potassium carbonate, potassium bis(trimethylsilyl)amide, sodium carbonate, potassium hydroxide, caesium carbonate, sodium hydroxide, sodium hydride and the like.

The compounds of the formula (I) can be isolated and purified as their free compounds, salts, hydrates, solvates, or polymorphic crystal substances thereof. The salts of the compound of the formula (I) can be prepared by carrying out a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties among the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compounds of the formula (I) was confirmed by the tests shown below.

TEST EXAMPLE

Inhibition of Beta-Secretase Activity

Test Example 1

Measurement of BACE1 Inhibition by Fluorescence Resonance Energy Transfer (FRET)

Potency of test compounds were determined by measurement of their inhibition of BACE1 activity toward a fluorescent substrate. Experiments were performed by reference to the procedure as described in Ermolieff, et al. (*Biochemistry* 39:12450-12456 (2000), the teachings of which are incorporated hereby in their entirety). Briefly, the recombinant protease unit of BACE1 was prepared from *E. coli* expression as inclusion bodies, refolded, and purified as described in Lin, et al., (*Proc. Nat. Acad. Sci.* 97:1456-1460 (2000)). Fluorogenic substrate, MCA-SEVNLDAEFK(DNP)-NH$_2$ (SEQ ID NO:1) was purchased. (M-2485, Bachem Americas, Torrance, Calif.). The substrate was derived from 10 amino acids of the human amyloid precursor protein (APP), with the Swedish variant amino acids at the beta-secretase cleavage site. The terminal amino acid was modified from arginine to lysine to facilitate derivatization with a functional group for detection by autofluorescence. The amino acid sequence of the "core" peptide of the substrate is SEVNLDAEFK (SEQ ID NO:2). The amino terminus was derivatized with (7-methoxycoumarin-4-yl)acetyl (MCA), and the epsilon amine of the lysine side chain of the terminal residue (K in sequence SEVNLDAEFK (SEQ ID NO:2)) was derivatized with 2,4-dinitrophenyl (DNP). Assays were performed in a buffer of 0.1 M sodium acetate, pH 4.4, 0.08% 3-[(3-Cholamidopropyl)dimethylammonio]propanesulfonate (CHAPS), 0.005% Tween80. BACE1 enzyme (final concentration 65 nM) was pre-incubated with test compounds for 15 minutes at room temperature. Fluorescence intensities were measured 60 minutes after addition of the substrate (final concentration 3 µM) by Tecan Safire2™. An excitation wavelength of 328 nm and an emission wavelength of 393 nm were used. For the calculation of % inhibition, fluorescence intensity without compounds was defined as the value for 0% inhibition and fluorescence intensity without the enzyme was defined as the value for 100% inhibition. The values of IC$_{50}$ were calculated by GraphPad Prism version 5.

Moreover, the inhibition constants, Ki, were determined as described in Ermolieff, et al. (*Biochemistry* 39:12450-12456 (2000)). Briefly, the hydrolysis of the fluorogenic substrate, for a series of mixtures with constant enzyme, but increasing inhibitor concentration was carried out in the same manner as described in the method for Test Example 1. Quantification of enzymes was achieved by active-site titration using a tight-binding inhibitor. The inhibition constant, Ki, was determined from plot of activity vs. inhibitor concentration based on the equation described in Ermolieff, et al. (*Biochemistry* 39:12450-12456 (2000)).

The results of the representative compounds are shown in [Table. 1] below.

The inhibition constants Ki of Example 89 and Example 98 compounds described in Pamphlet of International Publication WO2011/123674 were determined. In the result, the Ki value of Example 89 compound was 0.241 µM, and the Ki value of Example 98 compound was 4.087 µM.

Herein, the structure of Example 89 compound described in Pamphlet of International Publication WO2011/123674 is

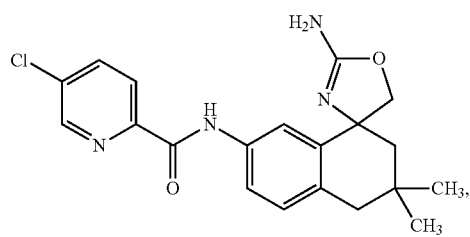 [SMILES: CC1(C)Cc2ccc(NC(=O)c3ccc(Cl)cn3)cc2C2(COC(N)=N2)C1]

and this compound is a racemic mixture.

The structure of Example 98 compound described in Pamphlet of International Publication WO2011/123674 is

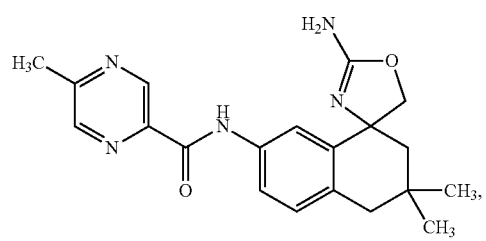 [SMILES: Cc1cnc(C(=O)Nc2ccc3c(c2)C2(COC(N)=N2)CC(C)(C)C3)cn1]

and this compound is a racemic mixture.

The results of the representative compounds are shown in [Table. 1] below.

Test Example 2

Measurement of BACE1 Inhibition by Time Resolved Fluorescence Resonance Energy Transfer (TR-FRET)

Potency of compounds were also measured using another fluorogenic substrate, TruPoint BACE1 Substrate Eu-CEVNLDAEFK-QSY 7 (SEQ ID NO:3) (AD0258, PerkinElmer, Boston Mass.). This substrate also has Swedish variant amino acids at the β-secretase cleavage site, with a fluorescent europium (Eu) chelate coupled to one end and a quencher of europium fluorescence (QSY7) coupled to the other end via lysine. If the sample contains BACE1 activity, the Eu chelate and the quencher will be separated as the substrate is cleaved. The Eu-signal increases and it can be measured by time-resolved fluorometry, EnVision™, 30 minutes after the substrate (final concentration 300 nM) was added.

The experiment was basically conducted in a way similar to Test Example 1 above.

The results of the representative compounds are shown in [Table. 1] below.

Test Example 3

Measurement of Aβ Production Inhibition in Cell

The potency of compounds against BACE1 activity was determined in a cellular assay of Aβ production. Human SK-N-BE(2) neuroblastoma cells (ATCC No. CRL-2271) were plated at 96,000 cells/well/100 μL in 96-well plates in RPMI1640 medium/10% fetal bovine serum (FBS)/penicillin-streptomycin and cultured for 24 hours at 37° C., 5% $CO_2$. Test compounds were dissolved in dimethyl sulfoxide and diluted with dimethyl sulfoxide and put into RPMI1640/5% FBS/penicillin-streptomycin media (final dimethyl sulfoxide concentration is 0.5%). The culture media in 96-well plates were replaced by 125 μL/well of the media containing test compounds. After incubation for 6 hours at 37° C., 5% $CO_2$, 30 μL of the media were transferred into a fresh 96-well plate and used for Aβ40 assay by an enzyme-linked immunosorbent assay (ELISA) kit (#27718, Immuno-Biological Laboratories, Japan) according to the manufacturer's protocol. Cell viability was measured by CellTiter-Glo™ Luminescent Cell Viability Assay (#7571, Promega) after removal of 30 μL of the media for the Aβ assay. CellTiter-Glo Substrate was dissolved into CellTiter-Glo Buffer and added to the plates in 95 μL/well. After shaking the plates for 2 minutes, the whole sample was transferred into a white 96-well plate and luminescence was measured for ATP quantification as the cell viability. Aβ concentration measured by ELISA was normalized by the viability of the corresponding cells. The values of $IC_{50}$ were calculated by GraphPad Prism version 5.

The results of the representative compounds are shown in [Table. 1] below.

Test Example 4

Brain Aβ Reduction in Rats

Effects on brain Aβ reduction in rats were determined with reference to the method described in the WO2012/054510. It was confirmed that some of the compounds of the formula (I) exhibit brain Aβ reduction in rats. Concretely, the test was conducted with the method as below.

Formulation

Test compounds were prepared in a vehicle of 35% HPβCD in $H_2O$. The test compound was formulated the same day as oral dosing. Doses (see [Table. 1]) were based on the free base equivalent. Sonication was used where required to facilitate the formulation.

Test Species

Male Sprague-Dawley rats (150-300 grams) were obtained from Charles River Japan (Atsugi, Japan) and were given approximately 4 days of acclimation. Food and water was made available ad libitum throughout the study. Animals were visually inspected for health before being included into the study group, and were randomly assigned to the treatment and control groups to achieve similar group mean body weights. The dosing solution (dose volume 5 mL/kg) was administered directly into the stomach using a rodent gavage needle. Control animals received oral administration of equivalent volume of the vehicle.

Sampling Methods

At a time post-dose (e.g., 3 hours; see [Table. 1]), animals were euthanized with isoflurane. Blood was collected from the inferior vena cava using syringe flushed with EDTA 2K and placed on ice. Plasma was separated using centrifugation at 15,000 rpm (20,400×g) for 5 minutes at 4° C. and subsequently stored at −80° C. After blood sampling, CSF (cerebrospinal fluid) was carefully withdrawn from the cisterna magna using a 29 gauge needle after a quick dissection to expose the atlantooccipital membrane. The CSF samples were centrifuged at 15,000 rpm (20,400×g) for 5 minutes to confirm free of blood contamination and stored at −80° C. Immediately after decapitation, the hippocampus were isolated on ice, and quickly frozen in liquid nitrogen and stored at −80° C.

Extraction of Brain Aβ42

Fragments of the hippocampus were weighed while frozen. A 10-fold volume (w:v) of TBS (Tris-buffered saline) supplemented with a Complete Mini protease inhibitor tablet (catalog number: 11 836 153 001, Roche Diagnostics, In, USA) was added. The hippocampus were homogenized using sonication on ice in microcentrifuge tube. Resulting homogenates were centrifuged at 100,000×g for 1 hour in a refrigerated centrifuge at 4° C. Supernatants were collected as soluble fraction.

Determination of Aβ42

Concentration of Aβ42 in the extract of hippocampus, plasma, and CSF were analyzed using ELISA (Human/Rat Aβ42 ELISA, catalog number 292-64501, Wako Pure Chemical Industries, Ltd. Japan). Each concentration of Aβ42 was divided by the mean concentration of Aβ42 of vehicle-treated group, and these ratios were converted to percentages.

The results of the representative compounds are shown in [Table. 1] below.

Test Example 5 hERG (Human Ether-a-go-go Related Gene) Analysis hERG Inhibition

The hERG potassium current was measured in a hERG-stably-expressing Chinese hamster ovary K1 (CHO) cells. The experiments were performed using an automated planar patch-clamp system QPatch HTX (Sophion Bioscience A/S). The application of pressure for forming gigaseals and whole-cell patch clamp configuration were established using the QPatch assay software. Patch-clamp experiments were performed in voltage-clamp mode and whole-cell currents were recorded. The following stimulation protocol was applied to investigate the effects of compounds on hERG potassium channel.

The membrane potential was held at −80 mV and repetitively (every 15 seconds) depolarized to +20 mV for 4800 milliseconds after the pulse to −50 mV for 20 milliseconds served to define the baseline, followed by repolarizing step to −50 mV for 5000 milliseconds to evaluate of the tail current amplitude. Experiments were conducted at room temperature.

Effects of compounds were determined from cumulative applications of increasing 6 concentrations and calculated as percent of blocked current. The data points were fitted with Hill equation to calculate half-maximal inhibition concentrations ($IC_{50}$). The maximum compound concentration tested in the assay was 10 µM for some compounds. If less than 50% inhibition was achieved at the 10 µM compound concentration, the $IC_{50}$ is reported as >10 µM.

The test solution includes:
Extracellular solution: 2 mM of $CaCl_2$, 1 mM of $MgCl_2$, 10 mM of HEPES, 4 mM of KCl, 145 mM of NaCl, and 10 mM of glucose; and pH adjusted to 7.4 with NaOH,
Intracellular solution: 5.374 mM of $CaCl_2$, 1.75 mM of $MgCl_2$, 10 mM of HEPES, 10 mM of EGTA, 120 mM of KCl, and 4 mM of ATP, and pH adjusted to 7.2 with KOH.
hERG selectivity Selectivity of BACE1 inhibition over hERG inhibition was calculated by dividing hERG $IC_{50}$ by BACE1 Ki. The results of the representative compounds are shown in [Table. 1] below. As mentioned above, some results from the hERG assay are necessarily reported as >10 µM. Using these values in the calculation of selectivity will necessarily cause the selectivity values to be characterized as ">" or "greater than" the calculated ratio.

The hERG $IC_{50}$ values of Example 89 and Example 98 compounds described in Pamphlet of International Publication WO2011/123674 were determined. In the result, the $IC_{50}$ value of Example 89 compound was 0.44 µM, and the $IC_{50}$ value of Example 98 compound was 9.46 µM. Moreover, selectivity values of BACE1 inhibition over hERG inhibition of these compounds were calculated. In the result, the selectivity value of Example 89 compound was 1.8, and the selectivity value of Example 98 compound was 2.3.

It is considered to be desirable that compounds show their primary pharmacological effect with selectivity over hERG inhibition (Jamieson et al. *J. Med. Chem.* 2006, 49, 5029). Compounds with lower hERG selectivity are considered to have higher risk to cause QTc prolongation, which may eventually lead to drug-induced arrhythmia and sudden deaths. For example, hERG selectivity around or less than 10-fold over hERG inhibition are recognized to have a concern for high risk of QTc prolongation (Kongsamut et al. *Eur. J. Pharmacol.* 2002, 450, 37. and Minotti, *Cardiotoxicity of Non-Cardiovascular Drugs*, Wiley, 2010. p. 65), whereas compounds with selectivity around or larger than 100-fold are recognized to be more favorable (Pajouhesh et al. *Bioorg. Med. Chem. Lett.* 2012, 22, 4153; Micheli et al. *J. Med. Chem.* 2010, 53, 374).

The results of the representative compounds are shown in [Table. 1] below.

In [Table. 1], Ex means Example Number, and "Test Example X" refers to the protocol described above used to obtain the data. Moreover, RP prefixed before the numeral shows the compound of Reference Example.

TABLE 1

| Ex. | Test Example 1 $IC_{50}$ (µM) | Test Example 1 BACE1 MCA Ki (µM) | Test Example 2 $IC_{50}$ (µM) | Test Example 3 $IC_{50}$ (µM) | Test Example 4 Aβ42 reduction (%) | Test Example 5 hERG $IC_{50}$ (µM) | Test Example 5 hERG selectivity |
|---|---|---|---|---|---|---|---|
| RP 1a | 73.3 | | | | | | |
| RP 1b | 138 | | | | | | |
| RP 2 | 59.6 | | | | | | |
| RP 3 | 33.8 | | | | | | |
| RP 4 | 12.6 | | | 7.2 | | >10 | |
| RP 5 | 1.56 | | | 0.59 | | >10 | |
| RP 6 | 11.7 | | | 3.9 | | >10 | |
| RP 7a | 39.0 | | | | | | |
| RP 7b | 39.7 | | | | | | |
| RP 9a | 17.3 | | | | | >10 | |
| RP 9b | 24.4 | | | | | >10 | |
| RP 8 | 61.3 | | | | | | |
| RP 10 | 7.21 | | | | | >10 | |
| RP 11a | 15.6 | | | | | | |
| RP 11b | 17.4 | | | | | | |

TABLE 1-continued

| Ex. | Test Example 1 IC$_{50}$ (μM) | Test Example 1 BACE1 MCA Ki (μM) | Test Example 2 IC$_{50}$ (μM) | Test Example 3 IC$_{50}$ (μM) | Test Example 4 Aβ42 reduction (%) | Test Example 5 hERG IC$_{50}$ (μM) | Test Example 5 hERG selectivity |
|---|---|---|---|---|---|---|---|
| RP 12a | 38.7 | | | | | | |
| RP 12b | 81.3 | | | | | | |
| RP 13a | 11.1 | | | | | | |
| RP 13b | 19.3 | | | | | | |
| RP 14a | 19.0 | | | | | | |
| RP 14b | 44.2 | | | | | | |
| RP 15a | 1.72 | | | 1.1 | | >10 | |
| RP 15b | 1.01 | | | 0.44 | | 7.93 | |
| RP 16a | 9.54 | | | | | >10 | |
| RP 16b | 4.57 | | | 4.8 | | >10 | |
| RP 17 | 30.2 | | | | | >10 | |
| RP 18 | 41.3 | | | | | | |
| RP 19 | 2.31 | | | 0.43 | | | |
| RP 20 | | | 2.71 | 0.58 | | | |
| RP 21 | | | 1.35 | 0.41 | | | |
| RP 22 | | | 2.60 | 2.9 | | | |
| RP 23 | 0.519 | | | 0.90 | | | |
| RP 24 | 37.9 | | 32.9 | | | | |
| RP 25 | 36.9 | | | | | | |
| RP 26 | 3.75 | | | 0.069 | | | |
| 27 | 0.0822 | 0.0382 | | 0.0094 | | >10 | >262 |
| 28 | 0.154 | 0.117 | | 0.019 | | >10 | >86 |
| RP 29 | 0.276 | 0.240 | | 0.022 | | >10 | >42 |
| 30 | 0.0975 | 0.0515 | | 0.0023 | | >10 | >194 |
| RP 31 | 1.06 | 1.03 | | 0.061 | | >10 | >10 |
| RP 32 | 0.418 | 0.378 | | 0.022 | | 2.17 | 6 |
| RP 33 | 1.52 | | | 0.95 | | | |
| RP 34 | 1.24 | | | 0.26 | | >10 | |
| RP 35 | 26.0 | | | | | | |
| RP 36 | 2.90 | | | 0.81 | | | |
| RP 37 | | | 55.4 | | | | |
| RP 38 | 17.3 | | | | | | |
| RP 40 | 46.9 | | | | | | |
| RP 41 | 24.8 | | | >30 | | | |
| RP 42 | 16.1 | | | 5.9 | | >10 | |
| RP 43 | 1.96 | | | 1.4 | | >10 | |
| RP 44 | 0.602 | | | 0.098 | | | |
| RP 45 | 1.04 | | | 0.057 | | >10 | |

TABLE 1-continued

| Ex. | Test Example 1 IC$_{50}$ (μM) | Test Example 1 BACE1 MCA Ki (μM) | Test Example 2 IC$_{50}$ (μM) | Test Example 3 IC$_{50}$ (μM) | Test Example 4 Aβ42 reduction (%) | Test Example 5 hERG IC$_{50}$ (μM) | Test Example 5 hERG selectivity |
|---|---|---|---|---|---|---|---|
| RP 46 | 8.94 | | | 1.4 | | >10 | |
| RP 47 | 2.33 | | | 1.4 | | | |
| RP 48 | 1.13 | | | 0.69 | | | |
| RP 51a | 48.6 | | | | | >10 | |
| RP 51b | 0.172 | 0.137 | | 0.072 | | >10 | |
| RP 52a | 0.161 | | | 0.075 | | 4.83 | |
| RP 53b | 0.157 | 0.123 | | 0.099 | | >10 | |
| RP 54 | 0.406 | | | 0.079 | | >10 | |
| RP 56 | | | | 0.74 | | >10 | |
| RP 57 | 3.69 | | | 0.61 | | 3.48 | |
| RP 58 | 1.48 | | | 0.18 | | 5.81 | |
| RP 59 | 1.11 | | | 0.076 | | 6.9 | |
| RP 60 | 1.48 | | | 0.16 | | 2.78 | |
| RP 61 | | | | 0.35 | | 9.22 | |
| RP 62 | | | 1.33 | 1.0 | | 4.43 | |
| RP 63 | 7.90 | | | 3.3 | | 4.48 | |
| RP 64 | 6.12 | | | 2.3 | | 1.67 | |
| RP 65 | | | 0.388 | 0.049 | | 9.77 | |
| RP 66 | | | 135 | | | >10 | |
| RP 67 | | | 96.5 | | | >10 | |
| RP 68 | 0.345 | | | 0.50 | | 6.05 | |
| RP 69 | 0.397 | | | 0.040 | | >10 | |
| RP 70 | 1.75 | | | 0.96 | | >10 | |
| RP 71 | 1.08 | | | 0.11 | | >10 | |
| RP 72 | 0.817 | | | 0.068 | | 8.22 | |
| RP 73 | 0.827 | | | 0.070 | | | |
| RP 74 | 35.4 | | | | | | |
| RP 75 | 3.67 | | | 1.1 | | >10 | |
| RP 76 | 13.4 | | | | | >10 | |
| RP 77 | 1.43 | | | 0.92 | | >10 | |
| RP 78 | 2.05 | | | 1.3 | | >10 | |
| RP 79 | 1.69 | | | 0.45 | | >10 | |
| RP 80 | 1.91 | | | 0.71 | | >10 | |
| RP 81 | 1.89 | | | 0.51 | | >10 | |
| RP 82 | 0.348 | | | 0.036 | | >10 | |
| RP 83 | 0.285 | 0.255 | | 0.047 | | >10 | |
| RP 84 | 0.735 | | | 0.41 | | >10 | |

TABLE 1-continued

| Ex. | Test Example 1 IC$_{50}$ (μM) | Test Example 1 BACE1 MCA Ki (μM) | Test Example 2 IC$_{50}$ (μM) | Test Example 3 IC$_{50}$ (μM) | Test Example 4 Aβ42 reduction (%) | Test Example 5 hERG IC$_{50}$ (μM) | Test Example 5 hERG selectivity |
|---|---|---|---|---|---|---|---|
| RP 85 | 0.319 | | | 0.077 | | >10 | |
| RP 86 | 0.143 | 0.107 | | 0.058 | | 7.94 | |
| RP 87 | 1.55 | | | 0.43 | | | |
| RP 88 | 2.51 | | | 1.4 | | >10 | |
| RP 89 | 4.67 | | | | | >10 | |
| RP 90 | 0.901 | | | 0.50 | | >10 | |
| RP 91 | 0.656 | | | 0.34 | | >10 | |
| RP 92 | 0.124 | 0.0879 | | 0.037 | | 5.34 | |
| RP 93 | 0.629 | | | 0.37 | | >10 | |
| RP 94 | 0.862 | | | 0.38 | | >10 | |
| RP 95 | 0.740 | | | 0.41 | | >10 | |
| RP 96 | 0.126 | 0.868 | | 0.022 | | >1 | |
| RP 97 | 20.2 | | | 2.6 | | >10 | |
| RP 98 | 64.1 | | | | | >10 | |
| RP 99 | 2.97 | | | 1.9 | | >10 | |
| RP 100 | 2.62 | | | 0.25 | | >10 | |
| RP 101 | 7.65 | | | | | 5.28 | |
| RP 102 | 1.61 | | | 0.24 | | >10 | |
| RP 103 | 2.19 | | | 0.45 | | >10 | |
| RP 104 | | | 1.13 | 0.30 | | 3.25 | |
| RP 105 | 2.94 | | | 0.34 | | 7.9 | |
| RP 106 | 1.83 | | | 0.16 | | 5.75 | |
| RP 107 | 1.06 | | | 0.46 | | 2.91 | |
| RP 108 | 0.383 | 0.354 | 0.316 | 0.096 | | 9.4 | |
| RP 109 | 0.152 | 0.120 | | 0.048 | | >1 | |
| RP 110 | 0.137 | 0.0904 | | 0.0092 | | >1 | |
| RP 111 | 0.287 | 0.252 | | 0.14 | | 1.98 | |
| RP 112 | 0.400 | | | 0.66 | | 4.32 | |
| RP 113 | 1.11 | | | 0.47 | | | |
| RP 114 | 68.3 | | | | | | |
| RP 115 | 3.31 | | | 1.1 | | >10 | |
| RP 116 | 1.27 | | | 0.70 | | >10 | |
| RP 117 | 4.40 | | | 3.0 | | >10 | |
| RP 118 | 1.81 | | | 0.99 | | >10 | |
| RP 119 | 3.56 | | | | | | |
| RP 120 | 1.89 | | | 2.3 | | | |
| RP 121 | 3.37 | | | | | | |

TABLE 1-continued

| Ex. | Test Example 1 IC$_{50}$ (μM) | Test Example 1 BACE1 MCA Ki (μM) | Test Example 2 IC$_{50}$ (μM) | Test Example 3 IC$_{50}$ (μM) | Test Example 4 Aβ42 reduction (%) | Test Example 5 hERG IC$_{50}$ (μM) | Test Example 5 hERG selectivity |
|---|---|---|---|---|---|---|---|
| RP 122 | 2.74 | | | 1.1 | | | |
| RP 123 | 3.39 | | | | | | |
| RP 124 | 3.59 | | | | | | |
| RP 125 | 2.31 | | | 0.58 | | | |
| RP 126 | 0.696 | | | 1.2 | | | |
| RP 127 | 2.27 | | | 1.8 | | | |
| RP 128 | 1.68 | | | 1.5 | | | |
| RP 129 | 2.21 | | | 7.3 | | | |
| RP 130 | 1.87 | | | 1.7 | | | |
| RP 131 | 2.02 | | | 3.2 | | | |
| RP 132 | 2.45 | | | 1.2 | | | |
| RP 133 | 1.67 | | | 2.8 | | | |
| RP 134 | 3.63 | | | | | | |
| RP 135 | 3.27 | | | 1.8 | | | |
| RP 136 | 0.635 | | | 0.66 | | | |
| RP 137 | 0.773 | | | 0.83 | | | |
| RP 138 | 1.67 | | | 1.5 | | | |
| RP 139 | 0.252 | 0.215 | | 0.14 | | | |
| RP 140 | 0.389 | | | 0.41 | | | |
| RP 141 | 0.903 | | | 1.30 | | | |
| RP 142 | 0.401 | | | 0.15 | | >1 | |
| RP 143 | 1.26 | | | | | | |
| RP 144 | 0.879 | | | 0.46 | | | |
| RP 145 | 0.933 | | | | | | |
| RP 146 | 0.226 | 0.188 | | 0.21 | | | |
| RP 147 | 0.621 | | | 0.17 | | | |
| RP 148 | 0.614 | | | 0.48 | | | |
| RP 149 | | | 1.593 | 1.1 | | | |
| RP 150 | | | 0.759 | 0.45 | | | |
| RP 151 | 1.36 | | | 0.28 | | | |
| RP 152 | 0.688 | | | 0.11 | | | |
| RP 153 | 1.13 | | | 0.13 | | | |
| RP 154 | | | 0.313 | 0.032 | | >1 | |
| RP 155 | | | 0.786 | 0.63 | | | |
| RP 156 | 2.61 | | | 0.18 | | | |
| RP 157 | 2.80 | | | 0.66 | | | |
| RP 158 | 0.930 | | | 0.37 | | | |

TABLE 1-continued

| Ex. | Test Example 1 IC$_{50}$ (μM) | Test Example 1 BACE1 MCA Ki (μM) | Test Example 2 IC$_{50}$ (μM) | Test Example 3 IC$_{50}$ (μM) | Test Example 4 Aβ42 reduction (%) | Test Example 5 hERG IC$_{50}$ (μM) | Test Example 5 hERG selectivity |
|---|---|---|---|---|---|---|---|
| RP 159 | 2.12 | | | | | | |
| RP 160 | 0.981 | | | | | | |
| RP 161 | 1.41 | | | | | | |
| RP 162 | 1.04 | | | | | | |
| RP 163 | | | 1.064 | | | | |
| RP 164 | | | 2.314 | | | | |
| RP 165 | 0.760 | | | | | | |
| RP 166 | 3.63 | | | | | | |
| RP 167 | 0.869 | | | | | | |
| RP 168 | | | 0.760 | 0.31 | | | |
| RP 169 | 1.41 | | 0.859 | 0.90 | | | |
| RP 170 | 1.00 | | 0.588 | 0.40 | | | |
| RP 171 | 2.24 | | 3.04 | 3.1 | | | |
| RP 172 | 2.24 | | 2.16 | | | | |
| RP 173 | 0.401 | | 0.239 | 0.073 | | | |
| RP 174 | 3.35 | | 2.18 | 3.4 | | | |
| RP 175 | 3.23 | | 1.55 | | | | |
| RP 176 | | | 0.994 | 0.85 | | | |
| RP 177 | | | 2.12 | 1.5 | | | |
| RP 178 | 1.15 | | 0.747 | 0.81 | | | |
| RP 179 | 3.24 | | 2.06 | 1.4 | | | |
| RP 180 | 2.03 | | 1.77 | 0.49 | | | |
| RP 181 | 2.59 | | 2.13 | 0.82 | | | |
| RP 182 | | | 1.45 | 2.5 | | | |
| RP 183 | 1.08 | | 0.880 | | | | |
| RP 184 | 2.82 | | 2.72 | | | | |
| RP 185 | 2.05 | | 1.27 | 0.76 | | | |
| RP 186 | | | 2.42 | | | | |
| RP 187 | 3.16 | | 1.92 | | | | |
| RP 188 | 50.6 | | | | | >10 | |
| RP 189 | 0.661 | 0.623 | | 0.043 | | >10 | >16 |
| 190 | 0.125 | 0.0835 | | 0.0041 | | >10 | >120 |
| RP 191 | 0.248 | 0.215 | | 0.027 | | >10 | >47 |
| RP 192 | 0.318 | 0.280 | | 0.030 | | >10 | >36 |
| RP 193 | 1.04 | | | 0.081 | | >10 | >120 |
| RP 194 | 0.349 | 0.313 | | 0.028 | | 4.91 | 16 |
| 195 | 0.109 | 0.0645 | | 0.0032 | | >10 | >155 |

TABLE 1-continued

| Ex. | Test Example 1 IC$_{50}$ (μM) | Test Example 1 BACE1 MCA Ki (μM) | Test Example 2 IC$_{50}$ (μM) | Test Example 3 IC$_{50}$ (μM) | Test Example 4 Aβ42 reduction (%) | Test Example 5 hERG IC$_{50}$ (μM) | Test Example 5 hERG selectivity |
|---|---|---|---|---|---|---|---|
| RP 196 | 0.380 | 0.342 | | 0.053 | | 3.65 | 11 |
| 197 | 0.118 | 0.0720 | | 0.0057 | | >10 | >139 |
| RP 198 | 14.9 | | | | | >1 | |
| RP 199 | 0.736 | | | 0.24 | | 4.25 | |
| RP 200 | 0.128 | 0.0921 | | 0.026 | | >10 | |
| RP 201 | 0.113 | 0.0711 | | 0.0087 | | | |
| RP 202 | 0.145 | 0.113 | | 0.026 | | 7.73 | |
| RP 203 | 0.109 | 0.0676 | | 0.0049 | | | |
| RP 204 | 0.388 | | | 0.24 | | >10 | |
| RP 205 | 0.126 | 0.0825 | | 0.022 | | 5.22 | |
| RP 206 | 4.91 | | | >30 | | >10 | |
| RP 207 | 0.460 | | | 0.16 | | >10 | |
| RP 208 | 7.76 | | | 6.1 | | >10 | |
| RP 209 | 2.00 | | | 0.83 | | >10 | |
| RP 210 | | | 4.95 | | | 3.7 | |
| RP 211 | | | 19.4 | | | | |
| RP 212 | 17.6 | | | | | >10 | |
| RP 213 | | | 39.6 | 6.3 | | >10 | |
| RP 214 | 40.3 | | | | | | |
| RP 215 | 1.21 | | | 0.24 | | >10 | |
| RP 216 | 55.8 | | | | | | |
| 218 | 0.0447 | 0.0103 | | 0.00078 | 24% (3 mg/kg, 2.5 hours) 31% (10 mg/kg, 2.5 hours) | 20.67 | 2007 |
| 219 | 0.0444 | 0.0102 | 0.0418 | 0.0022 | | >10 | >980 |
| 220 | 0.0765 | 0.0429 | | 0.0031 | 21% (3 mg/kg, 1.5 hours) 27% (10 mg/kg, 1.5 hours) | >10 | >233 |
| 221 | 0.0818 | 0.0378 | | 0.00016 | 24% (1 mg/kg, 3 hours) 42% (3 mg/kg, 3 hours) | 3.25 | 86 |
| 222 | 0.138 | 0.0915 | | 0.00062 | | >10 | >109 |
| 223 | 0.0991 | 0.0612 | | 0.0031 | 19% (1 mg/kg, 3 hours) 34% (3 mg/kg, 3 hours) | 20.77 | 339 |
| 224 | 0.0914 | 0.0527 | | 0.00063 | 21% (1 mg/kg, 3 hours) 35% (3 mg/kg, 3 hours) | 15.1 | 287 |

TABLE 1-continued

| Ex. | Test Example 1 IC$_{50}$ (μM) | Test Example 1 BACE1 MCA Ki (μM) | Test Example 2 IC$_{50}$ (μM) | Test Example 3 IC$_{50}$ (μM) | Test Example 4 Aβ42 reduction (%) | Test Example 5 hERG IC$_{50}$ (μM) | Test Example 5 hERG selectivity |
|---|---|---|---|---|---|---|---|
| 227 | 0.107 | 0.0792 | | 0.0080 | | >10 | >126 |
| 228a | 30.3 | 30.2 | | | | >10 | >0.3 |
| 229a | 47.6% inhibition at 30 microM | | | | | | |

As described above, it was confirmed that the representative compounds of the formula (I) have β-secretase inhibitory activities, Aβ production inhibitory activities, and Aβ reduction activities and can be therefore used for diseases or conditions associated with and/or mediated by β-secretase activity, hydrolysis of a β-secretase cleavage site of an amyloid precursor protein, and/or β-amyloid protein accumulation, such as Glaucoma, MCI (Mild cognitive impairment) or Alzheimer's disease, especially, Alzheimer's disease, or the like.

Determination of Absolute Stereochemistry by Vibrational Circular Dichroism (VCD) Spectrometry Measurements The infrared and VCD spectra were recorded on a Bio tools ChiralIR-2X™ Vibrational Circular Dichroism (VCD) spectrometer.

The infrared and VCD spectra were measured in CDCl$_3$ solution placed in a 100 μm path length cell with BaF$_2$ windows at 4 cm$^{-1}$ resolution and their data collection was performed for 5 hours.

Calculations

Conformational searches were executed by using CONFLEX™ ver.6 program.

The geometry optimizations and the calculations of theoretical infrared and VCD spectra were implemented using density functional theory with B3LYP functional and 6-31G (d) basis set on Gaussian 09.

By comparison of measured and calculated spectra, absolute stereochemistry of Ex. 228a and 228b, Ex. 229a and 229b, Ex. 225a and 225b compounds were assigned. Based on the absolute stereochemistry of Ex. 228b and Ex. 229b compound, the absolute stereochemistry of their precursor, Reference Example 226 compound was determined.

Powder X-Ray Diffraction

The powder X-ray diffraction was measured using RIGAKU RINT-TTRII diffractometer under the conditions of a tube: Cu, a tube current: 300 mA, a tube voltage, 50 kV, a sampling width: 0.02°, a scanning speed: 4°/minute, a wavelength: 1.54056 angstroms, and a measurement diffraction angle (2θ): 2.5 to 40°.

Furthermore, the term "about" in the characteristic peaks of powder X-ray diffraction shown at angles 2θ denotes ±0.2°, in another embodiment, ±0.1°. Each crystal can be characterized by a powder X-ray diffraction spectrum, but with the powder X-ray diffraction, crystal lattice intervals and overall patterns are important for identification of crystals in terms of the properties of the data, and since the relative intensity may vary slightly depending on the direction of crystal growth, the particle size, and the measurement conditions, it should not be strictly construed.

Formulations

The pharmaceutical composition containing one or two or more kinds of the compound represented by the formula (I) or salts thereof as an active ingredient can be prepared using excipients that are usually used in the art, that is, excipients for pharmaceutical preparation, carriers for pharmaceutical preparation, and the like.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

Administration can be accomplished either by oral administration via tablets, pills, capsules, granules, powders, solutions, and the like, or parenteral administration, such as intraarticular, intravenous, or intramuscular injections, and the like, suppositories, ophthalmic solutions, eye ointments, transdermal liquid preparations, ointments, transdermal patches, transmucosal liquid preparations, transmucosal patches, inhalers, and the like.

The solid composition for use in the oral administration according to the present invention is used in the form of tablets, powders, granules, or the like. In such a solid composition, one or more active ingredient(s) are mixed with at least one inactive excipient. According to a conventional method, the composition may contain inactive additives, such as a lubricant such as magnesium stearate, a disintegrating agent such as sodium carboxymethyl starch and the like, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, and antiseptics.

The injections for parenteral administration include sterile aqueous or non-aqueous solution preparations, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizing agent, or a solubilizing aid. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, poultices, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizing agent, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, hydrofluoroalkane, carbon dioxide, and the like, or other forms.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compound of the formula (I) can be used in combination with various therapeutic or prophylactic agents for the diseases, in which the compound of the formula (I) is considered effective, as described above. The combined preparation may be administered simultaneously or separately and continuously, or at a desired time interval. The preparations to be co-administered may be a blend or prepared individually.

EXAMPLES

Hereinbelow, the preparation methods for the compound of the formula (I) will be described in more detail with reference to Examples. Further, the present invention is not limited to the preparation methods described in the specific Examples, Reference Examples and Preparation Examples as described below, but the compound of the formula (I) can be prepared by any combination of the preparation methods or the methods that are apparent to a skilled person in the art, particularly in view of the detailed teachings provided herein.

Furthermore, the following symbols are used in the Examples, Reference Examples, Preparation Examples, and Tables as described below.

Rf: Preparation Example Number,
RP: Reference Example Number,
Ex: Example Number,
No.: Compound No.,
Data: Physicochemical data,
ESI+: representing m/z values in ESI-MS (positive ions), and representing [M+H]$^+$ peaks unless otherwise specified,
APCI/ESI+: m/z value in APCI/ESI-MS (positive ions), and representing [M+H]$^+$ peaks unless otherwise specified,
EI: representing m/z values in EI-MS (positive ions), and representing [M]$^+$ peaks unless otherwise specified,
CI+: representing m/z values in CI-MS (positive ions), and representing [M+H]$^+$ peaks unless otherwise specified,
NMR-DMSO-d$_6$: δ (ppm) in $^1$H-NMR in DMSO-d$_6$,
NMR-CDCl$_3$: δ (ppm) in $^1$H-NMR in CDCl$_3$,
Structure: Structural formula (In case HCl is described in a structural formula, a compound represented by a structural formula forms a salt with HCl. Compounds having a double bond described by a cross line represents mixtures of a cis-compound and a trans-compound),
rel-: representing relative configuration,
Syn: Preparation method (in which E prefixed before the numeral shows that the compound is prepared by the similar preparation method as the compound having the Example Number, R prefixed before the numeral shows that the compound is prepared by the similar preparation method as the compound having the Preparation Example Number and RP prefixed before the numeral shows that the compound is prepared by the similar preparation method as the compound having the Reference Example Number),
Boc/BOC: tert-butoxycarbonyl,
CHCl$_3$: chloroform,
CH$_2$Cl$_2$: dichloromethane,
CO$_2$: carbon dioxide,
Cs$_2$CO$_3$: caesium carbonate,
CuBr: copper (I) bromide,
CuI: copper (I) iodide,
DAST: N,N-diethylaminosulfur trifluoride,
DBU: 1,8-diazabicyclo[5.4.0]undec-7-ene,
DIBAL-H: diisobutylaluminium hydride,
DMAP: N,N-dimethyl-4-aminopyridine,
DMF: N,N-dimethylformamide,
DMSO: dimethyl sulfoxide,
Et$_3$N: triethylamine,
AcOEt/EtOAc: ethyl acetate,
EtOH: ethanol,
Et$_2$O: diethyl ether,
HCOOH: formic acid,
HCl: hydrogen chloride,
H$_2$O: hydrogen oxide,
HPLC: high performance liquid chromatography,
IPE, iPr$_2$O: diisopropyl ether,
K$_2$CO$_3$: potassium carbonate,
K$_3$PO$_4$: potassium phosphate,
LiBH$_4$: lithium borohydride,
MeCN: acetonitrile,
MsCl: methanesulfonyl chloride,
MeMgBr: methylmagnesium bromide,
MeOH: methanol,
MgSO$_4$: anhydrous magnesium sulfate,
n-BuLi: n-butyllithium,
NMP: 1-methyl-2-pyrrolidone,
NaOH: sodium hydroxide,
NaHCO$_3$: sodium hydrogen carbonate,
Na$_2$CO$_3$: sodium carbonate,
Na$_2$S$_2$O$_3$: sodium thio sulfate,
Na$_2$SO$_4$: anhydrous sodium sulfate,
Na$_2$SO$_4$' 10H$_2$O: sodium sulfate decahydrate,
NH$_4$Cl: ammonium chloride,
PdCl$_2$(dppf): [1,1'-Bis(diphenylphosphino)ferrocene]palladium(II) dichloride,
Pd(OAc)$_2$: palladium(II) acetate,
Pd(PPh$_3$)$_4$: tetrakis(triphenylphosphine)palladium(0),
PdCl$_2$(PPh$_3$)$_2$: bis(triphenylphosphine)palladium (II) chloride,
PPh$_3$: triphenylphosphine, PtO$_2$: platinum (IV) oxide,
SiO$_2$: silicon dioxide,
THF: tetrahydrofuran,
TsOH.H$_2$O: p-toluenesulfonic acid monohydrate,
TMSOTf: Trimethylsilyl trifluoromethanesulfonate.

Preparation Example 1

To a mixture of 6-bromo-4-methylene-4H-spiro[chromene-3,3'-oxetane] (351 mg, 1.31 mmol), silver cyanate (295 mg, 1.97 mmol), EtOAc (1.7 mL), and MeCN (3.5 mL) was added a mixture of iodine (500 mg, 1.97 mmol) and EtOAc (5.3 mL) in an ice-water bath. After stirring for 1.5 hours at the same temperature, the mixture was stirred for 30 minutes at ambient temperature. The mixture was filtered through celite pad (washed with EtOAc), and the filtrate was washed with saturated aqueous Na$_2$S$_2$O$_3$ and brine, dried over MgSO$_4$ and filtered. After concentration of the filtrate at reduced pressure, tert-butyl alcohol (4.4 mL) and triethylamine (0.183 mL, 1.31 mmol) were added to the residue, and the mixture was stirred overnight under reflux. The reaction mixture was cooled down to ambient temperature, concentrated at reduced pressure to give crude 6'-bromo-2H-dispiro[1,3-oxazolidine-4,4'-chromene-3',3''-oxetan]-2-one.

Preparation Example 2

A mixture of di-tert-butyl[6'-(3-methoxyprop-1-yn-1-yl)dispiro[1,3-oxazole-4,4'-chromene-3',3''-oxetan]-2-yl]imidodicarbonate (34.7 mg, 0.067 mmol) and 10% palladium on carbon (7 mg) in EtOH (1.4 mL) was stirred for 13 hours under a hydrogen atmosphere (4.5 kgf/cm$^2$). The mixture was filtered off, and the filtrate was evaporated to give crude di-tert-butyl [6'-(3-methoxypropyl)dispiro[1,3-oxazole-4,4'-chromene-3',3''-oxetan]-2-yl]imidodicarbonate (34.7 mg).

Preparation Example 8

To a solution of 6'-bromo-2',2'-dimethyldispiro[1,3-oxazole-4,4'-chromene-3',3''-oxetan]-2-amine (643 mg, 1.82 mmol) in THF (12.9 mL) were added 4-dimethylaminopyridine (11 mg, 0.091 mmol) and di-tert-butyl dicarbonate (1.19 g, 5.46 mmol). The mixture was stirred overnight at ambient temperature. The reaction mixture was evaporated off at reduced pressure. The residue was purified with column chromatography on silica gel (hexane-EtOAc, a linear gradient of EtOAc from 0 to 20%) to give di-tert-butyl (6'-bromo-2',2'-dimethyldispiro[1,3-oxazole-4,4'-chromene-3',3''-oxetan]-2-yl)imidodicarbonate (890 mg).

Preparation Example 22

The mixture of 6'-bromodispiro[cyclopropane-1,3'-chromene-4',4''-[1,3]oxazol]-2''-amine (1.1 g, 3.4 mmol), di-tert-butyl dicarbonate (2.2 g, 10 mmol), and N,N-dimethylpyridin-4-amine (21 mg, 0.17 mmol) in THF (21 ml) was stirred for 3 hours at ambient temperature and for 5 hours at 50° C. The mixture was concentrated in vacuo. The residue was purified by silica gel chromatography (hexane:EtOAc=100:0-80:20) to give di-tert-butyl (6'-bromodispiro[cyclopropane-1,3'-chromene-4',4''-[1,3]oxazol]-2''-yl)imidodicarbonate (1.5 g).

Preparation Example 23

The mixture of 6'-bromodispiro[cyclobutane-1,3'-chromene-4',4''-[1,3]oxazol]-2''-amine (185 mg, 0.57 mmol), di-tert-butyl dicarbonate (374 mg, 1.7 mmol), N,N-dimethylpyridin-4-amine (3.4 mg, 0.029 mmol), and N,N-diethylethanamine (173 mg, 1.7 mmol) in THF (20 mL) was stirred overnight at ambient temperature. The mixture was concentrated in vacuo, and the residue was purified by silica gel chromatography (hexane:EtOAc=100:0-80:20) to give tert-butyl (6'-bromodispiro[cyclobutane-1,3'-chromene-4',4''-[1,3]oxazol]-2''-yl)carbamate (223 mg).

Preparation Example 24

To a solution of 6'-bromodispiro[oxetane-3,3'-chromene-4',4''-[1,3]thiazol]-2''-amine (214 mg, 0.627 mmol) in THF (2.1 mL) were added di-tert-butyl dicarbonate (411 mg, 1.88 mmol) and 4-dimethylaminopyridine (3.8 mg, 0.031 mmol). The mixture was stirred overnight at ambient temperature, and di-tert-butyl dicarbonate (68.4 mg, 0.314 mmol) was added to the reaction mixture. After stirring for 2 hours at ambient temperature, the mixture was partitioned between EtOAc and 10 wt. % aqueous citric acid. The organic layer was washed with brine, dried over MgSO$_4$ and silica gel and filtered. The filtrate was evaporated off, and purification of the residue with column chromatography on silica gel (Hexane-EtOAc, a linear gradient of EtOAc from 0 to 50%) afforded di-tert-butyl (6'-bromodispiro[oxetane-3,3'-chromene-4',4''-[1,3]thiazol]-2''-yl)imidodicarbonate (279 mg).

Preparation Example 26

The mixture of 4-bromo-2-iodophenol (3.30 g, 11.04 mmol), 1-bromo-5-chloropentan-2-one (75% purity, 3.9 g, 14.66 mmol), and K$_2$CO$_3$ (2.3 g, 16.64 mmol) in acetone (66 mL) was stirred for 48 hours at ambient temperature. The insoluble material was removed by filtration and washed with EtOAc. The filtrate was evaporated in vacuo. The residue was purified by silicagel column chromatography (EtOAc-hexane, a linear gradient of EtOAc from 0 to 25%) afforded 1-(4-bromo-2-iodophenoxy)-5-chloropentan-2-one (2.12 g).

Preparation Example 27

A solution of potassium tert-butoxide (441 mg, 3.93 mmol) in THF (5 mL) was added to a suspension of 6-bromospiro[chromene-2,1'-cyclobutan]-4(3H)-one (500 mg, 1.87 mmol) and 1H-benzotriazole-1-methanol (586 mg, 3.93 mmol) in THF (5 mL) over 10 minutes in a dry ice-acetone bath under an argon atmosphere. The mixture was stirred for 0.5 hours in an ice bath, and then diluted with EtOAc (10 mL). After stirring for 0.5 hours, the mixture was filtered off. The filtrate was washed with 0.2 M aqueous NaOH (two times), water and brine, dried over MgSO$_4$ and silicagel, filtered off. The filtrate was evaporated to give crude 6-bromo-3,3-bis(hydroxymethyl)spiro[chromene-2,1'-cyclobutan]-4(3H)-one (641 mg).

Preparation Example 29

A mixture of di-tert-butyl (6'-bromodispiro[1,3-oxazole-4,4'-chromene-3',3''-oxetan]-2-yl)imidodicarbonate (300 mg, 0.571 mmol), 3-methoxypyridin-2-amine (354 mg, 2.86 mmol), tris(dibenzylideneacetone)dipalladium(0) (105 mg, 0.114 mmol), (9,9-dimethyl-9H-xanthene-4,5-diyl)bis(diphenylphosphine) (198 mg, 0.343 mmol), Cs$_2$CO$_3$ (558 mg, 1.71 mmol) and dioxane (15 mL) was stirred for 48 hours at 100° C. The reaction mixture was cooled down to ambient temperature, and partitioned with CHCl$_3$ and water. The organic layer was dried over Na$_2$SO$_4$, and filtered. The filtrate was concentrated at reduced pressure, to give crude di-tert-butyl {6'-[(3-methoxypyridin-2-yl)amino]dispiro[1,3-oxazole-4,4'-chromene-3',3''-oxetan]-2-yl}imidodicarbonate, which was used for the next reaction without further purification.

Preparation Example 30

To a mixture of (4-amino-6-bromo-4H-spiro[chromene-3,3'-oxetan]-4-yl)methanol (280 mg, 0.933 mmol), $CH_2Cl_2$ (10 mL) and saturated aqueous $NaHCO_3$ (10 mL) was added a mixture of chloroacetyl chloride (0.083 mL, 1.02 mmol) and $CH_2Cl_2$ (1 mL) at ambient temperature. After stirring for 30 minutes at ambient temperature, chloroacetyl chloride (0.016 mL, 0.197 mmol) was added to the reaction mixture. The mixture was stirred for 10 minutes at ambient temperature, diluted with $CH_2Cl_2$ and separated. The organic layer was washed with water, dried over $MgSO_4$ and filtered. Concentration of the filtrate at reduced pressure gave crude N-[6-bromo-4-(hydroxymethyl)-4H-spiro[chromene-3,3'-oxetan]-4-yl]-2-chloroacetamide, which was used for the next reaction without further purification.

Preparation Example 31

To a mixture of crude N-[6-bromo-4-(hydroxymethyl)-4H-spiro[chromene-3,3'-oxetan]-4-yl]-2-chloroacetamide (351 mg, 0.933 mmol) and 2-methylbutan-2-ol (6.3 mL) was added potassium tert-butoxide (356 mg, 3.17 mmol) at ambient temperature, and the mixture was stirred for 1 hour at the same temperature. MeOH (3.2 mL) was added to the reaction mixture, and the mixture was concentrated at reduced pressure. Purification of the residue with column chromatography on silica gel (Hexane-EtOAc, a linear gradient of EtOAc from 50 to 100%) afforded 6'-bromo-5H-dispiro[1,4-oxazinane-3,4'-chromene-3',3''-oxetan]-5-one (277 mg).

Preparation Example 36

To a suspension of methyl(triphenyl)phosphonium bromide (8.13 g, 22.3 mmol) in THF (44 mL) was added n-butyllithium (1.65 M in n-hexane, 13.5 mL, 22.3 mmol) in a dry ice-acetone bath under argon atmosphere. The mixture was stirred for 60 minutes in an ice bath. To the mixture was added a mixture of 6-bromo-2,2-dimethyl-4H-spiro[chromene-3,3'-oxetan]-4-one (2.21 g, 7.44 mmol) and THF (11 mL) in an ice bath. The mixture was stirred for 1 hour at ambient temperature. The reaction was quenched by adding water in an ice-water bath. The mixture was partitioned between EtOAc-hexane (1:2) and water. The organic layer was washed with brine, dried over $MgSO_4$, filtered, and the filtrate was evaporated. Purification using silica gel column chromatography (EtOAc-hexane, a linear gradient of EtOAc from 0 to 20%) afforded 6-bromo-2,2-dimethyl-4-methylene-4H-spiro[chromene-3,3'-oxetane] (2.02 g).

Preparation Example 48

To a mixture of 6-bromo-2,2-dimethyl-2,3-dihydro-4H-chromen-4-one (1.00 g, 3.92 mmol) and dioxane (10 mL) were added formaldehyde (37 wt. % in water, 2.95 mL, 39.2 mmol) and $Na_2CO_3$ (831 mg, 7.84 mmol) at room temperature. After stirring overnight at the same temperature, the reaction mixture was filtered. The filtrate was diluted with $CHCl_3$, washed with 1M aqueous HCl and water, dried over $MgSO_4$ and filtered. The filtrate was concentrated at reduced pressure, and the residue was purified with column chromatography on silica gel (hexane-EtOAc, a linear gradient of EtOAc from 0 to 50%) to afford 6-bromo-3,3-bis(hydroxymethyl)-2,2-dimethyl-2,3-dihydro-4H-chromen-4-one (1.07 g).

Preparation Example 58

To a solution of 1-(4-bromo-2-iodophenoxy)-5-chloropentan-2-one (1.61 g, 3.86 mmol) in THF (35 mL) was added vinylmagnesium bromide (1M solution in THF, 4.3 mL) at −78° C. under an argon atmosphere. After stirring for 1 hour at −78° C., the mixture was gradually warmed up to −30° C. over 1 hour. The reaction was quenched by adding saturated aqueous $NH_4Cl$ solution and extracted with EtOAc. The combined organic layer were washed with brine, dried over $Na_2SO_4$, filtered, and the filtrate was evaporated. The residue was purified by silicagel column chromatography (EtOAc-hexane, a linear gradient of EtOAc from 0 to 20%) afforded 3-[(4-bromo-2-iodophenoxy)methyl]-6-chlorohex-1-en-3-ol (1.35 g).

Preparation Example 59

The mixture of 3-[(4-bromo-2-iodophenoxy)methyl]-6-chlorohex-1-en-3-ol (1.53 g, 3.43 mmol), $Pd(OAc)_2$ (77 mg, 0.343 mmol), $PPh_3$ (360 mg, 1.37 mmol), and $K_2CO_3$ (2.84 g, 20.55 mmol) in MeCN (45 mL) was heated at 85° C. for 18 hours under an argon atmosphere. After addition of $Pd(OAc)_2$ (23 mg, 0.102 mmol) and $PPh_3$ (108 mg, 0.412 mmol), the mixture was heated at 85° C. for 30 hours. The reaction mixture was cooled to room temperature, and the insoluble material was removed by filtration and washed with EtOAc. The filtrate was evaporated in vacuo. The residue was purified by silicagel column chromatography (EtOAc-hexane, a linear gradient of EtOAc from 0 to 15%) to afford a mixture of 6-bromo-4-methylene-4',5'-dihydro-3'H,4H-spiro[chromene-3,2'-furan] and a reaction intermediate (598 mg). To the mixture dissolved in MeCN (30 mL) were added $Pd(OAc)_2$ (23 mg, 0.102 mmol), $PPh_3$ (108 mg, 0.412 mmol), and $K_2CO_3$ (947 mg, 6.85 mmol) and the reaction mixture was heated at 85° C. for 2 hours under an argon atmosphere. The reaction mixture was cooled to room temperature, and the insoluble material was removed by filtration and washed with AcOEt. The filtrate was evaporated in vacuo. The residue was purified by silicagel column chromatography (EtOAc-hexane, a linear gradient of EtOAc from 0 to 15%) to afford 6-bromo-4-methylene-4',5'-dihydro-3'H,4H-spiro[chromene-3,2'-furan] (460 mg).

Preparation Example 60

To a mixture of 6'-bromo-5H-dispiro[1,4-oxazinane-3,4'-chromene-3',3''-oxetan]-5-one (275 mg, 0.808 mmol) and dioxane (11 mL) was added 2,4-bis(4-methoxyphenyl)-1,3,2,4-dithiadiphosphetane 2,4-disulfide (236 mg, 0.566 mmol) at ambient temperature. After stirring for 2 hours at 80° C., the reaction mixture was cooled down to ambient temperature and concentrated at reduced pressure. The residue was purified with column chromatography on silica gel (hexane-EtOAc, a linear gradient of EtOAc from 0 to 50%) to afford 6'-bromo-5H-dispiro[1,4-oxazinane-3,4'-chromene-3',3''-oxetane]-5-thione (259 mg).

Preparation Example 62

To a solution of ethyl 1-(hydroxymethyl)cyclobutanecarboxylate (1.0 g, 6.3 mmol) and N,N-diethylethanamine (1.5 g, 8.2 mmol) in CH$_2$Cl$_2$ (30 ml) was added methanesulfonyl chloride (869 mg, 7.6 mmol). The mixture was stirred for 6 hours at ambient temperature. After dilution with CHCl$_3$ and H$_2$O, the organic layer was washed with H$_2$O, dried over MgSO$_4$, and concentrated in vacuo to give ethyl 1-{[(methylsulfonyl)oxy]methyl}cyclobutanecarboxylate (1.2 g).

Preparation Example 63

To a mixture of 6'-bromo-2H-dispiro[1,3-oxazolidine-4,4'-chromene-3',3''-oxetan]-2-one (1.98 g, 6.07 mmol), EtOH (9.9 mL) and water (50 mL) was added lithium hydroxide monohydrate (2.68 g, 60.7 mmol), and the mixture was stirred overnight at 100° C. The reaction mixture was cooled down to ambient temperature and extracted with CH$_2$Cl$_2$. The organic layer was washed with water, dried over Na$_2$SO$_4$ and filtered. After concentration of the filtrate at reduced pressure, the residue was triturated with hexane, collected by filtration, washed with EtOAc-hexane (1:3) and dried at reduced pressure to afford (4-amino-6-bromo-4H-spiro[chromene-3,3'-oxetan]-4-yl)methanol (1.40 g).

Preparation Example 64

To a solution of di-tert-butyl (6'-bromodispiro[1,3-oxazole-4,4'-chromene-3',3''-oxetan]-2-yl)imidodicarbonate (300 mg, 0.571 mmol), 4,4,4',4',5,5,5',5'-octamethyl-2,2'-bi-1,3,2-dioxaborolane (174 mg, 0.685 mmol), and PdCl$_2$(dppf) (21 mg, 0.029 mmol) in dioxane (6 mL) was added potassium acetate (112 mg, 1.14 mmol). The mixture was stirred for 3 hours at 110° C. The resulting precipitate was removed by filtration and the filtrate was evaporated. Silicagel column chromatography (MeOH—CHCl$_3$, a linear gradient of MeOH from 3 to 10%) afforded di-tert-butyl[6'-(4,4,5,5-tetramethyl-1,3,2-dioxaborolan-2-yl)dispiro[1,3-oxazole-4,4'-chromene-3',3''-oxetan]-2-yl]imidodicarbonate (305 mg).

Preparation Example 66

To a mixture of di-tert-butyl (6'-bromodispiro[cyclopropane-1,3'-chromene-4',4''-[1,3]oxazol]-2''-yl)imidodicarbonate (200 mg, 0.393 mmol), bis(dibenzylideneacetone)palladium (0) (22.6 mg, 0.039 mmol), and tri-tert-butylphosphonium tetrafluoroborate (11.6 mg, 0.039 mmol) was added lithium bis(trimethylsilyl)amide (1 M in toluene, 1.96 mL, 1.96 mmol) at ambient temperature. After stirring for 1 hour at 100° C., the mixture was cooled down to ambient temperature. To the mixture were added 1M aqueous HCl (1.96 mL) and MeOH (1.96 mL) at ambient temperature, and the mixture was stirred for 30 minutes at the same temperature. The mixture was extracted with CHCl$_3$, and the organic layer was dried over Na$_2$SO$_4$ and filtered. The filtrate was concentrated at reduced pressure and purified with column chromatography on silica gel (hexane-EtOAc, a linear gradient of EtOAc from 0 to 90%) to afford tert-butyl (6'-aminodispiro[cyclopropane-1,3'-chromene-4',4''-[1,3]oxazol]-2''-yl)carbamate (103 mg).

Preparation Example 67

Under argon atmosphere, to a mixture of di-tert-butyl (6'-bromo-2',2'-dimethyldispiro[1,3-oxazole-4,4'-chromene-3',3''-oxetan]-2-yl)imidodicarbonate (1.00 g, 1.81 mmol), bis (dibenzylideneacetone)palladium (0) (104 mg, 0.181 mmol) and tri-tert-butylphosphonium tetrafluoroborate (53.5 mg, 0.181 mmol) was added lithium bis(trimethylsilyl)amide (1.0 M in toluene, 9.03 mL, 9.03 mmol) at ambient temperature. After stirring for 1 hour at 100° C., the reaction mixture was cooled down to ambient temperature. To the mixture were added 1.0 M hydrochloric acid (9.0 mL) and MeOH (9.0 mL) and the mixture was stirred for 30 minutes at ambient temperature. After extraction of the mixture with CHCl$_3$, the organic layer was dried over Na$_2$SO$_4$ and filtered. The filtrate was concentrated at reduced pressure and the residue was purified by column chromatography on silica gel (hexane-EtOAc, a linear gradient of EtOAc from 0 to 90%) to give tert-butyl (6'-amino-2',2'-dimethyldispiro[1,3-oxazole-4,4'-chromene-3',3''-oxetan]-2-yl)carbamate (616 mg).

Preparation Example 69

Under argon atmosphere, a mixture of 4,6-dichloropyrimidine (500 mg, 3.36 mmol), 1-(trimethylsilyl)-1-propyne (0.497 mL, 3.36 mmol), tetrabutylammonium fluoride (1 M in THF, 3.36 mL, 3.36 mmol), triethylamine (1.54 mL, 11.1 mmol), tetrakis(triphenylphosphine)palladium(0) (194 mg, 0.168 mmol), copper(I) iodide (192 mg, 1.01 mmol) and toluene (20 mL) was stirred for 9 hours at 60° C. The mixture was cooled down to ambient temperature, and water was added to the mixture. The mixture was extracted with CHCl$_3$, and the organic layer was dried over MgSO$_4$ and filtered. The filtrate was concentrated at reduced pressure, and purification of the residue with column chromatography on silica gel (hexane-EtOAc, a linear gradient of EtOAc from 0 to 20%) afforded 4-chloro-6-(prop-1-yn-1-yl)pyrimidine (207 mg).

Preparation Example 70

A mixture of tert-butyl (6'-aminodispiro[cyclopropane-1, 3'-chromene-4',4''-[1,3]oxazol]-2''-yl)carbamate (115 mg, 0.333 mmol), 5-fluoropyridine-2-carboxylic acid (62.3 mg, 0.433 mmol), N-(3-dimethylaminopropyl)-N'-ethylcarbodiimide hydrochloride (83.0 mg, 0.433 mmol), 1-hydroxybenzotriazole (58.5 mg, 0.433 mmol), N,N-diisopropylethylamine (0.074 mL, 0.433 mmol) and CH$_2$Cl$_2$ (1.2 mL) was stirred for 2.5 days at ambient temperature. The reaction mixture was purified with column chromatography on silica gel (hexane-EtOAc, a linear gradient of EtOAc from 10 to 90%) to afford tert-butyl (6'-{[(5-fluoropyridin-2-yl)carbonyl]amino}dispiro[cyclopropane-1,3'-chromene-4',4''-[1,3] oxazol]-2''-yl)carbamate (136 mg).

Preparation Example 73

A mixture of tert-butyl (6'-amino-2',2'-dimethyldispiro[1, 3-oxazole-4,4'-chromene-3',3''-oxetan]-2-yl)carbamate (878 mg, 2.25 mmol), 5-chloro-2-pyridinecarboxylic acid (476 mg, 2.93 mmol), N-(3-dimethylaminopropyl)-N'-ethylcarbodiimide hydrochloride (562 mg, 2.93 mmol), 1-hydroxybenzotriazole (396 mg, 2.93 mmol), N,N-diisopropylethylamine (0.502 mL, 2.93 mmol) and CH$_2$Cl$_2$ (8.78 mL) was stirred for 1.5 hours at ambient temperature. After concentration of the reaction mixture at reduced pressure, the residue was purified with column chromatography on silica gel (hexane-EtOAc, a linear gradient of EtOAc from 0 to 90%) to give tert-butyl (6'-{[(5-chloropyridin-2-yl)carbonyl]amino}-2',2'-dimethyldispiro[1,3-oxazole-4,4'-chromene-3',3''-oxetan]-2-yl)carbamate (976 mg).

Preparation Example 76

A mixture of di-tert-butyl (6'-bromodispiro[1,3-oxazole-4, 4'-chromene-3',3''-oxetan]-2-yl)imidodicarbonate (150 mg, 0.286 mmol) and 3-methoxyprop-1-yne (0.072 mL, 0.86 mmol) in Et$_3$N (1.5 mL) was purged with argon. To the mixture was added Pd(PPh$_3$)$_4$ (13 mg, 0.011 mmol) and CuBr (4.9 mg, 0.034 mmol), and the mixture was refluxed for 3 hours under an argon atmosphere. The mixture was partitioned between CHCl$_3$ and brine, and filtered through celite. The organic layer of the filtrate was dried over MgSO$_4$, filtered off, and the filtrate was evaporated. Silicagel column chromatography (EtOAc-hexane, a linear gradient of EtOAc from 0 to 25%) afforded di-tert-butyl[6'-(3-methoxyprop-1-yn-1-yl)dispiro[1,3-oxazole-4,4'-chromene-3',3''-oxetan]-2-yl]imidodicarbonate (34.7 mg).

Preparation Example 78

The mixture of 6-bromo-4H-spiro[chromene-3,1'-cyclopropan]-4-one (8.0 g, 32 mmol), 2-methylpropane-2-sulfinamide (12 g, 99 mmol), and titanium(IV) tetraethanolate (22 g, 95 mmol) in THF (160 ml) was stirred for 48 hours at 80° C. To the mixture was added H$_2$O (20 ml), filtered through Celite and washed by EtOAc (50 ml). The filtrate was concentrated in vacuo. The residue was purified by silica gel chromatography (hexane:EtOAc=100:0-0:100) to give N-(6-bromo-4H-spiro[chromene-3,1'-cyclopropan]-4-ylidene)-2-methylpropane-2-sulfinamide (6.5 g).

Preparation Example 83

A mixture of di-tert-butyl (6'-bromodispiro[1,3-oxazole-4,4'-chromene-3',3''-oxetan]-2-yl)imidodicarbonate (300 mg, 0.571 mmol), 4-(4,4,5,5-tetramethyl-1,3,2-dioxaborolan-2-yl)-3,6-dihydro-2H-pyran (360 mg, 1.71 mmol), bis(triphenylphosphine)palladium(II) dichloride (40.1 mg, 0.057 mmol) and Na$_2$CO$_3$ (182 mg, 1.71 mmol) in dioxane (3.6 mL) and water (0.9 mL) was stirred for 1 hour at 100° C. The mixture was cooled down to ambient temperature and partitioned between EtOAc and water. The organic layer was washed with brine, dried over MgSO$_4$, diluted with hexane, and filtered through silica gel pad (eluted with 50% EtOAc in hexane). The filtrate was concentrated at reduced pressure to give crude di-tert-butyl[6'-(3,6-dihydro-2H-pyran-4-yl)dispiro[1,3-oxazole-4,4'-chromene-3',3''-oxetan]-2-yl]imidodicarbonate which was used for the next reaction without further purification.

Preparation Example 85

Under argon atmosphere, a mixture of di-tert-butyl[6'-(4,4,5,5-tetramethyl-1,3,2-dioxaborolan-2-yl)dispiro[1,3-oxazole-4,4'-chromene-3',3''-oxetan]-2-yl]imidodicarbonate (213 mg, 0.372 mmol), 3-bromo-5-(3-methoxyprop-1-yn-1-yl)pyridine (252 mg, 1.12 mmol), Na$_2$CO$_3$ (158 mg, 1.49 mmol), tetrakis(triphenylphosphine)palladium(0) (21.5 mg, 0.019 mmol), dioxane (3.4 mL) and water (0.85 mL) was stirred for 3 hours at 110° C. The reaction mixture was cooled down to ambient temperature, and water was added to the mixture. The mixture was extracted with MeOH—CHCl$_3$ (1:9), and the organic layer was dried over Na$_2$SO$_4$ prior to filtration. The filtrate was concentrated at reduced pressure to give crude di-tert-butyl {6'-[5-(3-methoxyprop-1-yn-1-yl)pyridin-3-yl]dispiro[1,3-oxazole-4,4'-chromene-3',3''-oxetan]-2-yl}imidodicarbonate, which was used for the next reaction without further purification.

Preparation Example 91

A mixture of di-tert-butyl[6'-(5-bromopyridin-3-yl)dispiro[1,3-oxazole-4,4'-chromene-3',3''-oxetan]-2-yl]imidodicarbonate (232 mg, 0.385 mmol), ethynyl(trimethyl)silane (0.160 mL, 1.16 mmol), bis(triphenylphosphine)palladium(II) dichloride (13.5 mg, 0.019 mmol), copper(I) iodide (7.3 mg, 0.039 mmol) and triethylamine (3.2 mL) was stirred overnight at ambient temperature and for 6 days at 50° C. Ethynyl(triisopropyl)silane (0.257 mL, 1.16 mmol) was added to the reaction mixture at ambient temperature, and the mixture was stirred overnight at 85° C. The mixture was cooled down to ambient temperature, diluted with EtOAc and washed with saturated aqueous NH$_4$Cl. The organic layer was dried over MgSO$_4$ and filtered. The filtrate was concentrated at reduced pressure.

To a mixture of the residue and THF (4.6 mL) was added tetrabutylammonium fluoride (1M in THF, 1.54 mL, 1.54 mmol), and the mixture was stirred overnight at ambient temperature. The mixture was partitioned with EtOAc and saturated aqueous NH$_4$Cl, and the organic layer was washed with brine, dried over anhydrous MgSO$_4$ and filtered. The filtrate was concentrated at reduced pressure, and purification of the residue with column chromatography on silica gel (hexane-EtOAc, a linear gradient of EtOAc from 0 to 50%) afforded di-tert-butyl[6'-(5-ethynylpyridin-3-yl)dispiro[1,3-oxazole-4,4'-chromene-3',3''-oxetan]-2-yl]imidodicarbonate (59.9 mg).

Preparation Example 92

To a solution of 6-bromo-4H-chromen-4-one (12 g, 53 mmol) in CH$_2$Cl$_2$ (24 mL) was added TMSOTf (12.5 mL, 69.18 mmol) at ambient temperature. After stirring for 1 hour, THF (210 mL) was added to the mixture at ambient temperature and cooled to −78° C. To the mixture was added n-propylmagnesium bromide (1.05M solution in THF, 66 mL, 69 mmol). After stirring for 1 hour at −78° C., 1M aqueous NH$_4$Cl was added to the mixture. The mixture was warmed to ambient temperature and stirred overnight. The organic and the aqueous layers were separated, and the organic layer was dried over Na$_2$SO$_4$, filtered, and the filtrate was concentrated in vacuo. The residue was purified by silicagel column chromatography (EtOAc-hexane, a linear gradient of EtOAc from 0 to 10%) to afford 6-bromo-2-propyl-2,3-dihydro-4H-chromen-4-one (11.42 g).

Preparation Example 94

A mixture of 4-(methoxymethyl)-1H-pyrazole (145 mg, 1.29 mmol), 6'-bromo-4'H-dispiro[cyclobutane-1,2'-chromene-3',3''-oxetan]-4'-one (200 mg, 0.647 mmol), trans-N,N'-dimethylcyclohexane-1,2-diamine (74 mg, 0.52 mmol) and K$_2$CO$_3$ (268 mg, 1.94 mmol) in NMP (2 mL) was purged with argon. To the mixture was added CuI (49 mg, 0.26 mmol), and the mixture was sealed and stirred for 1 hour at 150° C. and 0.5 hours at 170° C. under a microwave irradiation. The mixture was partitioned between EtOAc and saturated aqueous NH$_4$Cl. The organic layer was washed with water (two times) and brine, dried over MgSO$_4$, filtered, and the filtrate was evaporated. Silicagel column chromatography (EtOAc-hexane, a linear gradient of EtOAc from 0 to 45%) afforded 6'-[4-(methoxymethyl)-1H-pyrazol-1-yl]-4'H-dispiro[cyclobutane-1,2'-chromene-3',3''-oxetan]-4'-one (97 mg).

Preparation Example 96

To a mixture of 6-bromo-3,3-bis(hydroxymethyl)-2,2-dimethyl-2,3-dihydro-4H-chromen-4-one (6.76 g, 21.4 mmol), zinc bis(dimethyldithiocarbamate) (26.2 g, 85.8 mmol) and triphenylphosphine (8.44 g, 32.2 mmol) in THF (0.20 L) was added diisopropyl azodicarboxylate (1.9 M solution in toluene, 16.9 mL, 32.2 mmol) in an ice-water bath. The mixture was stirred overnight at ambient temperature. The mixture was diluted with toluene (0.20 L), and the mixture was filtered off. The filtrate was washed with 1 M aqueous NaOH (three times), water and brine, dried over MgSO$_4$ and filtered. The filtrate was evaporated to give a crude product. The crude product was purified with column chromatography on silica gel (Hexane-EtOAc, a linear gradient of EtOAc from 0 to 20%) to afford 6-bromo-2,2-dimethyl-4H-spiro[chromene-3,3'-oxetan]-4-one (2.22 g).

Preparation Example 106

To a solution of ethyl 1-[(4-bromophenoxy)methyl]cyclobutanecarboxylate (1.1 g, 3.5 mmol) in EtOH (11 ml) was added 1M aqueous NaOH (11 ml, 11 mmol). The mixture was stirred for 7 hours at 60° C. The mixture was concentrated in vacuo, and to the solution was added 1M aqueous HCl.

The resulting precipitate was collected by filtration, washed with H$_2$O and dried in vacuo to give crude 1-[(4-bromophenoxy)methyl]cyclobutanecarboxylic acid (0.91 g).

Preparation Example 108

To a mixture of 1-(5-bromo-2-hydroxyphenyl)ethanone (10.0 g, 46.5 mmol) and MeOH (0.20 L) were added 3-methylbutanal (7.54 mL, 69.8 mmol) and pyrrolidine (5.77 mL, 69.8 mmol) at ambient temperature, and the mixture was stirred for 3 days at the same temperature. After concentration of the reaction mixture at reduced pressure, the residue was diluted with EtOAc, acidified to pH 3-4 with 1M aqueous HCl, and extracted with EtOAc. The organic layer was washed with water and brine, dried over MgSO$_4$, and filtered. After concentration of the filtrate at reduced pressure, purification of the residue with column chromatography on silica gel (EtOAc-hexane, a linear gradient of EtOAc from 0 to 10%) afforded 6-bromo-2-isobutyl-2,3-dihydro-4H-chromen-4-one (9.02 g).

Preparation Example 111

The mixture of 1-(5-bromo-2-hydroxyphenyl)ethanone (10 g, 46.50 mmol), propionaldehyde (6.7 mL, 93 mmol), pyrrolidine (3.9 mL, 47 mmol), and acetic acid (3.2 mL, 56 mmol) in toluene (20 mL) was heated to 60° C. for 18 hours. After cooling to room temperature, the mixture was concentrated in vacuo. The mixture was diluted with diethyl ether and 1M aqueous HCl. The phases were separated. The organic phase was washed with 1M aqueous NaOH, then brine. The organic phase was dried over Na$_2$SO$_4$, filtered, and concentrated in vacuo. Purification with silicagel column chromatography (EtOAc-hexane, a linear gradient of EtOAc from 1 to 10%) afforded 6-bromo-2-ethyl-2,3-dihydro-4H-chromen-4-one (3.92 g).

Preparation Example 112

The mixture of ethyl 1-{[(methylsulfonyl)oxy]methyl}cyclobutanecarboxylate (1.50 g, 6.3 mmol), 4-bromophenol (1.2 g, 7.0 mmol), and caesium carbonate (4.13 g, 7.0 mmol) in DMF (15 ml) was stirred for 6 hours at 135° C. After dilution with EtOAc and H$_2$O, the organic layer was washed with H$_2$O, dried over MgSO$_4$, and concentrated in vacuo. The residue was purified by silica gel chromatography (hexane:EtOAc=100:0-70:30) to give ethyl 1-[(4-bromophenoxy)methyl]cyclobutanecarboxylate (919 mg).

Preparation Example 114

To sulfuric acid (5 mL) was added 1-[(4-bromophenoxy)methyl]cyclobutanecarboxylic acid (1.9 g, 6.6 mmol) at 0° C. in an ice bath. After stirring for 1 hour at room temperature, ice was added to the mixture portionwise. The mixture was diluted with water, and extracted with EtOAc. The organic layer was washed with brine, dried over MgSO$_4$, and concentrated in vacuo. The residue was purified by silica gel chromatography (hexane:EtOAc=100:0-70:30) to give 6-bromo-4H-spiro[chromene-3,1'-cyclobutan]-4-one (649 mg).

Preparation Example 116

To a stirred solution of 3,5-dibromopyridine (251 mg, 1.061 mmol) and di-tert-butyl (6'-bromotrispiro[cyclobutane-1,2'-chromene-4',4"-[1,3]oxazole-3',3"'-oxetan]-2"-yl)imidodicarbona to (200 mg, 0.354 mmol) in dioxane (1.6 ml) were added 4,4,4',4',5,5,5',5'-octamethyl-2,2'-bi-1,3,2-dioxaborolane (93 mg, 0.364 mmol), potassium acetate (69 mg, 0.707 mmol) and PdCl$_2$(PPh$_3$)$_2$ (50 mg, 0.071 mmol) at room temperature and the mixture was stirred at 100° C. for 8 hours before the starting molecule was completely consumed to give the corresponding boronate intermediate. To this mixture was added Na$_2$CO$_3$ (150 mg, 1.42 mmol) and H$_2$O (400 µl) and the mixture was stirred at 100° C. for 6 hours before the boronate intermediate was completely consumed. The mixture was cooled to room temperature and evaporated to give a crude, which was purified with column chromatography (EtOAc in hexane=0 to 50%) to give di-tert-butyl[6'-(5-bromopyridin-3-yl)trispiro[cyclobutane-1,2'-chromene-4',4"-[1,3]oxazole-3',3'''-oxetan]-2"-yl]imidodicarbonate (48 mg).

Preparation Example 117

The mixture of 4-bromo-1-[(3,3-dimethoxy-1-vinylcyclobutyl)methoxy]-2-iodobenzene (3.16 g, 6.98 mmol) and 1M aqueous HCl (14 mL) in THF (31 mL) was stirred for ambient temperature for 1 hour. Then the mixture was stirred for 4 hours at 50° C. The mixture was cooled to room temperature and added saturated aqueous NaHCO$_3$ and extracted with EtOAc. The combined organic extracts were washed with brine, dried over Na$_2$SO$_4$, filtered, and evaporated under reduced pressure to give 3-[(4-bromo-2-iodophenoxy)methyl]-3-vinylcyclobutanone (2.91 g).

Preparation Example 119

To a solution of diisopropylamine (3.2 mL, 22.67 mmol) in THF (45 mL) was added n-BuLi (2.69 M in hexane, 7.7 mL, 20.71 mmol) at −78° C. under argon. The mixture was stirred for 10 minutes at 0° C., then cooled to −78° C. and added a solution of methyl 3,3-dimethoxycyclobutanecarboxylate (3.0 g, 17.22 mmol) in THF (10 mL). The mixture was stirred for 30 minutes at −78° C., then added a solution of acetaldehyde (1.9 mL, 33.86 mmol) in THF (10 mL). The mixture was stirred for 30 minutes at −78° C., and water was added. The aqueous layer was extracted with EtOAc. Combined organic layers were washed with brine, dried over Na$_2$SO$_4$, filtered, and evaporated under reduced pressure to give methyl 1-(1-hydroxyethyl)-3,3-dimethoxycyclobutanecarboxylate (3.33 g).

Preparation Example 128

Under ice cooling, to a solution of 2-(4-amino-6-bromo-4H-spiro[chromene-3,1'-cyclopropan]-4-yl)-2,2-difluoroethanol (2.24 g, 6.46 mmol) in acetone (45 mL) was added benzoyl isothiocyanate (1.16 g, 7.10 mmol), and the mixture was stirred for 2 hours at room temperature and stirred for 13 hours at 40° C. After concentration, the residue was purified by silica gel chromatography (EtOAc/hexane=1:99-30:70) followed by purification using silica gel chromatography (NH-silicagel, EtOH/CHCl$_3$=0:100-10:90) to give N-{[6-bromo-4-(1,1-difluoro-2-hydroxyethyl)-4H-spiro[chromene-3,1'-cyclopropan]-4-yl]carbamothioyl}benzamide (684 mg).

Preparation Example 131

To an ice chilled solution of 6-bromo-4-methylene-3'H,4H-spiro[chromene-3,1'-cyclobutan]-3'-one (148 mg, 0.53 mmol) in CH$_2$Cl$_2$ (4.4 mL) was added DAST (0.20 mL, 1.53 mmol), and the mixture was stirred at room temperature for 4.5 hours. Another portion of DAST (0.10 mL, 0.76 mmol) was added to the reaction mixture and the mixture was stirred at room temperature for 19.5 hours. The mixture was cooled at 0° C. and added to saturated aqueous NaHCO$_3$ and the resulting mixture was extracted with CHCl$_3$. The combined organic extracts were dried over Na$_2$SO$_4$, filtered, and concentrated in vacuo. The residue was purified by silica gel chromatography (hexane/EtOAc=100:0-90:10) to give 6-bromo-3',3'-difluoro-4-methylene-4H-spiro[chromene-3,1'-cyclobutane] (65 mg).

Preparation Example 132

To a solution of N-{[6-bromo-4-(1,1-difluoro-2-hydroxyethyl)-4H-spiro[chromene-3,1'-cyclopropan]-4-yl]carbamothioyl}benzamide (340 mg, 0.684 mmol) in MeOH (1.7 mL) was added methylamine (9.8M MeOH solution, 698 µL, 6.84 mmol). The mixture was stirred for 3 hours at ambient temperature. The mixture was concentrated azeotropically with toluene 3 times to give crude 1-[6-bromo-4-(1,1-difluoro-2-hydroxyethyl)-4H-spiro[chromene-3,1'-cyclopropan]-4-yl]thiourea (268 mg).

Preparation Example 133

Under ice cooling, to a solution of N-[6-bromo-4-(1,1-difluoro-2-hydroxyethyl)-4H-spiro[chromene-3,1'-cyclopropan]-4-yl]-2-methylpropane-2-sulfinamide (4.60 g, 10.5 mmol) in THF-EtOH (50% v/v, 46 mL) was added 4M HCl/dioxane (13.1 mL, 52.5 mmol), and the mixture was stirred for 3 hours at room temperature. Under ice cooling, saturated aqueous NaHCO$_3$, H$_2$O and brine were added to the mixture, and then the mixture was extracted with EtOAc. The organic layer was dried over MgSO$_4$ and concentrated. The residue was purified by silica gel chromatography (EtOAc/hexane=50:50-100:0) to give 2-(4-amino-6-bromo-4H-spiro[chromene-3,1'-cyclopropan]-4-yl)-2,2-difluoroethanol (2.28 g).

Preparation Example 134

To a solution of methyl 3,3-dimethoxy-1-vinylcyclobutanecarboxylate (2.02 g, 10.09 mmol) in THF (20 mL) was added DIBAL-H (1.04M in toluene, 29 mL, 30.16 mmol) at 0° C. under argon, and the mixture was stirred for 30 minutes at 0° C. To the mixture was carefully added MeOH (29 mL) and Na$_2$SO$_4$.10H$_2$O (29 g), and the mixture was stirred overnight. The mixture was filtered and evaporated under reduced pressure. And the residue was diluted with hexane/EtOAc=1:1 and filtrated through the pad of silica gel and concentrated in vacuo to give (3,3-dimethoxy-1-vinylcyclobutyl)methanol (1.42 g).

Preparation Example 137

Under ice cooling, to a solution of LiBH$_4$ (458 mg, 21.0 mmol) in THF (30 mL) was added a solution of ethyl {6-bromo-4-[(tert-butylsulfinyl)amino]-4H-spiro[chromene-3,1'-cyclopropan]-4-yl}(difluoro)acetate (5.05 g, 10.5 mmol) in THF (20 mL), and the mixture was stirred for 15 minutes at same temperature and stirred for 2 hours at room temperature. After adding H$_2$O and brine, the mixture was extracted with EtOAc. The organic layer was dried over MgSO$_4$ and concentrated to obtain crude N-[6-bromo-4-(1,1-difluoro-2-hydroxyethyl)-4H-spiro[chromene-3,1'-cyclopropan]-4-yl]-2-methylpropane-2-sulfinamide. The desired compound (4.6 g) was applied to the next step without further purification.

Preparation Example 149

To a suspension of activated zinc (3.44 g, 52.5 mmol) in Et$_2$O-THF (50% v/v, 80 ml) under reflux was slowly added a solution of ethyl bromodifluoroacetate (8.00 g, 39.4 mmol) and N-(6-bromo-4H-spiro[chromene-3,1'-cyclopropan]-4-ylidene)-2-methylpropane-2-sulfinamide (4.68 g, 13.1 mmol) in Et$_2$O-THF (50% v/v, 80 ml) over 40 minutes, and the mixture was stirred for 4 hours at the same temperature. After cooling, the mixture was filtrated through celite pad and washed with EtOAc. To the filtrate were added saturated aqueous NH$_4$Cl and EtOAc. After separation, the water layer was extracted with EtOAc. The combined organic layer was dried over MgSO$_4$ and concentrated. The residue was purified by silica gel chromatography (EtOAc:hexane=20:80-100:0) to give ethyl {6-bromo-4-[(tert-butylsulfinyl)amino]-4H-spiro[chromene-3,1'-cyclopropan]-4-yl}(difluoro)acetate (6.08 g).

Preparation Example 151

To a solution of methyl 1-(1-hydroxyethyl)-3,3-dimethoxycyclobutanecarboxylate (3.28 g, 15.03 mmol) and pyridine (2.4 mL, 29.83 mmol) in CH$_2$Cl$_2$ (65 mL) was added trifluoromethanesulfonic anhydride (3.0 mL, 17.86 mmol) at −78° C. The mixture was stirred for 10 minutes and then warmed to 0° C. After stirring for 15 minutes at 0° C., DBU (9.0 mL, 60.18 mmol) was added to the reaction mixture and the resulting mixture was stirred for 1 hour at room temperature. The mixture was partially evaporated under reduced pressure and filtrated through the pad of silica gel and washed with CH$_2$Cl$_2$. The filtrate was washed with saturated aqueous NaHCO$_3$, dried over Na$_2$SO$_4$, filtered, and evaporated. The residue was diluted with hexane/EtOAc=4:1 and added small amount of CHCl$_3$ and filtrated through the pad of silica gel to give methyl 3,3-dimethoxy-1-vinylcyclobutanecarboxylate (2.21 g).

Preparation Example 152

Under ice cooling, to a solution of N-{[6-bromo-4-(1,1-difluoro-2-hydroxyethyl)-4H-spiro[chromene-3,1'-cyclopropan]-4-yl]carbamothioyl}benzamide (340 mg, 0.684 mmol) in CH$_2$Cl$_2$ (9 mL) was added 1-chloro-N,N,2-trimethylprop-1-en-1-amine (206 mg, 1.54 mmol), and the mixture was stirred for 17 hours at room temperature. Ice was added and the mixture was neutralized by 10% aqueous K$_2$CO$_3$ and extracted with CH$_2$Cl$_2$. The organic layer was washed with brine and dried over MgSO$_4$ and concentrated. The residue was purified by silica gel chromatography (EtOAc/hexane=1:99-40:60) to afford N-(6'-bromo-5",5"-difluoro-5",6"-dihydrodispiro[cyclopropane-1,3'-chromene-4',4"-[1,3]thiazin]-2"-yl)benzamide (198 mg).

Preparation Example 154

To a solution of (4S)-6'-bromo-2',2'-dimethyldispiro[1,3-oxazole-4,4'-chromene-3',3"-oxetan]-2-amine (4.41 g, 12.5 mmol) in THF (44 mL) were added di-tert-butyl dicarbonate (6.54 g, 30.0 mmol) and 4-dimethylaminopyridine (76 mg, 0.62 mmol). After stirring for 16 hours at ambient temperature, the mixture was concentrated at reduced pressure. The residue was purified by column chromatography on silica gel (hexane-EtOAc, a linear gradient of EtOAc from 10 to 30%) to afford di-tert-butyl[(4S)-6'-bromo-2',2'-dimethyldispiro[1,3-oxazole-4,4'-chromene-3',3"-oxetan]-2-yl]imidodicarbonate (6.95 g).

Preparation Example 155

To a solution of (4'R)-6'-bromo-2',2'-dimethyldispiro[cyclopropane-1,3'-chromene-4',4"-[1,3]oxazol]-2"-amine (1.54 g, 4.57 mmol) in tetrahydrofuran (21 ml) were added di-tert-butyl dicarbonate (2.49 g, 11.4 mmol) and N,N-dimethylpyridin-4-amine (28 mg, 0.23 mmol). The mixture was stirred at room temperature overnight and concentrated in vacuo. The residue was purified by silica gel column chromatography (hexane/ethyl acetate=3:1) to afford di-tert-butyl[(4'R)-6'-bromo-2',2'-dimethyldispiro[cyclopropane-1,3'-chromene-4',4"-[1,3]oxazol]-2"-yl]imidodicarbonate (1.99 g).

Preparation Example 156

A 3-necked-flask was charged with dimethylsulfoxide (17 ml) and potassium hydroxide (0.84 g, 15 mmol). Then trimethylsulfoxonium iodide (3.3 g, 15 mmol) was added and the mixture was stirred at room temperature for 30 minutes. To this mixture, 6-bromo-2,2-dimethyl-3-methylene-2,3-dihydro-4H-chromen-4-one (2.0 g, 7.5 mmol) and dimethylsulfoxide (3 ml) were added. The mixture was stirred at room temperature for 15 hours and then water (30 ml) was added. The mixture was extracted with a mixture of hexane (70 ml) and ethyl acetate (70 ml). The organic layer was washed with water (50 ml) twice and then with brine (30 ml), dried over anhydrous magnesium sulfate, and concentrated in vacuo. The residue was purified by silica gel column chromatography (NH-silica gel, hexane/ethyl acetate=100:1-20:1) to afford 6-bromo-2,2-dimethyl-4H-spiro[chromene-3,1'-cyclopropan]-4-one (1.2 g).

Preparation Example 157

To a mixture of di-tert-butyl[(4S)-6'-bromo-2',2'-dimethyldispiro[1,3-oxazole-4,4'-chromene-3',3"-oxetan]-2-yl]imidodicarbonate (3.40 g, 6.14 mmol), bis(dibenzylideneacetone)palladium(0) (353 mg, 0.614 mmol), and tri-tert-butylphosphonium tetrafluoroborate (179 mg, 0.617 mmol) was added lithium bis(trimethylsilyl)amide (1M solution in toluene, 31 mL, 31 mmol) at ambient temperature under argon atmosphere. After stirring for 1.5 hours at 60° C., the mixture was cooled in an ice-water bath and 1M aqueous HCl (31 mL) was added. After stirring for 10 minutes at ambient temperature, to the mixture was added CHCl$_3$, and the mixture was filtered through a pad of celite. The filtrate was separated and the aqueous layer was extracted with CHCl$_3$. The combined organic layer was dried over Na$_2$SO$_4$ and filtered. The filtrate was concentrated at reduced pressure. To the residue were added MeOH (34 mL) and silica gel (neutral; 17 g) at ambient temperature. After stirring for 1 hour at 40° C., the mixture was concentrated at reduced pressure. The residue was purified with column chromatography on silica gel (hexane-EtOAc, a linear gradient of EtOAc from 10 to 100%) to afford tert-butyl[(4S)-6'-amino-2',2'-dimethyldispiro[1,3-oxazole-4,4'-chromene-3',3"-oxetan]-2-yl]carbamate (2.38 g).

Preparation Example 158

To a mixture of di-tert-butyl[(4'R)-6'-bromo-2',2'-dimethyldispiro[cyclopropane-1,3'-chromene-4',4"-[1,3]oxazol]-2"-yl]imidodicarbonate (1.98 g, 3.68 mmol), bis(dibenzylideneacetone)palladium(0) (212 mg, 0.369 mmol), and tri-tert-butylphosphonium tetrafluoroborate (108 mg, 0.371 mmol) was added lithium bis(trimethylsilyl)amide (1M solution in toluene, 18 ml, 18 mmol) at room temperature under argon atmosphere. The mixture was stirred at 60° C. for 2 hours and then quenched with saturated aqueous ammonium chloride. The mixture was extracted with chloroform. The organic layer was dried over anhydrous magnesium sulfate, and concentrated in vacuo. The residue was purified by silica gel column chromatography (hexane/ethyl acetate=100:0-50:50-0:100) to afford tert-butyl[(4'R)-6'-amino-2',2'-dimethyldispiro[cyclopropane-1,3'-chromene-4',4"-[1,3]oxazol]-2"-yl]carbamate (1.37 g).

Preparation Example 159

N,N,N',N'-tetramethylmethanediamine (4.8 g, 47 mmol) was added to a solution of 6-bromo-2,2-dimethyl-2,3-dihydro-4H-chromen-4-one (3.0 g, 12 mmol) and acetic acid (0.67 ml, 12 mmol) in tetrahydrofuran (43 ml), and the mixture was stirred at 70° C. for 24 hours. To the mixture was added acetic anhydride (4.4 ml, 47 mmol), and the mixture was stirred at 70° C. for 4 hours and concentrated in vacuo. The residue was directly purified by silica gel column chromatography (hexane/ethyl acetate=20:1) to afford 6-bromo-2,2-dimethyl-3-methylene-2,3-dihydro-4H-chromen-4-one (2.8 g).

Preparation Example 160

To a suspension of methyl(triphenyl)phosphonium bromide (20.8 g, 58.2 mmol) in tetrahydrofuran (168 ml) was added n-butyllithium (2.69 M solution in hexane, 21.6 ml, 58.2 mmol) under dry ice-acetone bath cooling and argon atmosphere. The mixture was stirred for 1 hour at 0° C. To the mixture was added 6-bromo-2,2-dimethyl-4H-spiro[chromene-3,1'-cyclopropan]-4-one (8.18 g, 29 mmol). The mixture was stirred for 1 hour at 0° C. The reaction was quenched by adding water and extracted with ethyl acetate. The organic layer was washed with brine, dried over anhydrous magnesium sulfate, and concentrated in vacuo. The residue was purified by silicagel column chromatography (hexane/ethyl acetate=20:1-10:1) to afford 6-bromo-2,2-dimethyl-4-methylene-4H-spiro[chromene-3,1'-cyclopropane] (7.69 g).

Preparation Example 161

To a mixture of tert-butyl[(4S)-6'-amino-2',2'-dimethyldispiro[1,3-oxazole-4,4'-chromene-3',3"-oxetan]-2-yl]carbamate (1.00 g, 2.57 mmol) and CH$_2$Cl$_2$ (10 mL) were added 5-chloro-2-pyridinecarboxylic acid (526 mg, 3.34 mmol), N-(3-dimethylaminopropyl)-N'-ethylcarbodiimide hydrochloride (640 mg, 3.34 mmol), 1-hydroxybenzotriazole (451 mg, 3.34 mmol) and N,N-diisopropylethylamine (0.571 mL, 3.34 mmol) at ambient temperature. After stirring overnight at the same temperature, the reaction mixture was purified with column chromatography on silica gel (hexane-EtOAc, a linear gradient of EtOAc from 0 to 90%) and then on NH-silica gel (hexane-EtOAc, a linear gradient of EtOAc from 0 to 90%) to give tert-butyl[(4S)-6'-{[(5-chloropyridin-2-yl)carbonyl]amino}-2',2'-dimethyldispiro[1,3-oxazole-4,4'-chromene-3',3"-oxetan]-2-yl]carbamate (1.02 g).

Preparation Example 165

To a mixture of tert-butyl[(4'R)-6'-amino-2',2'-dimethyldispiro[cyclopropane-1,3'-chromene-4',4"-[1,3]oxazol]-2"-yl]carbamate (100 mg, 0.268 mmol), 5-methoxypyrazine-2-carboxylic acid (45 mg, 0.30 mmol) and 1H-benzotriazol-1-ol (40 mg, 0.29 mmol) in dichloromethane (2 mL) was added N-[3-(dimethylamino)propyl]-N'-ethylcarbodiimide hydrochloride (57 mg, 0.30 mmol). The mixture was stirred at room temperature for 3 hours and directly purified by silica gel column chromatography (precolumn: NH-silica gel, main column: neutral silica gel, hexane/ethyl acetate=2:1-1:1-0:1) to afford tert-butyl[(4'R)-6'-{[(5-methoxypyrazin-2-yl)carbonyl]amino}-2',2'-dimethyldispiro[cyclopropane-1,3'-chromene-4',4"-[1,3]oxazol]-2"-yl]carbamate (108 mg).

Preparation Example 167

To an ice-water cooled mixture of tert-butyl[(4'R)-6'-amino-2',2'-dimethyldispiro[cyclopropane-1,3'-chromene-4',4"-[1,3]oxazol]-2"-yl]carbamate (430 mg, 1.15 mmol), 5-(difluoromethyl)pyrazine-2-carboxylic acid (221 mg, 1.27 mmol) and 1H-benzotriazol-1-ol (170 mg, 1.26 mmol) in chloroform (8.6 ml) was added N-[3-(dimethylamino)propyl]-N'-ethylcarbodiimide hydrochloride (244 mg, 1.28 mmol). The mixture was stirred at room temperature overnight and directly purified by silica gel column chromatography (precolumn: basic silica gel, main column: neutral silica gel, hexane/ethyl acetate=2:1-1:1-0:100) to afford tert-butyl[(4'R)-6'-({[5-(difluoromethyl)pyrazin-2-yl]carbonyl}amino)-2',2'-dimethyldispiro[cyclopropane-1,3'-chromene-4',4"-[1,3]oxazol]-2"-yl]carbamate (373 mg).

Preparation Example 169

A mixture of 6-bromo-2,3-dihydro-4H-chromen-4-one (0.3 g, 1.3 mmol), paraformaldehyde (0.48 g), L-proline (61 mg, 0.53 mmol), and 0.2 M aqueous sodium hydroxide (6 mL) was stirred at room temperature for 16 hours. The mixture was extracted with CHCl$_3$ and concentrated in vacuo. The residue was purified with silica-gel column chromatography (CHCl$_3$/MeOH=100:0 to 90:10) to give 6-bromo-3,3-bis(hydroxymethyl)-2,3-dihydro-4H-chromen-4-one (0.33 g).

Preparation Example 171

To a solution of 6-bromo-4H-spiro[chromene-3,3'-oxetan]-4-one (143 mg, 0.531 mmol) in THF (2 mL) was added Tebbe reagent ((C$_5$H$_5$)$_2$TiCH$_2$ClAl(CH$_3$)$_2$, μ-Chloro[di(cyclopenta-2,4-dien-1-yl)]dimethyl(μ-methylene)titaniumaluminum, 0.5 M in toluene, 2 mL) under ice-water bath cooling. After the reaction mixture was stirred at the same temperature for 2 hours and then room temperature for 4 hours, 1M aqueous NaOH (1 mL) was added. After dilution with water and filtration with Celite, the insoluble material was washed with CHCl$_3$. The aqueous phase was extracted with CHCl$_3$ and combined organic layer was concentrated in vacuo. The residue was purified with silica-gel column chromatography to give 6-bromo-4-methylene-4H-spiro[chromene-3,3'-oxetane] (0.10 g).

Preparation Example 173

Under nitrogen, MeMgBr solution (2.9 M in 2-methyltetrahydrofuran solution, 3.06 L, 8.88 mol) was diluted by adding into THF (8 L) at 0-5° C. A solution of 6-bromo-3,3-bis(hydroxymethyl)-2,2-dimethyl-2,3-dihydro-4H-chromen-4-one (700 g, 2.22 mol) in THF (5 L) was added dropwise via a dropping funnel to the diluted MeMgBr solution maintaining the temperature below 5° C. After the addition was complete, the reaction mixture was allowed to warm to room temperature and stirred for 30 minutes. Then the reaction mixture was heated under reflux overnight. The mixture was cooled to room temperature followed by cooling with an ice-water bath and 6 M hydrochloric acid (3.7 L, 22.2 mol) was added dropwise via a dropping funnel over 30 minutes maintaining the temperature below 10° C. After the addition was complete, the mixture was allowed to warm to room temperature and stirred for 20 minutes. The mixture was extracted with toluene (5 L×2) and the combined extracts were washed with brine, dried over Na$_2$SO$_4$ and concentrated under reduced pressure. The residue was treated with a mixture of hexane/toluene (5:1, 2 L) and the resulting suspension was stirred for 30 minutes. The precipitate was collected by filtration, washed with hexane and dried under vacuum to give (6-bromo-2,2-dimethyl-4-methylene-3,4-dihydro-2H-chromene-3,3-diyl)dimethanol (500 g).

Preparation Example 174

Under nitrogen, to a solution of (6-bromo-2,2-dimethyl-4-methylene-3,4-dihydro-2H-chromene-3,3-diyl)dimethanol (800 g, 2.55 mol) and MsCl (877.9 g, 7.66 mol) in THF (4.0 L) was added Et$_3$N (851 g, 8.41 mol) over 45 minutes maintaining the temperature below 0-10° C. The reaction mixture was allowed to warm to room temperature and stirred for 1 hour. EtOH (8 L) and NaOH (1021.8 g, 25.55 mol) were added and the reaction mixture was heated under reflux for 16 hours. Water (4 L) was added and a clear solution was obtained. Most of the solvent was removed under reduced pressure and the resulting residue was extracted with ethyl acetate (1.5 L×2). The combined extracts were washed with brine, dried over Na$_2$SO$_4$ and concentrated under reduced pressure. The residue was dissolved in MeOH (640 mL) at 60° C. and the resulting solution was allowed to cool to room temperature. The precipitation formed was filtered-off. The filtrate was concentrated under reduced pressure and the residue was re-dissolved in MeOH (500 mL) at 60° C. The resulting solution was allowed to cool to room temperature and then further to 0-5° C. The mixture was stirred at 0-5° C. overnight and the precipitated yellow solid was collected by filtration to give 6-bromo-2,2-dimethyl-4-methylene-4H-spiro[chromene-3,3'-oxetane] (197.2 g). The filtrate was concentrated under reduced pressure and the residue was purified by column chromatography on silica gel (petroleum ether/ethyl acetate=50:1) to give another batch of 6-bromo-2,2-dimethyl-4-methylene-4H-spiro[chromene-3,3'-oxetane] (143.6 g).

The compounds of Preparation Examples shown in Tables below were prepared using the respective corresponding starting materials in the same manner as the methods of Preparation Examples above. The structures and the preparation methods are shown in [Table. 2] below, and the physicochemical data for the compounds of Preparation Examples are shown in [Table. 3] below.

TABLE 2

| Rf | Syn | Structure |
|---|---|---|
| 1 | R1 | 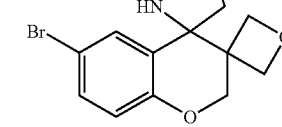 |
| 2 | R2 | 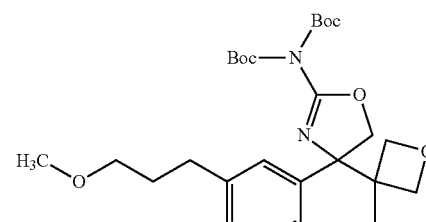 |
| 3 | R2 | 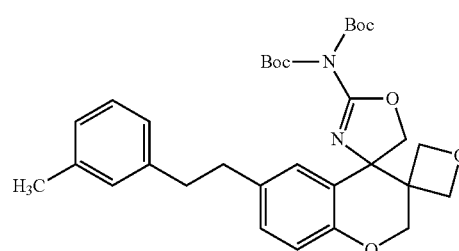 |
| 4 | R22 | 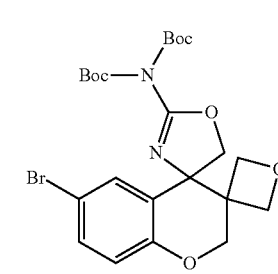 |
| 5 | R22 | 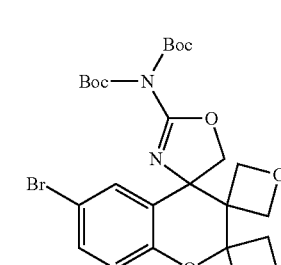 |

TABLE 2-continued

| Rf | Syn | Structure |
|---|---|---|
| 6 | R22 | 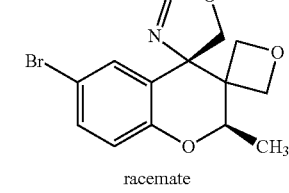<br>racemate |
| 7 | R22 | 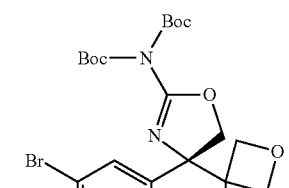<br>racemate |
| 8 | R8 or R22 | 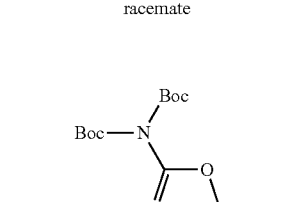 |
| 9 | R22 | 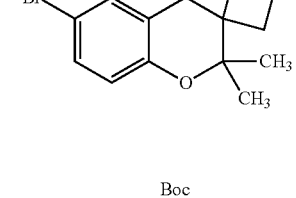 |
| 10 | R22 | 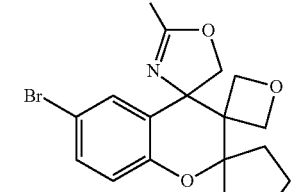 |

TABLE 2-continued
| Rf | Syn | Structure |
|---|---|---|
| 11 | R22 | 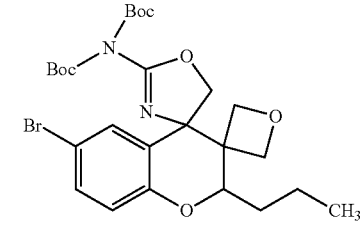 |
| 12 | R22 | 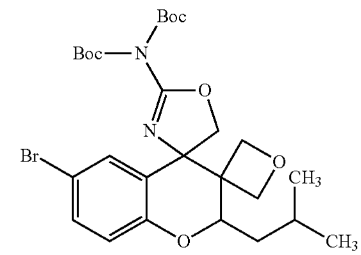 |
| 13 | R22 | 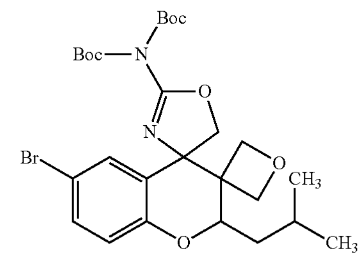 [SMILES: CC(C)CC1Oc2ccc(Br)cc2C2(COC(N(C(=O)OC(C)(C)C)C(=O)OC(C)(C)C)=N2)C12COC2] |
| 14 | R22 | 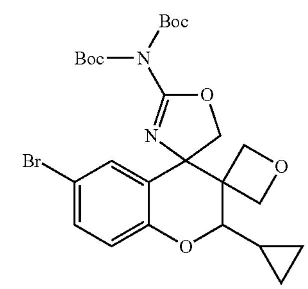 [SMILES: CC(C)(C)OC(=O)N(C(=O)OC(C)(C)C)C1=NC2(CO1)c1cc(Br)ccc1OC(C1CC1)C21COC1] |
| 15 | R22 | 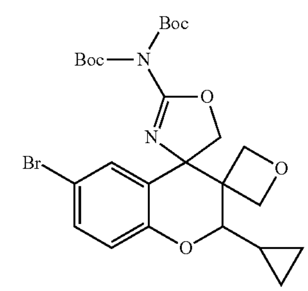 [SMILES: CC(C)(C)OC(=O)N(C(=O)OC(C)(C)C)C1=NC2(CO1)c1cc(Br)ccc1OC(C1CC1)C21COC1] |
| 16 | R22 | 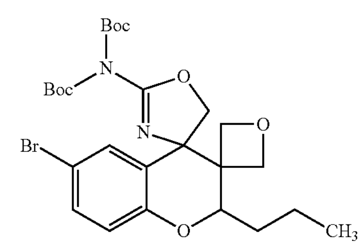 [SMILES: CCCC1Oc2ccc(Br)cc2C2(COC(N(C(=O)OC(C)(C)C)C(=O)OC(C)(C)C)=N2)C12COC2] |
TABLE 2-continued
| Rf | Syn | Structure |
|---|---|---|
| 17 | R22 | 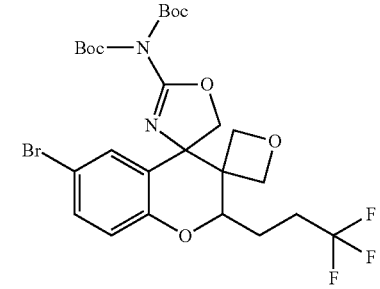 [SMILES: CC(C)(C)OC(=O)N(C(=O)OC(C)(C)C)C1=NC2(CO1)c1cc(Br)ccc1OC(CCC(F)(F)F)C21COC1] |
| 18 | R22 | |
| 19 | R22 | |
| 20 | R22 | |
| 21 | R22 | |
| 22 | R22 | |

TABLE 2-continued

| Rf | Syn | Structure |
|---|---|---|
| 23 | R23 | 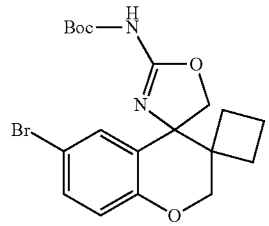 [SMILES: CC(C)(C)OC(=O)NC1=NC2(CO1)c1cc(Br)ccc1OCC21CCC1] |
| 24 | R24 | 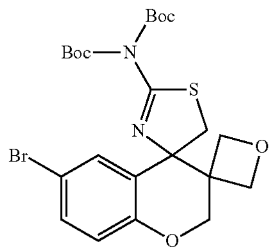 [SMILES: CC(C)(C)OC(=O)N(C(=O)OC(C)(C)C)C1=NC2(CS1)c1cc(Br)ccc1OCC21COC1] |
| 25 | R24 | 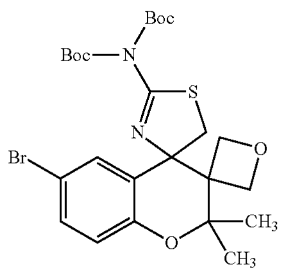 |
| 26 | R26 | 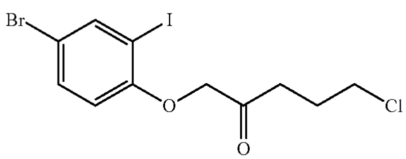 [SMILES: O=C(CCCCl)COc1ccc(Br)cc1I] |
| 27 | R27 | 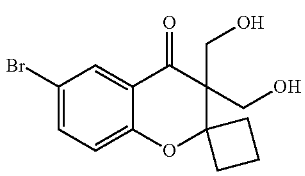 [SMILES: O=C1c2cc(Br)ccc2OC2(CCC2)C1(CO)CO] |
| 28 | R29 | 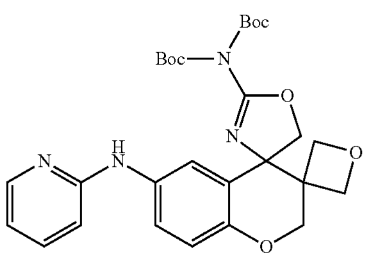 [SMILES: CC(C)(C)OC(=O)N(C(=O)OC(C)(C)C)C1=NC2(CO1)c1cc(Nc3ccccn3)ccc1OCC21COC1] |
| 29 | R29 | 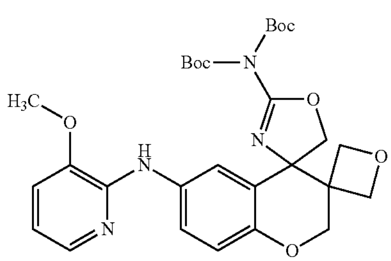 [SMILES: COc1cccnc1Nc1ccc2c(c1)C1(COC(N(C(=O)OC(C)(C)C)C(=O)OC(C)(C)C)=N1)C1(COC1)CO2] |
| 30 | R30 | 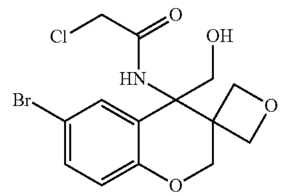 [SMILES: O=C(CCl)NC1(CO)c2cc(Br)ccc2OCC12COC2] |
| 31 | R31 | 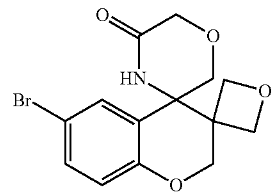 [SMILES: O=C1COCC2(N1)c1cc(Br)ccc1OCC21COC1] |
| 32 | R36 | 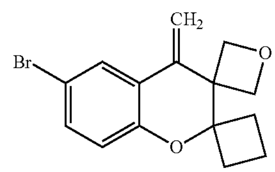 [SMILES: C=C1c2cc(Br)ccc2OC2(CCC2)C12COC2] |
| 33 | R36 | 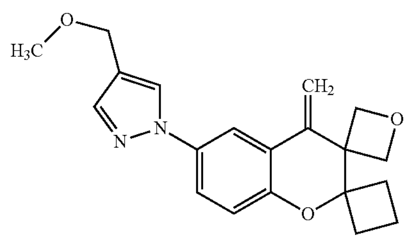 [SMILES: C=C1c2cc(-n3cc(COC)cn3)ccc2OC2(CCC2)C12COC2] |
| 34 | R36 | 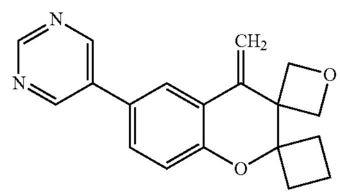 [SMILES: C=C1c2cc(-c3cncnc3)ccc2OC2(CCC2)C12COC2] |
| 35 | R36 | 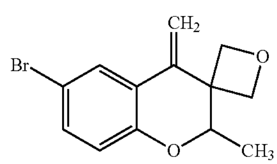 |
| 36 | R36 | 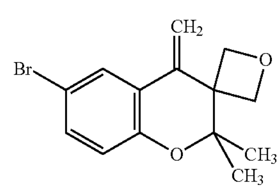 [SMILES: C=C1c2cc(Br)ccc2OC(C)(C)C12COC2] |
| 37 | R36 | 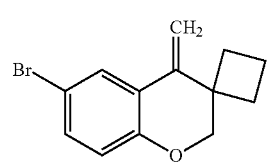 |

TABLE 2-continued

| Rf | Syn | Structure |
|---|---|---|
| 38 | R36 | (structure) |
| 39 | R36 | (structure) |
| 40 | R36 | (structure) |
| 41 | R36 | (structure) |
| 42 | R36 | (structure) |
| 43 | R36 | (structure) |
| 44 | R36 | (structure) |
| 45 | R36 | (structure) |
| 46 | R36 | (structure) |
| 47 | R36 | (structure) |
| 48 | R48 | (structure) |
| 49 | R48 | (structure) |
| 50 | R48 | (structure) |
| 51 | R48 | (structure) |
| 52 | R48 | (structure) |
| 53 | R48 | (structure) |
| 54 | R48 | (structure) |

TABLE 2-continued

| Rf | Syn | Structure |
|---|---|---|
| 55 | R48 | 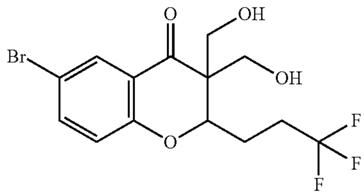 [SMILES: O=C1c2cc(Br)ccc2OC(CCC(F)(F)F)C1(CO)CO] |
| 56 | R48 | 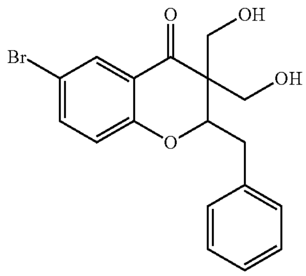 [SMILES: O=C1c2cc(Br)ccc2OC(Cc2ccccc2)C1(CO)CO] |
| 57 | R48 | 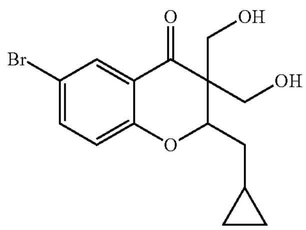 [SMILES: O=C1c2cc(Br)ccc2OC(CC2CC2)C1(CO)CO] |
| 58 | R58 | 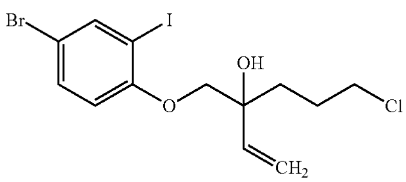 [SMILES: C=CC(O)(CCCCl)COc1ccc(Br)cc1I] |
| 59 | R59 | 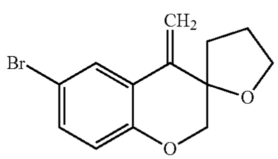 [SMILES: C=C1c2cc(Br)ccc2OCC12CCCO2] |
| 60 | R60 | 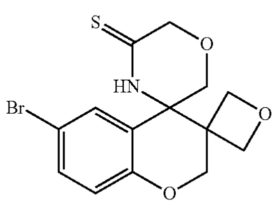 [SMILES: S=C1COCC2(N1)c1cc(Br)ccc1OCC21COC1] |
| 61 | R62 | 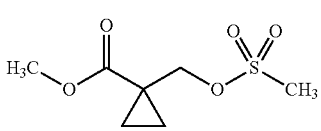 |
| 62 | R62 | 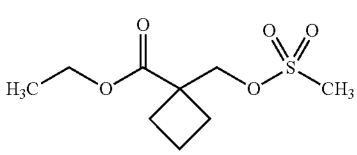 |
| 63 | R63 | |
| 64 | R64 | |
| 65 | R64 | |
| 66 | R66 | |
| 67 | R66 or R67 | |
| 68a | R69 | |
| 68b | R69 | |

TABLE 2-continued

| Rf | Syn | Structure |
|---|---|---|
| 69 | R69 | 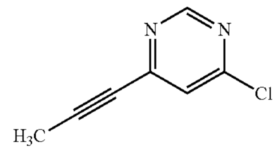 |
| 70 | R70 | 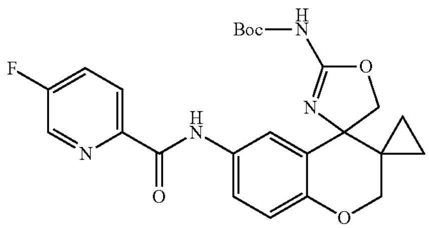 [SMILES: CC(C)(C)OC(=O)NC1=NC2(CO1)c1cc(NC(=O)c3ccc(F)cn3)ccc1OCC21CC1] |
| 71 | R70 | 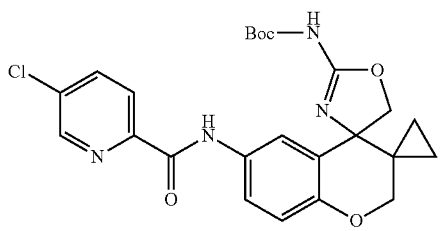 [SMILES: CC(C)(C)OC(=O)NC1=NC2(CO1)c1cc(NC(=O)c3ccc(Cl)cn3)ccc1OCC21CC1] |
| 72 | R70 | 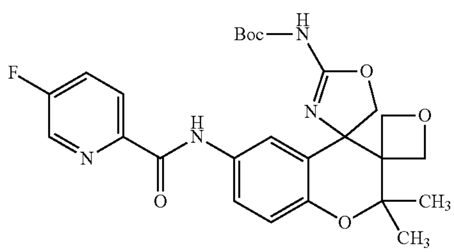 [SMILES: CC(C)(C)OC(=O)NC1=NC2(CO1)c1cc(NC(=O)c3ccc(F)cn3)ccc1OC(C)(C)C21COC1] |
| 73 | R70 or R73 | 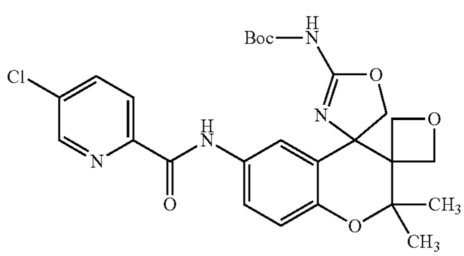 [SMILES: CC(C)(C)OC(=O)NC1=NC2(CO1)c1cc(NC(=O)c3ccc(Cl)cn3)ccc1OC(C)(C)C21COC1] |
| 74 | R70 | 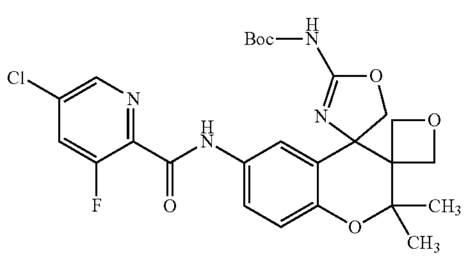 [SMILES: CC(C)(C)OC(=O)NC1=NC2(CO1)c1cc(NC(=O)c3ncc(Cl)cc3F)ccc1OC(C)(C)C21COC1] |
| 75 | R70 | 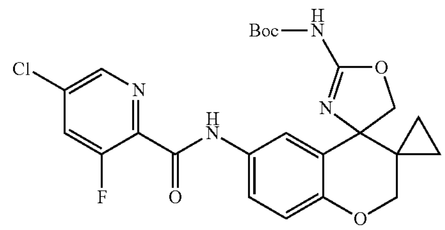 [SMILES: CC(C)(C)OC(=O)NC1=NC2(CO1)c1cc(NC(=O)c3ncc(Cl)cc3F)ccc1OCC21CC1] |
| 76 | R76 | 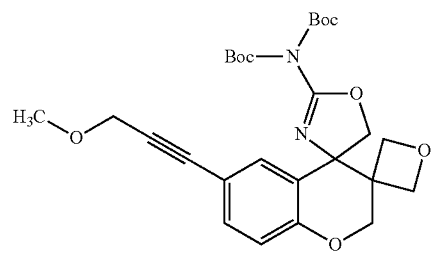 [SMILES: COCC#Cc1ccc2c(c1)C1(COC(N(C(=O)OC(C)(C)C)C(=O)OC(C)(C)C)=N1)C1(COC1)CO2] |
| 77 | R76 | 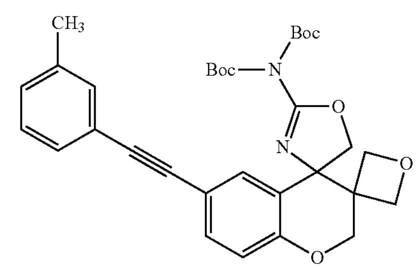 [SMILES: Cc1cccc(C#Cc2ccc3c(c2)C2(COC(N(C(=O)OC(C)(C)C)C(=O)OC(C)(C)C)=N2)C2(COC2)CO3)c1] |
| 78 | R78 | 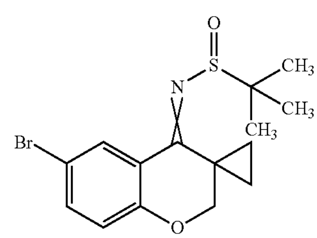 |
| 79 | R83 | 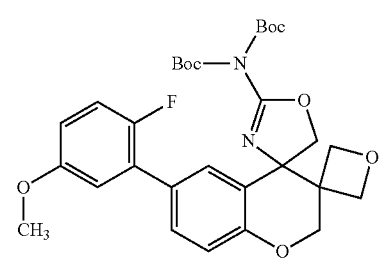 [SMILES: COc1ccc(F)c(-c2ccc3c(c2)C2(COC(N(C(=O)OC(C)(C)C)C(=O)OC(C)(C)C)=N2)C2(COC2)CO3)c1] |
| 80 | R83 | 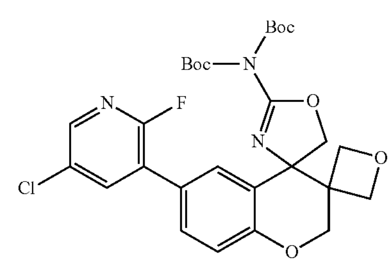 [SMILES: CC(C)(C)OC(=O)N(C(=O)OC(C)(C)C)C1=NC2(CO1)c1cc(-c3cc(Cl)cnc3F)ccc1OCC21COC1] |

TABLE 2-continued
| Rf | Syn | Structure |
|---|---|---|
| 81 | R83 | 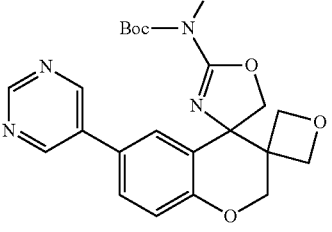 |
| 82 | R83 | 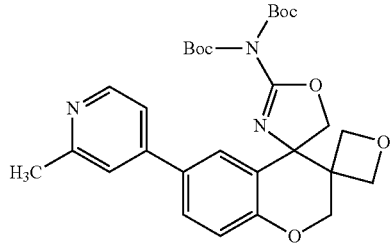 [SMILES: Cc1cc(-c2ccc3c(c2)C2(COC(N(C(=O)OC(C)(C)C)C(=O)OC(C)(C)C)=N2)C2(COC2)CO3)ccn1] |
| 83 | R83 | 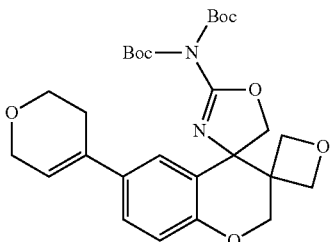 |
| 84 | R83 | 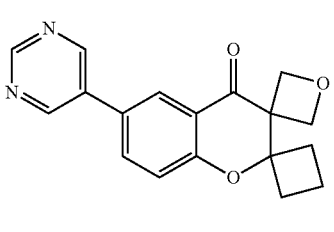 [SMILES: O=C1c2cc(-c3cncnc3)ccc2OC2(CCC2)C12COC2] |
| 85 | R85 | 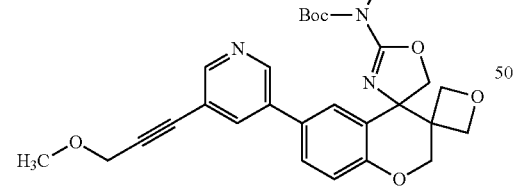 |
| 86 | R85 | 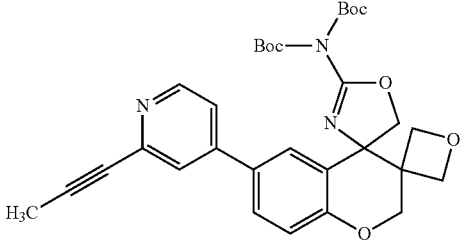 [SMILES: CC#Cc1cc(-c2ccc3c(c2)C2(COC(N(C(=O)OC(C)(C)C)C(=O)OC(C)(C)C)=N2)C2(COC2)CO3)ccn1] |
| 87 | R85 | 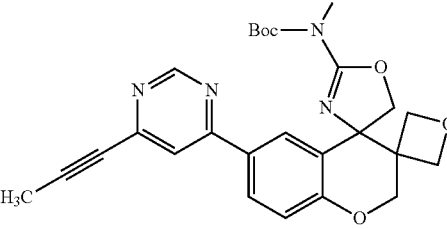 |
| 88 | R85 | 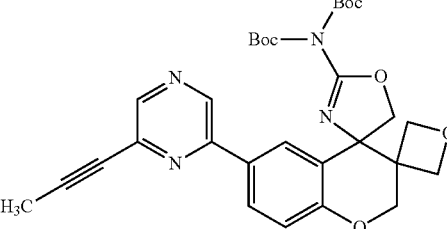 |
| 89 | R85 | 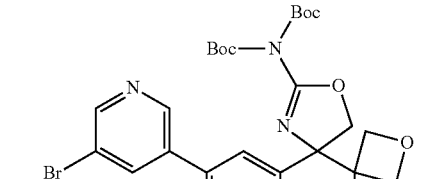 |
| 90 | R83 | 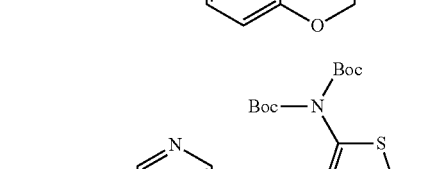 |
| 91 | R91 | 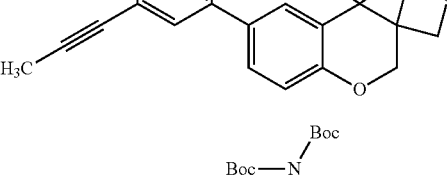 |
| 92 | R92 | 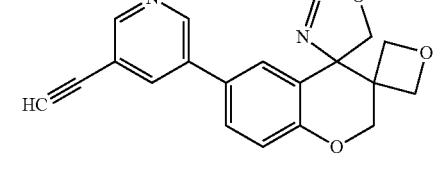 |
| 93 | R92 | 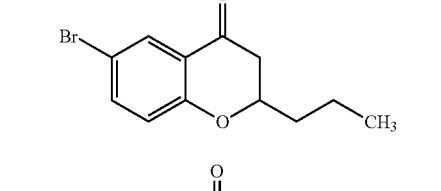 |

TABLE 2-continued

| Rf | Syn | Structure |
|----|-----|-----------|
| 94 | R94 | |
| 95 | R96 | |
| 96 | R96 | |
| 97 | R96 | |
| 98 | R96 | |
| 99 | R96 | |
| 100 | R96 | |
| 101 | R96 | |
| 102 | R96 | 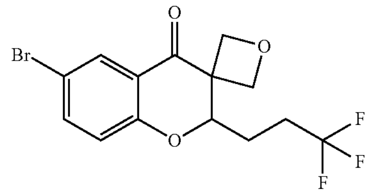 [SMILES: O=C1c2cc(Br)ccc2OC(CCC(F)(F)F)C12COC2] |
| 103 | R96 | 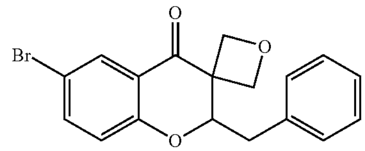 [SMILES: O=C1c2cc(Br)ccc2OC(Cc2ccccc2)C12COC2] |
| 104 | R96 | 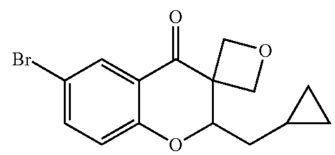 [SMILES: O=C1c2cc(Br)ccc2OC(CC2CC2)C12COC2] |
| 105 | R96 | 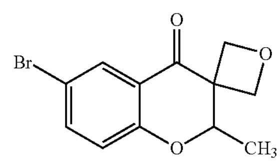 |
| 106 | R106 | 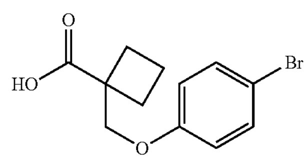 [SMILES: O=C(O)C1(COc2ccc(Br)cc2)CCC1] |
| 107 | R106 | 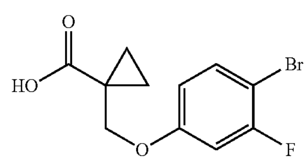 [SMILES: O=C(O)C1(COc2ccc(Br)c(F)c2)CC1] |
| 108 | R108 | 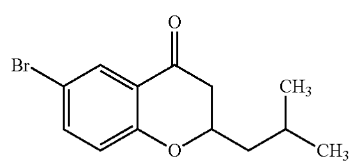 [SMILES: CC(C)CC1CC(=O)c2cc(Br)ccc2O1] |
| 109 | R108 | 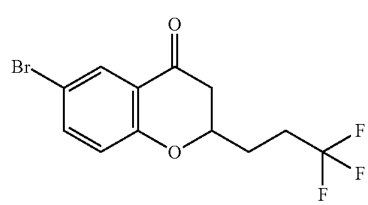 [SMILES: O=C1CC(CCC(F)(F)F)Oc2ccc(Br)cc21] |
| 110 | R108 | 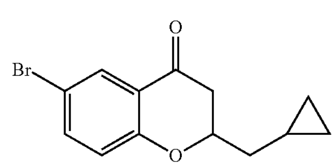 [SMILES: O=C1CC(CC2CC2)Oc2ccc(Br)cc21] |

TABLE 2-continued

| Rf | Syn | Structure |
|---|---|---|
| 111 | R111 | 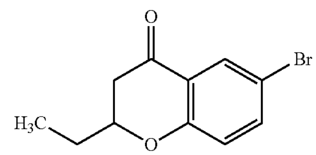 |
| 112 | R112 | 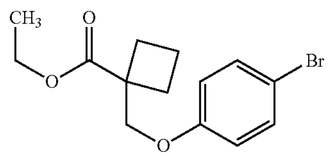 [SMILES: CCOC(=O)C1(COc2ccc(Br)cc2)CCC1] |
| 113 | R112 | 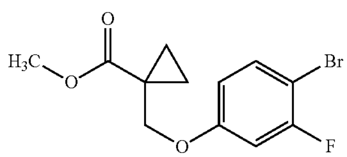 [SMILES: COC(=O)C1(COc2ccc(Br)c(F)c2)CC1] |
| 114 | R114 | 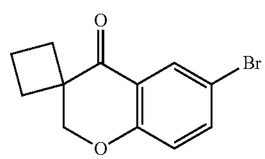 [SMILES: O=C1c2cc(Br)ccc2OCC12CCC2] |
| 115 | R114 | 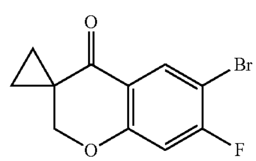 [SMILES: O=C1c2cc(Br)c(F)cc2OCC12CC2] |
| 116 | R116 | 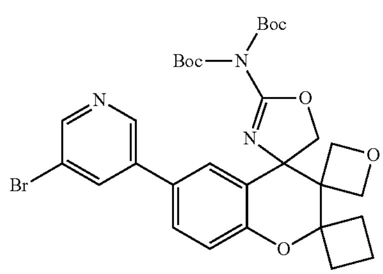 [SMILES: CC(C)(C)OC(=O)N(C(=O)OC(C)(C)C)C1=NC2(CO1)c1cc(-c3cncc(Br)c3)ccc1OC1(CCC1)C21COC1] |
| 117 | R117 | 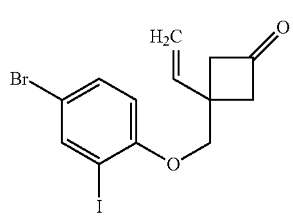 [SMILES: C=CC1(COc2ccc(Br)cc2I)CC(=O)C1] |
| 118 | R1 | 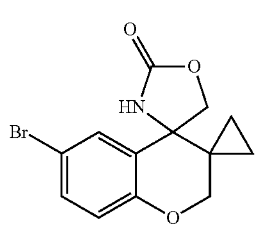 [SMILES: O=C1NC2(CO1)c1cc(Br)ccc1OCC21CC1] |
| 119 | R119 | 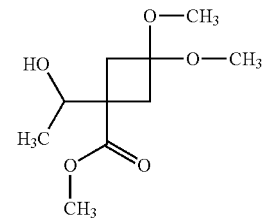 |
| 120 | R22 | 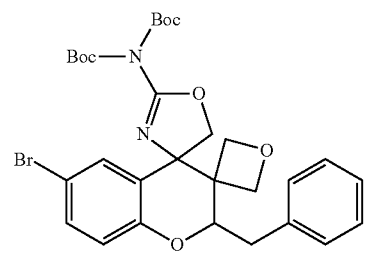 [SMILES: CC(C)(C)OC(=O)N(C(=O)OC(C)(C)C)C1=NC2(CO1)c1cc(Br)ccc1OC(Cc1ccccc1)C21COC1] |
| 121 | R22 | 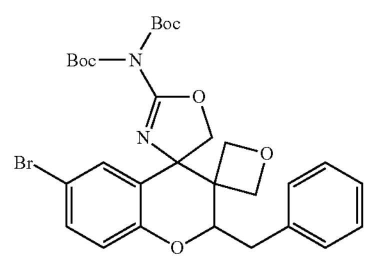 [SMILES: CC(C)(C)OC(=O)N(C(=O)OC(C)(C)C)C1=NC2(CO1)c1cc(Br)ccc1OC(Cc1ccccc1)C21COC1] |
| 122 | R22 | 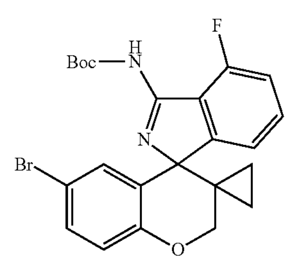 [SMILES: CC(C)(C)OC(=O)NC1=NC2(c3cc(Br)ccc3OCC23CC3)c2cccc(F)c21] |
| 123 | R22 | 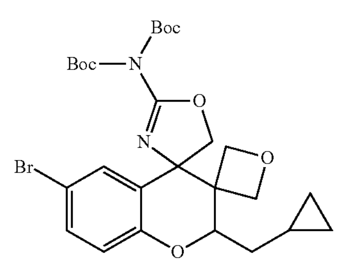 [SMILES: CC(C)(C)OC(=O)N(C(=O)OC(C)(C)C)C1=NC2(CO1)c1cc(Br)ccc1OC(CC1CC1)C21COC1] |
| 124 | R22 | 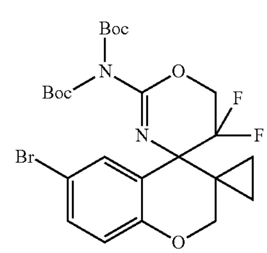 [SMILES: CC(C)(C)OC(=O)N(C(=O)OC(C)(C)C)C1=NC2(c3cc(Br)ccc3OCC23CC3)C(F)(F)CO1] |

TABLE 2-continued

| Rf | Syn | Structure |
|---|---|---|
| 125 | R22 | 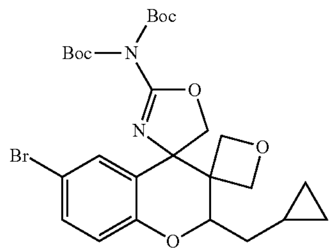 [SMILES: CC(C)(C)OC(=O)N(C(=O)OC(C)(C)C)C1=NC2(CO1)c1cc(Br)ccc1OC(CC1CC1)C21COC1] |
| 126 | R22 | 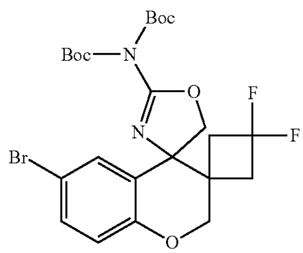 [SMILES: CC(C)(C)OC(=O)N(C(=O)OC(C)(C)C)C1=NC2(CO1)c1cc(Br)ccc1OCC21CC(F)(F)C1] |
| 127 | R22 | 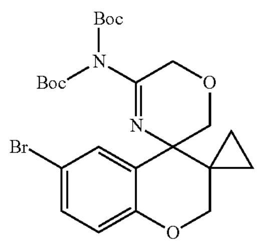 [SMILES: CC(C)(C)OC(=O)N(C(=O)OC(C)(C)C)C1=NC2(COC1)c1cc(Br)ccc1OCC21CC1] |
| 128 | R128 | 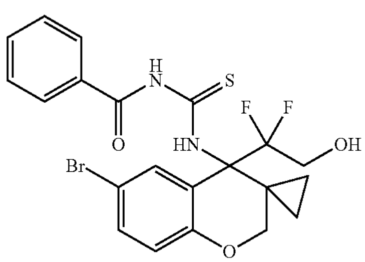 [SMILES: O=C(NC(=S)NC1(C(F)(F)CO)c2cc(Br)ccc2OCC12CC2)c1ccccc1] |
| 129 | R30 | 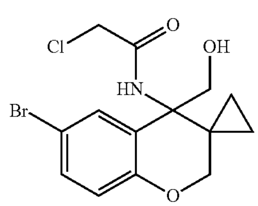 [SMILES: O=C(CCl)NC1(CO)c2cc(Br)ccc2OCC12CC2] |
| 130 | R31 | 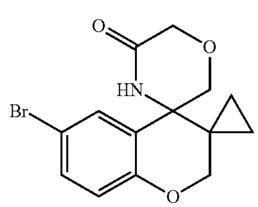 [SMILES: O=C1COCC2(N1)c1cc(Br)ccc1OCC21CC1] |
| 131 | R131 | 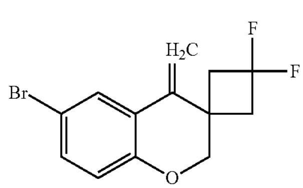 [SMILES: C=C1c2cc(Br)ccc2OCC12CC(F)(F)C2] |
| 132 | R132 | 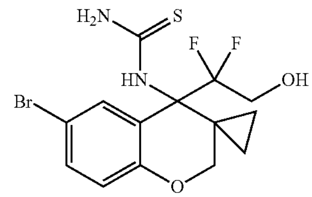 [SMILES: NC(=S)NC1(C(F)(F)CO)c2cc(Br)ccc2OCC12CC2] |
| 133 | R133 | 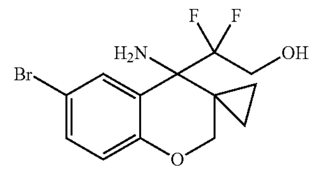 [SMILES: NC1(C(F)(F)CO)c2cc(Br)ccc2OCC12CC2] |
| 134 | R134 | 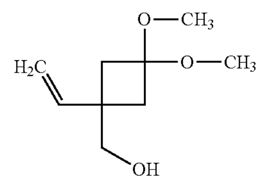 |
| 135 | R59 | 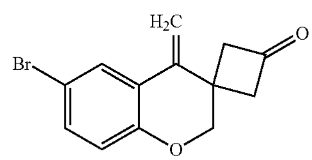 [SMILES: C=C1c2cc(Br)ccc2OCC12CC(=O)C2] |
| 136 | R60 | 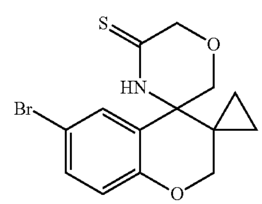 |
| 137 | R137 | 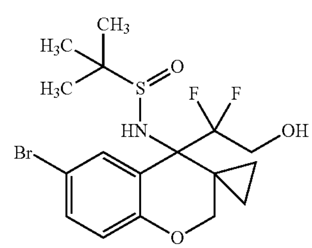 [SMILES: CC(C)(C)S(=O)NC1(C(F)(F)CO)c2cc(Br)ccc2OCC12CC2] |
| 138 | R62 | 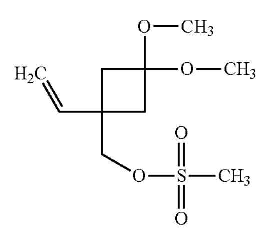 [SMILES: C=CC1(COS(C)(=O)=O)CC(OC)(OC)C1] |
| 139 | R63 | 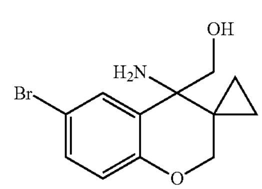 [SMILES: NC1(CO)c2cc(Br)ccc2OCC12CC2] |

TABLE 2-continued
| Rf | Syn | Structure |
|----|-----|-----------|
| 140 | R70 | 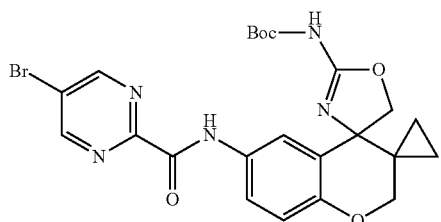 |
| 141 | R70 | 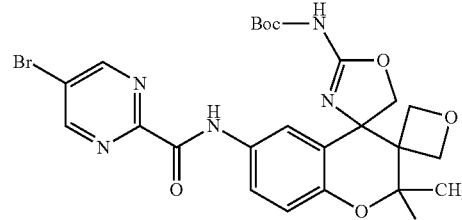 |
| 142 | R70 | 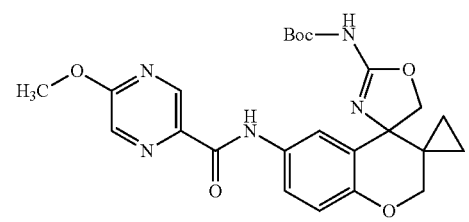 [SMILES: COc1cnc(C(=O)Nc2ccc3c(c2)C2(COC(NC(=O)OC(C)(C)C)=N2)C2(CC2)CO3)cn1] |
| 143 | R70 | 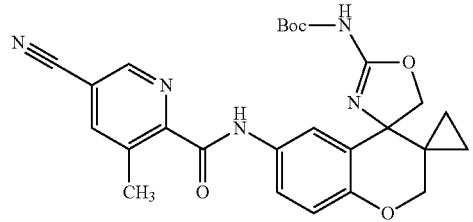 [SMILES: Cc1cc(C#N)cnc1C(=O)Nc1ccc2c(c1)C1(COC(NC(=O)OC(C)(C)C)=N1)C1(CC1)CO2] |
| 144 | R70 | 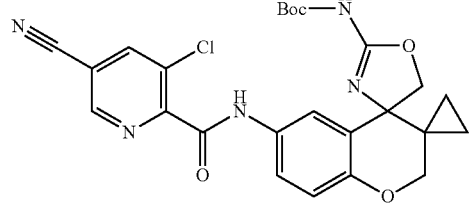 |
| 145 | R70 | 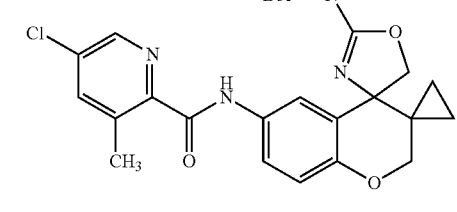 |
| 146 | R70 | 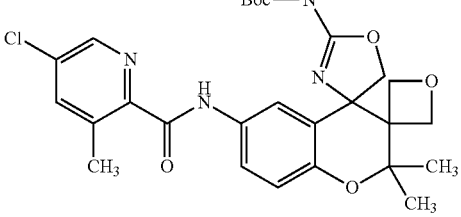 |
| 147 | R70 | 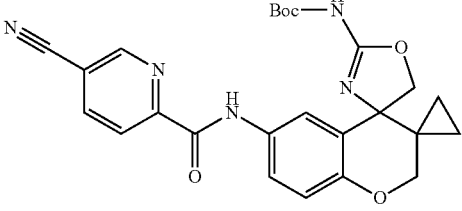 |
| 148 | R70 | 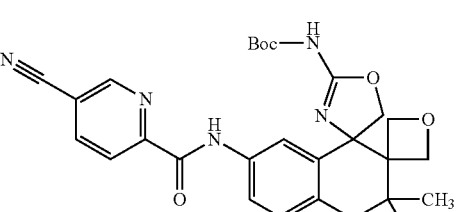 |
| 149 | R149 | 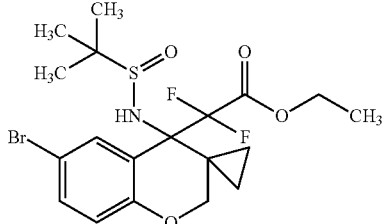 |
| 150 | R83 | 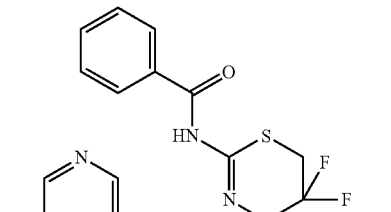 |
| 151 | R151 | 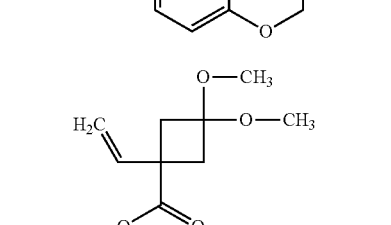 |

TABLE 2-continued
| Rf | Syn | Structure |
|---|---|---|
| 152 | R152 | 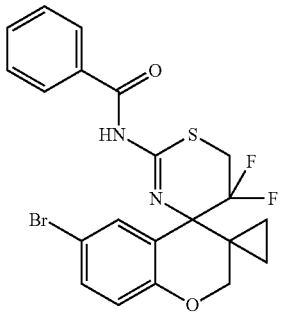 [SMILES: O=C(NC1=NC2(c3cc(Br)ccc3OCC23CC3)C(F)(F)CS1)c1ccccc1] |
| 153 | R112 | 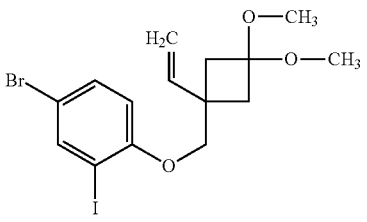 [SMILES: C=CC1(COc2ccc(Br)cc2I)CC(OC)(OC)C1] |
| 154 | R154 | 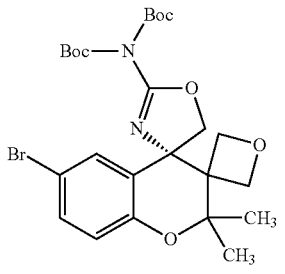 [SMILES: CC(C)(C)OC(=O)N(C(=O)OC(C)(C)C)C1=N[C@@]2(CO1)c1cc(Br)ccc1OC(C)(C)C21COC1] |
| 155 | R155 | 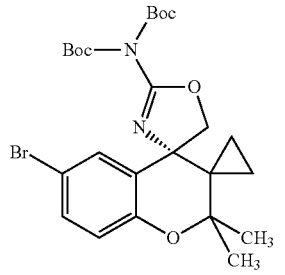 [SMILES: CC(C)(C)OC(=O)N(C(=O)OC(C)(C)C)C1=N[C@@]2(CO1)c1cc(Br)ccc1OC(C)(C)C21CC1] |
| 156 | R156 | 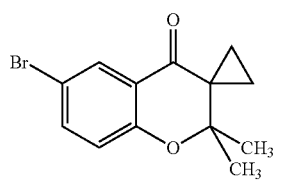 |
| 157 | R157 | 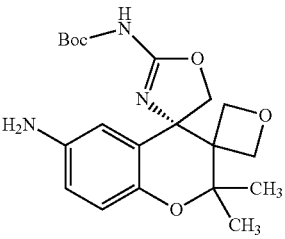 [SMILES: CC(C)(C)OC(=O)NC1=N[C@@]2(CO1)c1cc(N)ccc1OC(C)(C)C21COC1] |
| 158 | R158 | 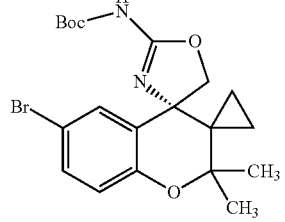 |
| 159 | R159 | 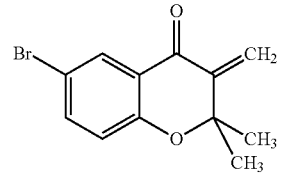 |
| 160 | R160 | 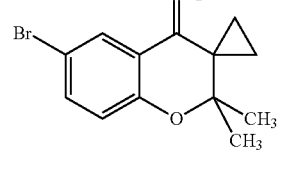 |
| 161 | R161 | 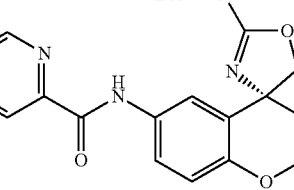 |
| 162 | R161 | 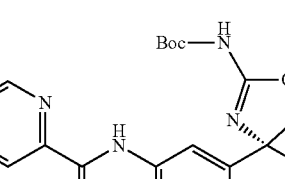 |
| 163 | R161 | 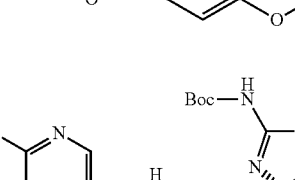 |
| 164 | R165 | 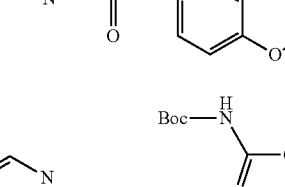 |

TABLE 2-continued

| Rf | Syn | Structure |
|---|---|---|
| 165 | R165 | 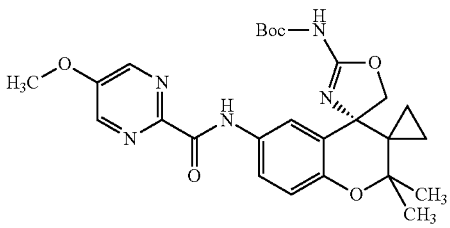 [SMILES: COc1cnc(C(=O)Nc2ccc3c(c2)[C@@]2(COC(NC(=O)OC(C)(C)C)=N2)C2(CC2)C(C)(C)O3)nc1] |
| 166 | R165 | 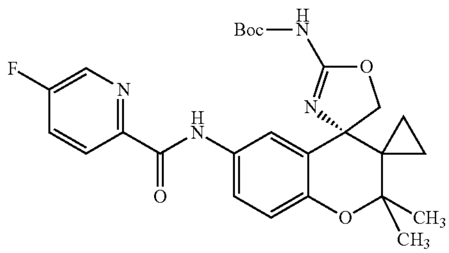 [SMILES: CC(C)(C)OC(=O)NC1=N[C@@]2(CO1)c1cc(NC(=O)c3ccc(F)cn3)ccc1OC(C)(C)C21CC1] |
| 167 | R167 | 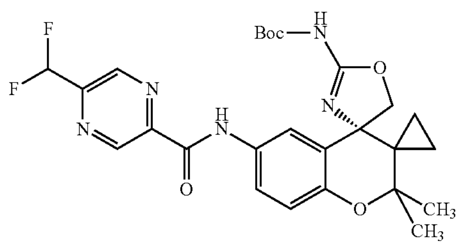 [SMILES: CC(C)(C)OC(=O)NC1=N[C@@]2(CO1)c1cc(NC(=O)c3cnc(C(F)F)cn3)ccc1OC(C)(C)C21CC1] |
| 168 | R161 | 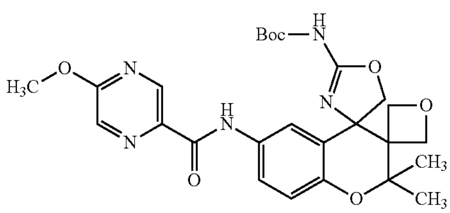 |
| 169 | R169 | 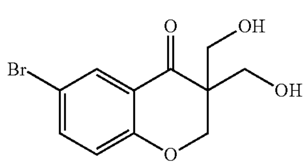 [SMILES: O=C1c2cc(Br)ccc2OCC1(CO)CO] |
| 170 | R96 | 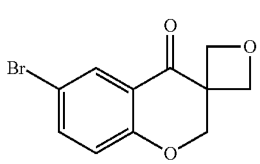 [SMILES: O=C1c2cc(Br)ccc2OCC12COC2] |
| 171 | R171 | 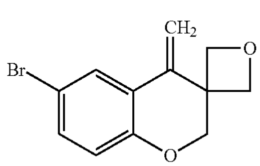 |
| 172 | R64 | |
| 173 | R173 | |
| 174 | R174 | |
| 175 | R64 | |
| 176 | R85 | |

TABLE 3

| Rf | Data |
|---|---|
| 1 | ESI+: 326, 328 |
| 2 | ESI+: 519 |
| 3 | ESI+: 565 |
| 4 | ESI+: 525, 527 |
| 5 | ESI+: 565, 567 |
| 6 | ESI+: 539, 541 |
| 7 | ESI+: 539, 541 |
| 8 | ESI+: 553, 555 |
| 9 | ESI+: 579, 581 |
| 10 | ESI+: 553, 555; a compound prepared from Reference Example 9a |
| 11 | ESI+: 553, 555; a compound prepared from Reference Example 9b |
| 12 | ESI+: 581, 583; a compound prepared from Reference Example 13a |

TABLE 3-continued

| Rf | Data |
|---|---|
| 13 | ESI+: 581, 583; a compound prepared from Reference Example 13b |
| 14 | ESI+: 565, 567; a compound prepared from Reference Example 12a |
| 15 | ESI+: 565, 567; a compound prepared from Reference Example 12b |
| 16 | ESI+: 567, 569; a compound prepared from Reference Example 11a |
| 17 | ESI+: 567, 569; a compound prepared from Reference Example 11b |
| 18 | ESI+: 621, 623; a compound prepared from Reference Example 14a |
| 19 | ESI+: 539, 541; a compound prepared from Reference Example 1a |
| 20 | ESI+: 539, 541; a compound prepared from Reference Example 1b |
| 21 | ESI+: 527, 529 |
| 22 | ESI+: 509, 511 |
| 23 | ESI+: 423, 425 |
| 24 | ESI+: 541, 543 |
| 25 | ESI+: 569, 571 |
| 26 | ESI+: 439, 441 [M + Na]+ |
| 27 | APCI/ESI+: 327 |
| 28 | ESI+: 539 |
| 29 | |
| 30 | ESI+: 376, 378 |
| 31 | ESI+: 340, 342 |
| 32 | EI: 306, 308 |
| 33 | APCI/ESI+: 339 |
| 34 | APCI/ESI+: 307 |
| 35 | EI: 280, 282 |
| 36 | EI: 294, 296 |
| 37 | EI: 264, 266 |
| 38 | EI: 294, 296 |
| 39 | ESI+: 321, 323 |
| 40 | ESI+: 309, 311 |
| 41 | ESI+: 307, 309 |
| 42 | ESI+: 323, 325 |
| 43 | EI: 362, 364 |
| 44 | ESI+: 357, 359 |
| 45 | EI: 268, 270 |
| 46 | ESI+: 321, 323 |
| 47 | EI: 250, 252 |
| 48 | ESI+: 315, 317 |
| 49 | ESI+: 301, 303 |
| 50 | ESI+: 315, 317 |
| 51 | ESI+: 341, 343 |
| 52 | ESI+: 329, 331 |
| 53 | ESI+: 327, 329 |
| 54 | ESI+: 365, 367 [M + Na]+ |
| 55 | ESI+: 383, 385 |
| 56 | ESI+: 377, 379 |
| 57 | ESI+: 341, 343 |
| 58 | EI: 444, 446 |
| 59 | ESI+: 281, 283 |
| 60 | APCI/ESI+: 356, 358 |
| 61 | ESI+: 209 |
| 62 | ESI+: 237 |
| 63 | ESI+: 300, 302 |
| 64 | |
| 65 | ESI+: 601 |
| 66 | ESI+: 346 |
| 67 | ESI+: 390 |
| 68a | ESI+: 196, 198 |
| 68b | ESI+: 196, 198 |
| 69 | ESI+: 153, 155 |
| 70 | ESI+: 469 |
| 71 | ESI+: 485, 487 |
| 72 | ESI+: 513 |
| 73 | ESI+: 529, 531 |
| 74 | ESI+: 547, 549 |
| 75 | ESI+: 503, 505 |
| 76 | ESI+: 515 |
| 77 | ESI+: 561 |
| 78 | ESI+: 356, 358 |
| 79 | ESI+: 571 |
| 80 | ESI+: 576 |
| 81 | ESI+: 525 |
| 82 | ESI+: 538 |
| 83 | |
| 84 | APCI/ESI+: 309 |
| 85 | |
| 86 | |
| 87 | |
| 88 | |
| 89 | ESI+: 602, 604 |
| 90 | |
| 91 | ESI+: 548 |
| 92 | EI: 268, 270 |
| 93 | EI: 316, 318 |
| 94 | APCI/ESI+: 341 |
| 95 | ESI+: 331, 333 [M + Na]+ |
| 96 | EI: 296, 298 |
| 97 | ESI+: 297, 299 |
| 98 | ESI+: 345, 347 [M + Na]+ |
| 99 | ESI+: 311, 313 |
| 100 | ESI+: 331, 333 [M + Na]+ |
| 101 | ESI+: 347, 349 [M + Na]+ |
| 102 | ESI+: 365, 367 |
| 103 | ESI+: 359, 361 |
| 104 | ESI+: 323, 325 |
| 105 | EI: 282, 284 |
| 106 | EI: 284, 286 |
| 107 | EI: 288, 290 |
| 108 | ESI+: 283, 285 |
| 109 | EI: 322, 324 |
| 110 | ESI+: 281, 283 |
| 111 | EI: 254, 256 |
| 112 | EI: 312, 314 |
| 113 | EI: 302, 304 |
| 114 | EI: 266, 268 |
| 115 | EI: 270, 272 |
| 116 | |
| 117 | EI: 406, 408 |
| 118 | |
| 119 | ESI+: 241 [M + Na]+ |
| 120 | ESI+: 615, 617; a compound prepared from Reference Example 15a |
| 121 | ESI+: 615, 617; a compound prepared from Reference Example 15b |
| 122 | ESI+: 473, 475 |
| 123 | ESI+: 579, 581; a compound prepared from Reference Example 16a |
| 124 | ESI+: 559, 561 |
| 125 | ESI+: 579, 581; a compound prepared from Reference Example 16b |
| 126 | ESI+: 559, 561 |
| 127 | ESI+: 523, 525 |
| 128 | ESI+: 497, 499 |
| 129 | ESI+: 360, 362 |
| 130 | ESI+: 324, 326 |
| 131 | EI: 300, 302 |
| 132 | |
| 133 | |
| 134 | ESI+: 195 [M + Na]+ |
| 135 | EI: 278, 280 |
| 136 | ESI+: 340, 342 |
| 137 | |
| 138 | ESI+: 273 [M + Na]+ |
| 139 | ESI+: 284, 286 |
| 140 | ESI+: 530, 532 |
| 141 | ESI+: 574, 576 |
| 142 | ESI+: 482 |
| 143 | ESI+: 490 |
| 144 | ESI+: 510, 512 |
| 145 | ESI+: 499, 501 |
| 146 | ESI+: 543, 545 |
| 147 | ESI+: 476 |
| 148 | ESI+: 520 |
| 149 | ESI+: 480, 482 |
| 150 | APCI/ESI+: 479 |
| 151 | ESI+: 223 [M + Na]+ |
| 152 | ESI+: 479, 481 |
| 153 | EI: 452, 454 |
| 154 | ESI+: 553, 555 |
| 155 | ESI+: 559, 561 [M + Na]+ |

TABLE 3-continued

| Rf | Data |
|---|---|
| 156 | ESI+: 281, 283 |
| 157 | ESI+: 390 |
| 158 | ESI+: 374 |
| 159 | CI+: 267, 269 |
| 160 | ESI+: 279, 281 |
| 161 | ESI+: 529, 531 |
| 162 | ESI+: 573, 575 |
| 163 | ESI+: 526 |
| 164 | ESI+: 513 |
| 165 | ESI+: 510 |
| 166 | ESI+: 497 |
| 167 | ESI+: 530 |
| 168 | ESI+: 526 |
| 169 | ESI+: 287, 289 |
| 170 | EI: 268, 270 |
| 171 | |
| 172 | ESI+: 613 |
| 173 | NMR-CDCl$_3$: 1.33 (s, 6H), 2.32 (br s, 2H), 3.90 (d, J = 11.1 Hz, 2H), 4.02 (d, J = 11.1 Hz, 2H), 5.51 (s, 1H), 5.86 (s 1H), 6.69 (d, J = 8.7 Hz, 1H), 7.31-7.27 (m, 1H), 7.68 (br s, 1 H) |
| 174 | NMR-CDCl$_3$: 1.46 (s, 6H), 4.55 (d, J = 6.6 Hz, 2H), 4.71 (d, J = 6.6 Hz, 2H), 5.33 (s, 1H), 5.73 (s, 1H), 6.70 (d, J = 8.7 Hz, 1H), 7.28 (dd, J = 2.4, 8.7 Hz, 1H), 7.65 (d, J = 2.4 Hz, 1H), |
| 175 | ESI+: 557 |
| 176 | ESI+: 554 |

Reference Example 1a,b

To an ice chilled solution of 6-bromo-4-methylene-4',5'-dihydro-3'H,4H-spiro[chromene-3,2'-furan] (497 mg, 1.77 mmol) in EtOAc (2.5 ml) and MeCN (2.5 ml) was added silver cyanate (397 mg, 2.65 mmol) in an ice bath under an argon atmosphere. To the mixture was added iodine (673 mg, 2.65 mmol). After stirring for 30 minutes in the ice bath and 30 minutes at ambient temperature, the mixture was filtered through celite. The filtrate was washed with saturated aqueous Na$_2$S$_2$O$_3$. The organic layer was washed with brine, dried over Na$_2$SO$_4$, filtered, and the filtrate was evaporated to give an oil. The oil was dissolved in THF (5 mL) and a 2M EtOH solution of NH$_3$ (4.5 ml, 9.0 mmol) was added under ice bath cooling. The mixture was stirred overnight under ice bath cooling and for 1 hour at 70° C. After concentration in vacuo, the residue was diluted with saturated aqueous NaHCO$_3$ and extracted with CHCl$_3$. The organic layer was washed with brine, dried over Na$_2$SO$_4$, filtered, and the filtrate was evaporated off. The residue was purified by silica gel chromatography (CHCl$_3$/EtOH=100:0-90:10) to give less polar diastereomer of 6'-bromo-4,5-dihydro-3H-dispiro[furan-2,3'-chromene-4',4"-[1,3]oxazol]-2"-amine (178 mg) and polar diastereomer of 6'-bromo-4,5-dihydro-3H-dispiro[furan-2,3'-chromene-4',4"-[1,3]oxazol]-2"-amine (367 mg).

Reference Example 6

Under an argon atmosphere, to a mixture of 6-bromo-2,2-dimethyl-4-methylene-4H-spiro[chromene-3,3'-oxetane] (504 mg, 1.71 mmol), silver cyanate (384 mg, 2.56 mmol) and EtOAc-MeCN (1:1, 5.0 mL) was added iodine (649 mg, 2.56 mmol) over 5 minutes in an ice-water bath. After stirring for 30 minutes at the same temperature, the mixture was filtered through celite pad. The filtrate was washed with saturated aqueous Na$_2$S$_2$O$_3$ and brine, dried over MgSO$_4$ and filtered. After concentration of the filtrate at reduced pressure, the residue was dissolved in THF (5.0 mL). The solution was added to 2 M EtOH solution of ammonia (10.7 mL, 21.4 mmol) in an ice-water bath. The mixture was stirred for 1 hour in the bath and 3 hours at 70° C. After cooling down to ambient temperature, NH-silica gel was added to the reaction mixture, and the mixture was concentrated at reduced pressure. The residue was purified with column chromatography on silica gel (CHCl$_3$-EtOH, a linear gradient of EtOH from 0 to 20%) to afford 6'-bromo-2',2'-dimethyldispiro[1,3-oxazole-4,4'-chromene-3',3"-oxetan]-2-amine (483 mg).

Reference Example 19

A mixture of di-tert-butyl {6'-[5-(3-methoxyprop-1-yn-1-yl)pyridin-3-yl]dispiro[1,3-oxazole-4,4'-chromene-3',3"-oxetan]-2-yl}imidodicarbonate (220 mg, 0.372 mmol), silica gel (neutral; 660 mg) and toluene (2.2 mL) was stirred for 3 hours at 100° C. The mixture was cooled down to ambient temperature, and concentrated at reduced pressure. Purification of the residue with column chromatography on silica gel (CHCl$_3$-MeOH, a linear gradient of MeOH from 0 to 10%) afforded 6'-[5-(3-methoxyprop-1-yn-1-yl)pyridin-3-yl]dispiro[1,3-oxazole-4,4'-chromene-3',3"-oxetan]-2-amine (92.4 mg).

Example 27

A mixture of tert-butyl (6'-{[(5-chloropyridin-2-yl)carbonyl]amino}-2',2'-dimethyldispiro[1,3-oxazole-4,4'-chromene-3',3"-oxetan]-2-yl)carbamate (217 mg, 0.410 mmol), silica gel (neutral; 651 mg), and toluene (4 mL) was stirred for 80 minutes at 120° C. The reaction mixture was cooled down to ambient temperature and concentrated at reduced pressure. Purification of the residue with column chromatography on silica gel (eluted with EtOH/CHCl$_3$=0/100 to 20/80) afforded N-(2-amino-2',2'-dimethyldispiro[1,3-oxazole-4,4'-chromene-3',3"-oxetan]-6'-yl)-5-chloropyridine-2-carboxamide (144 mg).

Reference Example 31

To a mixture of tert-butyl (6'-{[(5-fluoropyridin-2-yl)carbonyl]amino}dispiro[cyclopropane-1,3'-chromene-4',4"-[1,3]oxazol]-2"-yl)carbamate (135 mg, 0.288 mmol) and CH$_2$Cl$_2$ (5.4 mL) was added trifluoroacetic acid (1.30 mL, 17.0 mmol) at ambient temperature. After stirring for 2 hours at the same temperature, the mixture was concentrated at reduced pressure. The residue was partitioned between CHCl$_3$ and saturated aqueous NaHCO$_3$. The organic layer was washed with water, dried over Na$_2$SO$_4$ and filtered. The filtrate was concentrated at reduced pressure, and the residue was purified with column chromatography on silica gel (CHCl$_3$-EtOH, a linear gradient of EtOH from 0 to 20%) to afford N-(2"-aminodispiro[cyclopropane-1,3'-chromene-4',4"-[1,3]oxazol]-6'-yl)-5-fluoropyridine-2-carboxamide (43.6 mg).

Reference Example 39

The mixture of di-tert-butyl[6'-(6-methoxypyridin-2-yl)dispiro[1,3-oxazole-4,4'-chromene-3',3"-oxetan]-2-yl]imidodicarbonate (160 mg, 0.289 mmol) and TsOH.H$_2$O (275 mg, 1.45 mmol) in MeCN (3.2 mL) was stirred for 4 hours at 40° C. After dilution with CHCl$_3$, the organic layer was washed with saturated aqueous NaHCO$_3$ and brine, dried over Na$_2$SO$_4$, and concentrated in vacuo. The residue was purified by silica gel chromatography (CHCl$_3$:MeOH=99:1-95:5) and then the residue was washed with EtOAc to afford 6'-(6-methoxypyridin-2-yl)dispiro[1,3-oxazole-4,4'-chromene-3',3"-oxetan]-2-amine (40 mg).

Reference Example 40

To a solution of 2-fluoro-6-iodobenzonitrile (1560 mg, 6.32 mmol) in THF (16 mL) at −78° C. was added n-butyllithium (2.64M solution in n-hexane, 2.39 ml, 6.32 mmol) dropwise. The mixture was stirred for 0.5 hour at −78° C. and to the solution was added a solution of N-(6-bromo-4H-spiro[chromene-3,1'-cyclopropan]-4-ylidene)-2-methylpropane-2-sulfinamide (1500 mg, 4.21 mmol) in THF (5 mL). The mixture was stirred for 1 hour at −78° C. and overnight at room temperature. To the mixture was added saturated aqueous $NH_4Cl$. The mixture was extracted with EtOAc and the organic layer was concentrated in vacuo. The residue was purified by silica gel chromatography (hexane/AcOEt=100:0-0:100, then $CHCl_3$:MeOH=85:15) to give 6'-bromo-4"-fluorodispiro[cyclopropane-1,3'-chromene-4',1"-isoindol]-3"-amine (469 mg).

Reference Example 41

6-Bromo-4-methylene-4H-spiro[chromene-3,3'-oxetane] (1.50 g, 5.62 mmol) was added to a mixture of silver thiocyanate (3.73 g, 22.5 mmol), iodine (2.85 g, 11.2 mmol) and toluene (15 mL) in an ice-water bath. After stirring overnight at ambient temperature, the mixture was filtered through celite pad (washed with EtOAc). The filtrate was washed with saturated aqueous $Na_2S_2O_3$ and brine, dried over $MgSO_4$ and filtered. The filtrate was concentrated at reduced pressure. A mixture of the residue and THF (15 mL) was added to ammonia (2.0 M in EtOH, 30 mL) in an ice-water bath. After stirring for 1 hour at the same temperature, the mixture was stirred for 2.5 days at ambient temperature. The mixture was partitioned with MeOH—$CHCl_3$ (1:9) and water. The organic layer was dried over $Na_2SO_4$ and filtered. The filtrate was concentrated at reduced pressure, and purification of the residue with column chromatography on silica gel ($CHCl_3$-EtOH, a linear gradient of EtOH from 0 to 5%) afforded 6'-bromodispiro[oxetane-3,3'-chromene-4',4"-[1,3]thiazol]-2"-amine (1.26 g).

Reference Example 43

The mixture of di-tert-butyl (6'-bromodispiro[1,3-oxazole-4,4'-chromene-3',3"-oxetan]-2-yl)imidodicarbonate (150 mg, 0.286 mmol), 3-chloropyridin-2-amine (184 mg, 1.43 mmol), (1E,4E)-1,5-diphenylpenta-1,4-dien-3-one-palladium (3:2) (52 mg, 0.057 mmol), di-tert-butyl(2',4',6'-triisopropylbiphenyl-2-yl)phosphine (97 mg, 0.23 mmol), and $Cs_2CO_3$(279 mg, 0.857 mmol) in 1,4-dioxane (7.5 ml) was stirred for 48 hours at 100° C. The reaction mixture was cooled down to ambient temperature, and partitioned with $CHCl_3$ and water. The organic layer was dried over $Na_2SO_4$, and filtered. The residue was dissolved in toluene, and was added silica gel (neutral), and stirred at 130° C. for 3 hours. The mixture was concentrated under reduced pressure, and purified by silica gel column chromatography ($CHCl_3$/MeOH=100:0-85:15) to give an amorphous, which was washed with $CHCl_3$/hexane to give 6'-(3-chloropyridin-2-yl)aminodispiro[1,3-oxazole-4,4'-chromene-3',3"-oxetane]-2-amine (28 mg).

Reference Example 46

To a stirred mixture of palladium (II) acetate (7.9 mg, 0.035 mmol) and biphenyl-2-yl(di-tert-butyl)phosphine (5.3 mg, 0.018 mmol) in THF (5 mL) under argon atmosphere was added di-tert-butyl (6'-bromotrispiro[cyclobutane-1,2'-chromene-4',4"-[1,3]oxazole-3',3'"-oxetan]-2"-yl)imidodicarbonate (100 mg, 0.177 mmol) followed by isobutylzinc bromide (0.5 M THF solution, 1.1 mL). The reaction mixture was stirred at room temperature for 17 hours, and then the reaction was quenched with $H_2O$ and brine. The resulting mixture was extracted with chloroform 3 times. The combined organic layer was dried over magnesium sulfate and concentrated under reduced pressure. The crude product was dissolved in toluene (6 mL). To the solution was added silica gel (neutral; 600 mg), and the resulting suspension was stirred at 100° C. for 1 hour. After cooling and concentration, the residue was purified by silica gel column chromatography (EtOH/$CHCl_3$=0:100-20:80) followed by column chromatography (NH-silica gel, EtOAc/hexane=20:80-100:0) to afford 6'-isobutyltrispiro[cyclobutane-1,2'-chromene-4',4"-[1,3]oxazole-3',3'"-oxetan]-2"-amine (20 mg).

Reference Example 48

To a stirred solution of di-tert-butyl[6'-(5-bromopyridin-3-yl)trispiro[cyclobutane-1,2'-chromene-4',4"-[1,3]oxazole-3',3'"-oxetan]-2"-yl]imidodicarbonate (48 mg, 0.075 mmol) in $Et_3N$ (0.67 ml) were added ethynylcyclopropane (0.063 mL, 0.75 mmol), $PdCl_2(PPh_3)_2$ (10 mg, 0.015 mmol) and CuI (5.7 mg, 0.030 mmol) at room temperature and the mixture was sealed and irradiated with microwave at 150° C. for 1 hour. To this mixture was added activated carbon (ca. 100 mg) and the mixture was stirred for 1 hour to remove palladium residues. The mixture was passed through a pad of Celite. The filtrate was evaporated to give a residue. To the solution of the residue in toluene (3 ml) was added silica gel (500 mg) and the mixture was refluxed for 2 hours. The mixture was passed through a pad of Celite and the filtrate was evaporated to give a crude product, which was purified with column chromatography (MeOH in $CHCl_3$=0 to 10%) to give 6'-[5-(cyclopropylethynyl)pyridin-3-yl]trispiro[cyclobutane-1,2'chromene-4',4"-[1,3]oxazole-3',3'"-oxetan]-2"-amine (5 mg).

Reference Example 49

A suspension of 6'-(2-methylimidazo[1,2-a]pyridin-6-yl)trispiro[cyclobutane-1,2'-chromene-4',4"-[1,3]oxazole-3',3'"-oxetan]-2"-amine (66 mg, 0.16 mmol), acetic acid (27 µl, 0.06 mmol) and $PtO_2$ (13 mg) in EtOH (3.3 ml) was stirred at room temperature under the hydrogen atmosphere at 3 atm for 8 hours. To the mixture was added acetic acid (63 µl), and the mixture was stirred at room temperature under hydrogen atmosphere at 3 atm for 38 hours. The mixture was filtrated through celite pad. And then the filtrate was concentrated under reduced pressure. The obtained residue was purified by silicagel column chromatography (28% $NH_4OH$/EtOH/$CHCl_3$=2:20:80) followed by trituration in $iPr_2O$ and filtration to give 6'-(2-methyl-5,6,7,8-tetrahydroimidazo[1,2-a]pyridin-6-yl)trispiro[cyclobutane-1,2'-chromene-4',4"-[1,3]oxazole-3',3'"-oxetan]-2"-amine (56 mg).

Reference Example 51a,b

2',2'-Dimethyl-6'-(pyrimidin-5-yl)dispiro[1,3-oxazole-4,4'-chromene-3',3"-oxetan]-2-amine (489 mg, 1.39 mmol) was subjected to chromatography using supercritical $CO_2$/[MeOH with 0.1% diethylamine] (70:30) on Chiralcel OD-H column (Daicel, 10×250 mm) eluting at a flow rate 10 mL/minute (40° C. column temperature). The first peak (retention time=3.44 minutes) provided an enantiomer of 2',2'- dimethyl-6'-(pyrimidin-5-yl)dispiro[1,3-oxazole-4,4'-chromene-3',3"-oxetan]-2-amine (220 mg), and the second peak (retention time=6.92 minutes) provided the other enantiomer of 2',2'-dimethyl-6'-(pyrimidin-5-yl)dispiro[1,3-oxazole-4,4'-chromene-3',3"-oxetan]-2-amine (215 mg).

Reference Example 52a,b

6'-[5-(prop-1-yn-1-yl)pyridin-3-yl]dispiro[cyclopropane-1,3'-chromene-4',4"-[1,3]oxazol]-2"-amine (330 mg, 0.96 mmol) was subjected to chromatography using supercritical $CO_2$/[EtOH with 0.1% diethylamine] (65/35) on Chiralcel OZ-H column (10×250 mm) eluting at a flow rate 10 mL/minute (40° C. column temperature). The first peak (retention time=3.62 minutes) was concentrated in vacuo, and dissolved in EtOAc (3 mL) and then hexane (20 mL) was added. The resulting precipitate was collected by filtration, washed with hexane and dried in vacuo to give an enantiomer of 6'-[5-(prop-1-yn-1-yl)pyridin-3-yl]dispiro[cyclopropane-1,3'-chromene-4',4"-[1,3]oxazol]-2"-amine (108 mg). The second peak (retention time=6.27 minutes) was concentrated in vacuo, and dissolved in EtOAc (3 mL) and hexane (20 mL) was added. The resulting precipitate was collected by filtration, washed with hexane and dried in vacuo to give the other enantiomer of 6'-[5-(prop-1-yn-1-yl)pyridin-3-yl]dispiro[cyclopropane-1,3'-chromene-4',4"-[1,3]oxazol]-2"-amine (80 mg).

Reference Example 53a,b

6'-[5-(prop-1-yn-1-yl)pyridin-3-yl]dispiro[1,3-oxazole-4,4'-chromene-3',3"-oxetan]-2-amine (400 mg, 1.39 mmol) was subjected to chromatography using supercritical $CO_2$/[MeOH with 0.1% diethylamine] (70:30) on Chiralcel AD-H column (10×250 mm) eluting at a flow rate 10 mL/minute (40° C. column temperature). The first peak (retention time=5.81 minutes) provided an enantiomer of 6'-[5-(prop-1-yn-1-yl)pyridin-3-yl]dispiro[1,3-oxazole-4,4'-chromene-3',3"-oxetan]-2-amine (160 mg), and the second peak (retention time=9.25 minutes) provided the other enantiomer of 6'-[5-(prop-1-yn-1-yl)pyridin-3-yl]dispiro[1,3-oxazole-4,4'-chromene-3',3"-oxetan]-2-amine (170 mg)

Reference Example 54

A mixture of di-tert-butyl (6'-bromo-2',2'-dimethyldispiro[oxetane-3,3'-chromene-4',4"-[1,3]thiazol]-2"-yl)imidodicarbonate (268 mg, 0.471 mmol), pyrimidin-5-ylboronic acid (175 mg, 1.41 mmol), bis(triphenylphosphine)palladium(II) dichloride (33.0 mg, 0.047 mmol) and $Na_2CO_3$ (150 mg, 1.41 mmol) in dioxane-water (4:1, 5.4 mL) was stirred for 1.5 hours at 100° C. Tetrakis(triphenylphosphine)palladium(0) (272 mg, 0.235 mmol) was added to the mixture and the mixture was stirred for 1.5 hours at 100° C. To the mixture was added charcoal and the mixture was stirred for 30 minutes at 50° C. The mixture was filtered through celite pad (eluted with EtOAc) and the filtrate was washed with water and brine. The organic layer was dried over $MgSO_4$ and filtered, and the filtrate was concentrated at reduced pressure. To the residue were added toluene (2.7 mL) and silica gel (neutral; 804 mg), and the mixture was stirred for 1 hour at 110° C. After concentration of the reaction mixture at reduced pressure, the residue was purified with column chromatography on silica gel ($CHCl_3$-EtOH, a linear gradient of EtOH from 0 to 20%), then re-purified with column chromatography on amino silica gel (Hexane-EtOAc, a linear gradient of EtOAc from 0 to 90%). The purified product was dissolved in dioxane (5.0 mL) and HCl (4 M in dioxane, 0.049 mL, 0.198 mmol) was added. The mixture was stirred for 2 hours at ambient temperature. After concentration at reduced pressure, the residue was triturated with IPE, collected by filtration and washed with IPE. The solid was dried under reduced pressure at 30° C. to afford 2',2'-dimethyl-6'-(pyrimidin-5-yl)dispiro[oxetane-3,3'-chromene-4',4"-[1,3]thiazol]-2"-amine hydrochloride (62.6 mg).

Reference Example 55

Under argon atmosphere, to a mixture of di-tert-butyl (6'-bromodispiro[1,3-oxazole-4,4'-chromene-3',3"-oxetan]-2-yl)imidodicarbonate (300 mg, 0.571 mmol), dioxane (3.0 mL) and water (1.5 mL) were added 1H-indazol-4-ylboronic acid (185 mg, 1.14 mmol), $K_2CO_3$ (237 mg, 1.71 mmol) and bis(triphenylphosphine)palladium(II) dichloride (40 mg, 0.057 mmol), and the mixture was stirred for 3 hours at 100° C. The reaction mixture was cooled down to ambient temperature, partitioned between $H_2O$ and 10% MeOH in $CHCl_3$. The organic layer was dried over $Na_2SO_4$ and filtered, and the filtrate was concentrated at reduced pressure. The residue was dissolved with dioxane (3.0 mL), and silica gel (neutral; 900 mg) was added to the mixture. After stirring for 2.5 hours at 110° C., the reaction mixture was cooled down to ambient temperature, and concentrated at reduced pressure. Purification of the residue with column chromatography on silica gel ($CHCl_3$-EtOH, a linear gradient of EtOH from 0 to 20%) afforded 6'-(1H-indazol-4-yl)dispiro[1,3-oxazole-4,4'-chromene-3',3"-oxetan]-2-amine (142 mg).

Reference Example 61

The mixture of di-tert-butyl[6'-(4,4,5,5-tetramethyl-1,3,2-dioxaborolan-2-yl)dispiro[cyclopropane-1,3'-chromene-4',4"-[1,3]oxazol]-2"-yl]imidodicarbonate (140 mg, 0.25 mmol), 5-bromo-1H-pyrrolo[2,3-b]pyridine (87 mg, 0.44 mmol), $Pd(PPh_3)_4$ (58 mg, 0.050 mmol), and $Na_2CO_3$ (80 mg, 0.76 mmol) in 1,4-dioxane-$H_2O$ (2.8 ml, 4:1) was stirred for 7 hours at 100° C. After dilution with EtOAc and $H_2O$, the organic layer was washed with $H_2O$, dried over $MgSO_4$, and concentrated in vacuo. The residue was purified by silica gel chromatography ($CHCl_3$:MeOH=100:0-85:15) to give white solid. The solid was washed by diisopropyl ether to give 6'-(1H-pyrrolo[2,3-b]pyridin-5-yl)dispiro[cyclopropane-1,3'-chromene-4',4"-[1,3]oxazol]-2"-amine (42 mg).

Reference Example 65

A mixture of di-tert-butyl[2',2'-dimethyl-6'-(4,4,5,5-tetramethyl-1,3,2-dioxaborolan-2-yl)dispiro[1,3-oxazole-4,4'-chromene-3',3"-oxetan]-2-yl]imidodicarbonate (282 mg, 0.470 mmol), 2-bromo-4-methoxypyridine (221 mg, 1.17 mmol), tetrakis(triphenylphosphine)palladium(0) (271 mg, 0.235 mmol) and $Na_2CO_3$ (149 mg, 1.41 mmol) in dioxane-water (4:1, 5.6 mL) was stirred for 8 hours at 100° C. The mixture was diluted with MeOH—$CHCl_3$ (1:9) and washed with water, then the organic layer was dried over $MgSO_4$ and filtered. The filtrate was concentrated at reduced pressure. To the residue were added toluene (2.8 mL) and silica gel (neutral; 846 mg), and the mixture was stirred for 3 hours at 120° C. After concentration of the reaction mixture at reduced pressure, the residue was purified with column chromatography on silica gel ($CHCl_3$-EtOH, a linear gradient of EtOH from 0 to 20%) afforded 6'-(4-methoxypyridin-2-yl)-2',2'-dimethyldispiro[1,3-oxazole-4,4'-chromene-3',3"-oxetan]-2-amine (146 mg).

Reference Example 75

A mixture of di-tert-butyl (6'-bromotrispiro[cyclobutane-1,2'-chromene-4',4"-[1,3]oxazole-3',3"'-oxetan]-2"-yl)imidodicarbona to (300 mg, 0.531 mmol), 5-methylpyridine-3-boronic acid (145 mg, 1.06 mmol), bis(triphenylphosphine)palladium(II) dichloride (37 mg, 0.053 mmol) and $Na_2CO_3$ (169 mg, 1.59 mmol) in dioxane-$H_2O$ (4:1, 6.0 mL) was stirred for 1 hour at 100° C. To the mixture was added charcoal and the mixture was stirred for 10 minutes at 50° C. The mixture was filtered through celite pad (eluted with EtOAc) and the filtrate was washed with $H_2O$ and brine. The organic layer was dried over $MgSO_4$ and filtered, and the filtrate was concentrated under reduced pressure. To the residue were added toluene (3.0 mL) and silica gel (neutral; 900 mg), and the mixture was stirred for 3 hours at 120° C. After concentration of the reaction mixture at reduced pressure, the residue was purified with column chromatography on silica gel ($CHCl_3$-EtOH, a linear gradient of EtOH from 0 to 20%) to afford 6'-(5-methylpyridin-3-yl)trispiro[cyclobutane-1,2'-chromene-4',4"-[1,3]oxazole-3',3"'-oxetan]-2"-amine (151 mg).

Reference Example 108

The mixture of 6'-bromodispiro[1,3-oxazole-4,4'-chromene-3',3"-oxetan]-2-amine (650 mg, 2.00 mmol), [5-(prop-1-yn-1-yl)pyridin-3-yl]boronic acid (644 mg, 4.00 mmol), (1E,4E)-1,5-diphenylpenta-1,4-dien-3-one-palladium (3:2) (92 mg, 0.10 mmol), dicyclohexyl(2',6'-dimethoxybiphenyl-2-yl)phosphine (164 mg, 0.400 mmol), and $K_3PO_4$ (1.70 g, 8.00 mmol) in DMF (13 mL) was stirred for 16 hours at 110° C. under argon atmosphere. The precipitate formed was removed by filtration with celite and washed with $CHCl_3$. The filtrate was concentrated in vacuo. The residue was purified by silica gel chromatography ($CHCl_3$:MeOH=99:1-95:5) to give 6'-[5-(prop-1-yn-1-yl)pyridin-3-yl]dispiro[1,3-oxazole-4,4'-chromene-3',3"-oxetan]-2-amine (310 mg).

Reference Example 114

A mixture of 6'-bromo-5H-dispiro[1,4-oxazinane-3,4'-chromene-3',3"-oxetane]-5-thione (200 mg, 0.561 mmol) and ammonia (2 M in EtOH, 6.0 mL) was stirred for 1 week at ambient temperature. The reaction mixture was concentrated at reduced pressure, and the residue was purified with column chromatography on amino silica gel ($CHCl_3$-EtOAc, a linear gradient of EtOAc from 0 to 50% then $CHCl_3$-EtOH, a linear gradient of EtOH from 0 to 20%) to afford 6'-bromo-6H-dispiro[1,4-oxazine-3,4'-chromene-3',3"-oxetan]-5-amine (123 mg).

Reference Example 115

A mixture of di-tert-butyl (6'-bromotrispiro[cyclobutane-1,2'-chromene-4',4"-[1,3]oxazole-3',3"'-oxetan]-2"-yl)imidodicarbonate (300 mg, 0.531 mmol), 4,4,4',4',5,5,5',5'-octamethyl-2,2'-bi-1,3,2-dioxaborolane (150 mg, 0.584 mmol), potassium acetate (91.1 mg, 0.928 mmol) and bis(triphenylphosphine)palladium(II) dichloride (37 mg, 0.053 mmol) in dioxane (2.4 mL) was stirred for 7 hours at 100° C. To the mixture was added 3-bromo-2-cyanopyridine (243 mg, 1.33 mmol), $Na_2CO_3$ (225 mg, 2.12 mmol) and water (0.60 mL), and the mixture was stirred for 2 hours at 100° C. The mixture was treated with charcoal, and filtered off. The filtrate was partitioned between EtOAc and water. The organic layer was washed with brine, dried over $MgSO_4$, filtered, and the filtrate was evaporated to give a pale brown oil. The oil was dissolved in toluene (3.0 mL) and to the mixture was added silica gel (neutral; 900 mg). The mixture was refluxed for 1 hour. The solvent was evaporated off. Silica gel column chromatography ($CHCl_3$-EtOH, a linear gradient of EtOH from 0 to 10%) afforded a solid. The solid was triturated in $Et_2O$, collected by filtration, washed with $Et_2O$ and dried at reduced pressure at 70° C. to give 3-(2"-amino-trispiro[cyclobutane-1,2'-chromene-4',4"-[1,3]oxazole-3',3"'-oxetan]-6'-yl)pyridine-2-carbonitrile (141 mg).

Reference Example 116

A mixture of 3-bromo-2-fluoro-5-methylpyridine (202 mg, 1.06 mmol), 4,4,4',4',5,5,5',5'-octamethyl-2,2'-bi-1,3,2-dioxaborolane (300 mg, 1.17 mmol), potassium acetate (208 mg, 2.12 mmol) and $PdCl_2(PPh_3)_2$ (37 mg, 0.053 mmol) in dioxane (4 mL) was stirred for 3 hours at 100° C. To the mixture was added di-tert-butyl (6'-bromotrispiro[cyclobutane-1,2'-chromene-4',4"-[1,3]oxazole-3',3"'-oxetan]-2"-yl) imidodicarbonate (300 mg, 0.531 mmol), sodium carbonate (225 mg, 2.12 mmol) and $H_2O$ (1 mL), and the mixture was stirred for 1.5 hours at 100° C. The mixture was treated with charcoal, and filtered off. The filtrate was partitioned between EtOAc and water. The organic layer was washed with brine, dried over $MgSO_4$, filtered, and the filtrate was evaporated to give a pale brown oil. The oil was dissolved in toluene (5 mL) and to the mixture was added silicagel (neutral; 600 mg). The mixture was refluxed for 1 hour. The solvent was evaporated off. Silicagel column chromatography ($CHCl_3$-EtOH, linear gradient of EtOH from 0 to 20%) afforded a solid. The solid was triturated in $Et_2O$ and collected by filtration, washed with $Et_2O$ and dried in vacuo at 70° C. to give 6'-(2-fluoro-5-methylpyridin-3-yl)trispiro[cyclobutane-1,2'-chromene-4',4"-[1,3]oxazole-3',3"'-oxetan]-2"-amine (130 mg).

Reference Example 136

A mixture of di-tert-butyl (6'-bromotrispiro[cyclobutane-1,2'-chromene-4',4"-[1,3]oxazole-3',3"'-oxetan]-2"-yl)imidodicarbonate (14.1 mg), 2-fluoro-5-methoxyphenylboronic acid (12.7 mg), $PdCl_2(PPh_3)_2$ (5.3 mg) and 1M aqueous $Na_2CO_3$ (0.1 mL) in dioxane (0.4 mL) was stirred for 2 hours at 100° C. The mixture was filtered by using Chem Elut cartridges (Agilent Technologies) and washed with $CHCl_3$. The filtrate was evaporated to give a brown oil. The oil was dissolved in toluene (0.5 mL) and to the mixture was added silicagel (neutral; 50 mg). The mixture was stirred for 1 hour at 100° C. The mixture was filtered and washed with $CHCl_3$. The filtrate was evaporated. The residue was purified with HPLC (Column: Waters SunFire™ Prep $C_{18}$ OBD™ 5 micrometer, 19×100 mm; MeOH/0.1% aqueous HCOOH 11/89 to 95/5(v/v)) and afforded 6'-(2-fluoro-5-methoxyphenyl)trispiro[cyclobutane-1,2'-chromene-4',4"-[1,3]oxazole-3',3"'-oxetan]-2"-amine (1.5 mg).

Reference Example 146

A mixture of di-tert-butyl (6'-bromo-2',2'-dimethyldispiro [1,3-oxazole-4,4'-chromene-3',3"-oxetan]-2-yl)imidodicarbonate (13.8 mg), 3-chloro-5-fluorophenylboronic acid (8.7 mg), $Pd(PPh_3)_4$ (2.9 mg) and 1M aqueous $Na_2CO_3$ (0.063 mL) in dioxane (0.25 mL) was stirred for 12 hours at 100° C. The mixture was filtered by using Chem Elut cartridges and washed with $CHCl_3$. The filtrate was evaporated. The residue was purified with HPLC (Column: Waters SunFire™ Prep $C_{18}$ OBD™ 5 micrometer, 19×100 mm; MeOH/0.1% aqueous HCOOH 11/89 to 95/5(v/v)) and afforded 6'-(3-chloro-5-fluorophenyl)-2',2'-dimethyldispiro[1,3-oxazole-4,4'-chromene-3',3"-oxetan]-2-amine (4.6 mg).

Reference Example 174

A mixture of di-tert-butyl (6'-bromo-2',2'-dimethyldispiro[1,3-oxazole-4,4'-chromene-3',3"-oxetan]-2-yl)imidodicarbonate (13.8 mg), indole-5-boronic acid (8.1 mg), $PdCl_2$ (dppf) (2.0 mg) and 1M aqueous $K_2CO_3$ (0.063 mL) in dioxane (0.25 mL) was stirred for 12 hours at 100° C. The mixture was filtered by using Chem Elut cartridges and washed with $CHCl_3$. The filtrate was evaporated. The residue was purified with HPLC (Column: Waters SunFire™ Prep $C_{18}$ OBD™ 5 micrometer, 19×100 mm; MeOH/0.1% aqueous HCOOH 11/89 to 95/5(v/v)) and afforded 6'-(1H-indol-5-yl)-2',2'-dimethyldispiro[1,3-oxazole-4,4'-chromene-3',3"-oxetan]-2-amine (4.5 mg).

Reference Example 198

To a solution of N-[5",5"-difluoro-6'-(pyrimidin-5-yl)-5",6"-dihydrodispiro[cyclopropane-1,3'-chromene-4',4"-[1,3]thiazin]-2"-yl]benzamide (76 mg, 0.16 mmol) in ethanol (4 mL) were added N-hydroxymethanamine hydrochloride (133 mg, 1.59 mmol) and pyridine (126 mg, 1.59 mmol), and the mixture was stirred for 27 hours at 70° C. After cooling, $H_2O$ and brine were added and the mixture was extracted with chloroform. The organic layer was dried over $MgSO_4$ and concentrated. The residue was purified by silica gel chromatography (EtOAc/hexane=50:50-100:0 and then EtOH/$CHCl_3$=5:95) and a resultant solid was washed with $iPr_2O$ to give 5",5"-difluoro-6'-(pyrimidin-5-yl)-5",6"-dihydrodispiro[cyclopropane-1,3'-chromene-4',4"-[1,3]thiazin]-2"-amine (36 mg).

Reference Example 214

A suspension of 6'-bromo-5"H-dispiro[cyclopropane-1,3'-chromene-4',3"-[1,4]oxazinane]-5"-thione (391 mg, 1.15 mmol) in 2M solution of ammonia in ethanol (60 mL, 120 mmol) was treated with tert-butylhydroperoxide (5.0-6.0 M solution in decane, 4.60 mL). The mixture was stirred at room temperature for 1 hour, followed by the addition of methanol (10 mL). After stirring at room temperature for 5 hours, insoluble material was filtered off. The filtrate was poured into saturated aqueous sodium hydrogen carbonate and extracted with chloroform. The organic layer was washed three times with saturated aqueous sodium hydrogen carbonate, dried over sodium sulfate, and evaporated. The residue was purified by silica gel chromatography (NH-silica gel, hexane:EtOAc=100:0-0:100) to give 6'-bromo-6"H-dispiro[cyclopropane-1,3'-chromene-4',3"-[1,4]oxazin]-5"-amine (247 mg).

Reference Example 215

In the same manner as in the method of Preparation Example 83 and Reference Example 31, 6'-(pyrimidin-5-yl)-6"H-dispiro[cyclopropane-1,3'-chromene-4',3"-[1,4]oxazin]-5"-amine was prepared with using di-tert-butyl (6'-bromo-6"H-dispiro[cyclopropane-1,3'-chromene-4',3"-[1,4]oxazin]-5"-yl)imidodicarbonate as a starting material.

Reference Example 216

To a solution of 1-[6-bromo-4-(1,1-difluoro-2-hydroxyethyl)-4H-spiro[chromene-3,1'-cyclopropan]-4-yl]thiourea (268 mg, 0.682 mmol) in MeOH (2.7 mL) were added methyliodide (967 mg, 6.82 mmol) and 1M aqueous NaOH (0.68 mL, 0.68 mmol). The mixture was stirred for 3 hours at 60° C. After cooling, to the mixture were added $H_2O$ and brine. The mixture was extracted with $CH_2Cl_2$. The extract was dried over $MgSO_4$ and concentrated.

Purification using silicagel column chromatography (EtOAc-hexane, a linear gradient of EtOAc from 1 to 100%) afforded a solid (177 mg). To a solution of the solid in MeOH (2.7 mL) was added 1M aqueous NaOH (0.68 mL, 0.68 mmol). The mixture was stirred for 5 hours at 60° C. After cooling, to the mixture were added $H_2O$ and brine. The mixture was extracted with EtOAc. The extract was dried over $MgSO_4$ and concentrated. Purification using silicagel column chromatography (EtOAc-hexane, a linear gradient of EtOAc from 1 to 100%) afforded 6'-bromo-5",5"-difluoro-5",6"-dihydrodispiro[cyclopropane-1,3'-chromene-4',4"-[1,3]oxazin]-2"-amine (145 mg).

Reference Example 217

To a solution of 6-bromo-2,2-dimethyl-4-methylene-4H-spiro[chromene-3,1'-cyclopropane] (6.72 g, 24 mmol) in ethyl acetate (67.2 ml) and acetonitrile (67.2 ml) was added silver cyanate (5.4 g, 36 mmol) under cooling with an ice bath under an argon atmosphere. To the mixture was added iodine (9.17 g, 36 mmol). The mixture was stirred at 0° C. for 2 hours and filtered. The cake was washed with ethyl acetate and the filtrate was partitioned between ethyl acetate and saturated aqueous sodium thiosulfate. The organic layer was washed with brine, dried over anhydrous magnesium sulfate, and concentrated in vacuo.

The residue was dissolved in tetrahydrofuran (69 mL) and the solution was added to 2 M ethanolic ammonia (151 mL, 302 mmol) under cooling with an ice bath. The mixture was stirred at room temperature overnight, and concentrated in vacuo.

The residue was dissolved in MeOH (30 ml) and saturated aqueous sodium bicarbonate was added. The mixture was stirred at room temperature for 1 hour and the resulting precipitate was collected and dried in vacuo. The residue was triturated with a mixture of ethyl acetate/diisopropyl ether and filtered to afford 6'-bromo-2',2'-dimethyldispiro[cyclopropane-1,3'-chromene-4',4"-[1,3]oxazol]-2"-amine (8.12 g).

Example 218

A mixture of tert-butyl[(4S)-6'-{[(5-chloropyridin-2-yl)carbonyl]amino}-2',2'-dimethyldispiro[1,3-oxazole-4,4'-chromene-3',3"-oxetan]-2-yl]carbamate (1.02 g, 1.93 mmol), silica gel (neutral; 3.06 g) and toluene (20.4 mL) was stirred for 3 hours at 120° C. The reaction mixture was cooled down to ambient temperature and concentrated at reduced pressure. The residue was purified with column chromatography on silica gel ($CHCl_3$-EtOH, a linear gradient of EtOH from 0 to 15%) and then with NH-silica gel (Hexane-EtOAc, a linear gradient of EtOAc from 50 to 100%). The purified product was recrystallized from EtOH/$H_2O$ (1:1), and the solid was collected by filtration and dried at reduced pressure to give a hydrate of N-[(4S)-2-amino-2',2'-dimethyldispiro[1,3-oxazole-4,4'-chromene-3',3"-oxetan]-6'-yl]-5-chloropyridine-2-carboxamide (547 mg) as a crystal.

Example 223

To a solution of tert-butyl[(4'R)-6'-{[(5-methoxypyrazin-2-yl)carbonyl]amino}-2',2'-dimethyldispiro[cyclopropane- 1,3'-chromene-4',4''-[1,3]oxazol]-2''-yl]carbamate (392 mg, 0.769 mmol) in chloroform (3 ml) was added trifluoroacetic acid (1.8 ml), and the mixture was stirred at room temperature for 2 hours. The mixture was concentrated in vacuo, and the residue was purified by silica gel column chromatography (precolumn: NH-silica gel, main column: neutral silica gel, chloroform/methanol=10:0-10:1). To the purified product was added a mixture of hexane/ethyl acetate (4:1) and the mixture was stirred at room temperature over night. The precipitate was collected, washed with mixture of hexane/ethyl acetate (4:1), and dried in vacuo to afford N-[(4'R)-2''-amino-2',2'-dimethyldispiro[cyclopropane-1,3'-chromene-4',4''-[1,3]oxazol]-6'-yl]-5-methoxypyrazine-2-carboxamide (246 mg).

Example 224

To a solution of tert-butyl[(4'R)-6'-({[5-(difluoromethyl)pyrazin-2-yl]carbonyl}amino)-2',2'-dimethyldispiro[cyclopropane-1,3'-chromene-4',4''-[1,3]oxazol]-2''-yl]carbamate (373 mg, 0.704 mmol) in chloroform (6 ml) was added trifluoroacetic acid (2 ml). The mixture was stirred at room temperature for 2 hours and concentrated in vacuo. The residue was purified by silica gel column chromatography (precolumn: NH-silica gel, main column: neutral silica gel, chloroform/methanol=100:0-10:1). To the purified product was added a mixture of hexane and ethyl acetate (4:1), and the mixture was stirred at room temperature over night. The resulting precipitate was collected, washed with a mixture of hexane and ethyl acetate (4:1), and dried in vacuo to afford N-[(4'R)-2''-amino-2',2'-dimethyldispiro[cyclopropane-1,3'-chromene-4',4''-[1,3]oxazol]-6'-yl]-5-(difluoromethyl)pyrazine-2-carboxamide (253 mg).

Reference Example 225a,b

To a solution of 6'-bromo-2',2'-dimethyldispiro[cyclopropane-1,3'-chromene-4',4''-[1,3]oxazol]-2''-amine (3.7 g, 11 mmol) in methanol (50 ml) was added (+)-dibenzoyl-D-tartaric acid monohydrate (4.1 g, 11 mmol). The mixture was stirred at room temperature for 5 minutes and concentrated in vacuo. To the residue was added dioxane (25 ml). The mixture was heated under reflux for 5 minutes, cooled to room temperature and stirred at room temperature overnight. The resulting precipitate was collected, washed with dioxane, and dried in vacuo. The resulting powder was dissolved in saturated aqueous sodium hydrogen carbonate and chloroform. The mixture was extracted with chloroform, and the organic layer was dried over anhydrous magnesium sulfate, and concentrated in vacuo to afford (4'R)-6'-bromo-2',2'-dimethyldispiro[cyclopropane-1,3'-chromene-4',4''-[1,3]oxazol]-2''-amine (1.5 g). The mother liquor was concentrated in vacuo and purified by NH-silica gel column chromatography (CHCl₃/MeOH=20:1). The purified material was treated with (−)-dibenzoyl-L-tartaric acid monohydrate (2.0 g, 5.4 mmol) in the same manner as described above which lead to isolation of (4'S)-6'-bromo-2',2'-dimethyldispiro[cyclopropane-1,3'-chromene-4',4''-[1,3]oxazol]-2''-amine (1.2 g).

Reference Example 226

A mixture of racemic 6'-bromo-2',2'-dimethyldispiro[1,3-oxazole-4,4'-chromene-3',3''-oxetan]-2-amine (155 g, 0.44 mol) and L-camphorsulfonic acid (102 g, 0.44 mol) in ethanol (2.7 L) and water (340 mL) was heated at 50° C. till a clear solution was formed. The mixture was allowed to cool to room temperature and stood for 48 hours. The precipitate was collected by filtration, washed with ethanol and dried under reduced pressure to afford a salt with L-camphorsulfonic acid (65.0 g). The salt was dissolved in water (500 mL) and 10% aqueous Na₂CO₃ (400 mL) was added. The mixture was stirred for 1 hour and extracted with dichloromethane twice. The combined extracts were washed with brine (40 mL), dried over Na₂SO₄ and concentrated under reduced pressure to provide (4S)-6'-bromo-2',2'-dimethyldispiro[1,3-oxazole-4,4'-chromene-3',3''-oxetan]-2-amine (38.0 g).

Example 228a,b

N-(2-amino-2',2'-dimethyldispiro[1,3-oxazole-4,4'-chromene-3',3''-oxetan]-6'-yl)-5-chloro pyridine-2-carboxamide (352 mg, 0.821 mmol) was subjected to chromatography using supercritical CO₂ (supercritical CO₂/[EtOH with 0.1% diethylamine]=60:40) on Chiralcel OD-H column (10× 250 mm) eluting at a flow rate 10 mL/minute (40° C. column temperature). After concentration of collected fractions of the first peak (retention time=5.23 minutes) at reduced pressure, recrystallization of the residue with EtOH/water (1:1) provided a hydrate of N-[(4R)-2-amino-2',2'-dimethyldispiro[1,3-oxazole-4,4'-chromene-3',3''-oxetan]-6'-yl]-5-chloropyridine-2-carboxamide (153 mg, 44%) as a crystal. After concentration of collected fractions of the second peak (retention time=8.16 minutes) at reduced pressure, recrystallization of the residue with EtOH/water (1:1) provided a hydrate of N-[(4S)-2-amino-2',2'-dimethyldispiro[1,3-oxazole-4,4'-chromene-3',3''-oxetan]-6'-yl]-5-chloropyridine-2-carboxamide (152 mg) as a crystal.

Example 229a,b

N-[2-amino-2',2'-dimethyldispiro[1,3-oxazole-4,4'-chromene-3',3''-oxetan]-6'-yl]-5-methoxypyrazine-2-carboxamide (100 mg, 0.235 mmol) was chromatographed using supercritical CO₂ (supercritical CO₂/EtOH=60:40) on Chiralcel OD-H column (10×250 mm) eluting at a flow rate 10 mL/minute (40° C. column temperature). After concentration of collected fractions of the first peak (retention time=5.25 minutes) under reduced pressure, trituration of the residue with EtOAc/hexane provided N-[(4S)-2-amino-2',2'-dimethyldispiro[1,3-oxazole-4,4'-chromene-3',3''-oxetan]-6'-yl]-5-methoxypyrazine-2-carboxamide (35 mg). After concentration of collected fractions of the second peak (retention time=8.08 minutes) under reduced pressure, trituration of the residue with EtOAc/hexane provided N-[(4R)-2-amino-2',2'-dimethyldispiro[1,3-oxazole-4,4'-chromene-3',3''-oxetan]-6'-yl]-5-methoxypyrazine-2-carboxamide (35 mg).

Example 230

To a solution of tert-butyl[(4'R)-6'-{[(5-methoxypyrazin-2-yl)carbonyl]amino}-2',2'-dimethyldispiro[cyclopropane-1,3'-chromene-4',4''-[1,3]oxazol]-2''-yl]carbamate (13.75 g, 26.98 mmol) in chloroform (140 ml) was added trifluoroacetic acid (68 ml) in an ice-water bath, and the mixture was stirred at room temperature for 3 hours. The mixture was concentrated in vacuo, and the residue was purified by silica gel column chromatography (pre-column: NH-silica gel; main column: neutral silica gel, chloroform/methanol=100:0-10:1). To the purified product was added saturated aqueous sodium hydrogen carbonate and extracted with chloroform. The organic layer were washed with brine, dried over anhydrous sodium sulfate, filtered, and the filtrate was evaporated in vacuo. The residue was purified by silica gel column chromatography (pre-column: basic silica gel; main column: neutral silica gel, chloroform/methanol=100:0-10:1). The purified product was triturated with a mixture of hexane/ethyl acetate (4:1) (300 mL), and the mixture was stirred at 60° C. for 1 hour and room temperature for 4 days. The precipitate was collected, washed with mixture of hexane/ethyl acetate (4:1) (200 mL), and dried in vacuo at 50° C. to afford N-[(4'R)-2''-amino-2',2'-dimethyldispiro[cyclopropane-1,3'-chromene-4',4''-[1,3]oxazol]-6'-yl]-5-me thoxypyrazine-2-carboxamide (8.38 g) as a crystal.

Example 231

To a solution of N-[(4'R)-2''-amino-2',2'-dimethyldispiro [cyclopropane-1,3'-chromene-4',4''-[1,3]oxazol]-6'-yl]-5-(difluoromethyl)pyrazine-2-carboxamide (800 mg, 1.86 mmol) in MeOH (10 mL) was added 4M solution of hydrogen chloride in ethyl acetate (0.5 mL, 2 mmol) and the mixture was concentrated in vacuo. The residue was triturated with EtOH (10 mL), and the mixture was refluxed for 30 minutes and stirred at room temperature overnight. The precipitate was collected, washed with EtOH (2 mL), and dried under reduced pressure at 70° C. overnight to afford N-[(4'R)-2''-amino-2',2'-dimethyldispiro[cyclopropane-1,3'-chromene-4',4''-[1,3]oxazol]-6'-yl]-5-(difluoromethyl)pyrazine-2-carboxamide hydrochloride (449 mg) as a crystal.

The compounds of Examples and Reference Examples shown in Tables below were prepared using the respective corresponding starting materials in the same manner as the methods of Examples or Reference Examples above. The structures and the preparation methods are shown in [Table. 4] below, and the physicochemical data for the compounds of Examples or Reference Examples are shown in [Table. 5] below.

TABLE 4

| Ex | Syn | Structure |
|---|---|---|
| RP 1a | RP 1a,b | |
| RP 1b | RP 1a,b | |
| RP 2 | RP6 | |
| RP 3 | RP6 | 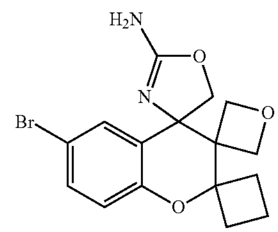 [SMILES: NC1=NC2(CO1)c1cc(Br)ccc1OC1(CCC1)C21COC1] |
| RP 4 | RP6 | 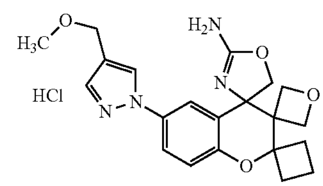 [SMILES: Cl ; COCc1cnn(-c2ccc3c(c2)C2(COC(N)=N2)C2(COC2)C2(CCC2)O3)c1] |
| RP 5 | RP6 | 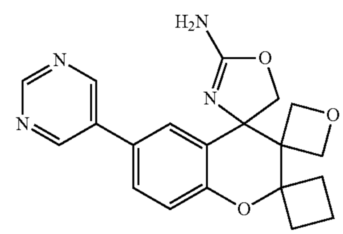 [SMILES: NC1=NC2(CO1)c1cc(-c3cncnc3)ccc1OC1(CCC1)C21COC1] |
| RP 6 | RP6 | 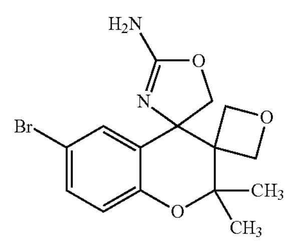 [SMILES: CC1(C)Oc2ccc(Br)cc2C2(COC(N)=N2)C12COC2] |
| RP 7a | RP 1a,b | 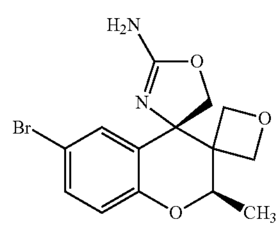 |
| RP 7b | RP 1a,b | 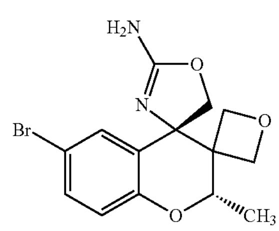 |

TABLE 4-continued

| Ex | Syn | Structure |
|---|---|---|
| RP 8 | RP6 | (structure) |
| RP 9a | RP 1a,b | (structure) |
| RP 9b | RP 1a,b | (structure) |
| RP 10 | RP6 | (structure) |
| RP 11a | RP 1a,b | (structure) |
| RP 11b | RP 1a,b | (structure) |
| RP 12a | RP 1a,b | (structure) |
| RP 12b | RP 1a,b | (structure) |
| RP 13a | RP 1a,b | (structure) |
| RP 13b | RP 1a,b | (structure) |
| RP 14a | RP 1a,b | (structure) |
| RP 14b | RP 1a,b | (structure) |
| RP 15a | RP 1a,b | (structure) |

TABLE 4-continued

| Ex | Syn | Structure |
|---|---|---|
| RP 15b | RP 1a,b | 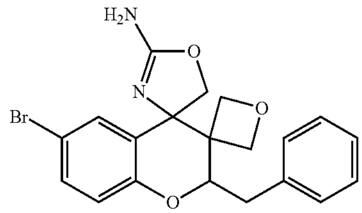 [SMILES: NC1=NC2(CO1)c1cc(Br)ccc1OC(Cc1ccccc1)C21COC1] |
| RP 16a | RP 1a,b | 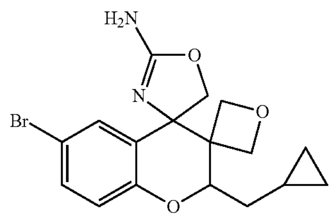 [SMILES: NC1=NC2(CO1)c1cc(Br)ccc1OC(CC1CC1)C21COC1] |
| RP 16b | RP 1a,b | 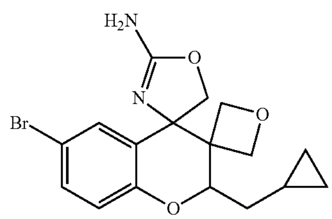 [SMILES: NC1=NC2(CO1)c1cc(Br)ccc1OC(CC1CC1)C21COC1] |
| RP 17 | RP6 | 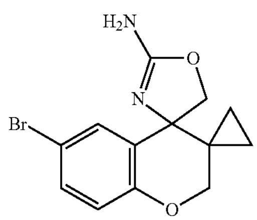 [SMILES: NC1=NC2(CO1)c1cc(Br)ccc1OCC21CC1] |
| RP 18 | RP6 | 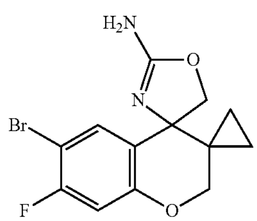 [SMILES: NC1=NC2(CO1)c1cc(Br)c(F)cc1OCC21CC1] |
| RP 19 | RP19 | 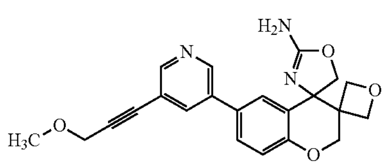 [SMILES: COCC#Cc1cncc(-c2ccc3c(c2)C2(COC(N)=N2)C2(COC2)CO3)c1] |
| RP 20 | RP19 | 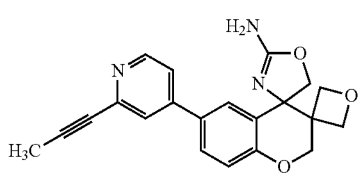 [SMILES: CC#Cc1cc(-c2ccc3c(c2)C2(COC(N)=N2)C2(COC2)CO3)ccn1] |
| RP 21 | RP19 | 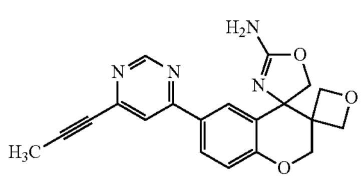 [SMILES: CC#Cc1cc(-c2ccc3c(c2)C2(COC(N)=N2)C2(COC2)CO3)ncn1] |
| RP 22 | RP19 | |
| RP 23 | RP19 | |
| RP 24 | RP19 | |
| RP 25 | RP19 | |
| RP 26 | RP19 | |
| 27 | E27 | |
| 28 | E27 | |
| RP 29 | E27 | |

TABLE 4-continued

| Ex | Syn | Structure |
|---|---|---|
| 30 | E27 | (structure) |
| RP 31 | RP31 | (structure) |
| RP 32 | RP31 | (structure) |
| RP 33 | RP39 | (structure) |
| RP 34 | RP39 | (structure) |
| RP 35 | RP39 | (structure) HCl |
| RP 36 | RP39 | (structure) |
| RP 37 | RP39 | (structure) |
| RP 38 | RP39 | (structure) |
| RP 39 | RP39 | (structure) |
| RP 40 | RP40 | (structure) |
| RP 41 | RP41 | (structure) |
| RP 42 | RP41 | (structure) |
| RP 43 | RP43 | (structure) |
| RP 44 | RP43 | (structure) |

TABLE 4-continued

| Ex | Syn | Structure |
|---|---|---|
| RP 45 | RP43 | 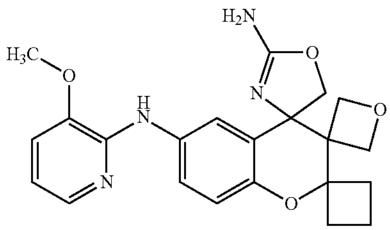 [SMILES: COc1cccnc1Nc1ccc2c(c1)C1(COC(N)=N1)C1(COC1)C1(CCC1)O2] |
| RP 46 | RP46 | 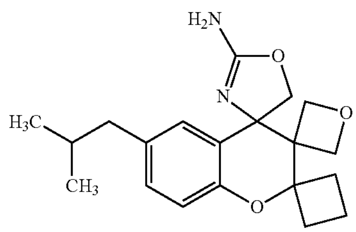 [SMILES: CC(C)Cc1ccc2c(c1)C1(COC(N)=N1)C1(COC1)C1(CCC1)O2] |
| RP 47 | RP46 | 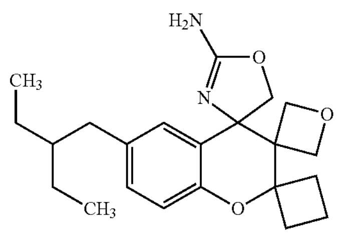 [SMILES: CCC(CC)Cc1ccc2c(c1)C1(COC(N)=N1)C1(COC1)C1(CCC1)O2] |
| RP 48 | RP48 | 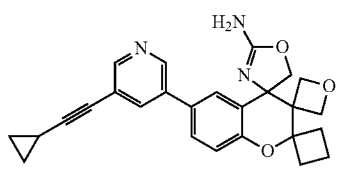 [SMILES: NC1=NC2(CO1)c1cc(-c3cncc(C#CC4CC4)c3)ccc1OC1(CCC1)C21COC1] |
| RP 49 | RP49 | 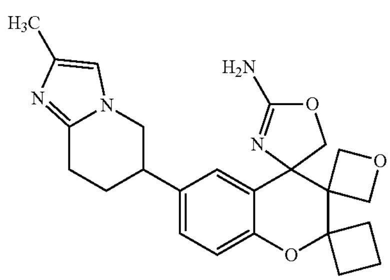 [SMILES: Cc1cn2c(n1)CCC(c1ccc3c(c1)C1(COC(N)=N1)C1(COC1)C1(CCC1)O3)C2] |
| RP 50 | RP49 | 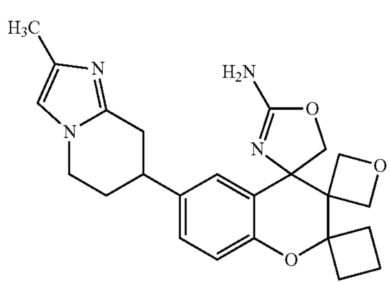 [SMILES: Cc1cn2c(n1)CC(c1ccc3c(c1)C1(COC(N)=N1)C1(COC1)C1(CCC1)O3)CC2] |
| RP 51a | RP 51a,b | 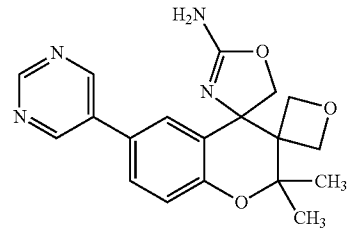 [SMILES: CC1(C)Oc2ccc(-c3cncnc3)cc2C2(COC(N)=N2)C12COC2] |
| RP 51b | RP 51a,b | 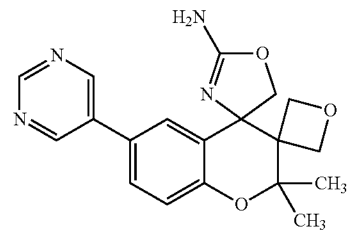 [SMILES: CC1(C)Oc2ccc(-c3cncnc3)cc2C2(COC(N)=N2)C12COC2] |
| RP 52a | RP 52a,b | 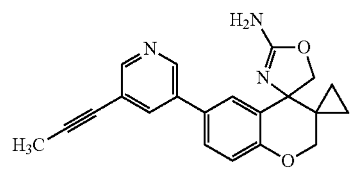 [SMILES: CC#Cc1cncc(-c2ccc3c(c2)C2(COC(N)=N2)C2(CC2)CO3)c1] |
| RP 52b | RP 52a,b | 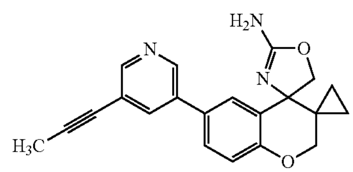 [SMILES: CC#Cc1cncc(-c2ccc3c(c2)C2(COC(N)=N2)C2(CC2)CO3)c1] |
| RP 53a | RP 53a,b | 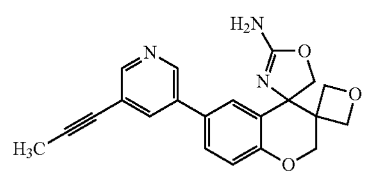 |
| RP 53b | RP 53a,b | 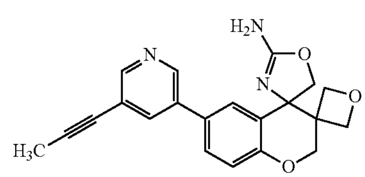 [SMILES: CC#Cc1cncc(-c2ccc3c(c2)C2(COC(N)=N2)C2(COC2)CO3)c1] |
| RP 54 | RP 54 | HCl |

TABLE 4-continued

| Ex | Syn | Structure |
|---|---|---|
| RP 55 | RP 55 | (structure) |
| RP 56 | RP 61 | (structure) |
| RP 57 | RP 61 | (structure) |
| RP 58 | RP 61 | (structure) |
| RP 59 | RP 61 | (structure) |
| RP 60 | RP 61 | (structure) |
| RP 61 | RP 61 | (structure) |
| RP 62 | RP 61 | (structure) |
| RP 63 | RP 61 | (structure) |
| RP 64 | RP 61 | (structure) |
| RP 65 | RP 65 | (structure) |
| RP 66 | RP 65 | (structure) |
| RP 67 | RP 65 | (structure) |
| RP 68 | RP 19 | (structure) |
| RP 69 | RP75 | (structure) |

TABLE 4-continued

| Ex | Syn | Structure |
|---|---|---|
| RP 70 | RP75 | (structure) |
| RP 71 | RP75 | (structure) |
| RP 72 | RP75 | (structure) |
| RP 73 | RP75 | (structure) |
| RP 74 | RP75 | (structure) |
| RP 75 | RP75 | (structure) |
| RP 76 | RP75 | (structure) |
| RP 77 | RP75 | (structure) racemate |
| RP 78 | RP75 | (structure) racemate |
| RP 79 | RP75 | (structure) racemate |
| RP 80 | RP75 | (structure) racemate |
| RP 81 | RP75 | (structure) racemate |
| RP 82 | RP75 | (structure) |

TABLE 4-continued

| Ex | Syn | Structure |
|---|---|---|
| RP 83 | RP75 | |
| RP 84 | RP75 | |
| RP 85 | RP75 | |
| RP 86 | RP75 | |
| RP 87 | RP75 | |
| RP 88 | RP75 | |
| RP 89 | RP75 | |
| RP 90 | RP75 | 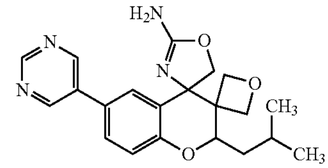 |
| RP 91 | RP75 | 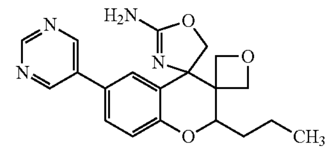 [SMILES: CCCC1Oc2ccc(-c3cncnc3)cc2C2(COC(N)=N2)C12COC2] |
| RP 92 | RP75 | 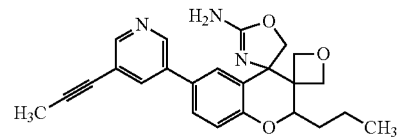 [SMILES: CC#Cc1cncc(-c2ccc3c(c2)C2(COC(N)=N2)C2(COC2)C(CCC)O3)c1] |
| RP 93 | RP75 | 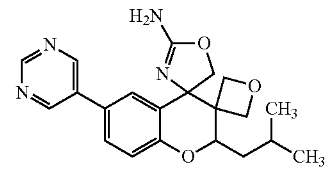 [SMILES: CC(C)CC1Oc2ccc(-c3cncnc3)cc2C2(COC(N)=N2)C12COC2] |
| RP 94 | RP75 | 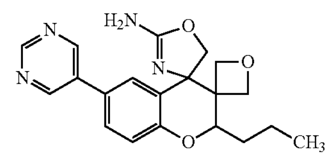 [SMILES: CCCC1Oc2ccc(-c3cncnc3)cc2C2(COC(N)=N2)C12COC2] |
| RP 95 | RP75 | 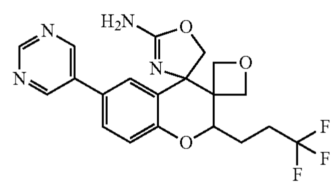 [SMILES: NC1=NC2(CO1)c1cc(-c3cncnc3)ccc1OC(CCC(F)(F)F)C21COC1] |
| RP 96 | RP75 | 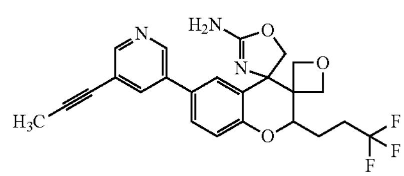 [SMILES: CC#Cc1cncc(-c2ccc3c(c2)C2(COC(N)=N2)C2(COC2)C(CCC(F)(F)F)O3)c1] |
| RP 97 | RP75 | 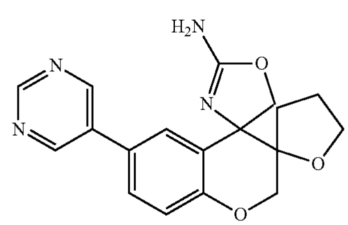 [SMILES: NC1=NC2(CO1)c1cc(-c3cncnc3)ccc1OCC21CCCO1] |

TABLE 4-continued
| Ex | Syn | Structure |
|---|---|---|
| RP 98 | RP75 | 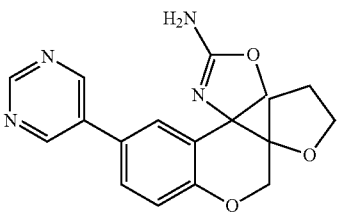 [SMILES: NC1=NC2(CO1)c1cc(-c3cncnc3)ccc1OCC21CCCO1] |
| RP 99 | RP75 | 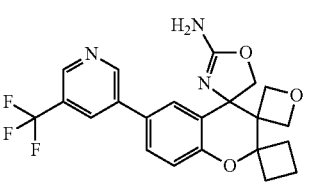 [SMILES: NC1=NC2(CO1)c1cc(-c3cncc(C(F)(F)F)c3)ccc1OC1(CCC1)C21COC1] |
| RP 100 | RP75 | 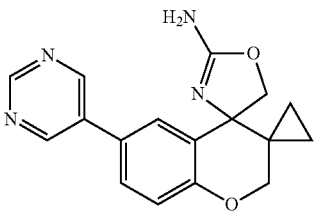 [SMILES: NC1=NC2(CO1)c1cc(-c3cncnc3)ccc1OCC21CC1] |
| RP 101 | RP75 | 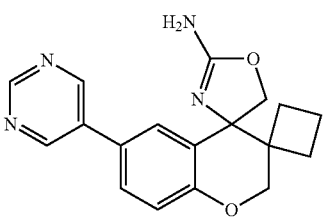 [SMILES: NC1=NC2(CO1)c1cc(-c3cncnc3)ccc1OCC21CCC1] |
| RP 102 | RP75 | 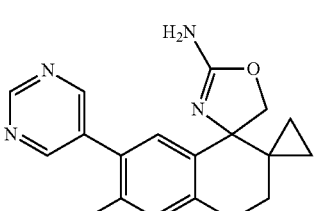 |
| RP 103 | RP75 | 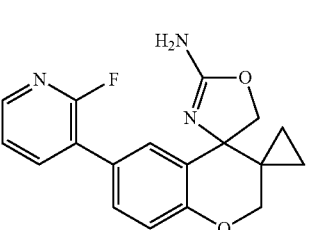 |
| RP 104 | RP75 | 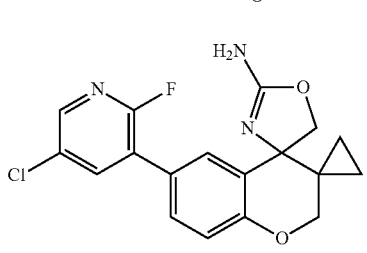 |
| RP 105 | RP75 | 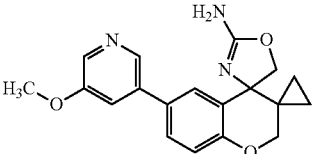 |
| RP 106 | RP75 | 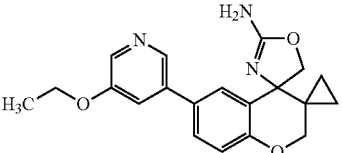 |
| RP 107 | RP75 | 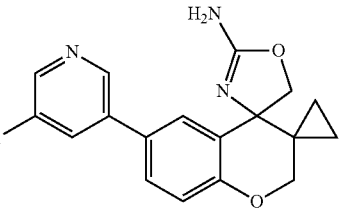 |
| RP 108 | RP108 | 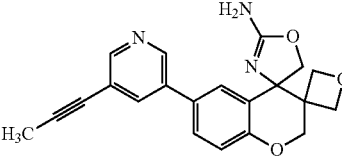 |
| RP 109 | RP108 | 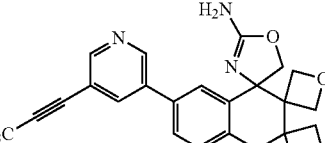 |
| RP 110 | RP108 | 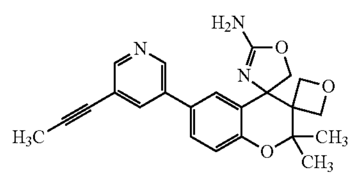 [SMILES: CC#Cc1cncc(-c2ccc3c(c2)C2(COC(N)=N2)C2(COC2)C(C)(C)O3)c1] |
| RP 111 | RP108 | 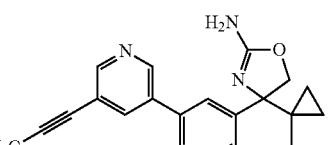 |
| RP 112 | RP108 | 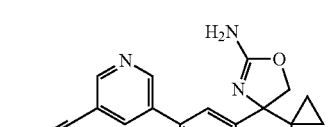 |

TABLE 4-continued
| Ex | Syn | Structure |
|---|---|---|
| RP 113 | RP108 | 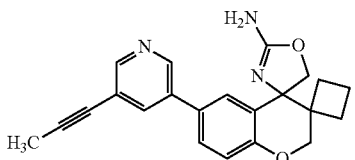 |
| RP 114 | RP114 | 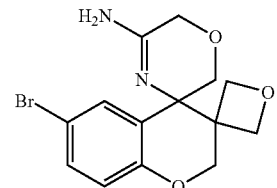 |
| RP 115 | RP115 | 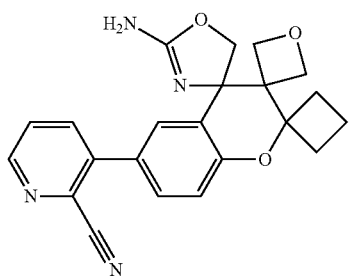 [SMILES: N#Cc1ncccc1-c1ccc2c(c1)C1(COC(N)=N1)C1(COC1)C1(CCC1)O2] |
| RP 116 | RP116 | 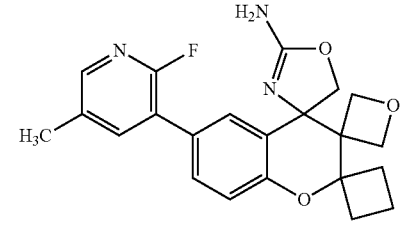 [SMILES: Cc1cnc(F)c(-c2ccc3c(c2)C2(COC(N)=N2)C2(COC2)C2(CCC2)O3)c1] |
| RP 117 | RP116 | 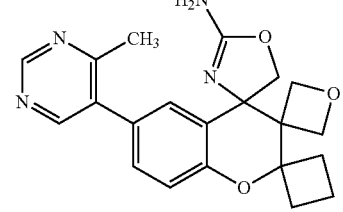 |
| RP 118 | RP116 | 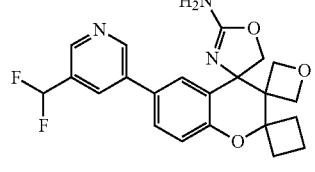 |
| RP 119 | RP136 | 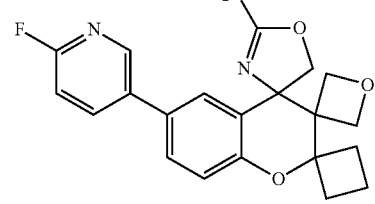 |
| RP 120 | RP136 | 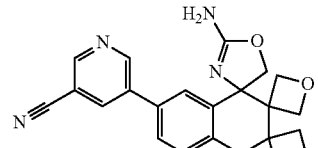 |
| RP 121 | RP136 | 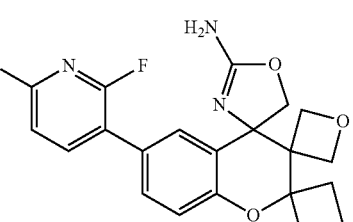 |
| RP 122 | RP136 | 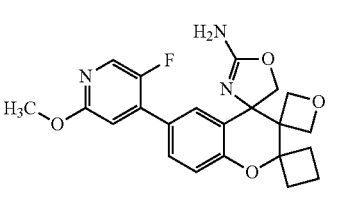 [SMILES: COc1cc(-c2ccc3c(c2)C2(COC(N)=N2)C2(COC2)C2(CCC2)O3)c(F)cn1] |
| RP 123 | RP136 | 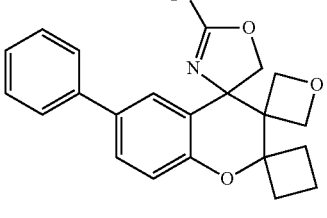 |
| RP 124 | RP136 | 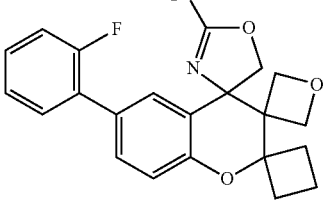 |
| RP 125 | RP136 | 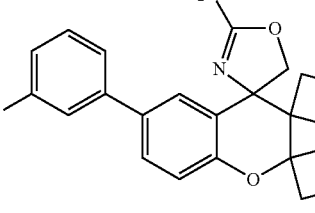 |
| RP 126 | RP136 | 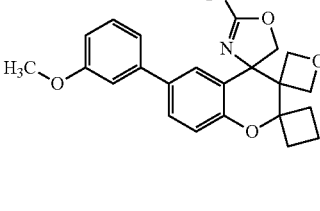 |

TABLE 4-continued

| Ex | Syn | Structure |
|---|---|---|
| RP 127 | RP136 | 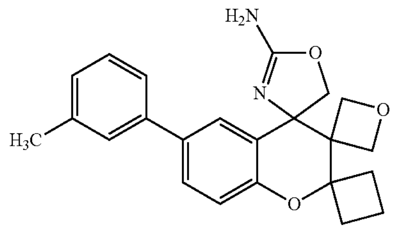 [SMILES: Cc1cccc(-c2ccc3c(c2)C2(COC(N)=N2)C2(COC2)C2(CCC2)O3)c1] |
| RP 128 | RP136 | 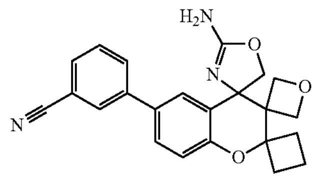 [SMILES: N#Cc1cccc(-c2ccc3c(c2)C2(COC(N)=N2)C2(COC2)C2(CCC2)O3)c1] |
| RP 129 | RP136 | 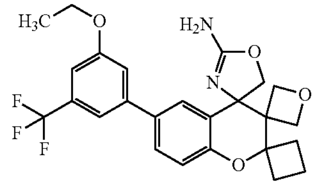 [SMILES: CCOc1cc(-c2ccc3c(c2)C2(COC(N)=N2)C2(COC2)C2(CCC2)O3)cc(C(F)(F)F)c1] |
| RP 130 | RP136 | 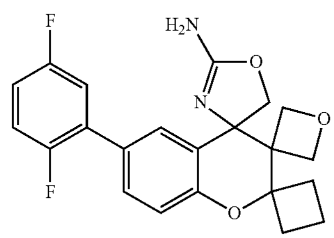 [SMILES: NC1=NC2(CO1)c1cc(-c3cc(F)ccc3F)ccc1OC1(CCC1)C21COC1] |
| RP 131 | RP136 | 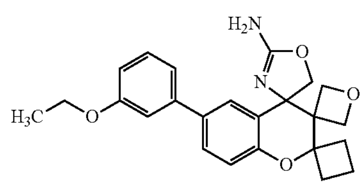 [SMILES: CCOc1cccc(-c2ccc3c(c2)C2(COC(N)=N2)C2(COC2)C2(CCC2)O3)c1] |
| RP 132 | RP136 | 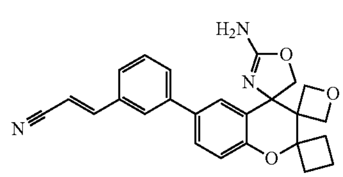 [SMILES: N#C/C=C/c1cccc(-c2ccc3c(c2)C2(COC(N)=N2)C2(COC2)C2(CCC2)O3)c1] |
| RP 133 | RP136 | 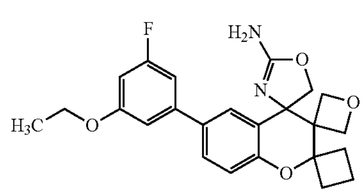 [SMILES: CCOc1cc(F)cc(-c2ccc3c(c2)C2(COC(N)=N2)C2(COC2)C2(CCC2)O3)c1] |
| RP 134 | RP136 | 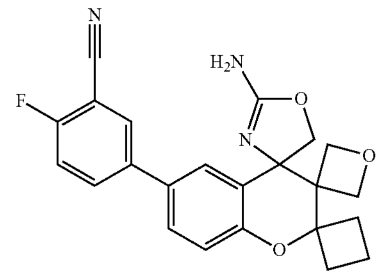 [SMILES: N#Cc1cc(-c2ccc3c(c2)C2(COC(N)=N2)C2(COC2)C2(CCC2)O3)ccc1F] |
| RP 135 | RP136 | 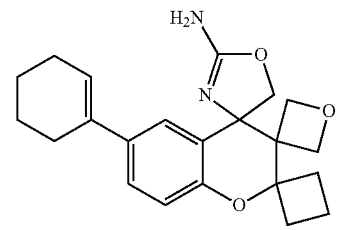 [SMILES: NC1=NC2(CO1)c1cc(C3=CCCCC3)ccc1OC1(CCC1)C21COC1] |
| RP 136 | RP136 | 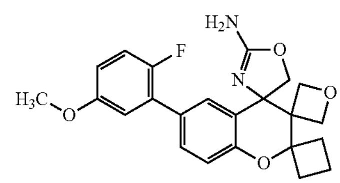 [SMILES: COc1ccc(F)c(-c2ccc3c(c2)C2(COC(N)=N2)C2(COC2)C2(CCC2)O3)c1] |
| RP 137 | RP136 | 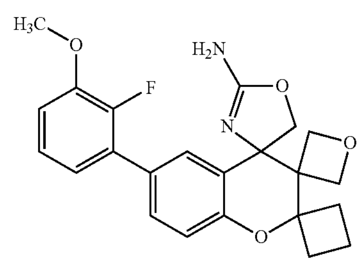 [SMILES: COc1cccc(-c2ccc3c(c2)C2(COC(N)=N2)C2(COC2)C2(CCC2)O3)c1F] |
| RP 138 | RP136 | 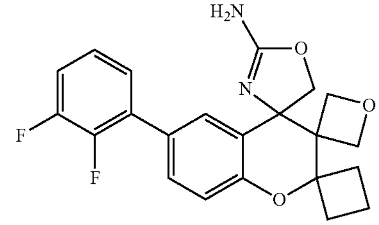 [SMILES: NC1=NC2(CO1)c1cc(-c3cccc(F)c3F)ccc1OC1(CCC1)C21COC1] |
| RP 139 | RP146 | 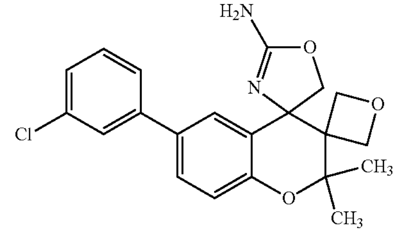 [SMILES: CC1(C)Oc2ccc(-c3cccc(Cl)c3)cc2C2(COC(N)=N2)C12COC2] |

TABLE 4-continued

| Ex | Syn | Structure |
|---|---|---|
| RP 140 | RP146 | (3-cyclopropylphenyl substituted spiro chromane oxazole) |
| RP 141 | RP146 | (3-trifluoromethylphenyl substituted spiro chromane oxazole) |
| RP 142 | RP146 | (3-methoxyphenyl substituted spiro chromane oxazole) |
| RP 143 | RP146 | (3-(2,2,2-trifluoroethoxy)phenyl substituted spiro chromane oxazole) |
| RP 144 | RP146 | (3-ethoxyphenyl substituted spiro chromane oxazole) |
| RP 145 | RP146 | (3-(methylthiomethyl)phenyl substituted spiro chromane oxazole) |
| RP 146 | RP146 | (3-chloro-5-fluorophenyl substituted spiro chromane oxazole) |
| RP 147 | RP146 | (3,5-difluorophenyl substituted spiro chromane oxazole) |
| RP 148 | RP146 | (3-fluoro-5-methylphenyl substituted spiro chromane oxazole) |
| RP 149 | RP146 | (4-fluoropyridin-2-yl substituted spiro chromane oxazole) |
| RP 150 | RP146 | (6-chloropyrazin-2-yl substituted spiro chromane oxazole) |
| RP 151 | RP146 | (2-chloro-5-methylpyridin-3-yl substituted spiro chromane oxazole) |
| RP 152 | RP146 | (2,5-dichloropyridin-3-yl substituted spiro chromane oxazole) |

TABLE 4-continued
| Ex | Syn | Structure |
|---|---|---|
| RP 153 | RP146 | 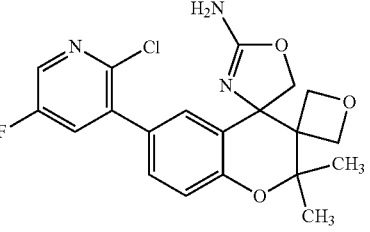 |
| RP 154 | RP146 | 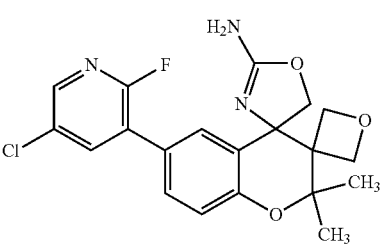 [SMILES: CC1(C)Oc2ccc(-c3cc(Cl)cnc3F)cc2C2(COC(N)=N2)C12COC2] |
| RP 155 | RP146 | 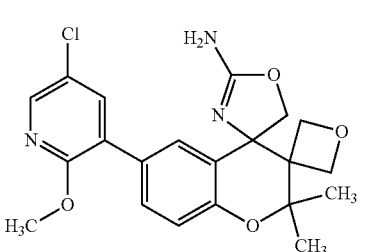 |
| RP 156 | RP146 | 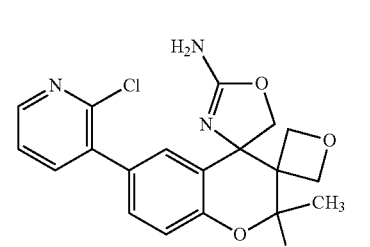 |
| RP 157 | RP146 | 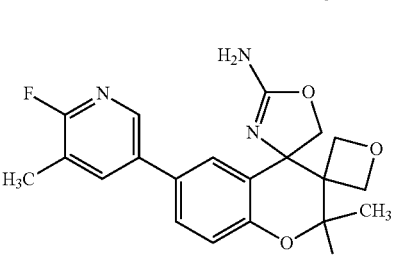 |
| RP 158 | RP146 | 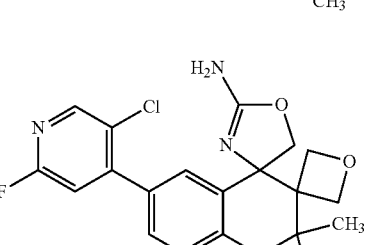 |
| RP 159 | RP146 | 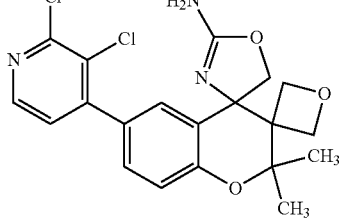 |
| RP 160 | RP146 | 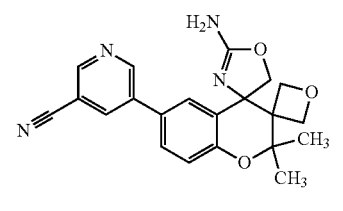 |
| RP 161 | RP146 | 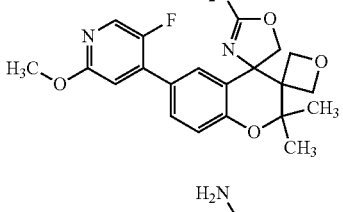 |
| RP 162 | RP146 | 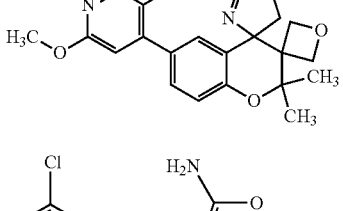 |
| RP 163 | RP146 | 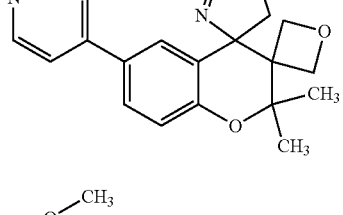 |
| RP 164 | RP146 | 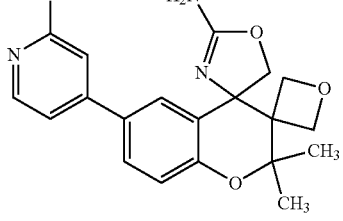 |
| RP 165 | RP146 | 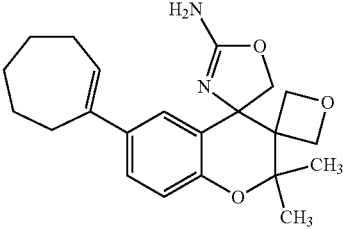 [SMILES: CC1(C)Oc2ccc(C3=CCCCCC3)cc2C2(COC(N)=N2)C12COC2] |

TABLE 4-continued

| Ex | Syn | Structure |
|---|---|---|
| RP 166 | RP146 | 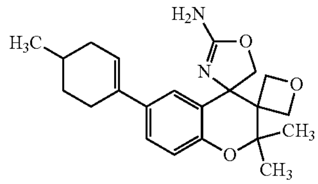 [SMILES: CC1CC=C(c2ccc3c(c2)C2(COC(N)=N2)C2(COC2)C(C)(C)O3)CC1] |
| RP 167 | RP146 | 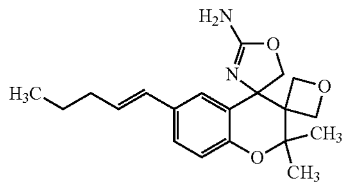 [SMILES: CCC/C=C/c1ccc2c(c1)C1(COC(N)=N1)C1(COC1)C(C)(C)O2] |
| RP 168 | RP146 | 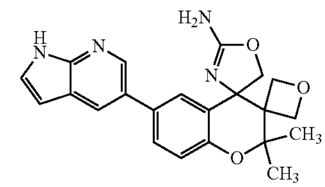 [SMILES: CC1(C)Oc2ccc(-c3cnc4[nH]ccc4c3)cc2C2(COC(N)=N2)C12COC2] |
| RP 169 | RP174 | 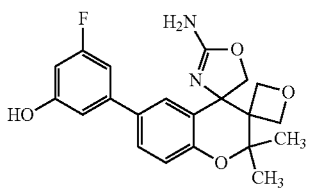 [SMILES: CC1(C)Oc2ccc(-c3cc(O)cc(F)c3)cc2C2(COC(N)=N2)C12COC2] |
| RP 170 | RP174 | 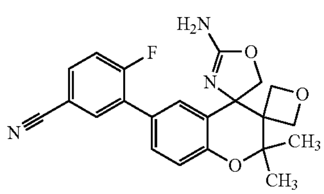 [SMILES: CC1(C)Oc2ccc(-c3cc(C#N)ccc3F)cc2C2(COC(N)=N2)C12COC2] |
| RP 171 | RP174 | 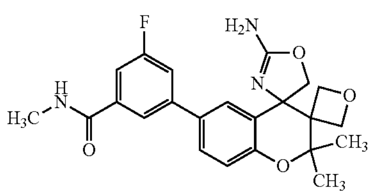 [SMILES: CNC(=O)c1cc(F)cc(-c2ccc3c(c2)C2(COC(N)=N2)C2(COC2)C(C)(C)O3)c1] |
| RP 172 | RP174 | 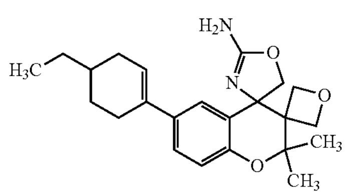 [SMILES: CCC1CC=C(c2ccc3c(c2)C2(COC(N)=N2)C2(COC2)C(C)(C)O3)CC1] |
| RP 173 | RP174 | 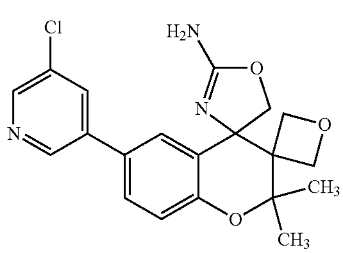 [SMILES: CC1(C)Oc2ccc(-c3cncc(Cl)c3)cc2C2(COC(N)=N2)C12COC2] |
| RP 174 | RP174 | |
| RP 175 | RP174 | |
| RP 176 | RP174 | |
| RP 177 | RP174 | |
| RP 178 | RP174 | |
| RP 179 | RP174 | |

TABLE 4-continued

| Ex | Syn | Structure |
|---|---|---|
| RP 180 | RP174 | 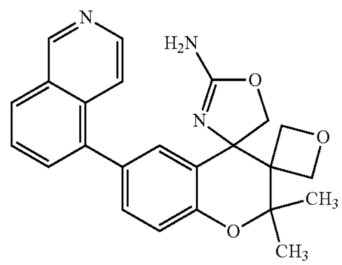 [SMILES: CC1(C)Oc2ccc(-c3cccc4cnccc34)cc2C2(COC(N)=N2)C12COC2] |
| RP 181 | RP174 | 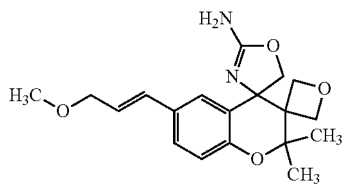 [SMILES: COC/C=C/c1ccc2c(c1)C1(COC(N)=N1)C1(COC1)C(C)(C)O2] |
| RP 182 | RP174 | 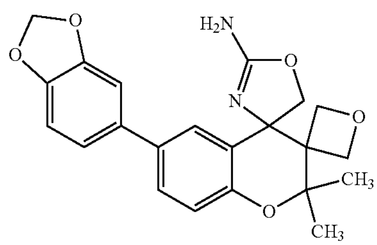 [SMILES: CC1(C)Oc2ccc(-c3ccc4c(c3)OCO4)cc2C2(COC(N)=N2)C12COC2] |
| RP 183 | RP174 | 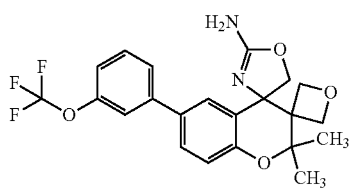 [SMILES: CC1(C)Oc2ccc(-c3cccc(OC(F)(F)F)c3)cc2C2(COC(N)=N2)C12COC2] |
| RP 184 | RP174 | 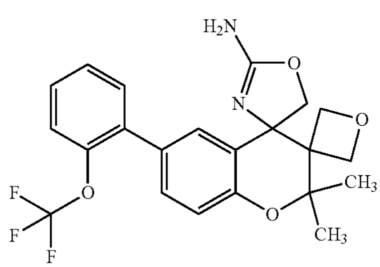 [SMILES: CC1(C)Oc2ccc(-c3ccccc3OC(F)(F)F)cc2C2(COC(N)=N2)C12COC2] |
| RP 185 | RP174 | 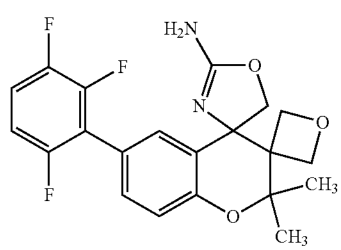 [SMILES: CC1(C)Oc2ccc(-c3c(F)ccc(F)c3F)cc2C2(COC(N)=N2)C12COC2] |

TABLE 4-continued

| Ex | Syn | Structure |
|---|---|---|
| RP 186 | RP174 | 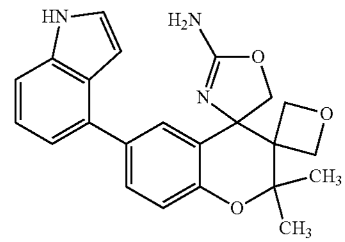 [SMILES: CC1(C)Oc2ccc(-c3cccc4[nH]ccc34)cc2C2(COC(N)=N2)C12COC2] |
| RP 187 | RP174 | 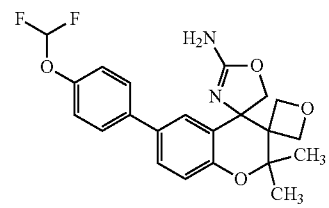 [SMILES: CC1(C)Oc2ccc(-c3ccc(OC(F)F)cc3)cc2C2(COC(N)=N2)C12COC2] |
| RP 188 | RP6 | 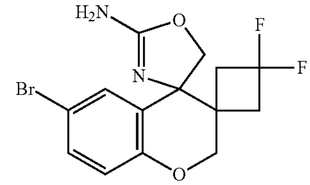 [SMILES: NC1=NC2(CO1)c1cc(Br)ccc1OCC21CC(F)(F)C1] |
| RP 189 | E27 | 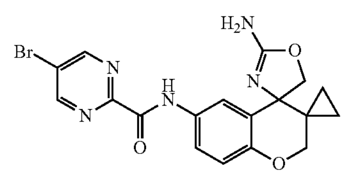 [SMILES: NC1=NC2(CO1)c1cc(NC(=O)c3ncc(Br)cn3)ccc1OCC21CC1] |
| RP 190 | E27 | |
| RP 191 | E27 | 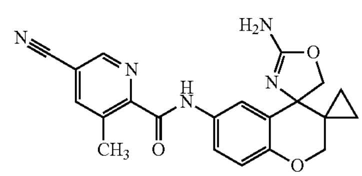 [SMILES: Cc1cc(C#N)cnc1C(=O)Nc1ccc2c(c1)C1(COC(N)=N1)C1(CC1)CO2] |
| RP 192 | E27 | 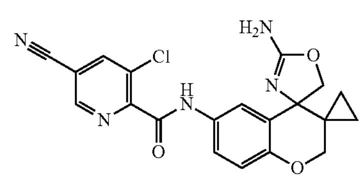 [SMILES: N#Cc1cnc(C(=O)Nc2ccc3c(c2)C2(COC(N)=N2)C2(CC2)CO3)c(Cl)c1] |
| RP 193 | E27 | 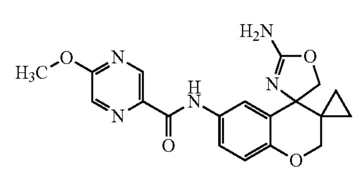 [SMILES: COc1cnc(C(=O)Nc2ccc3c(c2)C2(COC(N)=N2)C2(CC2)CO3)cn1] |

TABLE 4-continued

| Ex | Syn | Structure |
|---|---|---|
| RP 194 | E27 | 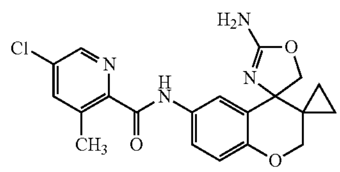 [SMILES: Cc1cc(Cl)cnc1C(=O)Nc1ccc2c(c1)C1(COC(N)=N1)C1(CC1)CO2] |
| 195 | E27 | 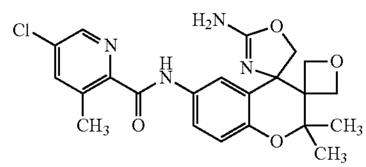 [SMILES: Cc1cc(Cl)cnc1C(=O)Nc1ccc2c(c1)C1(COC(N)=N1)C1(COC1)C(C)(C)O2] |
| RP 196 | E27 | 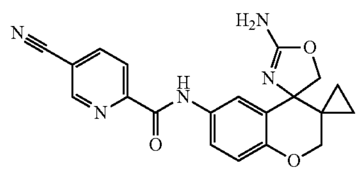 [SMILES: N#Cc1ccc(C(=O)Nc2ccc3c(c2)C2(COC(N)=N2)C2(CC2)CO3)nc1] |
| 197 | E27 | 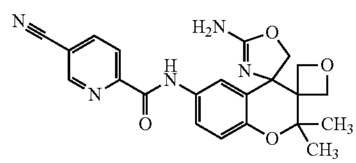 [SMILES: CC1(C)Oc2ccc(NC(=O)c3ccc(C#N)cn3)cc2C2(COC(N)=N2)C12COC2] |
| RP 198 | RP198 | 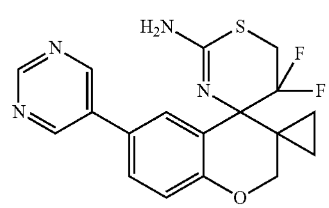 [SMILES: NC1=NC2(c3cc(-c4cncnc4)ccc3OCC23CC3)C(F)(F)CS1] |
| RP 199 | RP55 | 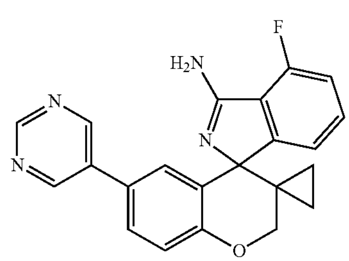 [SMILES: NC1=NC2(c3cc(-c4cncnc4)ccc3OCC23CC3)c2cccc(F)c21] |
| RP 200 | RP75 | 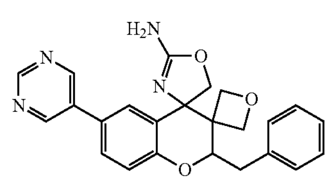 [SMILES: NC1=NC2(CO1)c1cc(-c3cncnc3)ccc1OC(Cc1ccccc1)C21COC1] |
| RP 201 | RP75 | 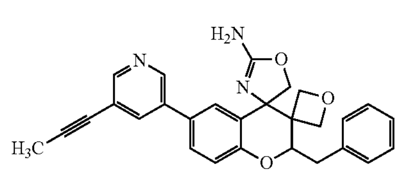 [SMILES: CC#Cc1cncc(-c2ccc3c(c2)C2(COC(N)=N2)C2(COC2)C(Cc2ccccc2)O3)c1] |
| RP 202 | RP75 | |
| RP 203 | RP75 | |
| RP 204 | RP75 | |
| RP 205 | RP75 | |
| RP 206 | RP75 | |
| RP 207 | RP75 | |
| RP 208 | RP75 | |
| RP 209 | RP75 | |

TABLE 4-continued

| Ex | Syn | Structure |
|---|---|---|
| RP 210 | RP75 | (structure) |
| RP 211 | RP75 | (structure) |
| RP 212 | RP75 | (structure) |
| RP 213 | RP75 | (structure) |
| RP 214 | RP214 | (structure) |
| RP 215 | RP215 | (structure) |
| RP 216 | RP216 | (structure) |

TABLE 4-continued

| Ex | Syn | Structure |
|---|---|---|
| RP 217 | RP217 | (structure) |
| 218 | E218 | (structure) H₂O |
| 219 | E218 | (structure) |
| 220 | E218 | (structure) |
| 221 | E223 | (structure) |
| 222 | E223 | (structure) |
| 223 | E223 | (structure) |
| 224 | E224 | (structure) |

TABLE 4-continued

| Ex | Syn | Structure |
|---|---|---|
| RP 225a | RP225 a,b | (structure: 6-bromo-2,2-dimethylchroman spiro cyclopropane with aminooxazoline) |
| RP 225b | RP225 a,b | (structure: 6-bromo-2,2-dimethylchroman spiro cyclopropane with aminooxazoline, other diastereomer) |
| RP 226 | RP226 | (structure: 6-bromo-2,2-dimethylchroman spiro oxetane with aminooxazoline) |
| 227 | E218 | (structure: 5-methoxypyrazine-2-carboxamide linked to 2,2-dimethylchroman spiro oxetane with aminooxazoline) |
| 228a | E228a,b | (structure: 5-chloropyridine-2-carboxamide linked to 2,2-dimethylchroman spiro oxetane with aminooxazoline · H₂O) |
| 228b | E228a,b | (structure: 5-chloropyridine-2-carboxamide linked to 2,2-dimethylchroman spiro oxetane with aminooxazoline · H₂O, other diastereomer) |
| 229a | E229a,b | (structure: 5-methoxypyrazine-2-carboxamide linked to 2,2-dimethylchroman spiro oxetane with aminooxazoline) |
| 229b | E229a,b | (structure: 5-methoxypyrazine-2-carboxamide linked to 2,2-dimethylchroman spiro oxetane with aminooxazoline, other diastereomer) |
| 230 | E230 | (structure: 5-methoxypyrazine-2-carboxamide linked to 2,2-dimethylchroman spiro cyclopropane with aminooxazoline) |
| 231 | E231 | (structure: 5-(difluoromethyl)pyrazine-2-carboxamide linked to 2,2-dimethylchroman spiro cyclopropane with aminooxazoline) |

TABLE 5

| Ex | Data |
|---|---|
| RP 1a | ESI+: 339, 341 less polar diastereomer |
| RP 1b | ESI+: 339, 341 polar diastereomer |
| RP2 | ESI+: 325, 327 |
| RP3 | ESI+: 365, 367 |
| RP4 | ESI+: 397 |
| RP5 | ESI+: 365 |
| RP6 | ESI+: 353, 355 |
| RP 7a | ESI+: 339, 341 |
| RP 7b | ESI+: 339, 341 |
| RP8 | ESI+: 323, 325 |
| RP 9a | ESI+: 353, 355 a diastereomer with higher Rf value on TLC (CHCl₃/EtOAc 9:1, NH silicagel) |
| RP 9b | ESI+: 353, 355 a diastereomer with lower Rf value on TLC (CHCl₃/EtOAc 9:1, NH silicagel) |
| RP 10 | ESI+: 379, 381 |

TABLE 5-continued

| Ex | Data |
|---|---|
| RP 11a | ESI+: 367, 369<br>a diastereomer with higher Rf value on TLC (CHCl$_3$/EtOAc 9:1, NH silicagel) |
| RP 11b | ESI+: 367, 369<br>a diastereomer with lower Rf value on TLC (CHCl$_3$/EtOAc 9:1, NH silicagel) |
| RP 12a | ESI+: 365, 367<br>a diastereomer with higher Rf value on TLC (CHCl$_3$/EtOAc 9:1, NH silicagel) |
| RP 12b | ESI+: 365, 367<br>a diastereomer with lower Rf value on TLC (CHCl$_3$/EtOAc 9:1, NH silicagel) |
| RP 13a | ESI+: 381, 383<br>a diastereomer with higher Rf value on TLC (CHCl$_3$/EtOAc 9:1, NH silicagel) |
| RP 13b | ESI+: 381, 383<br>a diastereomer with lower Rf value on TLC (CHCl$_3$/EtOAc 9:1, NH silicagel) |
| RP 14a | ESI+: 421, 423<br>a diastereomer with higher Rf value on TLC (CHCl$_3$/EtOAc 9:1, NH silicagel) |
| RP 14b | ESI+: 421, 423<br>a diastereomer with lower Rf value on TLC (CHCl$_3$/EtOAc 9:1, NH silicagel) |
| RP 15a | ESI+: 415, 417<br>a diastereomer with higher Rf value on TLC (CHCl$_3$/EtOAc 9:1, NH silicagel) |
| RP 15b | ESI+: 415, 417<br>NMR-CDCl$_3$: 3.43 (1H, dd, J = 9.0, 14.7 Hz), 3.53 (1H, dd, J = 3.1, 14.7 Hz), 3.99 (1H, d, J = 8.5 Hz), 4.10-4.18 (2H, m), 4.47-4.55 (4H, m), 4.64 (1H, d, J = 6.7 Hz), 4.81 (1H, d, J = 6.3 Hz), 6.63 (1H, d, J = 8.7 Hz), 7.21 (1H, dd, J = 2.4, 8.7 Hz), 7.25-7.41 (6H, m)<br>a diastereomer with lower Rf value on TLC (CHCl$_3$/EtOAc 9:1, NH silicagel) |
| RP 16a | ESI+: 379, 381<br>a diastereomer with higher Rf value on TLC (CHCl$_3$/EtOAc 9:1, NH silicagel) |
| RP 16b | ESI+: 379, 381<br>a diastereomer with lower Rf value on TLC (CHCl$_3$/EtOAc 9:1, NH silicagel) |
| RP 17 | ESI+: 309, 311 |
| RP 18 | ESI+: 327, 329 |
| RP 19 | ESI+: 392<br>NMR-DMSO-d$_6$: 3.37 (3H, s), 4.16-4.28 (5H, m), 4.37-4.39 (3H, m), 4.60 (1H, d, J = 5.4 Hz), 4.71 (1H, d, J = 11.4 Hz), 6.40 (2H, s), 6.88 (1H, d, J = 8.4 Hz), 7.48 (1H, d, J = 2.3 Hz), 7.54 (1H, dd, J = 8.5, 2.4 Hz), 8.02-8.03 (1H, m), 8.60 (1H, d, J = 1.9 Hz), 8.76 (1H, d, J = 2.3 Hz) |
| RP 20 | ESI+: 362<br>NMR-DMSO-d$_6$: 2.10 (3H, s), 4.17 (2H, m), 4.23-4.28 (3H, m), 4.38 (1H, d, J = 6.4 Hz), 4.60 (1H, d, J = 5.3 Hz), 4.73 (1H, d, J = 11.4 Hz), 6.44 (2H, s), 6.88 (1H, d, J = 8.5 Hz), 7.51 (1H, dd, J = 5.3, 1.8 Hz), 7.55 (1H, d, J = 2.3 Hz), 7.58-7.61 (2H, m), 8.52 (1H, d, J = 5.2 Hz) |
| RP 21 | ESI+: 363<br>NMR-DMSO-d$_6$: 2.16 (3H, s), 4.10-4.17 (2H, m), 4.23-4.30 (3H, m), 4.38 (1H, d, J = 6.4 Hz), 4.59 (1H, d, J = 5.4 Hz), 4.75 (1H, d, J = 11.5 Hz), 6.46 (2H, s), 6.89 (1H, d, J = 8.6 Hz), 7.97-8.00 (2H, m), 8.17 (1H, d, J = 2.3 Hz), 9.09 (1H, d, J = 1.2 Hz) |
| RP 22 | ESI+: 363 |
| RP 23 | ESI+: 348<br>NMR-DMSO-d$_6$: 4.16-4.28 (5H, m), 4.38 (1H, d, J = 6.4 Hz), 4.49 (1H, s), 4.60 (1H, d, J = 5.4 Hz), 4.71 (1H, d, J = 11.4 Hz), 6.40 (2H, s), 6.88 (1H, d, J = 8.5 Hz), 7.48 (1H, d, J = 2.3 Hz), 7.53 (1H, dd, J = 8.4, 2.4 Hz), 8.04-8.05 (1H, m), 8.61 (1H, d, J = 1.9 Hz), 8.78 (1H, d, J = 2.3 Hz) |
| RP 24 | ESI+: 329 |
| RP 25 | ESI+: 339 |
| RP 26 | ESI+: 369<br>NMR-DMSO-d$_6$: 3.85 (3H, s), 4.07 (1H, d, J = 8.8 Hz), 4.13-4.16 (2H, m), 4.21-4.24 (2H, m), 4.34 (1H, d, J = 6.3 Hz), 4.56-4.61 (2H, m), 6.31 (2H, s), 6.63 (1H, d, J = 8.8 Hz), 6.67 (1H, dd, J = 7.8, 5.0 Hz), 7.13 (1H, dd, J = 7.9, 1.4 Hz), 7.56 (1H, d, J = 2.6 Hz), 7.61-7.64 (2H, m), 7.97 (1H, s) |
| 27 | ESI+: 429, 431<br>NMR-DMSO-d$_6$: 1.18 (3H, s), 1.73 (3H, s), 4.13-4.19 (2H, m), 4.30-4.32 (2H, m), 4.36 (1H, d, J = 6.8 Hz), 4.90 (1H, d, J = 5.6 Hz), 6.33 (2H, s), 6.66 (1H, d, J = 8.8 Hz), 7.57 (1H, dd, J = 8.8, 2.7 Hz), 7.70 (1H, d, J = 2.5 Hz), 8.13 (1H, dd, J = 8.5, 0.7 Hz), 8,18 (1H, dd, J = 8.4, 2.4 Hz), 8.75 (1H, dd, J = 2.3, 0.8 Hz), 10.52 (1H, s) |
| 28 | ESI+: 413<br>NMR-DMSO-d$_6$: 1.18 (3H, s), 1.73 (3H, s), 4.13-4.19 (2H, m), 4.30-4.32 (2H, m), 4.36 (1H, d, J = 6.8 Hz), 4.90 (1H, d, J = 5.6 Hz), 6.32 (2H, s), 6.66 (1H, d, J = 8.8 Hz), 7.55 (1H, dd, J = 8.8, 2.6 Hz), 7.70 (1H, d, J = 2.5 Hz), 7.96 (1H, td, J = 8.7, 2.9 Hz), 8.20 (1H, dd, J = 8.7, 4.6 Hz), 8.70 (1H, d, J = 2.8 Hz), 10.46 (1H, s) |
| RP 29 | ESI+: 403, 405<br>NMR-DMSO-d$_6$: 0.37-0.43 (3H, m), 0.82-0.85 (1H, m), 3.58 (1H, d, J = 11.6 Hz), 4.09 (1H, d, J = 8.1 Hz), 4.31 (1H, d, J = 8.2 Hz), 4.34-4.38 (1H, m), 6.18 (2H, s), 6.73-6.75 (1H, m), 7.55-7.57 (2H, m), 8.29 (1H, dd, J = 10.2, 1.9 Hz), 8.62-8.63 (1H, m), 10.47 (1H, s) |

TABLE 5-continued

| Ex | Data |
|---|---|
| 30 | ESI+: 447, 449<br>NMR-DMSO-$d_6$: 1.18 (3H, s), 1.73 (3H, s), 4.13-4.18 (2H, m), 4.31 (2H, d, J = 6.0 Hz), 4.36 (1H, d, J = 6.8 Hz), 4.89 (1H, d, J = 5.6 Hz), 6.34 (2H, s), 6.65-6.68 (1H, m), 7.52-7.55 (2H, m), 8.29 (1H, dd, J = 10.2, 2.0 Hz), 8.62-8.63 (1H, m), 10.51 (1H, s) |
| RP 31 | ESI+: 369<br>NMR-DMSO-$d_6$: 0.36-0.43 (3H, m), 0.82-0.88 (1H, m), 3.58 (1H, d, J = 11.6 Hz), 4.09 (1H, d, J = 8.1 Hz), 4.30-4.37 (2H, m), 6.17 (2H, s), 6.73 (1H, d, J = 8.8 Hz), 7.58 (1H, dd, J = 8.8, 2.6 Hz), 7.71 (1H, d, J = 2.6 Hz), 7.96 (1H, td, J = 8.7, 2.9 Hz), 8.18-8.21 (1H, m), 8.70 (1H, d, J = 2.9 Hz), 10.41 (1H, s) |
| RP 32 | ESI+: 385, 387<br>NMR-DMSO-$d_6$: 0.36-0.44 (3H, m), 0.82-0.88 (1H, m), 3.58 (1H, d, J = 11.6 Hz), 4.09 (1H, d, J = 8.1 Hz), 4.31 (1H, d, J = 8.1 Hz), 4.35 (1H, dd, J = 11.5, 1.4 Hz), 6.17 (2H, s), 6.73 (1H, d, J = 8.8 Hz), 7.59 (1H, dd, J = 8.8, 2.6 Hz), 7.71 (1H, d, J = 2.6 Hz), 8.12 (1H, dd, J = 8.4, 0.7 Hz), 8.18 (1H, dd, J = 8.5, 2.3 Hz), 8.75 (1H, dd, J = 2.3, 0.7 Hz), 10.47 (1H, s) |
| RP 33 | ESI+: 371 |
| RP 34 | ESI+: 376 |
| RP 35 | ESI+: 319 |
| RP 36 | ESI+: 325 |
| RP 37 | ESI+: 338 |
| RP 38 | ESI+: 365 |
| RP 39 | ESI+: 354 |
| RP 40 | ESI+: 373, 375 |
| RP 41 | ESI+: 341, 343 |
| RP 42 | ESI+: 369, 371 |
| RP 43 | ESI+: 373, 375<br>NMR-DMSO-$d_6$: 4.05-4.36 (6H, m), 4.57-4.65 (2H, m), 6.32 (2H, brs), 6.67-6.75 (2H, m), 7.39-7.42 (2H, m), 7.70-7.72 (1H, m), 7.97-7.99 (1H, m), 8.26 (1H, s) |
| RP 44 | ESI+: 413, 415<br>NMR-DMSO-$d_6$: 1.82-1.88 (2H, m), 2.13-2.24 (2H, m), 2.32-2.43 (1H, m), 2.92-2.98 (1H, m), 3.95-4.06 (1H, m), 4.16-4.21 (2H, m), 4.44-4.51 (2H, m), 4.62-4.66 (1H, m), 6.29 (2H, brs), 6.71-6.74 (2H, m), 7.31-7.38 (2H, m), 7.70-7.71 (1H, m), 7.98-7.99 (1H, m), 8.25 (1H, s) |
| RP 45 | ESI+: 409<br>NMR-DMSO-$d_6$: 1.80-1.88 (2H, m), 2.12-2.40 (3H, m), 2.89-2.97 (1H, m), 3.76-3.94 (4H, m), 4.17-4.24 (2H, m), 4.49-4.64 (3H, m), 6.29 (2H, brs), 6.67-6.72 (2H, m), 7.13 (1H, d, J = 7.6 Hz), 7.57-7.70 (3H, m), 8.00 (1H, brs) |
| RP 46 | ESI+: 343 |
| RP 47 | APCI/ESI+: 371 |
| RP 48 | ESI+: 428<br>NMR-DMSO-$d_6$: 0.77-0.82 (2H, m), 0.90-0.96 (2H, m), 1.57-1.64 (1H, m), 1.80-1.95 (2H, m), 2.12-2.34 (2H, m), 2.38-2.50 (1H, m), 2.93-3.04 (1H, m), 4.11-4.21 (3H, m), 4.49-4.53 (2H, m), 4.65 (1H, d, J = 5.5 Hz), 6.39 (2H, brs), 6.91 (1H, d, J = 8.5 Hz), 7.27 (1H, d, J = 2.2 Hz), 7.50 (1H, dd, J = 8.5, 2.4 Hz), 7.86-7.87 (1H, m), 8.49 (1H, d, J = 1.9 Hz), 8.65 (1H, d, J = 2.3 Hz) |
| RP 49 | ESI+: 421 |
| RP 50 | APCI/ESI+: 421 |
| RP 51a | ESI+: 353<br>retention time = 3.44 minutes |
| RP 51b | ESI+: 353<br>NMR-DMSO-$d_6$: 1.22 (3H, s), 1.77 (3H, s), 4.20 (1H, d, J = 8.9 Hz), 4.29-4.34 (3H, m), 4.39 (1H, d, J = 6.9 Hz), 4.91 (1H, d, J = 5.6 Hz), 6.35 (2H, s), 6.85 (1H, d, J = 8.5 Hz), 7.35 (1H, d, J = 2.4 Hz), 7.54 (1H, dd, J = 8.4, 2.4 Hz), 8.97 (2H, s), 9.14 (1H, s)<br>retention time = 6.92 minutes |
| RP 52a | ESI+: 346<br>NMR-DMSO-$d_6$: 0.38-0.46 (3H, m), 0.81-0.88 (1H, m), 2.11 (3H, s), 3.65 (1H, d, J = 11.7 Hz), 4.21 (1H, d, J = 8.1 Hz), 4.34 (1H, d, J = 8.1 Hz), 4.41-4.45 (1H, m), 6.21 (2H, brs), 6.87 (1H, d, J = 8.5 Hz), 7.37-7.41 (1H, m), 7.50-7.53 (1H, m), 7.91-7.92 (1H, t, J = 2.1 Hz), 8.51 (1H, d, J = 2.1 Hz), 8.70 (1H, d, J = 2.1 Hz);<br>retention time = 3.62 minutes |
| RP 52b | ESI+: 346<br>retention time = 6.27 minutes |
| RP 53a | ESI+: 362<br>retention time = 5.81 minutes |

TABLE 5-continued

| Ex | Data |
|---|---|
| RP 53b | ESI+: 362<br>NMR-DMSO-$d_6$: 2.11 (3H, s), 4.15-4.21 (2H, m), 4.24-4.27 (3H, m), 4.38 (1H, d, J = 6.4 Hz), 4.60 (1H, d, J = 5.3 Hz), 4.71 (1H, d, J = 11.4 Hz), 6.41 (2H, s), 6.87 (1H, d, J = 8.5 Hz), 7.46 (1H, d, J = 2.3 Hz), 7.51 (1H, dd, J = 2.3, 8.5 Hz), 7.92-7.94 (1H, m), 8.52 (1H, d, J = 1.9 Hz), 8.70 (1H, d, J = 2.2 Hz);<br>retention time = 9.25 minutes |
| RP 54 | ESI+: 369 |
| RP 55 | ESI+: 363 |
| RP 56 | ESI+: 362<br>NMR-DMSO-$d_6$: 2.12 (3H, s), 4.10-4.17 (2H, m), 4.24-4.27 (3H, m), 4.38 (1H, d, J = 6.4 Hz), 4.59-4.61 (1H, m), 4.71 (1H, d, J = 11.4 Hz), 6.43 (2H, s), 6.83 (1H, d, J = 8.6 Hz), 7.24 (1H, dd, J = 5.0, 1.4 Hz), 7.756-7.762 (1H, m), 7.83 (1H, dd, J = 8.6, 2.4 Hz), 7.99 (1H, d, J = 2.3 Hz), 8.58 (1H, dd, J = 5.1, 0.8 Hz) |
| RP 57 | ESI+: 348<br>NMR-DMSO-$d_6$: 0.42 (3H, brs), 0.82 (3H, brs), 1.02-1.07 (2H, m), 1.98-2.02 (1H, m), 3.65 (1H, d, J = 11.3 Hz), 4.20-4.22 (1H, m), 4.32-4.36 (1H, m), 4.43 (1H, d, J = 11.3 Hz), 6.22 (2H, brs), 6.86 (1H, d, J = 8.4 Hz), 7.36 (1H, brs), 7.46-7.50 (2H, m), 8.32 (1H, s), 8.50 (1H, s) |
| RP 58 | ESI+: 406<br>NMR-DMSO-$d_6$: 0.41-0.46 (3H, m), 0.82-0.86 (1H, m), 3.65 (1H, d, J = 11.6 Hz), 4.21 (1H, d, J = 8.1 Hz), 4.34 (1H, d, J = 8.1 Hz), 4.44 (1H, d, J = 11.6 Hz), 4.92-4.99 (2H, m), 6.21 (2H, brs), 6.89 (1H, d, J = 8.5 Hz), 7.41-7.43 (1H, m), 7.51-7.54 (1H, m), 7.64-7.66 (1H, m), 8.34 (1H, d, J = 2.6 Hz), 8.43-8.46 (1H, m) |
| RP 59 | ESI+: 388<br>NMR-DMSO-$d_6$: 0.41-0.46 (3H, m), 0.82-0.88 (1H, m), 3.66 (1H, d, J = 11.7 Hz), 4.20 (1H, d, J = 8.16 Hz), 4.33 (1H, d, J = 8.16 Hz), 4.42-4.54 (3H, m), 6.20 (2H, brs), 6.29-6.58 (1H, m), 6.88 (1H, d, J = 8.5 Hz), 7.40-7.41 (1H, m), 7.51-7.53 (1H, m), 7.57-7.58 (1H, m), 8.29-8.30 (1H, m), 8.40-8.41 (1H, m) |
| RP 60 | ESI+: 374<br>NMR-DMSO-$d_6$: 0.40-0.45 (3H, m), 0.82-0.85 (1H, m), 3.66 (1H, d, J = 11.6 Hz), 4.20 (1H, d, J = 8.1 Hz), 4.34 (1H, d, J = 8.1 Hz), 4.44 (1H, d, J = 11.6 Hz), 6.21 (2H, brs), 6.90 (1H, d, J = 8.4 Hz), 7.21-7.58 (3H, m), 7.77-7.79 (1H, m), 8.42 (1H, d, J = 2.6 Hz), 8.66 (1H, d, J = 1.9 Hz) |
| RP 61 | ESI+: 347<br>NMR-DMSO-$d_6$: 0.41-0.46 (3H, m), 0.84-0.87 (1H, m), 3.62 (1H, d, J = 11.7 Hz), 4.21 (1H, d, J = 8.1 Hz), 4.34 (1H, d, J = 8.1 Hz), 4.42 (1H, d, J = 11.7 Hz), 6.20 (2H, brs), 6.48-6.50 (1H, m), 6.85 (1H, d, J = 8.4 Hz), 7.36-7.37 (1H, m), 7.43-7.46 (1H, m), 7.48-7.49 (1H, m), 8.03 (1H, d, J = 2.1 Hz), 8.37 (1H, d, J = 2.1 Hz), 11.6 (1H, brs) |
| RP 62 | ESI+: 381, 383 |
| RP 63 | ESI+: 336 |
| RP 64 | ESI+: 438 |
| RP 65 | ESI+: 382 |
| RP 66 | ESI+: 417 |
| RP 67 | ESI+: 417 |
| RP 68 | ESI+: 378<br>NMR-DMSO-$d_6$: 2.11 (3H, s), 3.34-3.40 (2H, m), 4.23-4.28 (2H, m), 4.43 (1H, d, J = 11.3 Hz), 4.54 (1H, d, J = 6.4 Hz), 4.63 (1H, d, J = 5.4 Hz), 4.74 (1H, d, J = 11.4 Hz), 6.87 (2H, s), 6.90 (1H, d, J = 8.5 Hz), 7.42 (1H, d, J = 2.3 Hz), 7.53 (1H, dd, J = 8.6, 2.3 Hz), 7.87 (1H, t, J = 2.1 Hz), 8.52 (1H, d, J = 1.9 Hz), 8.66 (1H, d, J = 2.2 Hz) |
| RP 69 | ESI+: 353<br>NMR-DMSO-$d_6$: 1.22 (3H, s), 1.77 (3H, s), 4.20 (1H, d, J = 8.9 Hz), 4.29-4.35 (3H, m), 4.39 (1H, d, J = 6.9 Hz), 4.91 (1H, d, J = 5.6 Hz), 6.35 (2H, s), 6.85 (1H, d, J = 8.5 Hz), 7.35 (1H, d, J = 2.3 Hz), 7.54 (1H, dd, J = 8.6, 2.3 Hz), 8.97 (2H, s), 9.14 (1H, s) |
| RP 70 | ESI+: 382 |
| RP 71 | ESI+: 382<br>NMR-DMSO-$d_6$: 1.82-1.94 (2H, m), 2.14-2.33 (2H, m), 2.39-2.51 (1H, m), 2.95-3.03 (1H, m), 4.06 (1H, d, J = 8.7 Hz), 4.17-4.20 (2H, m), 4.49-4.53 (2H, m), 4.65 (1H, d, J = 5.4 Hz), 6.38 (2H, s), 6.93 (1H, d, J = 8.5 Hz), 7.25-7.26 (1H, m), 7.37-7.40 (1H, m), 7.42-7.46 (1H, m), 7.96-8.01 (1H, m), 8.18-8.20 (1H, m) |
| RP 72 | ESI+: 394<br>NMR-DMSO-$d_6$: 1.81-1.94 (2H, m), 2.13-2.33 (2H, m), 2.38-2.51 (1H, m), 2.95-3.02 (1H, m), 3.89 (3H, s), 4.10 (1H, d, J = 8.6 Hz), 4.17-4.20 (2H, m), 4.50-4.54 (2H, m), 4.65 (1H, d, J = 5.4 Hz), 6.39 (2H, s), 6.92 (1H, d, J = 8.4 Hz), 7.28 (1H, d, J = 2.3 Hz), 7.43 (1H, dd, J = 2.6, 2.0 Hz), 7.50 (1H, dd, J = 8.4, 2.3 Hz), 8.25 (1H, d, J = 2.7 Hz), 8.32 (1H, d, J = 1.8 Hz) |
| RP 73 | ESI+: 416 |
| RP 74 | ESI+: 378 |

TABLE 5-continued

| Ex | Data |
|---|---|
| RP 75 | ESI+: 378 |
| RP 76 | ESI+: 379 |
| RP 77 | ESI+: 356 |
| RP 78 | ESI+: 339 |
| RP 79 | ESI+: 356 |
| RP 80 | ESI+: 339 |
| RP 81 | ESI+: 368 |
| RP 82 | ESI+: 370<br>NMR-DMSO-$d_6$: 1.22 (3H, s), 1.77 (3H, s), 4.18 (1H, d, J = 8.9 Hz), 4.24 (1H, d, J = 8.9 Hz), 4.32-4.33 (2H, m), 4.39 (1H, d, J = 6.9 Hz), 4.91 (1H, d, J = 5.6 Hz), 6.35 (2H, s), 6.82 (1H, d, J = 8.5 Hz), 7.27-7.28 (1H, m), 7.34-7.38 (1H, m), 7.44 (1H, ddd, J = 7.4, 4.9, 2.0 Hz), 7.99 (1H, ddd, J = 10.4, 7.5, 2.0 Hz), 8.18-8.20 (1H, m) |
| RP 83 | ESI+: 382<br>NMR-DMSO-$d_6$: 1.21 (3H, s), 1.77 (3H, s), 3.89 (3H, s), 4.18 (1H, d, J = 8.8 Hz), 4.28-4.33 (3H, m), 4.40 (1H, d, J = 6.9 Hz), 4.91 (1H, d, J = 5.6 Hz), 6.36 (2H, s), 6.81 (1H, d, J = 8.4 Hz), 7.30 (1H, d, J = 2.3 Hz), 7.44 (1H, dd, J = 2.7, 1.9 Hz), 7.47 (1H, dd, J = 8.5, 2.3 Hz), 8.25 (1H, d, J = 2.7 Hz), 8.32 (1H, d, J = 1.8 Hz) |
| RP 84 | ESI+: 353<br>NMR-DMSO-$d_6$: 1.12 (3H, t, J = 7.2 Hz), 1.59-1.74 (1H, m), 1.86-1.99 (1H, m), 4.20 (1H, d, J = 6.9 Hz), 4.38 (1H, d, J = 6.3 Hz), 4.42 (1H, d, J = 6.9 Hz), 4.45-4.52 (1H, m), 4.54-4.68 (3H, m), 6.22 (2H, bs), 6.91 (1H, d, J = 8.4 Hz), 7.48 (1H, d, J = 2.3 Hz), 7.56 (1H, dd, J = 2.3, 8.4 Hz), 9.02 (2H, s), 9.13 (1H, s)<br>a compound prepared from Ex. 9a |
| RP 85 | ESI+: 379<br>NMR-DMSO-$d_6$: 1.51-1.55 (1H, m), 1.60-1.77 (4H, m), 1.87-1.96 (1H, m), 2.13-2.21 (1H, m), 2.49-2.56 (1H, m), 4.19-4.24 (2H, m), 4.27-4.29 (2H, m), 4.43 (1H, d, J = 6.8 Hz), 4.83 (1H, d, J = 5.3 Hz), 6.36 (2H, s), 6.85 (1H, d, J = 8.5 Hz), 7.34 (1H, d, J = 2.3 Hz), 7.53 (1H, dd, J = 8.5, 2.4 Hz), 8.97 (2H, s), 9.14 (1H, s) |
| RP 86 | ESI+: 390<br>NMR-DMSO-$d_6$: 1.11 (3H, t, J = 7.1 Hz), 1.57-1.72 (1H, m), 1.84-1.97 (1H, m), 2.11 (3H, s), 4.20 (1H, d, J = 6.9 Hz), 4.37 (1H, d, J = 6.3 Hz), 4.41 (1H, d, J = 6.9 Hz), 4.44-4.51 (1H, m), 4.52-4.66 (3H, m), 6.23 (2H, bs), 6.87 (1H, d, J = 8.5 Hz), 7.41 (1H, d, J = 2.4 Hz), 7.50 (1H, dd, J = 2.4, 8.5 Hz), 7.93-7.97 (1H, m), 8.52 (1H, d, J = 1.9 Hz), 8.71 (1H, d, J = 2.3 Hz)<br>a compound prepared from Reference Example 9a |
| RP 87 | ESI+: 353<br>NMR-DMSO-$d_6$: 1.21 (3H, t, J = 7.3 Hz), 2.02-2.30 (2H, m), 3.95-4.13 (3H, m), 4.20-4.30 (1H, m), 4.33-4.45 (2H, m), 4.55 (1H, d, J = 5.5 Hz), 6.44 (2H, bs), 6.9 (1H, d, J = 8.5 Hz), 7.46 (1H, bs), 7.51-7.61 (1H, m), 8.99 (2H, bs), 9.13 (1H, s)<br>a compound prepared from Reference Example 9b |
| RP 88 | ESI+: 365<br>NMR-DMSO-$d_6$: 0.39-0.51 (2H, m), 0.67-0.81 (2H, m), 1.36-1.46 (1H, m), 3.80 (1H, d, J = 9.5 Hz), 4.15 (1H, d, J = 7.0 Hz), 4.50 (1H, d, J = 6.4 Hz), 4.64-4.66 (2H, m), 4.81 (2H, s), 6.21 (2H, s), 6.92 (1H, d, J = 8.4 Hz), 7.53-7.57 (2H, m), 9.04 (2H, s), 9.13 (1H, s)<br>a compound prepared from Reference Example 12a |
| RP 89 | ESI+: 365<br>a compound prepared from Reference Example 12b |
| RP 90 | ESI+: 381<br>NMR-DMSO-$d_6$: 1.01 (3H, d, J = 6.5 Hz), 1.07 (3H, d, J = 6.5 Hz), 1.88-1.95 (1H, m), 2.02-2.15 (2H, m), 4.02 (1H, d, J = 8.9 Hz), 4.11-4.14 (2H, m), 4.25 (1H, d, J = 5.5 Hz), 4.32 (1H, d, J = 6.5 Hz), 4.41 (1H, d, J = 6.6 Hz), 4.58 (1H, d, J = 5.5 Hz), 6.44 (2H, s), 6.88 (1H, d, J = 8.5 Hz), 7.45 (1H, d, J = 2.4 Hz), 7.54 (1H, dd, J = 8.5, 2.4 Hz), 8.98 (2H, s), 9.13 (1H, s)<br>a compound prepared from Reference Example 13b |
| RP 91 | ESI+: 367<br>NMR-DMSO-$d_6$: 0.98 (3H, t, J = 7.2 Hz), 1.42-1.58 (1H, m), 1.62-1.77 (2H, m), 1.78-1.90 (1H, m), 4.19 (1H, d, J = 6.8 Hz), 4.37 (1H, d, J = 6.4 Hz), 4.42 (1H, d, J = 6.8 Hz), 4.53-4.71 (4H, m), 6.23 (2H, bs), 6.90 (1H, d, J = 8.4 Hz), 7.49 (1H, d, J = 2.3 Hz), 7.55 (1H, dd, J = 2.3, 8.4 Hz), 9.02 (2H, s), 9.13 (1H, s)<br>a compound prepared from Reference Example 11a |
| RP 92 | ESI+: 404<br>NMR-DMSO-$d_6$: 0.98 (3H, t, J = 7.2 Hz), 1.43-1.58 (1H, m), 1.61-1.75 (2H, m), 1.76-1.89 (1H, m), 2.11 (3H, s), 4.20 (1H, d, J = 7.0 Hz), 4.32-4.47 (2H, m), 4.51-4.78 (4H, m), 6.24 (2H, bs), 6.86 (1H, d, J = 8.5 Hz), 7.31-7.60 (2H, m), 7.97 (1H, bs), 8.52 (1H, d, J = 1.9 Hz), 8.72 (1H, bs)<br>a compound prepared from Reference Example 11a |

TABLE 5-continued

| Ex | Data |
|---|---|
| RP 93 | ESI+: 381<br>NMR-DMSO-$d_6$: 0.98 (3H, d, J = 6.6 Hz), 1.01 (3H, d, J = 6.7 Hz), 1.62-1.68 (1H, m), 1.74-1.81 (1H, m), 1.93-2.03 (1H, m), 4.17 (1H, d, J = 7.0 Hz), 4.37 (1H, d, J = 6.5 Hz), 4.41 (1H, d, J = 7.0 Hz), 4.54 (1H, d, J = 6.5 Hz), 4.63-4.72 (3H, m), 6.23 (2H, s), 6.89 (1H, d, J = 8.5 Hz), 7.49 (1H, d, J = 2.3 Hz), 7.55 (1H, dd, J = 8.5, 2.3 Hz), 9.02 (2H, s), 9.14 (1H, s)<br>a compound prepared from Reference Example 13a |
| RP 94 | ESI+: 367<br>NMR-DMSO-$d_6$: 1.05 (3H, t, J = 7.4 Hz), 1.45-1.63 (1H, m), 1.73-1.89 (1H, m), 2.00-2.21 (2H, m), 3.94-4.15 (3H, m), 4.23 (1H, d, J = 5.5 Hz), 4.37 (1H, d, J = 6.5 Hz), 4.41 (1H, d, J = 6.5 Hz), 4.56 (1H, d, J = 5.5 Hz), 6.44 (2H, bs), 6.89 (1H, d, J = 8.5 Hz), 7.46 (1H, bs), 7.55 (1H, dd, J = 2.2, 8.5 Hz), 8.99 (2H, bs), 9.13 (1H, s)<br>a compound prepared from Reference Example 11b |
| RP 95 | ESI+: 421<br>NMR-DMSO-$d_6$: 1.90-2.07 (1H, m), 2.16-2.20 (1H, m), 2.52-2.69 (2H, m), 4.18 (1H, d, J = 7.2 Hz), 4.40 (1H, d, J = 6.8 Hz), 4.47 (1H, d, J = 7.2 Hz), 4.55 (1H, d, J = 6.8 Hz), 4.58-4.68 (1H, m), 4.73 (1H, d, J = 9.5 Hz), 4.75 (1H, d, J = 9.5 Hz), 6.21 (2H, bs), 6.96 (1H, d, J = 8.5 Hz), 7.53 (1H, d, J = 2.2 Hz), 7.58 (1H, dd, J = 2.2, 8.5 Hz), 9.04 (2H, s), 9.14 (1H, s)<br>a compound prepared from Reference Example 14a |
| RP 96 | ESI+: 458<br>NMR-DMSO-$d_6$: 1.89-2.05 (1H, m), 2.11 (3H, s), 2.14-2.29 (1H, m), 2.50-2.69 (2H, m), 4.18 (1H, d, J = 7.2 Hz), 4.39 (1H, d, J = 6.8 Hz), 4.46 (1H, d, J = 7.2 Hz), 4.56 (1H, d, J = 6.8 Hz), 4.58-4.65 (1H, m), 4.69 (1H, d, J = 9.2 Hz), 4.74 (1H, d, J = 9.2 Hz), 6.22 (2H, bs), 6.91 (1H, d, J = 8.5 Hz), 7.45 (1H, d, J = 2.3 Hz), 7.52 (1H, dd, J = 2.3, 8.5 Hz), 7.95-8.00 (1H, m), 8.52 (1H, d, J = 1.9 Hz), 8.72 (1H, d, J = 2.3 Hz)<br>a compound prepared from Reference Example 14a |
| RP 97 | ESI+: 339<br>a compound prepared from Reference Example 1a |
| RP 98 | ESI+: 339<br>a compound prepared from Reference Example 1b |
| RP 99 | ESI+: 432 |
| RP 100 | ESI+: 309<br>NMR-DMSO-$d_6$: 0.42-0.44 (3H, m), 0.81-0.83 (1H, m), 3.67 (1H, d, J = 11.6 Hz), 4.21 (1H, d, J = 7.8 Hz), 4.35 (1H, d, J = 7.8 Hz), 4.44 (1H, d, J = 11.6 Hz), 6.21 (2H, brs), 6.91-6.93 (1H, m), 7.45 (1H, s), 7.55-7.58 (1H, m), 8.99 (2H, s), 9.12 (1H, s) |
| RP 101 | ESI+: 323 |
| RP 102 | ESI+: 327<br>NMR-DMSO-$d_6$: 0.42-0.48 (3H, m), 0.81-0.86 (1H, m), 3.71 (1H, d, J = 11.7 Hz), 4.19 (1H, d, J = 8.2 Hz), 4.35 (1H, d, J = 8.2 Hz), 4.49 (1H, dd, J = 1.6, 11.7 Hz), 6.20 (2H, brs), 6.83 (1H, d, J = 12.0 Hz), 7.29 (1H, d, J = 9.0 Hz), 8.91 (2H, d, J = 1.4 Hz), 9.17 (1H, s) |
| RP 103 | ESI+: 326<br>NMR-DMSO-$d_6$: 0.39-0.46 (3H, m), 0.83-0.85 (1H, m), 3.65 (1H, d, J = 10.9 Hz), 4.16 (1H, d, J = 8.0 Hz), 4.33 (1H, d, J = 8.0 Hz), 4.44 (1H, d, J = 10.9 Hz), 6.20 (2H, brs), 6.89 (1H, d, J = 8.4 Hz), 7.33-7.34 (1H, m), 7.37-7.40 (1H, m), 7.42-7.45 (1H, m), 7.97-8.02 (1H, m), 8.17-8.18 (1H, m) |
| RP 104 | ESI+: 360, 362<br>NMR-DMSO-$d_6$: 0.42-0.46 (3H, m), 0.81-0.83 (1H, m), 3.67 (1H, d, J = 11.7 Hz), 4.16 (1H, d, J = 8.2 Hz), 4.34 (1H, d, J = 8.2 Hz), 4.45 (1H, dd, J = 11.7, 1.6 Hz), 6.21 (2H, brs), 6.89 (1H, d, J = 8.5 Hz), 7.37-7.38 (1H, m), 7.41-7.44 (1H, m), 8.16-8.19 (1H, m), 8.24-8.25 (1H, m) |
| RP 105 | ESI+: 338<br>NMR-DMSO-$d_6$: 0.41-0.45 (3H, m), 0.82-0.86 (1H, m), 3.65 (1H, d, J = 11.7 Hz), 3.89 (3H, s), 4.20 (1H, d, J = 8.1 Hz), 4.32 (1H, d, J = 8.1 Hz), 4.41-4.44 (1H, m), 6.21 (2H, brs), 6.87 (1H, d, J = 8.4 Hz), 7.37-7.38 (1H, m), 7.44-7.45 (1H, m), 7.48-7.51 (1H, m), 8.24 (1H, d, J = 2.8 Hz), 8.34 (1H, d, J = 1.9 Hz) |
| RP 106 | ESI+: 352<br>NMR-DMSO-$d_6$: 0.42-0.44 (3H, m), 0.82-0.84 (1H, m), 1.37 (3H, t, J = 7.0 Hz), 3.65 (1H, d, J = 11.7 Hz), 4.15-4.20 (3H, m), 4.32-4.34 (1H, m), 4.41-4.44 (1H, m), 6.21 (2H, brs), 6.87 (1H, d, J = 8.5 Hz), 7.38 (1H, s), 7.44 (1H, s), 7.48-7.50 (1H, m), 8.22 (1H, d, J = 2.7 Hz), 8.33 (1H, d, J = 1.2 Hz) |
| RP 107 | ESI+: 342, 344<br>NMR-DMSO-$d_6$: 0.38-0.48 (3H, m), 0.81-0.84 (1H, m), 3.67 (2H, d, J = 11.9 Hz), 4.20-4.25 (1H, m), 4.32-4.37 (1H, m), 4.45 (1H, d, J = 11.9 Hz), 6.21 (2H, brs), 6.89 (1H, d, J = 8.2 Hz), 7.42-7.45 (1H, m), 7.55-7.59 (1H, m), 8.09 (1H, brs), 8.55-8.56 (1H, m), 8.74 (1H, brs) |
| RP 108 | ESI+: 362 |
| RP 109 | ESI+: 402 |
| RP 110 | ESI+: 390 |
| RP 111 | ESI+: 346<br>NMR-DMSO-$d_6$: 0.41-0.45 (3H, m), 0.81-0.86 (1H, m), 2.11 (3H, s), 3.65 (1H, d, J = 11.6 Hz), 4.21 (1H, d, J = 8.1 Hz), 4.33 (1H, d, J = 8.1 Hz), 4.43 (1H, d, J = 11.6 Hz), 6.21 (2H, |

TABLE 5-continued

| Ex | Data |
|---|---|
| | brs), 6.87 (1H, d, J = 8.4 Hz), 7.39 (1H, d, J = 2.4 Hz), 7.50-7.53 (1H, m), 7.91 (1H, t, J = 2.1 Hz), 8.51 (1H, d, J = 2.1 Hz), 8.70 (1H, d, J = 2.1 Hz) |
| RP 112 | ESI+: 364 NMR-DMSO-$d_6$: 0.41-0.49 (3H, m), 0.81-0.88 (1H, m), 2.10 (3H, s), 3.69 (1H, d, J = 11.8 Hz), 4.18-4.41 (2H, m), 4.48 (1H, d, J = 11.8 Hz), 6.22 (2H, brs), 6.79 (1H, d, J = 11.8 Hz), 7.26 (1H, brs), 7.86 (1H, s), 8.56 (1H, d, J = 2.0 Hz), 8.59 (1H, s) |
| RP 113 | ESI+: 360 NMR-DMSO-$d_6$: 1.57-1.62 (2H, m), 1.68-1.76 (1H, m), 1.85-2.00 (2H, m), 2.11 (3H, s), 2.14-2.18 (1H, m), 3.97-4.10 (3H, m), 4.37-4.43 (1H, m), 6.26 (2H, brs), 6.83-6.86 (1H, m), 7.42 (1H, s), 7.48-7.50 (1H, m), 7.91 (1H, s), 8.50-8.51 (1H, m), 8.69 (1H, s) |
| RP 114 | ESI+: 339, 341 |
| RP 115 | ESI+: 389 NMR-DMSO-$d_6$: 1.82-1.97 (2H, m), 2.15-2.34 (2H, m), 2.44-2.52 (1H, m), 2.94-3.03 (1H, m), 4.10 (1H, d, J = 8.7 Hz), 4.20 (1H, d, J = 5.5 Hz), 4.26 (1H, d, J = 8.7 Hz), 4.48 (1H, d, J = 6.8 Hz), 4.53 (1H, d, J = 6.8 Hz), 4.66 (1H, d, J = 5.5 Hz), 6.36 (2H, s), 6.99 (1H, d, J = 8.5 Hz), 7.28 (1H, d, J = 2.3 Hz), 7.45 (1H, dd, J = 8.5, 2.3 Hz), 7.80 (1H, dd, J = 8.0, 4.7 Hz), 8.02 (1H, dd, J = 8.0, 1.6 Hz), 8.72 (1H, dd, J = 4.7, 1.6 Hz) |
| RP 116 | ESI+: 396 |
| RP 117 | ESI+: 379 |
| RP 118 | ESI+: 414 |
| RP 119 | ESI+: 382 |
| RP 120 | ESI+: 389 |
| RP 121 | ESI+: 400 |
| RP 122 | ESI+: 412 |
| RP 123 | ESI+: 363 |
| RP 124 | ESI+: 381 |
| RP 125 | ESI+: 381 |
| RP 126 | ESI+: 393 |
| RP 127 | ESI+: 377 |
| RP 128 | ESI+: 388 |
| RP 129 | ESI+: 475 |
| RP 130 | ESI+: 399 |
| RP 131 | ESI+: 407 |
| RP 132 | ESI+: 414 |
| RP 133 | ESI+: 425 |
| RP 134 | ESI+: 406 |
| RP 135 | ESI+: 367 |
| RP 136 | ESI+: 411 |
| RP 137 | ESI+: 411 |
| RP 138 | ESI+: 399 |
| RP 139 | ESI+: 385, 387 |
| RP 140 | ESI+: 391 |
| RP 141 | ESI+: 419 |
| RP 142 | ESI+: 381 |
| RP 143 | ESI+: 449 |
| RP 144 | ESI+: 395 |
| RP 145 | ESI+: 411 |

TABLE 5-continued

| Ex | Data |
|---|---|
| RP 146 | ESI+: 403, 405 |
| RP 147 | ESI+: 387 |
| RP 148 | ESI+: 383 |
| RP 149 | ESI+: 370 |
| RP 150 | ESI+: 387, 389 |
| RP 151 | ESI+: 400, 402 |
| RP 152 | ESI+: 420, 422 |
| RP 153 | ESI+: 404, 406 |
| RP 154 | ESI+: 404, 406 |
| RP 155 | ESI+: 416, 418 |
| RP 156 | ESI+: 386, 388 |
| RP 157 | ESI+: 384 |
| RP 158 | ESI+: 404, 406 |
| RP 159 | ESI+: 420, 422 |
| RP 160 | ESI+: 377 |
| RP 161 | ESI+: 400 |
| RP 162 | ESI+: 416, 418 |
| RP 163 | ESI+: 386, 388 |
| RP 164 | ESI+: 382 |
| RP 165 | ESI+: 369 |
| RP 166 | ESI+: 369 |
| RP 167 | ESI+: 343 |
| RP 168 | ESI+: 391 |
| RP 169 | ESI+: 385 |
| RP 170 | ESI+: 394 |
| RP 171 | ESI+: 426 |
| RP 172 | ESI+: 383 |
| RP 173 | ESI+: 386, 388 |
| RP 174 | ESI+: 390 |
| RP 175 | ESI+: 390 |
| RP 176 | ESI+: 391 |
| RP 177 | ESI+: 391 |
| RP 178 | ESI+: 393 |
| RP 179 | ESI+: 402 |
| RP 180 | ESI+: 402 |
| RP 181 | ESI+: 345 |
| RP 182 | ESI+: 395 |
| RP 183 | ESI+: 435 |
| RP 184 | ESI+: 435 |

TABLE 5-continued

| Ex | Data |
|---|---|
| RP 185 | ESI+: 405 |
| RP 186 | ESI+: 390 |
| RP 187 | ESI+: 417 |
| RP 188 | ESI+: 359, 361 |
| RP 189 | ESI+: 430, 432<br>NMR-DMSO-$d_6$: 0.32-0.46 (3H, m), 0.78-0.90 (1H, m), 3.58 (1H, d, J = 11.6 Hz), 4.09 (1H, d, J = 8.1 Hz), 4.31 (1H, d, J = 8.1 Hz), 4.36 (1H, dd, J = 1.3, 11.6 Hz), 6.18 (2H, bs), 6.71-6.77 (1H, m), 7.58-7.65 (2H, m), 9.19 (2H, s), 10.60 (1H, s) |
| RP 190 | ESI+: 474, 476<br>NMR-DMSO-$d_6$: 1.18 (3H, s), 1.73 (3H, s), 4.09-4.22 (2H, m), 4.25-4.42 (3H, m), 4.90 (1H, d, J = 5.6 Hz), 6.33 (2H, bs), 6.63-6.71 (1H, m), 7.54-7.63 (2H, m), 9.19 (2H, s), 10.64 (1H, s) |
| RP 191 | ESI+: 390<br>NMR-DMSO-$d_6$: 0.34-0.45 (3H, m), 0.78-0.86 (1H, m), 2.52 (3H, s), 3.58 (1H, d, J = 11.6 Hz), 4.08 (1H, d, J = 8.1 Hz), 4.31 (1H, d, J = 8.1 Hz), 4.36 (1H, dd, J = 1.5, 11.6 Hz), 6.18 (2H, bs), 6.71-6.76 (1H, m), 7.53-7.59 (2H, m), 8.34-8.38 (1H, m), 8.92-8.97 (1H, m), 10.49 (1H, s) |
| RP 192 | ESI+: 410, 412<br>NMR-DMSO-$d_6$: 0.35-0.45 (3H, m), 0.78-0.86 (1H, m), 3.58 (1H, d, J = 11.6 Hz), 4.09 (1H, d, J = 8.1 Hz), 4.31 (1H, d, J = 8.1 Hz), 4.37 (1H, dd, J = 1.4, 11.6 Hz), 6.20 (2H, bs), 6.76 (1H, d, J = 8.8 Hz), 7.45 (1H, d, J = 2.7 Hz), 7.55 (1H, dd, J = 2.7, 8.8 Hz), 8.77 (1H, d, J = 1.8 Hz), 9.07 (1H, d, J = 1.8 Hz), 10.64 (1H, s) |
| RP 193 | ESI+: 382<br>NMR-DMSO-$d_6$: 0.35-0.44 (3H, m), 0.80-0.88 (1H, m), 3.58 (1H, d, J = 11.5 Hz), 4.01 (3H, s), 4.09 (1H, d, J = 8.1 Hz), 4.31 (1H, d, J = 8.1 Hz), 4.34 (1H, br.d, J = 11.6 Hz), 6.16 (2H, s), 6.72 (1H, d, J = 8.8 Hz), 7.56 (1H, dd, J = 2.7, 8.8 Hz), 7.71 (1H, d, J = 2.6 Hz), 8.38 (1H, d, J = 1.3 Hz), 8.86 (1H, d, J = 1.3 Hz), 10.30 (1H, s) |
| RP 194 | ESI+: 399, 401<br>NMR-DMSO-$d_6$: 0.37-0.43 (3H, m), 0.82-0.88 (1H, m), 2.54 (3H, s), 3.57 (1H, d, J = 11.7 Hz), 4.08 (1H, d, J = 8.1 Hz), 4.31 (1H, d, J = 8.1 Hz), 4.34-4.37 (1H, m), 6.18 (2H, s), 6.72 (1H, d, J = 8.7 Hz), 7.54-7.58 (2H, m), 7.98-7.99 (1H, m), 8.536-8.543 (1H, m), 10.34 (1H, s) |
| RP 195 | ESI+: 443, 445<br>NMR-DMSO-$d_6$: 1.18 (3H, s), 1.73 (3H, s), 2.53 (3H, s), 4.13-4.18 (2H, m), 4.30 (2H, d, J = 6.1 Hz), 4.36 (1H, d, J = 6.8 Hz), 4.90 (1H, d, J = 5.6 Hz), 6.33 (2H, s), 6.64-6.66 (1H, m), 7.52-7.55 (2H, m), 7.99 (1H, dd, J = 2.4, 0.7 Hz), 8.54-8.55 (1H, m), 10.38 (1H, s) |
| RP 196 | ESI+: 376<br>NMR-DMSO-$d_6$: 0.36-0.44 (3H, m), 0.82-0.85 (1H, m), 3.58 (1H, d, J = 11.6 Hz), 4.09 (1H, d, J = 8.1 Hz), 4.30-4.37 (2H, m), 6.18 (2H, s), 6.74 (1H, d, J = 8.8 Hz), 7.61 (1H, dd, J = 8.8, 2.7 Hz), 7.74 (1H, d, J = 2.6 Hz), 8.26 (1H, dd, J = 8.2, 0.9 Hz), 8.56 (1H, dd, J = 8.2, 2.1 Hz), 9.16 (1H, dd, J = 2.1, 0.9 Hz), 10.64 (1H, s) |
| RP 197 | ESI+: 420<br>NMR-DMSO-$d_6$: 1.18 (3H, s), 1.73 (3H, s), 4.13-4.19 (2H, m), 4.30-4.37 (3H, m), 4.90 (1H, d, J = 5.6 Hz), 6.33 (2H, s), 6.67 (1H, d, J = 8.8 Hz), 7.59 (1H, dd, J = 8.8, 2.6 Hz), 7.74 (1H, d, J = 2.5 Hz), 8.26 (1H, dd, J = 8.2, 0.9 Hz), 8.56 (1H, dd, J = 8.2, 2.1 Hz), 9.16-9.17 (1H, m), 10.69 (1H, s) |
| RP 198 | ESI+: 375 |
| RP 199 | ESI+: 373<br>NMR-DMSO-$d_6$: 0.18-0.22 (1H, m), 0.39-0.46 (2H, m), 0.61-0.63 (1H, m), 4.14 (1H, d, J = 11.5 Hz), 4.58 (1H, d, J = 11.5 Hz), 6.47 (2H, brs), 6.82 (1H, s), 7.06 (1H, d, J = 8.7 Hz), 7.21-7.27 (2H, m), 7.42 (1H, s), 7.58 (1H, d, J = 8.7 Hz), 8.81 (2H, s), 9.05 (1H, s) |
| RP 200 | ESI+: 415<br>NMR-DMSO-$d_6$: 2.89-2.95 (1H, m), 3.26-3.32 (1H, m), 4.30 (1H, d, J = 7.0 Hz), 4.45 (1H, d, J = 6.3 Hz), 4.60-4.72 (4H, m), 4.79-4.83 (1H, m), 6.28 (2H, brs), 6.82 (1H, d, J = 8.4 Hz), 7.23-7.29 (1H, m), 7.32-7.37 (4H, m), 7.51 (1H, d, J = 2.3 Hz), 7.56 (1H, dd, J = 2.3, 8.4 Hz), 9.02 (2H, s), 9.14 (1H, s)<br>a compound prepared from Reference Example 15a |
| RP 201 | ESI+: 452<br>NMR-DMSO-$d_6$: 2.11 (3H, s), 2.87-2.94 (1H, m), 3.24-3.34 (1H, m), 4.31 (1H, d, J = 7.0 Hz), 4.44 (1H, d, J = 6.3 Hz), 4.59-4.71 (4H, m), 4.79 (1H, dd, J = 1.9, 10.7 Hz), 6.29 (2H, brs), 6.77 (1H, d, J = 8.5 Hz), 7.23-7.28 (1H, m), 7.32-7.37 (4H, m), 7.44 (1H, d, J = 2.3 Hz), 7.51 (1H, dd, J = 2.3, 8.5 Hz), 7.95-7.96 (1H, m), 8.52 (1H, d, J = 1.9 Hz), 8.71 (1H, d, J = 2.3 Hz)<br>a compound prepared from Reference Example 15a |
| RP 202 | ESI+: 415<br>NMR-DMSO-$d_6$: 3.31-3.39 (1H, m), 3.57 (1H, brd, J = 13.5 Hz), 4.10-4.17 (2H, m), 4.38-4.43 (2H, m), 4.48 (1H, d, J = 6.6 Hz), 4.53 (1H, d, J = 6.6 Hz), 4.63 (1H, d, J = 5.7 Hz), 6.45 (2H, brs), 6.76 (1H, d, J = 8.4 Hz), 7.24-7.28 (1H, m), 7.33-7.38 (2H, m), 7.46-7.53 (4H, m), 8.98 (2H, s), 9.13 (1H, s)<br>a compound prepared from Reference Example 15b |
| RP 203 | ESI+: 452<br>NMR-DMSO-$d_6$: 2.10 (3H, s), 3.31-3.38 (1H, m), 3.56 (1H, brd, J = 13.8 Hz), 4.10-4.15 (2H, m), 4.36-4.40 (1H, m), 4.42 (1H, d, J = 5.6 Hz), 4.47 (1H, d, J = 6.6 Hz), 4.53 (1H, d, J = 6.6 Hz), 4.63 (1H, d, J = 5.6 Hz), 6.46 (2H, brs), 6.71 (1H, d, J = 8.4 Hz), 7.23-7.28 |

TABLE 5-continued

| Ex | Data |
|---|---|
| | (1H, m), 7.33-7.51 (6H, m), 7.89-7.91 (1H, m), 8.51 (1H, d, J = 1.9 Hz), 8.67 (1H, d, J = 2.3 Hz)<br>a compound prepared from Reference Example 15b |
| RP 204 | ESI+: 379<br>NMR-DMSO-$d_6$: 0.11-0.24 (2H, m), 0.43-0.58 (2H, m), 1.00-1.08 (1H, m), 1.48-1.54 (1H, m), 1.82-1.90 (1H, m), 4.19 (1H, d, J = 6.9 Hz), 4.34 (1H, d, J = 6.3 Hz), 4.40 (1H, d, J = 6.9 Hz), 4.54-4.70 (4H, m), 6.24 (2H, brs), 6.92 (1H, d, J = 8.5 Hz), 7.48 (1H, d, J = 2.3 Hz), 7.57 (1H, dd, J = 2.3, 8.5 Hz), 9.02 (2H, s), 9.14 (1H, s)<br>a compound prepared from Reference Example 16a |
| RP 205 | ESI+: 416<br>NMR-DMSO-$d_6$: 0.11-0.24 (2H, m), 0.43-0.58 (2H, m), 0.98-1.08 (1H, m), 1.46-1.52 (1H, m), 1.80-1.87 (1H, m), 2.11 (3H, s), 4.19 (1H, d, J = 6.9 Hz), 4.33 (1H, d, J = 6.2 Hz), 4.39 (1H, d, J = 6.9 Hz), 4.51 (1H, d, J = 9.0 Hz), 4.58-4.63 (2H, m), 4.65-4.69 (1H, m), 6.25 (2H, brs), 6.87 (1H, d, J = 8.5 Hz), 7.41 (1H, d, J = 2.3 Hz), 7.51 (1H, dd, J = 2.3, 8.5 Hz), 7.95 (1H, dd, J = 1.9, 2.2 Hz), 8.52 (1H, d, J = 1.9 Hz), 8.71 (1H, d, J = 2.2 Hz)<br>a compound prepared from Reference Example 16a |
| RP 206 | ESI+: 359 |
| RP 207 | ESI+: 379<br>NMR-DMSO-$d_6$: 0.24-0.33 (2H, m), 0.44-0.50 (1H, m), 0.56-0.62 (1H, m), 1.09-1.19 (1H, m), 1.69-1.75 (1H, m), 2.30-2.37 (1H, m), 4.05-4.12 (2H, m), 4.15-4.18 (1H, m), 4.25 (1H, d, J = 5.5 Hz), 4.30 (1H, d, J = 6.6 Hz), 4.39 (1H, d, J = 6.6 Hz), 4.55 (1H, d, J = 5.5 Hz), 6.43 (2H, brs), 6.91 (1H, d, J = 8.4 Hz), 7.46 (1H, d, J = 2.4 Hz), 7.57 (1H, dd, J = 2.4, 8.4 Hz), 8.99 (2H, s), 9.13 (1H, s)<br>a compound prepared from Reference Example 16b |
| RP 208 | ESI+: 359 |
| RP 209 | ESI+: 364<br>NMR-DMSO-$d_6$: 1.80-1.95 (2H, m), 2.13-2.24 (1H, m), 2.24-2.34 (1H, m), 2.37-2.48 (1H, m), 2.94-3.04 (1H, m), 4.07-4.15 (1H, m), 4.15-4.23 (2H, m), 4.47-4.54 (2H, m), 4.66 (1H, d, J = 5.2 Hz), 6.40 (2H, brs), 6.92 (1H, d, J = 8.4 Hz), 7.28 (1H, s), 7.44-7.50 (2H, m), 7.90 (1H, d, J = 7.6 Hz), 8.52 (1H, d, J = 4.8 Hz), 8.73 (1H, s) |
| RP 210 | ESI+: 414 |
| RP 211 | ESI+: 414 |
| RP 212 | ESI+: 432 |
| RP 213 | ESI+: 361 |
| RP 214 | ESI+: 323, 325 |
| RP 215 | ESI+: 323<br>NMR-DMSO-$d_6$: 0.20-0.24 (1H, m), 0.42-0.54 (2H, m), 0.95-0.98 (1H, m), 3.51 (1H, d, J = 11.6 Hz), 3.73 (1H, d, J = 11.4 Hz), 3.84 (1H, d, J = 11.4 Hz), 3.97 (1H, d, J = 15.6 Hz), 4.13 (1H, d, J = 15.6 Hz), 4.61 (1H, dd, J = 1.8, 11.6 Hz), 5.69 (2H, brs), 6.89 (1H, d, J = 8.4 Hz), 7.31 (1H, d, J = 2.4 Hz), 7.53 (1H, dd, J = 2.4, 8.4 Hz), 8.99 (2H, s), 9.12 (1H, s) |
| RP 216 | ESI+: 359, 361 |
| RP 217 | ESI+: 337, 339 |
| 218 | ESI+: 429, 431<br>NMR-DMSO-$d_6$: 1.18 (3H, s), 1.73 (3H, s), 4.13-4.19 (2H, m), 4.30-4.32 (2H, m), 4.36 (1H, d, J = 6.8 Hz), 4.90 (1H, d, J = 5.6 Hz), 6.33 (2H, s), 6.66 (1H, d, J = 8.8 Hz), 7.57 (1H, dd, J = 8.8, 2.6 Hz), 7.70 (1H, d, J = 2.6 Hz), 8.13 (1H, dd, J = 8.5, 0.8 Hz), 8.18 (1H, dd, J = 8.5, 2.3 Hz), 8.75 (1H, dd, J = 2.4, 0.7 Hz), 10.52 (1H, s)<br>Melting point: 165° C. (differential scanning calorimetry onset temperature, Heating rate: 10° C./minute, under $N_2$ flow of 50 mL/minute)<br>Crystals having characteristic peaks of powder X-ray diffraction shown at angles 2θ (°) of about 5.7, 9.6, 11.4, 12.3, 13.7, 15.7, 15.9 and 25.0.<br>This is the same compound as Ex. 228b. |
| 219 | ESI+: 473, 475<br>NMR-DMSO-$d_6$: 1.18 (3H, s), 1.73 (3H, s), 4.13-4.19 (2H, m), 4.30-4.32 (2H, m), 4.36 (1H, d, J = 6.7 Hz), 4.90 (1H, d, J = 5.6 Hz), 6.33 (2H, s), 6.66 (1H, d, J = 8.8 Hz), 7.57 (1H, dd, J = 8.8, 2.6 Hz), 7.70 (1H, d, J = 2.5 Hz), 8.05 (1H, dd, J = 8.4, 0.3 Hz), 8.29-8.32 (1H, m), 8.82-8.85 (1H, m), 10.52 (1H, s) |
| 220 | ESI+: 426<br>NMR-DMSO-$d_6$: 1.18 (3H, s), 1.73 (3H, s), 4.01 (3H, s), 4.14 (1H, d, J = 8.8 Hz), 4.17 (1H, d, J = 8.8 Hz), 4.28-4.33 (2H, m), 4.35 (1H, d, J = 6.8 Hz), 4.90 (1H, d, J = 5.6 Hz), 6.32 (2H, s), 6.65 (1H, d, J = 8.8 Hz), 7.53 (1H, dd, J = 2.6, 8.8 Hz), 7.72 (1H, d, J = 2.5 Hz), 8.38 (1H, d, J = 1.3 Hz), 8.87 (1H, d, J = 1.4 Hz), 10.35 (1H, s)<br>This is the same compound as Ex. 229b. |
| 221 | ESI+: 413<br>NMR-CDCl$_3$: 0.42-0.55 (2H, m), 0.74-0.82 (1H, m), 1.18 (3H, s), 1.23-1.30 (1H, m), 1.33 (3H, s), 4.45 (br s), 4.46 (1H, d, J = 8.0 Hz), 4.57 (1H, d, J = 8.0 Hz), 6.81 (1H, d, J = 8.8 Hz), |

TABLE 5-continued

| Ex | Data |
|---|---|
| | 7.45 (1H, d, J = 2.6 Hz), 7.60 (1H, dd, J = 2.6, 8.8 Hz), 7.84 (1H, dd, J = 2.4, 8.4 Hz), 8.20-8.24 (1H, m), 8.50-8.54 (1H, m), 9.69 (1H, bs) |
| 222 | ESI+: 397<br>NMR-CDCl$_3$: 0.41-0.55 (2H, m), 0.73-0.82 (1H, m), 1.18 (3H, s), 1.23-1.30 (1H, m), 1.33 (3H, s), 4.45 (br s), 4.46 (1H, d, J = 8.0 Hz), 4.57 (1H, d, J = 8.0 Hz), 6.81 (1H, d, J = 8.8 Hz), 7.44-7.47 (1H, m), 7.52-7.63 (2H, m), 8.28-8.33 (1H, m), 8.41 (1H, d, J = 2.8 Hz), 9.67 (1H, bs) |
| 223 | ESI+: 410<br>NMR-DMSO-d$_6$: 0.23-0.32 (1H, m), 0.49-0.57 (1H, m), 0.59-0.68 (1H, m), 1.07-1.16 (1H, m), 1.11 (3H, s), 1.27 (3H, s), 4.01 (3H, s), 4.26 (1H, d, J = 8.0 Hz), 4.37 (1H, d, J = 8.0 Hz), 6.09 (2H, bs), 6.66 (1H, d, J = 8.7 Hz), 7.53 (1H, dd, J = 2.6, 8.7 Hz), 7.61 (1H, d, J = 2.6 Hz), 8.38 (1H, d, J = 1.3 Hz), 8.86 (1H, d, J = 1.3 Hz), 10.29 (1H, s)<br>This is the same compound as Ex. 230. |
| 224 | ESI+: 430<br>NMR-DMSO-d$_6$: 0.24-0.32 (1H, m), 0.50-0.58 (1H, m), 0.60-0.68 (1H, m), 1.08-1.16 (1H, m), 1.12 (3H, s), 1.27 (3H, s), 4.27 (1H, d, J = 8.0 Hz), 4.38 (1H, d, J = 8.0 Hz), 6.11(2H, bs), 6.69 (1H, d, J = 8.7 Hz), 7.24 (1H, t, J = 53.9 Hz), 7.59 (1H, dd, J = 2.6, 8.7 Hz), 7.65 (1H, d, J = 2.6 Hz), 9.06 (1H, s), 9.34-9.37 (1H, m), 10.71(1H, s)<br>This is the free form of Ex. 231. |
| RP 225a | ESI+:337, 339<br>HPLC retention time: 4.5 minutes (CHIRALCEL OD-RH, MeCN:20 mM aqueous KH$_2$PO$_4$ = 80:20; flow rate 1.0 ml/minute, detected by 254 nm UV absorption, 2nd peak of the enantiomer pair) |
| RP 225b | ESI+:337, 339<br>HPLC retention time: 2.4 minutes (CHIRALCEL OD-RH, MeCN:20 mM aqueous KH$_2$PO$_4$ = 80:20; flow rate 1.0 ml/minute, detected by 254 nm UV absorption, 1st peak of the enantiomer pair) |
| RP 226 | ESI+: 353, 355 |
| 227 | ESI+: 426 |
| 228a | ESI+: 429, 431<br>Supercritical fluid chromatography retention time: 5.23 minutes: (eluent: supercritical CO$_2$/(EtOH with 0.1% diethylamine) = 60:40; Column: CHIRALCEL OD-H column (10 × 250 mm); flow rate 10 mL/minute; column temperature: 40° C., 1st peak of the enantiomer pair) |
| 228b | ESI+: 429, 431<br>Supercritical fluid chromatography retention time: 8.16 minutes (eluent: supercritical CO$_2$/ (EtOH with 0.1% diethylamine) = 60:40; Column: CHIRALCEL OD-H column (10 × 250 mm); flow rate 10 mL/minute; column temperature: 40° C., 2nd peak of the enantiomer pair)<br>This is the same compound as Ex. 218. |
| 229a | ESI+: 426<br>Supercritical fluid chromatography retention time: 5.94 minutes (eluent: supercritical CO$_2$/EtOH = 60:40; Column: CHIRALCEL OD-H column (4.6 × 250 mm); flow rate 3 mL/minute; column temperature: 40° C., 2nd peak of the enantiomer pair) |
| 229b | ESI+: 426<br>Supercritical fluid chromatography retention time: 3.58 minutes (eluent: supercritical CO$_2$/ EtOH = 60:40; Column: CHIRALCEL OD-H column (4.6 × 250 mm); flow rate 3 mL/minute; column temperature: 40° C., 1st peak of the enantiomer pair)<br>This is the same compound as Ex. 220. |
| 230 | ESI+: 410<br>NMR-DMSO-d$_6$: 0.23-0.32 (1H, m), 0.49-0.57 (1H, m), 0.59-0.68 (1H, m), 1.07-1.16 (1H, m), 1.11 (3H, s), 1.27 (3H, s), 4.01 (3H, s), 4.26 (1H, d, J = 8.0 Hz), 4.37 (1H, d, J = 8.0 Hz), 6.10 (2H, bs), 6.66 (1H, d, J = 8.7 Hz), 7.53 (1H, dd, J = 2.6, 8.7 Hz), 7.61 (1H, d, J = 2.6 Hz), 8.38 (1H, d, J = 1.3 Hz), 8.86 (1H, d, J = 1.3 Hz), 10.29 (1H, s)<br>Melting point: 191° C. (differential scanning calorimetry onset temperature, Heating rate: 10° C./minute, under N$_2$ flow of 50 mL/minute)<br>Crystals having characteristic peaks of powder X-ray diffraction shown at angles 2θ (°) of about 5.0, 7.9, 8.0, 8.8, 12.6, 15.2, 16.3, 17.7 and 20.2.<br>This is the same compound as Ex. 223. |
| 231 | ESI+: 430<br>NMR-DMSO-d$_6$: 0.54-0.66 (1H, m), 0.76-0.92 (2H, m), 0.94-1.05 (1H, m), 1.18 (3H, s), 1.30 (3H, s), 5.07 (2H, s), 6.87 (1H, d, J = 8.9 Hz), 7.26 (1H, t, J = 53.9 Hz), 7.90 (1H, dd, J = 2.4, 8.9 Hz), 7.98 (1H, d, J = 2.4 Hz), 9.02-9.21 (2H, m), 9.37-9.41 (1H, m), 9.57 (1H, bs), 10.55 (1H, s), 10.98 (1H, s)<br>Melting point: 254° C. (differential scanning calorimetry onset temperature, Heating rate: 10° C./minute, under N$_2$ flow of 50 mL/minute)<br>Crystals having characteristic peaks of powder X-ray diffraction shown at angles 2θ (°) of about 4.8, 6.5, 8.4, 12.8, 16.0, 17.4, 23.4, 26.6 and 27.6.<br>This is the hydrochloride of Ex. 224. |

The compounds shown in Tables below can be prepared using tert-butyl (6'-aminodispiro[cyclopropane-1,3'-chromene-4',4''-[1,3]oxazol]-2''-yl)carbamate or tert-butyl (6'-amino-2',2'-dimethyldispiro[1,3-oxazole-4,4'-chromene-3',3''-oxetan]-2-yl)carbamate as a starting material in the same manner as the methods of Preparation Examples 70 and Reference Examples 19 or Examples 27 above. The structures, and the preparation methods, for the compounds are shown in [Table. 6] below.

TABLE 6

| No. | Structure | 1st_step | 2nd_step |
|---|---|---|---|
| P1 | 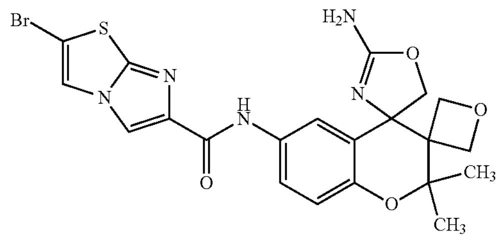 [SMILES: CC1(C)Oc2ccc(NC(=O)c3cn4cc(Br)sc4n3)cc2C2(COC(N)=N2)C12COC2] | R70 | E27 |
| P2 | 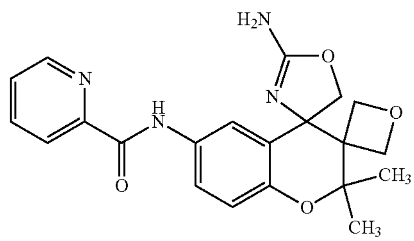 | R70 | E27 |
| P3 | 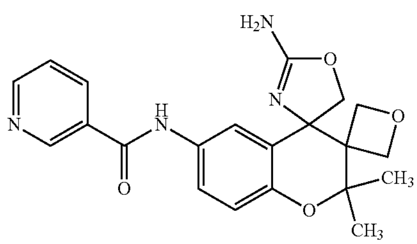 [SMILES: CC1(C)Oc2ccc(NC(=O)c3cccnc3)cc2C2(COC(N)=N2)C12COC2] | R70 | E27 |
| P4 | 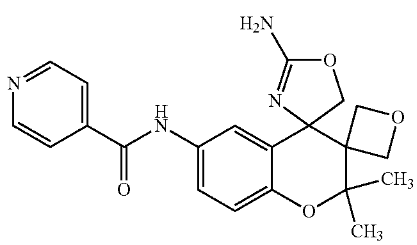 | R70 | E27 |
| P5 | 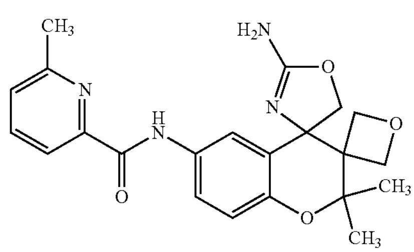 | R70 | E27 |
| P6 | 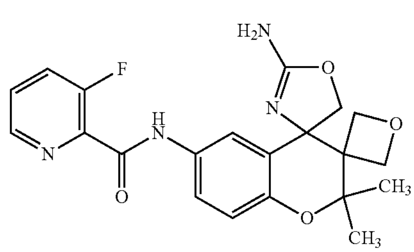 [SMILES: CC1(C)Oc2ccc(NC(=O)c3ncccc3F)cc2C2(COC(N)=N2)C12COC2] | R70 | E27 |

TABLE 6-continued

| No. | Structure | 1st_step | 2nd_step |
|---|---|---|---|
| P7 | 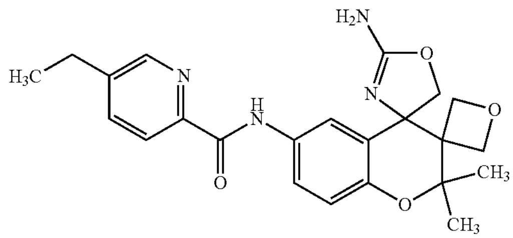 [SMILES: CCc1ccc(C(=O)Nc2ccc3c(c2)C2(COC(N)=N2)C2(COC2)C(C)(C)O3)nc1] | R70 | E27 |
| P8 | 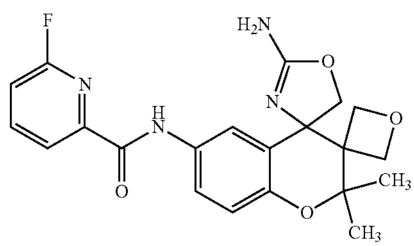 [SMILES: CC1(C)Oc2ccc(NC(=O)c3cccc(F)n3)cc2C2(COC(N)=N2)C12COC2] | R70 | E27 |
| P9 | 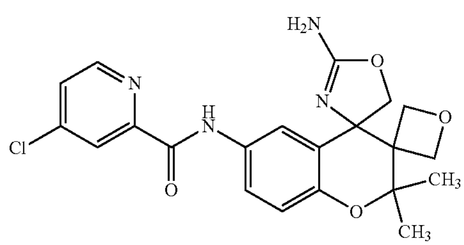 [SMILES: CC1(C)Oc2ccc(NC(=O)c3cc(Cl)ccn3)cc2C2(COC(N)=N2)C12COC2] | R70 | E27 |
| P10 | 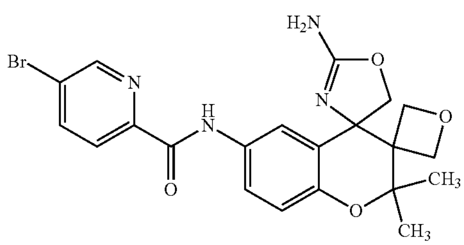 [SMILES: CC1(C)Oc2ccc(NC(=O)c3ccc(Br)cn3)cc2C2(COC(N)=N2)C12COC2] | R70 | E27 |
| P11 | 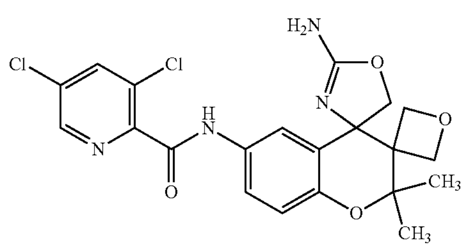 [SMILES: CC1(C)Oc2ccc(NC(=O)c3ncc(Cl)cc3Cl)cc2C2(COC(N)=N2)C12COC2] | R70 | E27 |
| P12 | 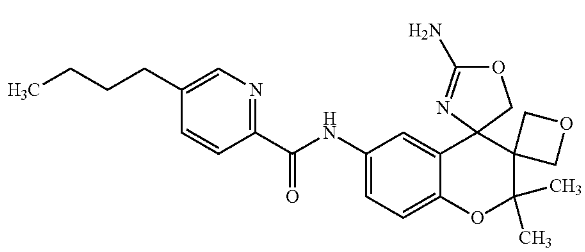 [SMILES: CCCCc1ccc(C(=O)Nc2ccc3c(c2)C2(COC(N)=N2)C2(COC2)C(C)(C)O3)nc1] | R70 | E27 |

TABLE 6-continued

| No. | Structure | 1st_step | 2nd_step |
|---|---|---|---|
| P13 | 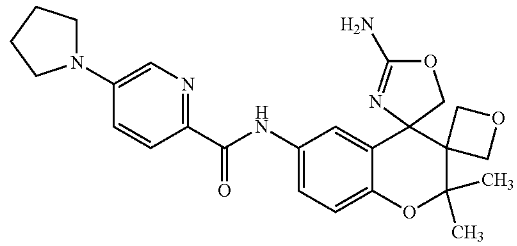 [SMILES: CC1(C)Oc2ccc(NC(=O)c3ccc(N4CCCC4)cn3)cc2C2(COC(N)=N2)C12COC2] | R70 | E27 |
| P14 | 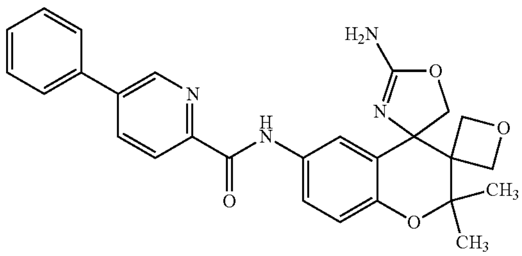 [SMILES: CC1(C)Oc2ccc(NC(=O)c3ccc(-c4ccccc4)cn3)cc2C2(COC(N)=N2)C12COC2] | R70 | E27 |
| P15 | 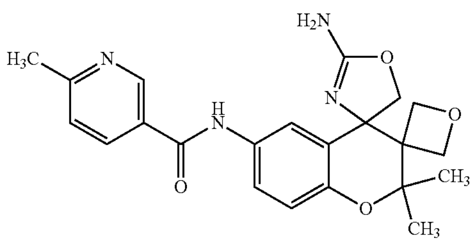 [SMILES: Cc1ccc(C(=O)Nc2ccc3c(c2)C2(COC(N)=N2)C2(COC2)C(C)(C)O3)cn1] | R70 | E27 |
| P16 | 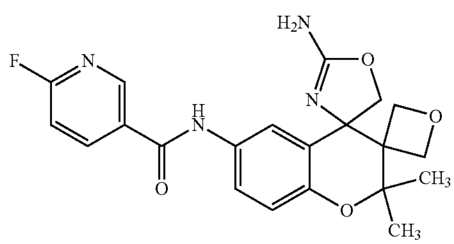 [SMILES: CC1(C)Oc2ccc(NC(=O)c3ccc(F)nc3)cc2C2(COC(N)=N2)C12COC2] | R70 | E27 |
| P17 | 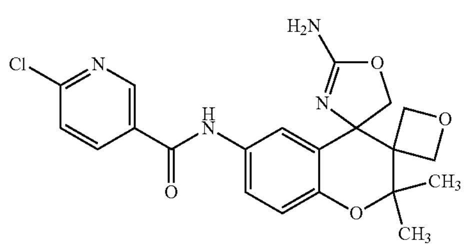 [SMILES: CC1(C)Oc2ccc(NC(=O)c3ccc(Cl)nc3)cc2C2(COC(N)=N2)C12COC2] | R70 | E27 |
| P18 | 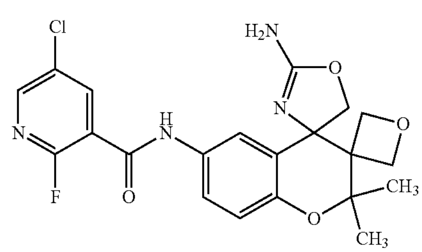 [SMILES: CC1(C)Oc2ccc(NC(=O)c3cc(Cl)cnc3F)cc2C2(COC(N)=N2)C12COC2] | R70 | E27 |

TABLE 6-continued
| No. | Structure | 1st_step | 2nd_step |
|---|---|---|---|
| P19 | 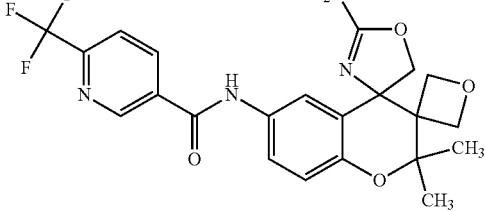 | R70 | E27 |
| P20 | 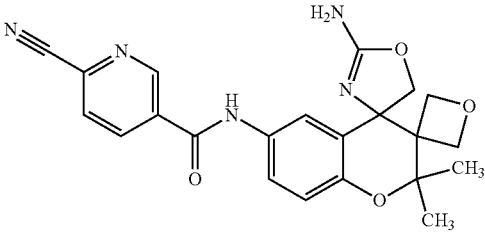 [SMILES: CC1(C)Oc2ccc(NC(=O)c3ccc(C#N)nc3)cc2C2(COC(N)=N2)C12COC2] | R70 | E27 |
| P21 | 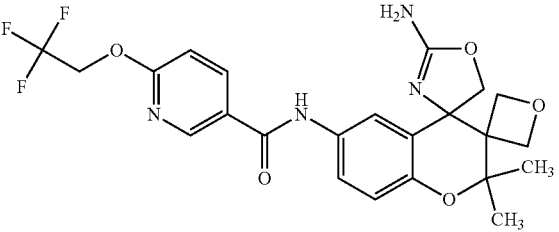 [SMILES: CC1(C)Oc2ccc(NC(=O)c3ccc(OCC(F)(F)F)nc3)cc2C2(COC(N)=N2)C12COC2] | R70 | E27 |
| P22 | 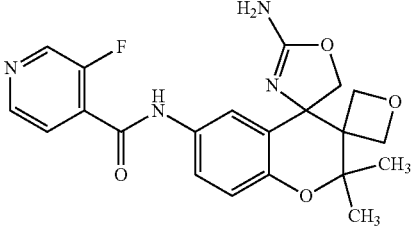 [SMILES: CC1(C)Oc2ccc(NC(=O)c3ccncc3F)cc2C2(COC(N)=N2)C12COC2] | R70 | E27 |
| P23 | 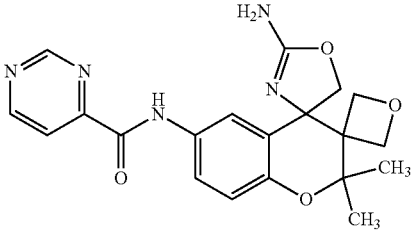 | R70 | E27 |
| P24 | 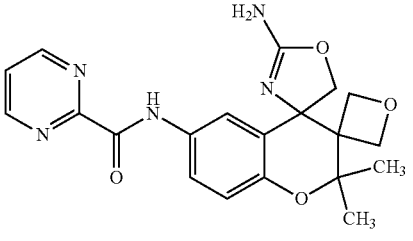 [SMILES: CC1(C)Oc2ccc(NC(=O)c3ncccn3)cc2C2(COC(N)=N2)C12COC2] | R70 | E27 |

TABLE 6-continued
| No. | Structure | 1st_step | 2nd_step |
|---|---|---|---|
| P25 | 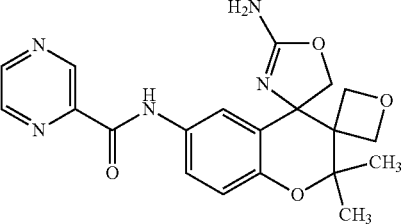 [SMILES: CC1(C)Oc2ccc(NC(=O)c3cnccn3)cc2C2(COC(N)=N2)C12COC2] | R70 | E27 |
| P26 | 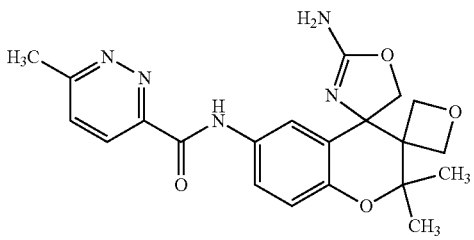 [SMILES: Cc1ccc(C(=O)Nc2ccc3c(c2)C2(COC(N)=N2)C2(COC2)C(C)(C)O3)nn1] | R70 | E27 |
| P27 | 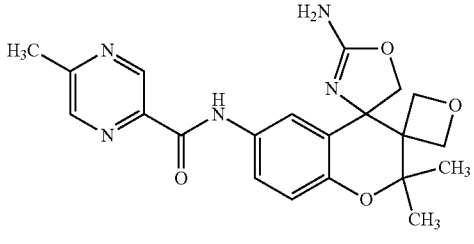 [SMILES: Cc1cnc(C(=O)Nc2ccc3c(c2)C2(COC(N)=N2)C2(COC2)C(C)(C)O3)cn1] | R70 | E27 |
| P28 | 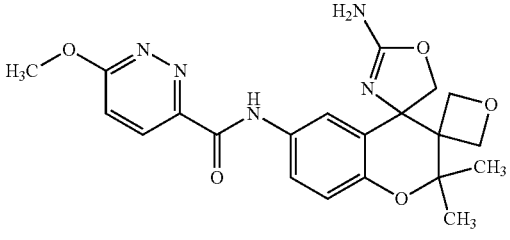 | R70 | E27 |
| P29 | 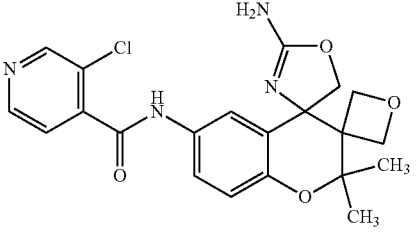 | R70 | E27 |
| P30 | 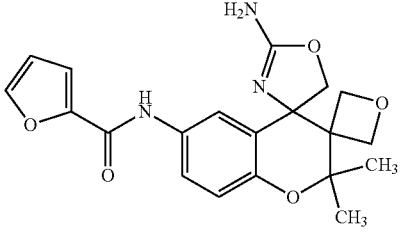 | R70 | E27 |

TABLE 6-continued

| No. | Structure | 1st_step | 2nd_step |
|---|---|---|---|
| P31 | 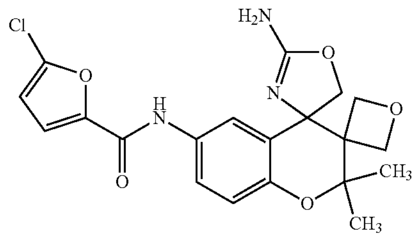 [SMILES: CC1(C)Oc2ccc(NC(=O)c3ccc(Cl)o3)cc2C2(COC(N)=N2)C12COC2] | R70 | E27 |
| P32 | 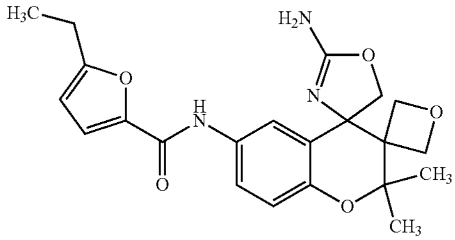 | R70 | E27 |
| P33 | 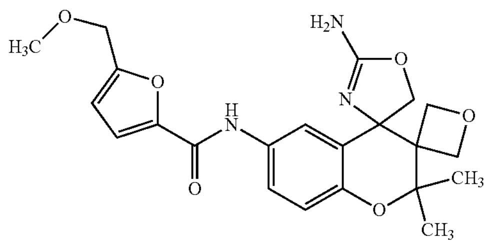 | R70 | E27 |
| P34 | 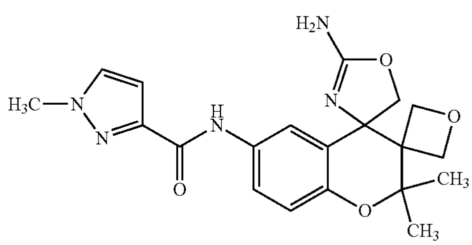 [SMILES: Cn1ccc(C(=O)Nc2ccc3c(c2)C2(COC(N)=N2)C2(COC2)C(C)(C)O3)n1] | R70 | E27 |
| P35 | 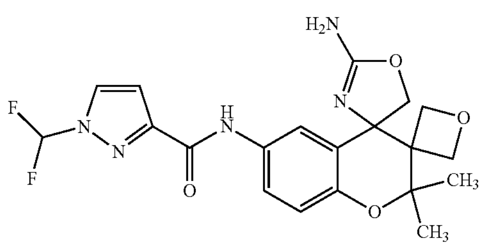 [SMILES: CC1(C)Oc2ccc(NC(=O)c3ccn(C(F)F)n3)cc2C2(COC(N)=N2)C12COC2] | R70 | E27 |
| P36 | 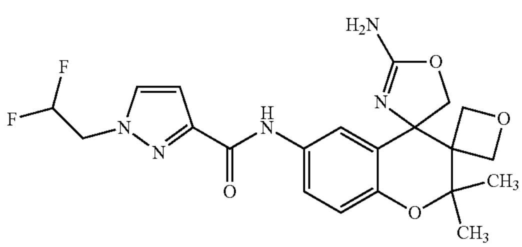 [SMILES: CC1(C)Oc2ccc(NC(=O)c3ccn(CC(F)F)n3)cc2C2(COC(N)=N2)C12COC2] | R70 | E27 |

TABLE 6-continued

| No. | Structure | 1st_step | 2nd_step |
|---|---|---|---|
| P37 | 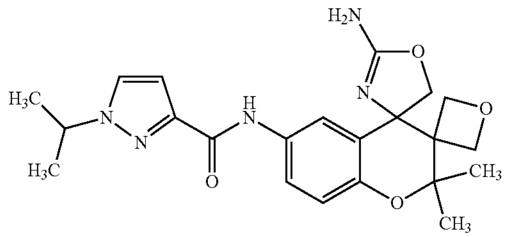 [SMILES: CC(C)n1ccc(C(=O)Nc2ccc3c(c2)C2(COC(N)=N2)C2(COC2)C(C)(C)O3)n1] | R70 | E27 |
| P38 | 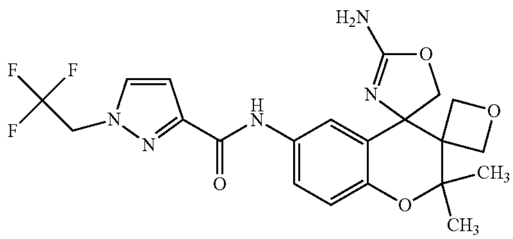 [SMILES: CC1(C)Oc2ccc(NC(=O)c3ccn(CC(F)(F)F)n3)cc2C2(COC(N)=N2)C12COC2] | R70 | E27 |
| P39 | 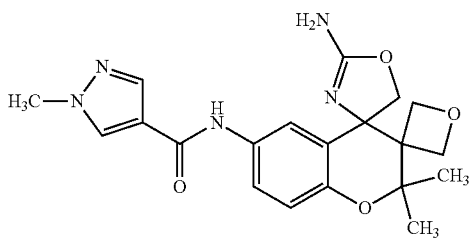 [SMILES: Cn1cc(C(=O)Nc2ccc3c(c2)C2(COC(N)=N2)C2(COC2)C(C)(C)O3)cn1] | R70 | E27 |
| P40 | 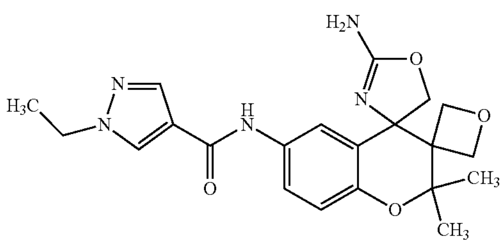 [SMILES: CCn1cc(C(=O)Nc2ccc3c(c2)C2(COC(N)=N2)C2(COC2)C(C)(C)O3)cn1] | R70 | E27 |
| P41 | 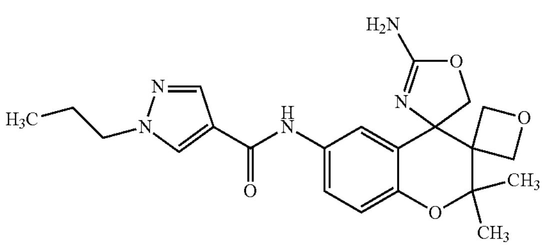 [SMILES: CCCn1cc(C(=O)Nc2ccc3c(c2)C2(COC(N)=N2)C2(COC2)C(C)(C)O3)cn1] | R70 | E27 |
| P42 | 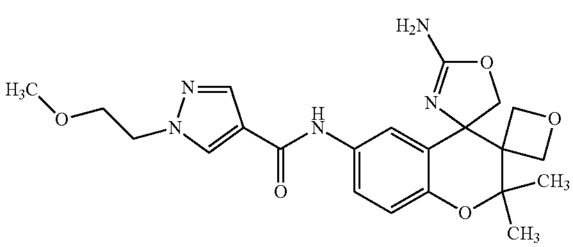 [SMILES: COCCn1cc(C(=O)Nc2ccc3c(c2)C2(COC(N)=N2)C2(COC2)C(C)(C)O3)cn1] | R70 | E27 |

TABLE 6-continued

| No. | Structure | 1st_step | 2nd_step |
|---|---|---|---|
| P43 | 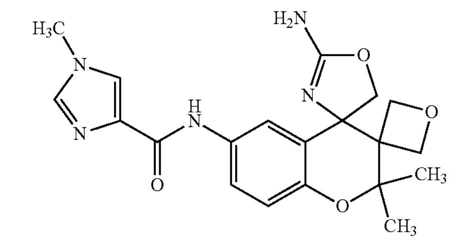 [SMILES: Cn1cnc(C(=O)Nc2ccc3c(c2)C2(COC(N)=N2)C2(COC2)C(C)(C)O3)c1] | R70 | E27 |
| P44 | 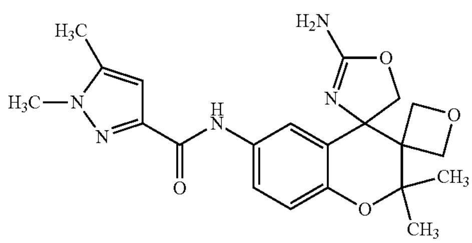 [SMILES: Cc1cc(C(=O)Nc2ccc3c(c2)C2(COC(N)=N2)C2(COC2)C(C)(C)O3)nn1C] | R70 | E27 |
| P45 | 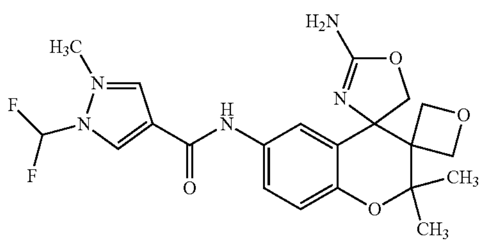 | R70 | E27 |
| P46 | 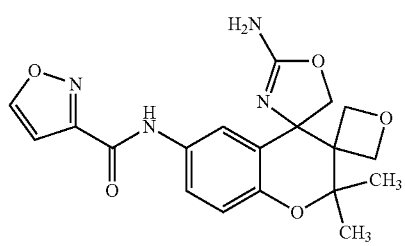 [SMILES: CC1(C)Oc2ccc(NC(=O)c3ccon3)cc2C2(COC(N)=N2)C12COC2] | R70 | E27 |
| P47 | 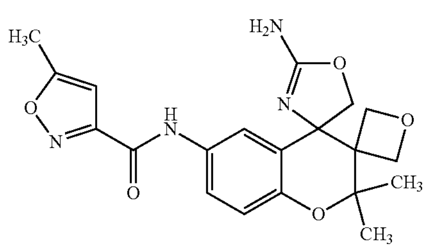 [SMILES: Cc1cc(C(=O)Nc2ccc3c(c2)C2(COC(N)=N2)C2(COC2)C(C)(C)O3)no1] | R70 | E27 |
| P48 | 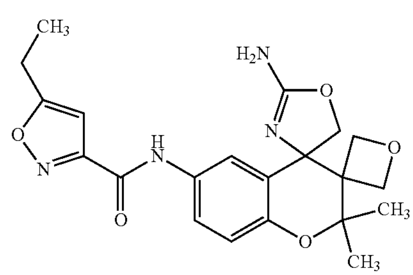 [SMILES: CCc1cc(C(=O)Nc2ccc3c(c2)C2(COC(N)=N2)C2(COC2)C(C)(C)O3)no1] | R70 | E27 |

TABLE 6-continued

| No. | Structure | 1st_step | 2nd_step |
|-----|-----------|----------|----------|
| P49 | 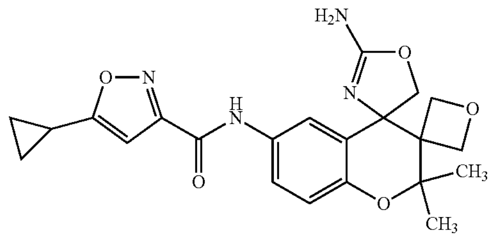 [SMILES: CC1(C)Oc2ccc(NC(=O)c3cc(C4CC4)on3)cc2C2(COC(N)=N2)C12COC2] | R70 | E27 |
| P50 | 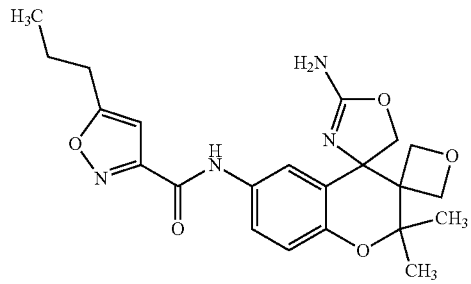 [SMILES: CCCc1cc(C(=O)Nc2ccc3c(c2)C2(COC(N)=N2)C2(COC2)C(C)(C)O3)no1] | R70 | E27 |
| P51 | 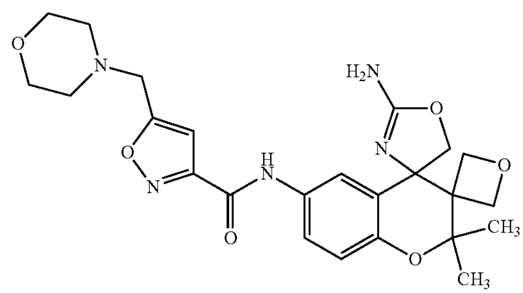 [SMILES: CC1(C)Oc2ccc(NC(=O)c3cc(CN4CCOCC4)on3)cc2C2(COC(N)=N2)C12COC2] | R70 | E27 |
| P52 | 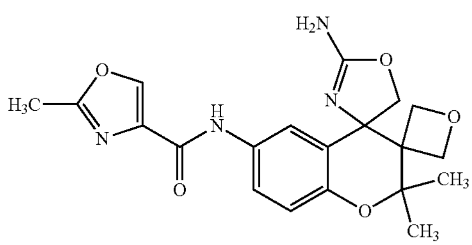 | R70 | E27 |
| P53 | 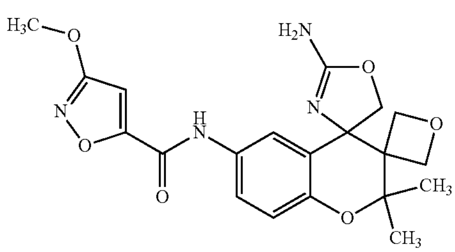 [SMILES: COc1cc(C(=O)Nc2ccc3c(c2)C2(COC(N)=N2)C2(COC2)C(C)(C)O3)on1] | R70 | E27 |
| P54 | 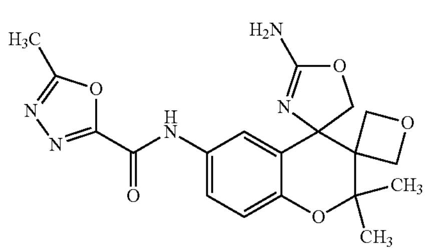 [SMILES: Cc1nnc(C(=O)Nc2ccc3c(c2)C2(COC(N)=N2)C2(COC2)C(C)(C)O3)o1] | R70 | E27 |

TABLE 6-continued

| No. | Structure | 1st_step | 2nd_step |
|-----|-----------|----------|----------|
| P55 | 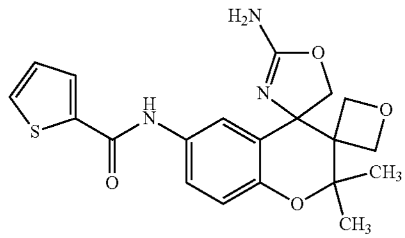 [SMILES: CC1(C)Oc2ccc(NC(=O)c3cccs3)cc2C2(COC(N)=N2)C12COC2] | R70 | E27 |
| P56 | 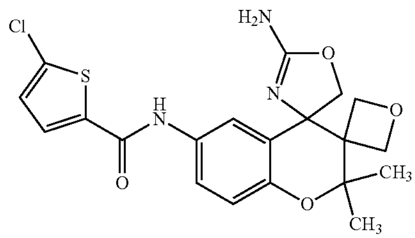 | R70 | E27 |
| P57 | 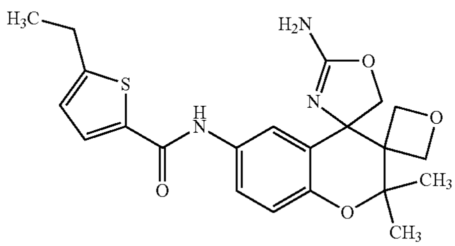 [SMILES: CCc1ccc(C(=O)Nc2ccc3c(c2)C2(COC(N)=N2)C2(COC2)C(C)(C)O3)s1] | R70 | E27 |
| P58 | 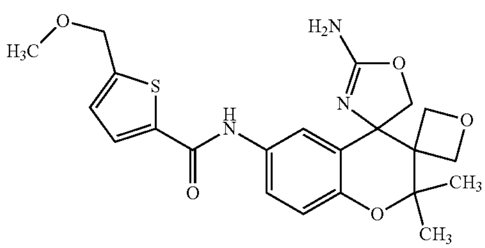 [SMILES: COCc1ccc(C(=O)Nc2ccc3c(c2)C2(COC(N)=N2)C2(COC2)C(C)(C)O3)s1] | R70 | E27 |
| P59 | 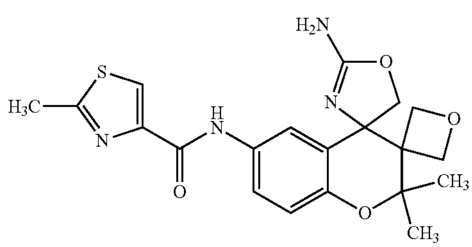 [SMILES: Cc1nc(C(=O)Nc2ccc3c(c2)C2(COC(N)=N2)C2(COC2)C(C)(C)O3)cs1] | R70 | E27 |
| P60 | 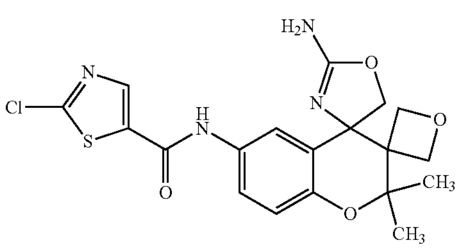 [SMILES: CC1(C)Oc2ccc(NC(=O)c3cnc(Cl)s3)cc2C2(COC(N)=N2)C12COC2] | R70 | E27 |

TABLE 6-continued
| No. | Structure | 1st_step | 2nd_step |
|---|---|---|---|
| P61 | 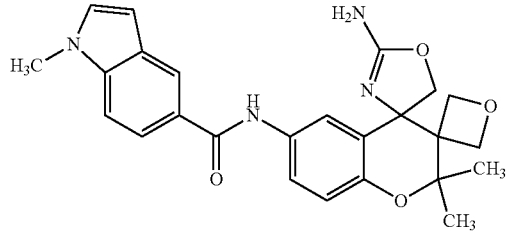 [SMILES: Cn1ccc2cc(C(=O)Nc3ccc4c(c3)C3(COC(N)=N3)C3(COC3)C(C)(C)O4)ccc21] | R70 | E27 |
| P62 | 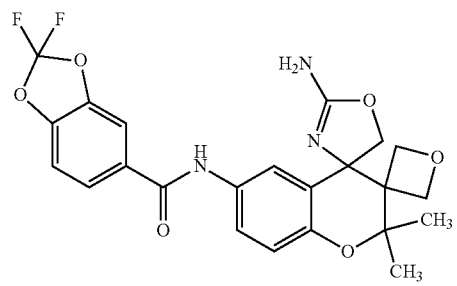 [SMILES: CC1(C)Oc2ccc(NC(=O)c3ccc4c(c3)OC(F)(F)O4)cc2C2(COC(N)=N2)C12COC2] | R70 | E27 |
| P63 | 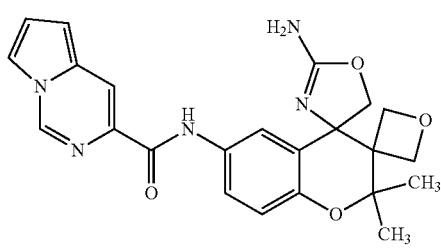 [SMILES: CC1(C)Oc2ccc(NC(=O)c3cc4cccn4cn3)cc2C2(COC(N)=N2)C12COC2] | R70 | E27 |
| P64 | 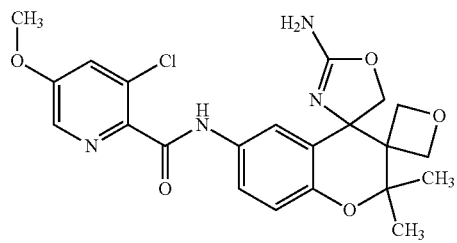 [SMILES: COc1cnc(C(=O)Nc2ccc3c(c2)C2(COC(N)=N2)C2(COC2)C(C)(C)O3)c(Cl)c1] | R70 | E27 |
| P65 | 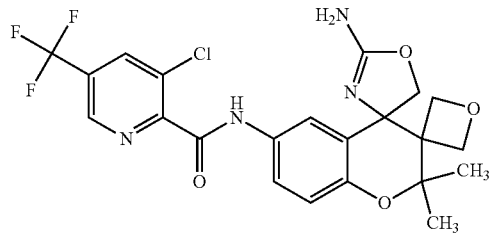 [SMILES: CC1(C)Oc2ccc(NC(=O)c3ncc(C(F)(F)F)cc3Cl)cc2C2(COC(N)=N2)C12COC2] | R70 | E27 |
| P66 | 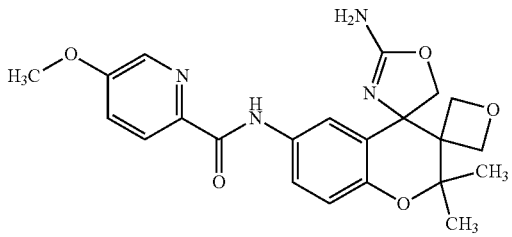 [SMILES: COc1ccc(C(=O)Nc2ccc3c(c2)C2(COC(N)=N2)C2(COC2)C(C)(C)O3)nc1] | R70 | E27 |

TABLE 6-continued

| No. | Structure | 1st_step | 2nd_step |
|---|---|---|---|
| P67 | 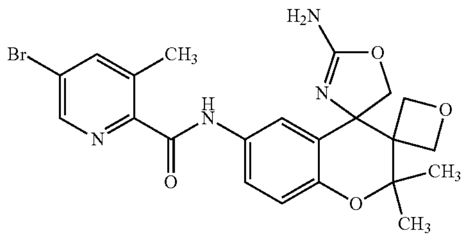 [SMILES: Cc1cc(Br)cnc1C(=O)Nc1ccc2c(c1)C1(COC(N)=N1)C1(COC1)C(C)(C)O2] | R70 | E27 |
| P68 | 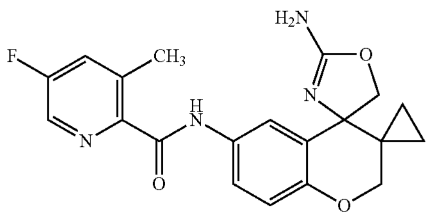 [SMILES: Cc1cc(F)cnc1C(=O)Nc1ccc2c(c1)C1(COC(N)=N1)C1(CC1)CO2] | R70 | E27 |
| P69 | 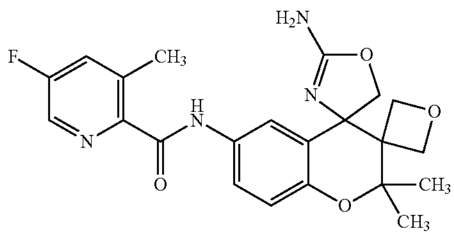 [SMILES: Cc1cc(F)cnc1C(=O)Nc1ccc2c(c1)C1(COC(N)=N1)C1(COC1)C(C)(C)O2] | R70 | E27 |
| P70 | 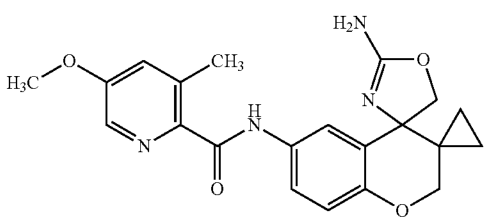 [SMILES: COc1cnc(C(=O)Nc2ccc3c(c2)C2(COC(N)=N2)C2(CC2)CO3)c(C)c1] | R70 | E27 |
| P71 | 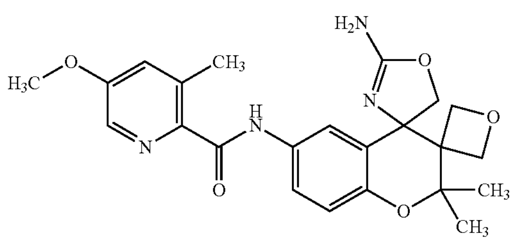 [SMILES: COc1cnc(C(=O)Nc2ccc3c(c2)C2(COC(N)=N2)C2(COC2)C(C)(C)O3)c(C)c1] | R70 | E27 |
| P72 | 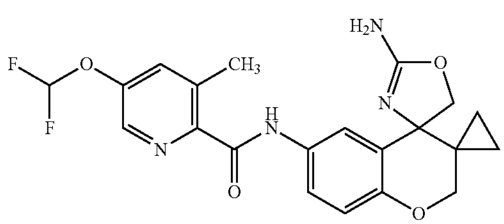 [SMILES: Cc1cc(OC(F)F)cnc1C(=O)Nc1ccc2c(c1)C1(COC(N)=N1)C1(CC1)CO2] | R70 | E27 |
| P73 | 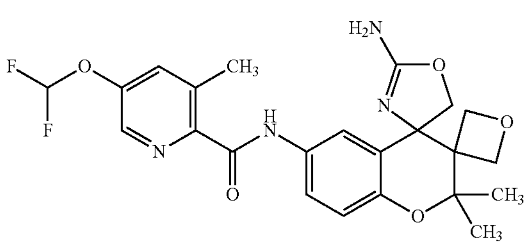 [SMILES: Cc1cc(OC(F)F)cnc1C(=O)Nc1ccc2c(c1)C1(COC(N)=N1)C1(COC1)C(C)(C)O2] | R70 | E27 |

TABLE 6-continued

| No. | Structure | 1st_step | 2nd_step |
|---|---|---|---|
| P74 | 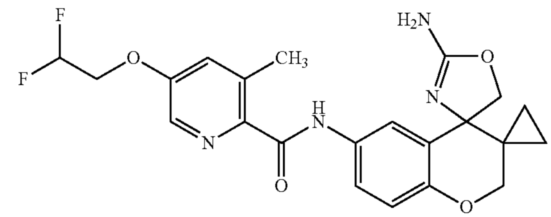 [SMILES: Cc1cc(OCC(F)F)cnc1C(=O)Nc1ccc2c(c1)C1(COC(N)=N1)C1(CC1)CO2] | R70 | E27 |
| P75 | 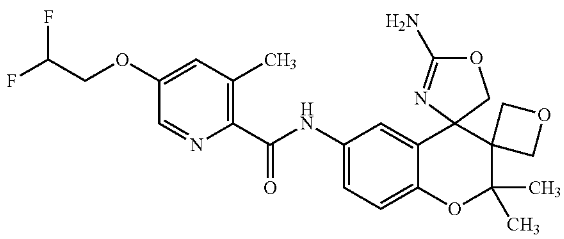 [SMILES: Cc1cc(OCC(F)F)cnc1C(=O)Nc1ccc2c(c1)C1(COC(N)=N1)C1(COC1)C(C)(C)O2] | R70 | E27 |
| P76 | 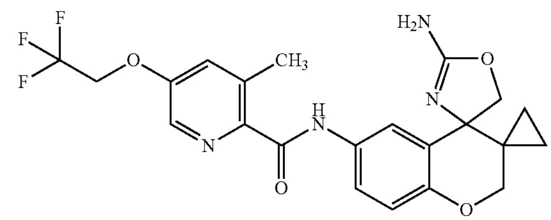 [SMILES: Cc1cc(OCC(F)(F)F)cnc1C(=O)Nc1ccc2c(c1)C1(COC(N)=N1)C1(CC1)CO2] | R70 | E27 |
| P77 | 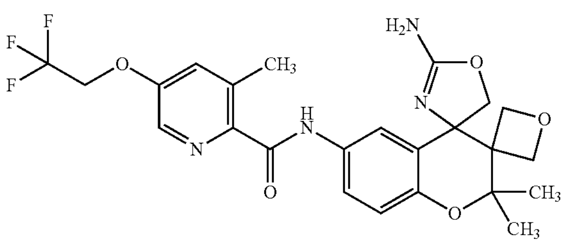 [SMILES: Cc1cc(OCC(F)(F)F)cnc1C(=O)Nc1ccc2c(c1)C1(COC(N)=N1)C1(COC1)C(C)(C)O2] | R70 | E27 |
| P78 | 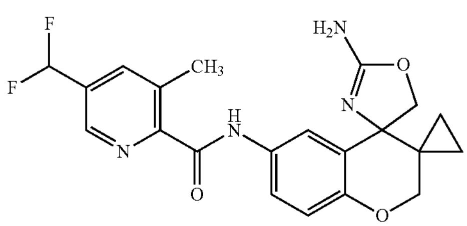 [SMILES: Cc1cc(C(F)F)cnc1C(=O)Nc1ccc2c(c1)C1(COC(N)=N1)C1(CC1)CO2] | R70 | E27 |
| P79 | 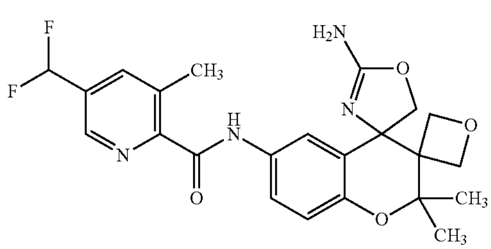 [SMILES: Cc1cc(C(F)F)cnc1C(=O)Nc1ccc2c(c1)C1(COC(N)=N1)C1(COC1)C(C)(C)O2] | R70 | E27 |

TABLE 6-continued
| No. | Structure | 1st_step | 2nd_step |
|---|---|---|---|
| P80 | 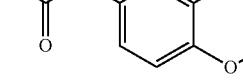 | R70 | E27 |
| P81 | 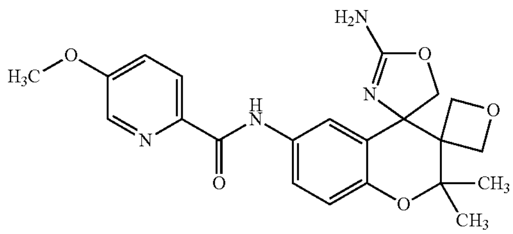 | R70 | E27 |
| P82 | 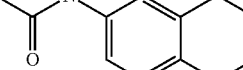 | R70 | E27 |
| P83 | 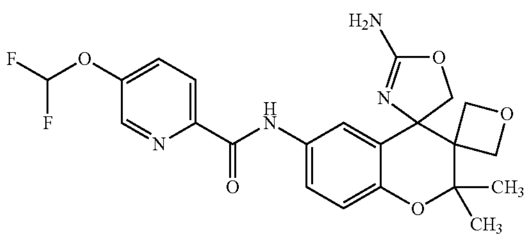 [SMILES: CC1(C)Oc2ccc(NC(=O)c3ccc(OC(F)F)cn3)cc2C2(COC(N)=N2)C12COC2] | R70 | E27 |
| P84 | 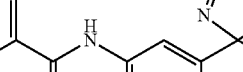 | R70 | E27 |
| P85 | 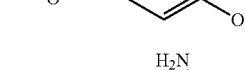 | R70 | E27 |
| P86 | 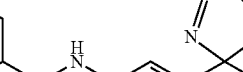 | R70 | E27 |

TABLE 6-continued

| No. | Structure | 1st_step | 2nd_step |
|---|---|---|---|
| P87 | 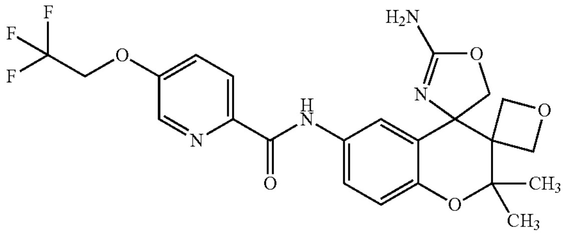 | R70 | E27 |
| P88 | 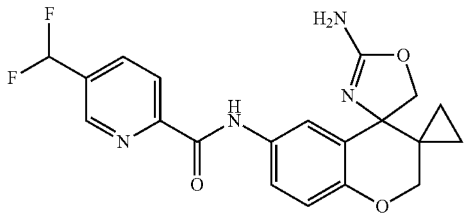 [SMILES: NC1=NC2(CO1)c1cc(NC(=O)c3ccc(C(F)F)cn3)ccc1OCC21CC1] | R70 | E27 |
| P89 | 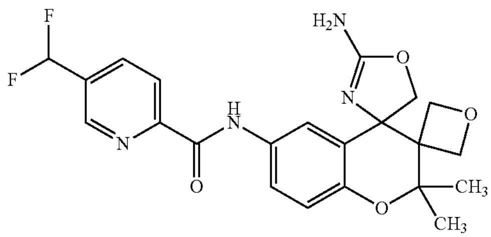 | R70 | E27 |
| P90 | 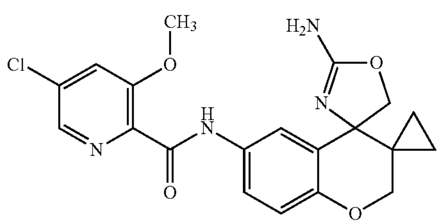 [SMILES: COc1cc(Cl)cnc1C(=O)Nc1ccc2c(c1)C1(COC(N)=N1)C1(CC1)CO2] | R70 | E27 |
| P91 | 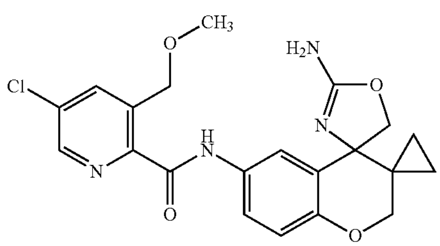 [SMILES: COCc1cc(Cl)cnc1C(=O)Nc1ccc2c(c1)C1(COC(N)=N1)C1(CC1)CO2] | R70 | E27 |
| P92 | 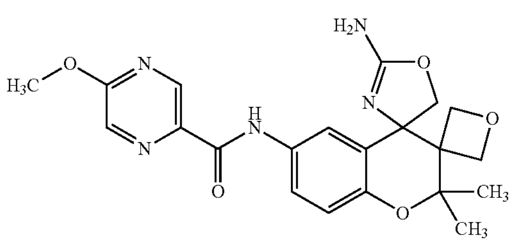 [SMILES: COc1cnc(C(=O)Nc2ccc3c(c2)C2(COC(N)=N2)C2(COC2)C(C)(C)O3)cn1] | R70 | E27 |

TABLE 6-continued

| No. | Structure | 1st_step | 2nd_step |
|---|---|---|---|
| P93 | 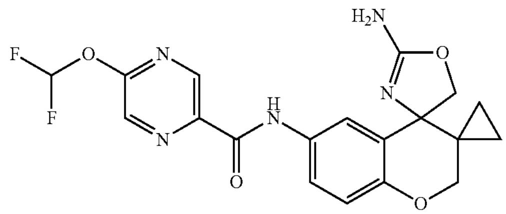 [SMILES: NC1=NC2(CO1)c1cc(NC(=O)c3cnc(OC(F)F)cn3)ccc1OCC21CC1] | R70 | E27 |
| P94 | 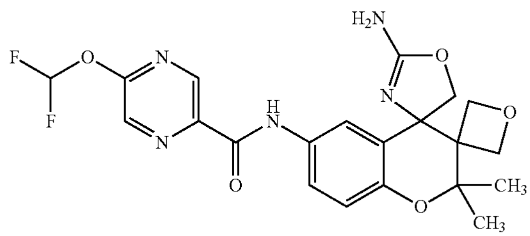 | R70 | E27 |
| P95 | 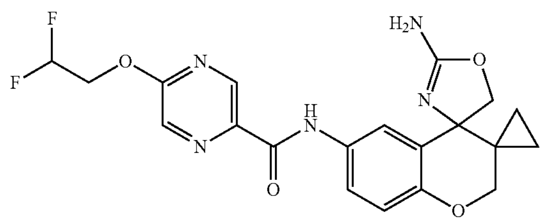 [SMILES: NC1=NC2(CO1)c1cc(NC(=O)c3cnc(OCC(F)F)cn3)ccc1OCC21CC1] | R70 | E27 |
| P96 | 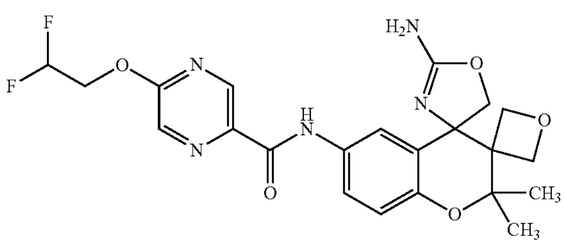 [SMILES: CC1(C)Oc2ccc(NC(=O)c3cnc(OCC(F)F)cn3)cc2C2(COC(N)=N2)C12COC2] | R70 | E27 |
| P97 | 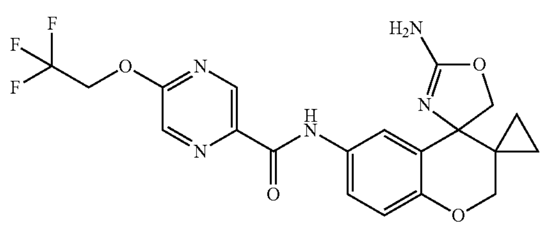 [SMILES: NC1=NC2(CO1)c1cc(NC(=O)c3cnc(OCC(F)(F)F)cn3)ccc1OCC21CC1] | R70 | E27 |
| P98 | 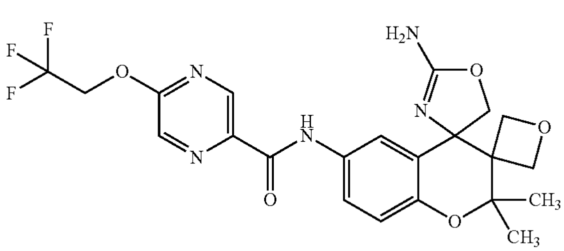 [SMILES: CC1(C)Oc2ccc(NC(=O)c3cnc(OCC(F)(F)F)cn3)cc2C2(COC(N)=N2)C12COC2] | R70 | E27 |

TABLE 6-continued

| No. | Structure | 1st_step | 2nd_step |
|---|---|---|---|
| P99 | 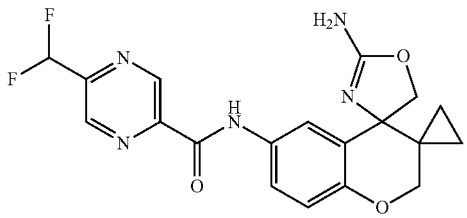 [SMILES: NC1=NC2(CO1)c1cc(NC(=O)c3cnc(C(F)F)cn3)ccc1OCC21CC1] | R70 | E27 |
| P100 | 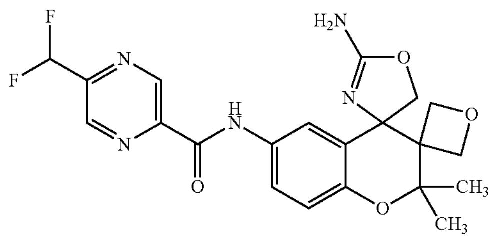 [SMILES: CC1(C)Oc2ccc(NC(=O)c3cnc(C(F)F)cn3)cc2C2(COC(N)=N2)C12COC2] | R70 | E27 |

The teachings of all references cited in this specification are incorporated herein in their entirety.

INDUSTRIAL APPLICABILITY

The compounds of the formula (I) or a salt thereof have a beta-secretase inhibitory activity, and therefore can be used as an agent for preventing or treating diseases or conditions associated with and/or mediated by β-secretase activity, hydrolysis of a β-secretase site of a β-amyloid precursor protein, and/or β-amyloid protein accumulation, such as Glaucoma, MCI (Mild cognitive impairment) or Alzheimer's disease, especially, Alzheimer's disease, or the like.

The invention claimed is:

1. A hydrate of N-[(4S)-2-amino-2',2'-dimethyldispiro[1, 3-oxazole-4,4'-chromene-3',3''-oxetan]-6'-yl]-5-chloropyridine-2-carboxamide, wherein a powder X-ray diffraction pattern for the hydrate comprises peaks at angles 2 theta of about 5.7°, 9.6°, 11.4°, 12.3°, 13.7°, 15.7°, 15.9°, and 25.0°.

2. A pharmaceutical composition comprising the hydrate of claim 1 and a pharmaceutically acceptable carrier.

* * * * *